(12) United States Patent
Passananti et al.

(10) Patent No.: US 10,286,085 B2
(45) Date of Patent: May 14, 2019

(54) COMPOSITIONS AND METHODS FOR TREATMENT OF MUSCULAR DYSTROPHY

(71) Applicant: CONSIGLIO NAZIONALE DELLE RICERCHE, Rome (IT)

(72) Inventors: Claudio Passananti, Rome (IT); Nicoletta Corbi, Rome (IT); Maria Grazia Di Certo, Rome (IT); Elisabetta Mattei, Rome (IT); Cinzia Pisani, Valmontone (IT); Georgios Strimpakos, Rome (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 279 days.

(21) Appl. No.: 14/909,854

(22) PCT Filed: Jul. 26, 2014

(86) PCT No.: PCT/EP2014/002051
§ 371 (c)(1),
(2) Date: Jul. 7, 2016

(87) PCT Pub. No.: WO2015/018503
PCT Pub. Date: Feb. 12, 2015

(65) Prior Publication Data
US 2016/0303255 A1 Oct. 20, 2016

(30) Foreign Application Priority Data
Aug. 5, 2013 (IT) .............................. TO2013A0669

(51) Int. Cl.
| | | |
|---|---|---|
| *A61K 48/00* | (2006.01) | |
| *C07K 14/47* | (2006.01) | |
| *G01N 33/68* | (2006.01) | |
| *C07K 14/005* | (2006.01) | |
| *C12N 15/86* | (2006.01) | |
| *A61K 38/00* | (2006.01) | |

(52) U.S. Cl.
CPC ........ *A61K 48/0058* (2013.01); *C07K 14/005* (2013.01); *C07K 14/4702* (2013.01); *C12N 15/86* (2013.01); *G01N 33/6893* (2013.01); *A61K 38/00* (2013.01); *C07K 14/4708* (2013.01); *C07K 2319/81* (2013.01); *C12N 2710/16632* (2013.01); *C12N 2750/14143* (2013.01); *C12N 2750/14171* (2013.01); *C12N 2830/008* (2013.01); *C12N 2830/34* (2013.01); *G01N 2800/2878* (2013.01)

(58) Field of Classification Search
None
See application file for complete search history.

(56) References Cited

U.S. PATENT DOCUMENTS

| | | | |
|---|---|---|---|
| 6,506,379 B1 * | 1/2003 | Clackson | ............. C07K 14/715 424/93.21 |
| 8,304,235 B2 | 11/2012 | Passananti et al. | |
| 2017/0218037 A1 | 8/2017 | Passananti et al. | |

FOREIGN PATENT DOCUMENTS

| | | |
|---|---|---|
| WO | WO-2005/118611 A2 | 12/2005 |
| WO | WO-2009/044383 A1 | 4/2009 |

OTHER PUBLICATIONS

Briguet et al., Neuromuscular Disorders, 2003, vol. 13, pp. 143-150.*
Mattei et al., PLoS ONE, 2007, vol. 2(8), pp. 1-8.*
Phillips et al., Methods Mol Biol, 2011, vol. 709, pp. 141-151.*
Barde et al., "Regulation of Episomal Gene Expression by KRAB/KAP1-Mediated Histone Modifications," J Virol. 83(11):5574-80 (2009).
Boisgérault et al., "The Skeletal Muscle Environment and Its Role in Immunity and Tolerance to AAV Vector-Mediated Gene Transfer," available in PMC Jul. 27, 2015, published in final edited form as: Curr Gene Ther. 15(4):381-94 (2015) (28 pages).
Communication Pursuant to Article 94(3) EPC for European Patent Application No. 14746954.8, dated Apr. 6, 2017 (6 pages).
Hirschfeld et al., "Targeting myofibroblasts in model systems of fibrosis by an artificial alpha-smooth muscle-actin promoter hybrid," Mol Biotechnol. 43(2):121-9 (2009).
International Search Report and Written Opinion for International Patent Application No. PCT/EP2014/002051, dated Nov. 5, 2014 (14 pages).
Lai et al., "Synthetic intron improves transduction efficiency of trans-splicing adeno-associated viral vectors," Hum Gene Ther. 17(10): 1036-42 (2006).
Li et al., "Sarcolemmal nNOS anchoring reveals a qualitative difference between dystrophin and utrophin," J Cell Sci. 123(Pt 12):2008-13 (2010).
Liu et al., "Therapeutic levels of factor IX expression using a muscle-specific promoter and adeno-associated virus serotype 1 vector," Hum Gene Ther. 15(8):783-92 (2004).
Onori et al., "UtroUp is a novel six zinc finger artificial transcription factor that recognises 18 base pairs of the utrophin promoter and efficiently drives utrophin upregulation," BMC Mol Bio. 14:3 (2013) (9 pages).
Strimpakos et al., "Novel adeno-associated viral vector delivering the utrophin gene regulator jazz counteracts dystrophic pathology in mdx mice," J Cell Physiol. 229(9): 1283-91 (2014).
Toscano et al., "Physiological and tissue-specific vectors for treatment of inherited diseases," Gene Ther. 18(2): 117-27 (2011).

* cited by examiner

*Primary Examiner* — Mindy G Brown
(74) *Attorney, Agent, or Firm* — Clark & Elbing LLP

(57) ABSTRACT

The present invention features recombinant adeno-associated vectors for delivery of genes to both skeletal and cardiac muscle and methods for treatment of muscle defects, including Duchenne's muscular dystrophy.

9 Claims, 30 Drawing Sheets

Specification includes a Sequence Listing.

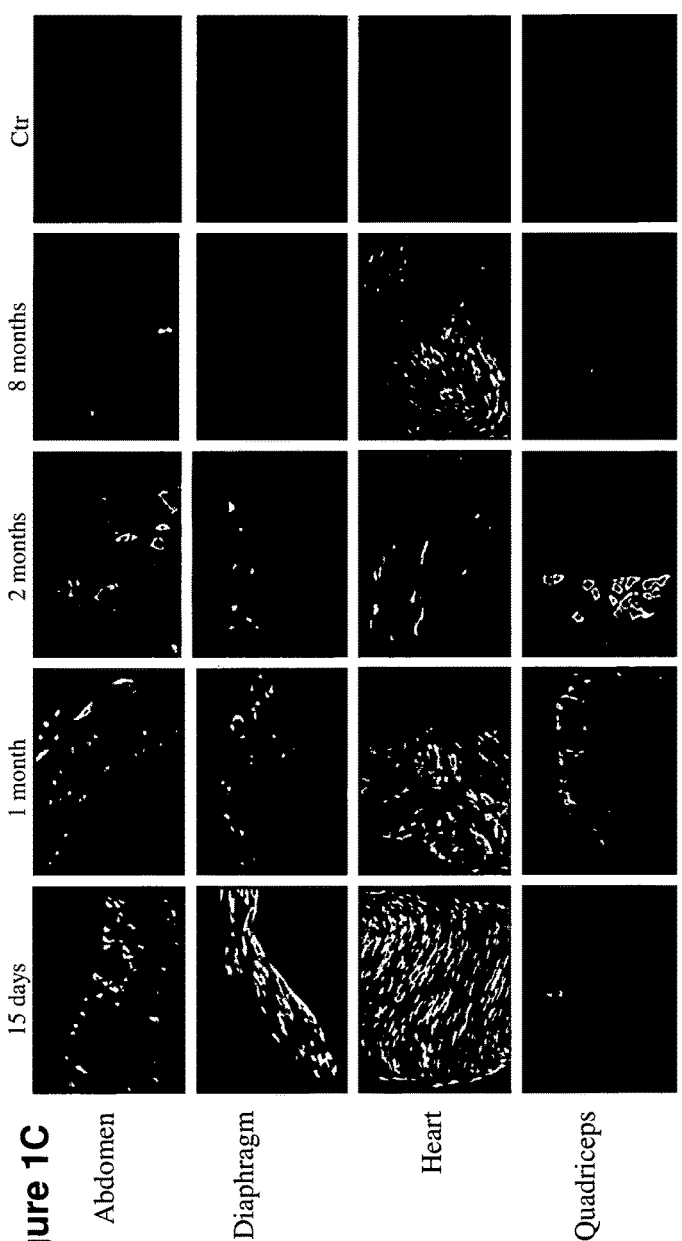
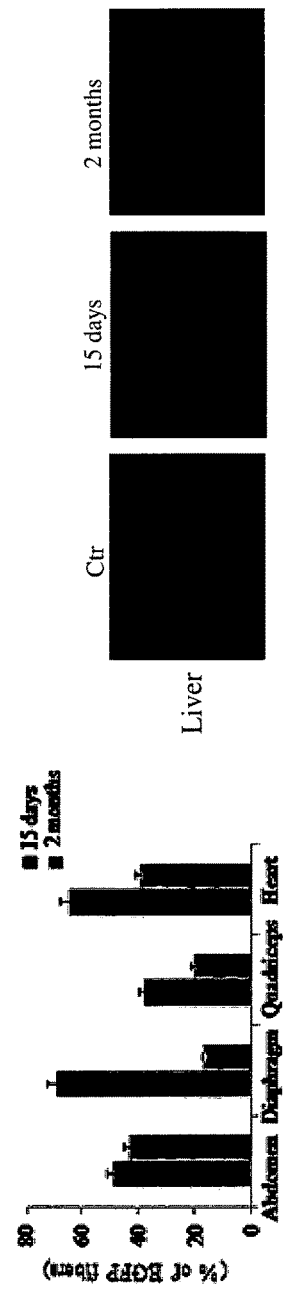
Figure 1C

Figure 12B

JZif1

MAAAKAEMQLMSPLQISDPFGSFPHSPTMDNYPKLEEMMLLSNGAPQFLGAAGAP

EGSGSNSSSSSGGGGGGGGSNSSSSSTFNPQADTGEQPYEHLTAESFPDISL

NNEKVLVETSYPSQTTRLPPITYTGRFSLEPAPNSGNTLWPEPLFSLVSGLVSMTNP

PASSSSAPSPAASSASASQSPPLSCAVPSNDSSPIYSAAPTFPTNTDIFPEPQSQAF

PGSAGTALQYPPPAYPAAKGGFQVPMIPDYLFPQQQGDLGLGTPDQKPFQGLESR

TQQPSLTPLSTIKAFATQSGSQDLKALNTSYQSQLIKPSRMRKYPNRPSKTPPHERP

ZF1   -1 2 3 4 5 6 7 8 9                   ZF2   -1 2 3 4 5 6 7 8 9
YACPVESCDRRFSRSDELTRHIRIHTGQKPFQCRICMRNFSSRDVLRRHNRIHTGE

ZF3   -1 2 3 4 5 6 7 8 9
KPFACDICGRKFASRDVLRRHNRIHLRQKDKKADKSVVASSATSSLSSYPSPVATSY

PSPVTTSYPSPATTSYPSPVPTSFSSPGSSTYPSPVHSGFPSPSVATTYSSVPPAFP

AQVSSFPSSAVTNSFSASTGLSDMTATFSPRTIEIC    (SEQ ID NO:38)

Figure 12C

JZif2

MAAAKAEMQLMSPLQISDPFGSFPHSPTMDNYPKLEEMMLLSNGAPQFLGAAGAP

EGSGSNSSSSGGGGGGGGSNSSSSSSTFNPQADTGEQPYEHLTAESFPDISL

NNEKVLVETSYPSQTTRLPPITYTGRFSLEPAPNSGNTLWPEPLFSLVSGLVSMTNP

PASSSSAPSPAASSASASQSPPLSCAVPSNDSSPIYSAAPTFPTNTDIFPEPQSQAF

PGSAGTALQYPPPAYPAAKGGFQVPMIPDYLFPQQQGDLGLGTPDQKPFQGLESR

TQQPSLTPLSTIKAFATQSGSQDLKALNTSYQSQLIKPSRMRKYPNRPSKTPPHERP

ZF1   -1 1 2 3 4 5 6 7 8 9                       ZF2   -1 1 2 3 4 5 6 7 8 9
YAC PVESC DRRF SRSDNLVRH IRIH TGQKPFQ CRICMRNF SRSDEL TTHIRIH TGE

ZF3   -1 1 2 3 4 5 6 7 8 9
KPFAC DICCRKF ADPGHLVRH NRIH LRQKDKKADKSVVASSATSSLSSYPSPVATSY

PSPVTTSYPSPATTSYPSPVPTSFSSPGSSTYPSSTYPSPVHSGFPSPSVATTYSSVPPAFP

AQVSSFPSSAVTNSFSASTGLSDMTATFSPRTIEIC    (SEQ ID NO:39)

Figure 13

Human and mouse Utrophin promoter "A"

```
human 272 AGAGACCTGTGTTTGCCTAAGGGACGTGACTCACATTTTCGGATAATCTGAATAAGGGGA
          ||||||||| ||||||||||||||||||||||||||||| ||||| |||||| |||||
mouse 292 AGAGACCTAGTGTGCCTAGAGGGGTGTGACACACATTTTCGGACAATTTGAATAAAGGGC human     ATTGTGTCTGCTCGAGGCATCCATTCTGGTTCGGTCTCCGGACTCCCGGCTCCCCGGCACG
          | |||  |||| ||||| ||| | |||||| |||  |||         ||||  |||||
mouse     ACGGTGCGTGCGCGGGTGACTATTCCAGCT---TCT--------GGCTTCCAGCACG human     CACGGTTCACTCTGGAGCGCCGCGCGCCCCCAGCGCCCAGCCCAGCGCCGAGCGCCGGCCGGGCTGCTGCGG
          |||| ||| ||||||||| |||| |||  ||| |||  ||||| ||||| |  |||||||||||||||
mouse     CACGACTGTTCCCGGATTCTCGCACCGCGCA---CC-GCACGGAGCC-GGGCTGCTGCGG
                                              N-Box human     GCTGGGAGGGGCGCCAGGGCCGGCTGATTGACGGGGCGGCAGTCAGGTGACTTGGGG
          ||||||||||||||||||||||||||||||||||||||||| ||||||||| ||||
mouse     GCTGGGAGGGCGCCCTAGGCCTAGCGCTGATTGACGCCGCGGTCAGTGACCCGAAG
                                                              E-Box human     CGCCAAGTTCCCGACGCGGTGGCGCGGTGACCGCGAGGCC-CGGACAGACGCTGACCCG
          |||||| ||| |||| || ||||| |||  || |||||| ||||| ||| || |||
mouse     CGCCACGTTCTGGGAGCCCGGCCGGTGGCTTCCCAGGCCGGGCAG--GACCGAACCC human     GGAACGTAGTGGGGCTGATCTTCC----GGAACAAAAGTTGCTGGGCGCGGGCGGG-
          || ||||| |||| ||| | |||     |||||||||||||||||| ||| |||||
mouse     GGAGCCGAGGGGGACTGGTCTCTCCCCGGAGAACAAAGTTGCCCGGCCTGGGGCCCCGGGG human     -GCGAGAGCGCCGAG  639  (SEQ ID NO:20)
           |||   |||||||
mouse     CGCGCGAGCGGCGAG  647  (SEQ ID NO:33)

---->> >> transcription ---->> >>
```

*diaphragm*

*abdomen*

COMPOSITIONS AND METHODS FOR TREATMENT OF MUSCULAR DYSTROPHY

CROSS-REFERENCE TO RELATED APPLICATIONS

This application claims priority to Italian provisional application TO2013A000669, filed on Aug. 5, 2013, the entirety of which is incorporated herein by reference.

BACKGROUND OF THE INVENTION

The present invention relates to compositions including recombinant adeno-associated vectors (AAVs) comprising genes to be expressed in skeletal and cardiac muscle tissue, as well as methods for treatment of muscular defects.

Duchenne's muscular dystrophy (DMD) is a severe X-linked muscle degenerative disease caused by the absence of the cytoskeletal protein dystrophin. The dystrophin protein provides stability to the sarcolemma (i.e., the cell membrane of muscle cells) by linking the intracellular cytoskeletal network to the extracellular matrix. In the absence of dystrophin, muscle contraction mechanically stresses the cell membrane, inducing progressive damage to the myofibers. Initially, skeletal muscles are predominantly affected; however, as the disease progresses, the damage extends to cardiac muscle and death is caused by respiratory or cardiac failure. DMD is one of the most common genetic diseases, affecting an estimated 1 out of every 3,600 male births each year. DMD is a debilitating disease that progressively worsens over the short (approximately 25 year) lifespan of those affected. Unfortunately, despite years of research, there are no curative treatments for muscular dystrophies including DMD. Current therapies are limited to managing symptoms.

Gene transfer by recombinant AAV has gained increasing value in recent years for experimental and human gene therapy. AAVs are small viruses that elicit a very mild immune response and do not cause any known human diseases. Additional advantages of these viral vectors include the existence of several serotypes ensuring a wide spectrum of tissue-specific tropism, as well as a robust, long-term transgene expression in vivo. Many successful preclinical studies on animal models have paved the way for the use of recombinant AAV-based gene delivery for clinical applications. However, the extremely large size of the dystrophin gene (approximately 2,400 kilobases or kb) has complicated efforts for gene therapy to treat DMD or related dystrophinopathies, because the packaging size of inserts into recombinant AAV vectors is limited to about 4.7 kb.

Therefore, a need exists for improved muscle-specific recombinant AAV vectors for delivery of genes to both skeletal and cardiac muscle. There also exists a long-standing need for compositions and methods for treating muscular dystrophies, especially DMD.

SUMMARY OF THE INVENTION

In a first aspect, the invention features a recombinant adeno-associated vector (AAV) for expression of a gene in skeletal or cardiac muscle tissue, the vector including a muscle-specific promoter and a gene encoding a fusion protein, wherein the fusion protein includes a) a transcriptional activation element and b) a DNA binding element, wherein the fusion protein, when expressed in the skeletal or cardiac muscle tissue, is capable of increasing utrophin expression.

In some embodiments of the first aspect, the gene is expressed in skeletal muscle. In some embodiments, the gene is expressed in cardiac muscle. In certain embodiments, the gene is expressed in skeletal and cardiac muscle. In some embodiments, the vector further includes at least one element selected from the group consisting of an inverted terminal repeat, a cap signal, a multicloning site, an intron splice-donor site, an intron splice-acceptor site, an epitope tag, a nuclear localization sequence, and a polyadenylation consensus sequence. In some embodiments, the epitope tag is a myc tag. In some embodiments, the intron splice-acceptor site is a beta-globin intron splice-acceptor site. In some embodiments, the transcriptional activation element is Vp16.

In some embodiments of the first aspect, the DNA binding element binds a mouse or human utrophin promoter. In some embodiments, the mouse or human utrophin promoter includes the sequence of SEQ ID NO:9. In some embodiments, the DNA binding element includes one or more zinc fingers. In certain embodiments, the DNA binding element is selected from the group consisting of Jazz, Bagly, and UtroUp or variants thereof. In some embodiments, the muscle-specific promoter is selected from the group consisting of alpha-actin, cardiac troponin C, myosin light chain 2A, skeletal beta-actin, CK6, dystrophin, and muscular creatine kinase. In some embodiments, the vector has a serotype of AAV8 or AAV9. In some embodiments, the transcriptional activation element is Vp16 and the DNA binding element is Jazz. In some embodiments, the muscle-specific promoter is alpha-actin, the transcriptional activation element is Vp16, and the DNA binding element is Jazz. In some embodiments, the vector includes the sequence of SEQ ID NO:83.

In a second aspect, the invention features a composition including any one of the preceding vectors and a pharmaceutically acceptable carrier.

In a third aspect, the invention features a method of treating Duchenne's Muscular Dystrophy in a subject in need thereof, the method including administering an effective amount of a composition of the second aspect. In some embodiments, the composition is administered intraperitoneally.

In a fourth aspect, the invention features a method of treating Duchenne's Muscular Dystrophy in a subject in need thereof, the method including contacting the utrophin gene of a muscle cell with a fusion protein, wherein the contacting results in an increase in utrophin expression. In some embodiments, the fusion protein binds to a promoter of the utrophin gene. In certain embodiments, the promoter includes a sequence selected from the group consisting of SEQ ID NO: 9, 10, 11, 12, 13, and 14. In some embodiments, the fusion protein includes a sequence selected from the group consisting of SEQ ID NO: 71, 72, and 73.

In a fifth aspect, the invention features a recombinant adeno-associated vector (AAV) for expression of a gene in skeletal or cardiac muscle tissue, the vector including a muscle-specific promoter and a gene encoding a fusion protein, wherein the fusion protein includes a) a transcriptional activation element and b) a DNA binding element, wherein the fusion protein, when expressed in the skeletal or cardiac muscle tissue, is capable of increasing utrophin expression, increasing muscle contractile force, or increasing muscle endurance.

In one embodiment of the fifth aspect, the transcriptional activation element is Vp16 and the DNA binding element is Jazz. In a second embodiment, the muscle-specific promoter is alpha-actin, the transcriptional activation element is Vp16, and the DNA binding element is Jazz. In a third embodiment, the vector includes the sequence of SEQ ID NO:83, 84, or 85.

In a sixth aspect, the invention features a recombinant adeno-associated vector (AAV) for expression of a gene in skeletal or cardiac muscle tissue, the vector including a muscle-specific promoter and a gene encoding a fusion protein, wherein the fusion protein includes: a) a transcriptional activation element and b) a DNA binding element, wherein the fusion protein, when expressed in the skeletal or cardiac muscle tissue, is capable of increasing utrophin expression, increasing muscle contraction force, or increasing muscle endurance, and wherein the vector does not include the sequence of SEQ ID NO:83. In one embodiment of the sixth aspect, the vector includes the sequence of SEQ ID NOs: 84 or 85.

In one embodiment of the fifth and sixth aspects, the gene is expressed in skeletal muscle. In some embodiments, the gene is expressed in cardiac muscle. In a second embodiment, the gene is expressed in skeletal and cardiac muscle. In a third embodiment of the fifth and sixth aspects, the vector further includes at least one element selected from a group consisting of an inverted terminal repeat, a cap signal, a multicloning site, an intron splice-donor site, an intron splice-acceptor site, an epitope tag, a nuclear localization sequence, and a polyadenylation consensus sequence. In certain embodiments, the intron splice-acceptor site is a beta-globin intron splice-acceptor site. In a fourth embodiment of the fifth and sixth aspects, the transcriptional activation element is selected from a group consisting of Vp16, Vp64, p65, SP1, Gal4, and CJ7. In a fifth embodiment of the fifth and sixth aspects, the DNA binding element binds to a promoter of the utrophin gene.

In certain embodiments, the utrophin promoter is a mouse or human utrophin "A" promoter, wherein the mouse or human utrophin "A" promoter includes the sequence of SEQ ID NO:9 or SEQ ID NO:14. In other embodiments, the human utrophin "A" promoter includes the sequence of SEQ ID NO:10 or SEQ ID NO:12. In yet other embodiments, the mouse utrophin "A" promoter includes the sequence of SEQ ID NO:11 or SEQ ID NO:13.

In another embodiment of the fifth and sixth aspects, the DNA binding element includes one or more zinc fingers. In yet another embodiment, the DNA binding element is selected from the group consisting of Jazz, Bagly, or UtroUp, or variants thereof. In yet other embodiments, the DNA binding element is Jazz or variants thereof.

In one embodiment of the fifth and sixth aspects, the muscle-specific promoter is constitutively expressed throughout differentiation. In a second embodiment, the muscle-specific promoter is selected from the group consisting of alpha-actin, cardiac troponin C, myosin light chain 2A, skeletal beta-actin, CK6, dystrophin, muscular creatine kinase, dMCK, tMCK, enh348MCK, synthetic C5-12 (Syn), Myf5, MLC1/3f. MyoD1, Myog, and Pax7. In a third embodiment of the fifth and sixth aspects, the vector has a serotype selected from the group consisting of AAV1, AAV2, AAV3, AAV4, AAV5, AAV6, AAV7, AAV8, and AAV9. In a fourth embodiment, the vector is muscle tropic. In a fifth embodiment, the vector has a serotype of AAV8 or AAV6.

In some embodiments of the fifth and sixth aspects, the muscle endurance is measured in a forced exercise assay, wherein the muscle endurance is increased in the range of about 5% to about 50% relative to baseline. In another embodiment of the fifth and sixth aspects, the utrophin expression is increased by at least 1.5 fold. In yet another embodiment of the fifth and sixth aspects, the muscle contractile force is increased by at least about 10%.

In a seventh aspect, the invention features a composition including any one of the vectors of the fifth and sixth aspects and a pharmaceutically acceptable carrier.

In an eight aspect, the invention features a method of treating a muscle disease in a subject in need thereof, the method including administering an effective amount of a composition of the seventh aspect. In some embodiments, the composition is administered systemically or locally. In some embodiments, the composition is administered intramuscularly, intravenously, subcutaneously, or intraperitoneally.

In a ninth aspect, the invention features a method of treating a muscle disease in a subject in need thereof, the method including contacting the utrophin gene of a muscle cell with a fusion protein, wherein the contacting results in an increase in utrophin expression, an increase in muscle contractile force, or an increase in muscle endurance. In some embodiments, the fusion protein includes a sequence selected from the group consisting of SEQ ID NOs:71, 72, and 73.

In a tenth aspect, the invention features a method of treating a muscle disease in a subject in need thereof, the method including contacting the utrophin gene of a muscle cell with a fusion protein, wherein the contacting results in an increase in utrophin expression, in increase in muscle contractile force, or an increase in muscle endurance, wherein the fusion protein does not include the sequence of SEQ ID NO:71. In some embodiments, the fusion protein includes a sequence selected from the group consisting of SEQ ID NOs:72 and 73.

In one embodiment of the ninth and tenth aspects, the fusion protein binds to a promoter of the utrophin gene. In some embodiments, the promoter is a mouse or human utrophin "A" promoter. In a second embodiment, the promoter includes a sequence selected from the group consisting of SEQ ID NOs: 9, 10, 11, 12, 13, and 14. In a third embodiment, the treating or the contacting results in an increase in muscle contractile force or an increase in muscle endurance. In a fourth embodiment, the muscle disease is a muscular dystrophy, wherein the muscular dystrophy is selected from the group consisting of: Duchenne's Muscular Dystrophy or Becker's Muscular Dystrophy, congenital muscular dystrophy, facioscapulohumeral muscular dystrophy, limb-girdle muscular dystrophy, myotonic muscular dystrophy, and oculopharyngeal muscular dystrophy.

The invention features a modified transcription factor including at least a first, a second, and a third zinc finger motif, wherein the transcription factor is capable of increasing utrophin expression when expressed in skeletal or cardiac muscle tissue. In some embodiments, the transcription factor further includes a fourth, a fifth, a sixth, a seventh, an eighth, or a ninth zinc finger motif. In certain embodiments, each zinc finger motif includes an alpha-helix. In some embodiments, the transcription factor is derived from a genomically-encoded human transcription factor. In some embodiments, the genomically-encoded transcription factor is Zif268.

In one embodiment, the first zinc finger motif can include a sequence having at least 80% sequence identity to SEQ ID NO:48, the second zinc finger motif can include a sequence having at least 80% sequence identity to SEQ ID NO:49, and the third zinc finger motif can include a sequence having at least 80% sequence identity to SEQ ID NO:50.

In a second embodiment, the first zinc finger motif can include SEQ ID NO:48, the second zinc finger motif can include SEQ ID NO:49, and the third zinc finger motif can include SEQ ID NO:50.

In a third embodiment, the transcription factor can include a sequence having at least 95% sequence identity to SEQ ID NO: 38 and wherein the transcription factor includes: i) a first zinc finger motif including an alpha-helix which contains an Arg residue at position −1, a Glu residue at position 3, and an Arg residue at position 6, ii) a second zinc finger motif including an alpha-helix which contains a Ser residue at position −1, an Arg residue at position 1, a Val residue at position 3, an Arg residue at position 5, and Arg residue at position 6, and an Asn residue at position 8, and iii) a third zinc finger motif including an alpha-helix which contains a Ser residue at position −1, an Arg residue at position 1, a Val residue at position 3, a Leu residue at position 4, an Arg residue at position 5, an Arg residue at position 6, an Asn residue at position 8, and an Arg residue at position 9

In a fourth embodiment, the first zinc finger motif can include a sequence having at least 80% sequence identity to SEQ ID NO:51, the second zinc finger motif can include a sequence having at least 80% sequence identity to SEQ ID NO:52, and the third zinc finger motif can include a sequence having at least 80% sequence identity to SEQ ID NO:53.

In a fifth embodiment, the first zinc finger motif can include SEQ ID NO:51, the second zinc finger motif can include SEQ ID NO:52, and the third zinc finger motif can include SEQ ID NO:53.

In a sixth embodiment, the transcription factor can include a sequence having at least 95% sequence identity to SEQ ID NO: 39 and wherein the transcription factor includes: i) a first zinc finger motif including an alpha-helix which contains an Arg residue at position −1, an Asn residue at position 3, a Val residue at position 5, and an Arg residue at position 6, ii) a second zinc finger motif including an alpha-helix which contains an Arg residue at position −1, a His residue at position 3, and a Thr residue at position 6, and iii) a third zinc finger motif including an alpha-helix which contains a Asp residue at position −1, a Pro residue at position 1, a Gly residue at position 2, a His residue at position 3, a Leu residue at position 4, a Val residue at position 5, an Arg residue at position 6, an Asn residue at position 8, and an Arg residue at position 9.

In some embodiments of the invention, the transcription factor can include an amino acid sequence of SEQ ID NO: 38 or SEQ ID NO: 39. In another embodiment of the invention, the transcription factor is substantially non-immunogenic when expressed in humans. In yet another embodiment, the transcription factor is capable of increasing muscle contractile force, wherein muscle contractile force is measured in an in vivo, ex vivo, or in situ assay. In a further embodiment, the transcription factor is capable of increasing muscle endurance, wherein muscle endurance is measured by a forced exercise assay. In some aspects of this embodiment, the muscle endurance is increased by at least 10% compared to reference.

The invention also features a recombinant adeno-associated vector (AAV) for expression of a gene in skeletal or cardiac muscle tissue, including a muscle-specific promoter and any of the preceding transcription factors. In some embodiments, the gene is expressed in skeletal and cardiac muscle tissue. In some embodiments, the muscle-specific promoter is constitutively expressed throughout differentiation. In certain embodiments, the muscle-specific promoter is selected from the group consisting of alpha-actin, cardiac troponin C, myosin light chain 2A, skeletal beta-actin, CK6, dystrophin, muscular creatine kinase, dMCK, tMCK, enh348MCK, synthetic C5-12 (Syn), Myf5, MLC1/3f, MyoD1, Myog, and Pax7.

In one embodiment, the vector can have a serotype selected from the group consisting of AAV1, AAV2, AAV3, AAV4, AAV5, AAV6, AAV7, AAV8, and AAV9. In some embodiments, the vector is muscle tropic. In certain embodiments, the vector has a serotype of AAV6 or AAV8. In another embodiment, the vector can further include at least one element selected from a group consisting of an inverted terminal repeat, a cap signal, a multicloning site, an intron splice-donor site, an intron splice-acceptor site, an epitope tag, a nuclear localization sequence, and a polyadenylation consensus sequence. In yet another embodiment, the vector includes the sequence of SEQ ID NO:86 or SEQ ID NO:87. In any embodiment of the invention, the transcription factor specifically binds to a promoter of the utrophin gene, wherein the utrophin promoter is a mouse or human utrophin "A" promoter. In certain aspects of this embodiment, the mouse or human utrophin "A" promoter includes the sequence of SEQ ID NO:9, SEQ ID NO:10, SEQ ID NO:11, or SEQ ID NO:40.

The invention also features a composition including any one of the preceding vectors and a pharmaceutically acceptable carrier. The invention further features a method of treating a muscle disease in a subject in need thereof, the method including administering an effective amount of the preceding composition. The invention also features a method of treating a muscle disease, the method including contacting the utrophin gene of a muscle cell with any one of the preceding modified transcription factors. In some embodiments, the contacting results in an increase in muscle contractile force or an increase in muscle endurance.

In some embodiments, the composition is administered systemically or locally. In other embodiments, the composition is administered intramuscularly, intravenously, subcutaneously, or intraperitoneally. In any of the preceding methods of the invention, the treating can result in an increase in muscle contractile force or an increase in muscle endurance. In any aspects of the invention, the muscle disease can be a muscular dystrophy, wherein the muscular dystrophy is selected from the group consisting of: Duchenne's Muscular Dystrophy or Becker's Muscular Dystrophy, congenital muscular dystrophy, facioscapulohumeral muscular dystrophy, limb-girdle muscular dystrophy, myotonic muscular dystrophy, and oculopharyngeal muscular dystrophy.

DEFINITIONS

The term "about" is used herein to mean a value that is ±10% of the recited value.

As used herein, by "administering" is meant a method of giving a dosage of a composition described herein (e.g., a composition comprising a recombinant AAV vector comprising a polynucleotide encoding a fusion protein or modified transcription factor capable of increasing utrophin expression) to a subject. The compositions utilized in the methods described herein can be administered by a route selected from, e.g., parenteral (for example, intravenous or intraperitoneal), dermal, transdermal, ocular, inhalation, buccal, sublingual, perilingual, nasal, rectal, topical, and oral. The compositions utilized in the methods described herein can also be administered locally or systemically. The preferred method of administration can vary depending on various factors (e.g., the components of the composition being administered and the severity of the condition being treated).

"Amino acid sequence" as used herein, refers to an oligopeptide, peptide, polypeptide, or protein sequence, and fragments or portions thereof, and to naturally occurring or synthetic molecules.

By "cardiac muscle" is meant the form of striated muscle tissue that is found in the heart which is under the control of the autonomic nervous system, i.e., it is involuntarily controlled. The cells that constitute cardiac muscle are called cardiomyocytes or myocardiocytes. The heart is an organ that is composed mostly of cardiac muscle and connective tissue.

By "modified transcription factor" is meant a transcription factor that is substantially derived from a genomically-encoded transcription factor. Modified transcription factors can be derived from transcription factors known in the art, for example, from zinc finger transcription factors. The zinc finger motifs of a transcription factor (e.g., a human transcription factor) can be replaced, modified, or engineered to change the target sequence that the transcription factor specifically recognizes and binds. Modified transcription factors derived from human transcription factors are referred to as "modified human transcription factors" herein. One exemplary human zinc finger transcription factor is Zif268, also known as "Early growth response protein 1," "Egr1," or "EGR-1". The protein encoded by Zif268 belongs to the EGR family of $C_2H_2$-type three-zinc-fingers containing proteins. Zif268 is a nuclear protein that functions as a transcriptional regulator. The principal isoform of human Zif268 protein contains 543 amino acids with a molecular weight of 57.5 kDa and binds the DNA target sequence: 5'-GCGTGGGCG-3' (SEQ ID NO: 44). An exemplary amino acid sequence of human Zif268 is shown in SEQ ID NO:41. An exemplary mRNA sequence of human Zif268 can be found, e.g., under NCBI Accession Number NM_001964 or in SEQ ID NO:19.

As used herein, "conservative variations" or "conservative modified variations" of a particular sequence refers to amino acids encoded by nucleic acids which encode identical or essentially identical amino acid sequences, or where the nucleic acid does not encode an amino acid sequence, to essentially identical sequences. Because of the degeneracy of the genetic code, a large number of functionally identical nucleic acids may encode any given peptide. Such nucleic acid variations are silent variations, which are one species of conservatively modified variations. One of skill will recognize that each codon in a nucleic acid (except AUG, which is ordinarily the only codon for methionine) can be modified to yield a functionally identical molecule by standard techniques. Accordingly, each silent variation of a nucleic acid which encodes a peptide is implicit in any described amino acid sequence. Furthermore, one of skill will recognize that individual substitutions, deletions or additions which alter, add or delete a single amino acid or a small percentage of amino acids in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

By "contact" or "contacting" as used herein is meant to allow or promote a state of immediate proximity or association between at least two elements. For example, the utrophin gene can be contacted with a fusion protein or modified transcription factor of the invention that specifically binds a target sequence in the utrophin "A" promoter, thereby increasing expression of utrophin.

A "deletion", as used herein, refers to a change in either amino acid or nucleotide sequence in which one or more amino acid or nucleotide residues, respectively, are absent.

By "DNA binding element" is meant an element capable of binding DNA. A DNA binding element may bind specifically to a target sequence or response element of a gene, e.g., in a promoter. Exemplary DNA binding elements include but are not limited to: zinc finger domains (e.g., domains that include zinc finger motifs), helix-turn-helix motifs, leucine zipper domains, winged helix domains, winged helix turn helix domains, helix-loop-helix domains, HMG box domains, Wor3 domains, immunoglobulin domains, B3 domains, TAL effector DNA-binding domains, RNA-guided DNA-binding domains, ZFP51, where the DNA target sequence of ZFP51 is represented by SEQ ID NO:15, and any described herein (e.g., Jazz, UtroUp, Bagly, or the zinc finger motifs of JZif1 or JZif2, or an element having the sequence of SEQ ID NO:16-18 or SEQ ID NO:42,43, or having at least 70% (e.g., 72%, 75%, 80%, 81%, 85%, 90%, 95%, 99%) identity to that of SEQ ID NO:16-18 or SEQ ID NO:42,43 or any of the zinc finger motifs described in Tables 2 and 6.

By "an effective amount of a composition" is meant the amount of a composition administered to improve, inhibit, or ameliorate a condition of a subject, or a symptom of a disorder or disease, e.g., a muscle disease, in a clinically relevant manner (e.g., improve, or ameliorate DMD, or inhibit degeneration of muscle tissue in DMD). Any improvement in the subject is considered sufficient to achieve treatment. Preferably, an amount sufficient to treat is an amount that reduces, inhibits, or prevents the occurrence or one or more symptoms of DMD or is an amount that reduces the severity of, or the length of time during which a subject suffers from, one or more symptoms of DMD (e.g., by at least 10%, 20%, or 30%, more preferably by at least 50%, 60%, or 70%, and most preferably by at least 80%, 90%, 95%, 99%, or more, relative to a control subject that is not treated with a composition of the invention). An effective amount of the pharmaceutical composition used to practice the methods described herein (e.g., the treatment of DMD) varies depending upon the manner of administration and the age, body weight, and general health of the subject being treated. A physician or researcher can decide the appropriate amount and dosage regimen.

As used herein, "expression vectors" or "expression plasmid", and similar terms, are defined herein as DNA sequences that are required for the transcription of cloned copies of genes and/or and the translation of their mRNAs in an appropriate host. Such vectors can be used to express viral, prokaryotic, or eukaryotic genes in a variety of hosts including, but not limited to, bacteria, for example, E. coli, blue-green algae, plant cells, insect cells, fungal cells including yeast cells, and animal cells.

As used herein, the term "fusion protein" includes a compound containing all or a portion of the amino acid sequences of two or more proteins. The modified transcription factors (e.g., modified human transcription factors) described herein are excluded from the definition of fusion proteins. For example, a fusion protein can comprise a DNA binding element (e.g., Jazz, Bagly, or UtroUp) and one or more transcriptional activation elements (e.g., Vp16, CJ7, SP1, or Gal4). The terms "protein" and "polypeptide" are used interchangeably herein. The term "portion" includes any region of a polypeptide, such as a fragment (e.g., a cleavage product or a recombinantly-produced fragment) or an element or a domain (a region of a polypeptide having an activity, such as, e.g., enzymatic activity or antigen- or DNA-binding capacity) that contains fewer amino acids than the full-length polypeptide (e.g., 5%, 10%, 12%, 15%, 20%, 30%, 40%, 50%, 60%, 70%, 80%, or 90% fewer). A fusion protein may include one or more linkers between the amino acid sequences of the proteins. Those skilled in the art will recognize that the terms "portion" and "fragment" are also used interchangeably herein.

By "host," "subject," or "patient," is meant any organism, such as a mammal (e.g., a human, a primate, dog, cat, cow, horse, pig, goat, rat, and mouse), a fish, or a bird. A host may also be a domestic animal (e.g., a farm animal) or a companion animal (e.g., a pet).

By "immunogenicity" is meant the ability of a particular substance (including, e.g., an antigen, an epitope, or a protein) to provoke an immune response in the body of a human or animal. An immune response may include a humoral or cell-mediated immune response. Immunogenicity is typically undesirable during treatment with therapeutic proteins, including artificial transcription factors of the invention, because some patients have or develop antibodies that bind and/or neutralize the therapeutic protein, leading to inactivation of the therapeutic protein and in some cases adverse effects. Factors including delivery route, delivery vehicle, dose regiment, aggregation, innate immune system activation, molecular size, epitope density, phylogenetic distance, protein structure, degradability, and the ability of the protein to interface with humoral (B cell) and cellular (T cell) responses can all affect the level of immunogenicity.

By "increasing muscle contractile force" is meant increasing the force that can be exerted by contraction of a muscle by at least at least 5%, 10%, 15%, 20%, 25%, 30%, 40%, 50%, 60%, 70%, 80%, 90%, 100%, 150%, or by 3-fold, 4-fold, 5-fold, or more compared to reference. The force generated by a muscle can be measured in vivo, in situ, or ex vivo, for example by ex vivo or in situ analysis of the contractile profile of a single intact limb muscle (e.g. the extensor digitorum longus or abdominal muscles for ex vivo assay and the tibialis anterior muscle for in situ assay), grip force analysis, downhill treadmill exercise, manual muscle testing, myometry (e.g. assessing upper and lower extremity strength using a myometer, including evaluation of knee flexors and extensors, elbow flexors and extensors, and shoulder abductors). sustained maximum voluntary contraction (MVC) assays or in any of the assays described in Hakim et al., *Methods Mol. Biol.* 709: 75-89, 2011; Sharma et al., *Neurology* 45: 306-310, 1995; and McDonald et al., *Muscle Nerve* 48: 343-356, 2013.

By "increasing muscle endurance" is meant increasing the ability of a muscle or group of muscles to sustain repeated contractions (e.g., an increase of at least 1%, 5%, 10%, 15%, 20%, 25%, 30%, 40%, 50%, 60%, 70%, 80%, 90%, 100%, 150%, 2-fold, 3-fold, 4-fold, 5-fold, 6-fold, 7-fold, 8-fold, 9-fold, 10-fold, or more compared to reference) over an extended period of time (e.g., a period of time in hours (e.g., 1, 2, 3, 4, 5, 6, 7, 8, 9, 10 hours), days (e.g., 1, 2, 3, 4, 5, 6, 7, 8, 9, 10 days), weeks (e.g. 1, 2, 3, 4, 5, 6, or 7 weeks), or months (e.g. 1, 2, 3, 4, 5, 6, 7, 8, 9, 10, 11, or 12 months)). Muscle endurance may be measured by assays including but not limited to treadmill exercise, 6-minute walk test (6MWT), timed function tests, (e.g., time taken to stand from a supine position, time taken to run/walk 10 m, or time taken to climb/descend 4 standard-sized stairs), by any of the tests suitable for testing muscular strength or endurance in mice including but not limited to enforced treadmill exercise, either at constant speed (e.g., any assay described in Radley-Crabb et al., *Neuromuscul. Disord.* 22(2):170-182, 2012) or at accelerated speed (see, e.g., Di Certo et al., *Hum. Mol. Genet.* 19:752-760, 2010 or Strimpakos et al., *J. Cell. Phys.* 229:1283-1291, 2014), voluntary wheel exercise, grip strength test, the hang wire test, the inverted grid test, and the rotarod test, or by any of the assays described in McDonald et al., *Muscle Nerve* 48: 343-356, 2013.

By "increasing utrophin expression" is meant to increase utrophin gene transcription, protein expression, and/or protein activity as compared to a normal or positive reference cell or tissue (e.g., an increase of at least 5%, 10%, 15%, 20%, 25%, 30%, 40%, 50%, 60%, 70%, 80%, 90%, 100%, 150%, 2-fold, 3-fold, 4-fold, 5-fold, 6-fold, 7-fold, 8-fold, 9-fold, 10-fold or more compared to a reference cell or tissue). The expression product can be an RNA transcribed from the gene (e.g. an mRNA) or a polypeptide translated from an mRNA transcribed from the gene. Typically, an increase in the level of an mRNA results in an increase in the level of a polypeptide translated therefrom. The level of expression and/or activity may be determined using standard techniques for detecting and measuring mRNA or protein, including but not limited to RT-PCR, Western blotting, enzyme-linked immunosorbant assay (ELISA), immunohistochemistry, immunofluorescence, and mass spectrometry.

An "insertion" or "addition," as used herein, refers to a change in an amino acid or nucleotide sequence resulting in the addition of one or more amino acid or nucleotide residues, respectively, as compared to the naturally occurring molecule.

The terms "linker," "linker region," or "linker domain," or similar, such descriptive terms as used herein refers to elements that are located between adjoined polynucleotide or polypeptide sequences. For example, stretches of polynucleotide or polypeptide sequence that are used in can be introduced during the construction of a cloning vector or fusion protein. Linkers can also be introduced by chemical conjugation, e.g., by 'click chemistry'-based approaches. Functions of a linker region can include introduction of cloning sites into the nucleotide sequence, introduction of a flexible component or space-creating region between two protein domains, or creation of an affinity tag for specific molecular interaction. A linker region may be introduced into a fusion protein as a product of the recombinant nucleic acid production.

By "muscle-specific promoter" is meant any sequence of DNA that can promote expression of a gene preferentially in muscle tissue compared to a variety of other tissue types. Typically, a muscle-specific promoter is present upstream of the transcription initiation site of a gene. For example, a muscle-specific promoter may increase expression of a gene in a muscle at least 2-fold, 3-fold, 4-fold, 5-fold, 10-fold, 15-fold, 20-fold, 30-fold, 50-fold, 100-fold or more compared to a reference non-muscle tissue. Some muscle-specific promoters are constitutively expressed throughout differentiation. Exemplary muscle-specific promoters include but are not limited to: alpha-actin, cardiac troponin C, myosin light chain 2A, skeletal beta-actin, CK6, dystrophin, muscular creatine kinase, dMCK, tMCK, enh348MCK, synthetic C5-12 (Syn), Myf5, MLC1/3f, MyoD1, Myog, and Pax7. See, for example, U.S. Patent Application 2011/0212529, McCarthy et al., *Skeletal Muscle* 2:8, 2012; and Wang et al., *Gene Ther.* 15:1489-1499, 2008, the entirety of which are incorporated herein by reference.

By "muscular dystrophy" is meant the group of muscle diseases that weaken the musculoskeletal system and hamper locomotion. Muscular dystrophies are characterized by progressive deterioration of muscle function (e.g., weakness), defects in muscle proteins, and death of muscle cells and tissue. Some types of muscular dystrophy are characterized as dystrophinopathy, which includes a spectrum of muscle diseases in which there is insufficient dystrophin protein produced in the muscle cells, resulting in instability in the structure of the muscle cell membrane. Non-limiting examples of dystrophinopathies include Duchenne's muscular dystrophy (DMD) and Becker's muscular dystrophy (BMD, also known as Benign pseudohypertrophic muscular dystropy). DMD and BMD are X-linked recessive diseases caused by mutations in the dystrophin gene, which encodes the protein dystrophin. DMD is more severe than BMD because typically no dystrophin protein is produced in the affected muscle cells in DMD, whereas in BMD, defective dystrophin is produced. Other examples of muscular dystrophies include but are not limited to: congenital muscular dystrophy, facioscapulohumeral muscular dystrophy, limb-girdle muscular dystrophy, myotonic muscular dystrophy, and oculopharyngeal muscular dystrophy.

"Nucleic acid sequence" as used herein, refers to an oligonucleotide, nucleotide, or polynucleotide, and fragments or portions thereof, and to DNA or RNA of genomic or synthetic origin which may be single- or double-stranded, and represent the sense or antisense strand.

As used herein, the term "operable linkage" or "operably linked" refers to a physical or functional juxtaposition of the components so described as to permit them to function in their intended manner. More specifically, for example, two DNA sequences operably linked means that the two DNAs are arranged (cis or trans) in such a relationship that at least one of the DNA sequences is able to exert a physiological effect upon the other sequence. For example, a muscle specific promoter can be operably linked with a gene to promote muscle-specific transcription of the gene.

By "pharmaceutical composition" is meant any composition that contains a therapeutically or biologically active agent (e.g., at least one nucleic acid molecule that encodes all or part of a fusion protein comprising a transcriptional activation element and a DNA binding element either incorporated into a viral vector or independent of a viral vector (e.g., incorporated into a liposome, microparticle, or nanoparticle)) that is suitable for administration to a subject. The compositions utilized in the methods described herein can be administered by a route selected from, e.g., parenteral (e.g., intravenous or intraperitoneal), dermal, transdermal, ocular, inhalation, buccal, sublingual, perilingual, nasal, rectal, topical, and oral. The compositions utilized in the methods described herein can also be administered locally or systemically. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique. A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation. Any of these formulations can be prepared by well-known and accepted methods of art. See, for example, *Remington: The Science and Practice of Pharmacy* ($21^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered. For injection, formulations can be prepared in conventional forms as liquid solutions or suspensions or as solid forms suitable for solution or suspension in liquid prior to injection or as emulsions. Acceptable carriers, excipients, or stabilizers for intravenous administration are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG). Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth. Other physiologically acceptable diluents, excipients, carriers, or adjuvants and their formulations are known to one skilled in the art.

By "recombinant adeno-associated vector (AAV)" is meant a recombinantly produced virus or viral particle that comprises a polynucleotide to be delivered into a host cell, either in vivo, ex vivo or in vitro. AAV is a nonpathogenic human parvovirus which is commonly used for gene transfer in mammals. The AAV genome is built of single stranded DNA, and comprises inverted terminal repeats (ITRs) at both ends of the DNA strand, and two open reading frames: rep and cap, encoding replication and capsid proteins, respectively. A foreign polynucleotide can replace the native rep and cap genes. AAVs can be made with a variety of different serotype capsids which have varying transduction profiles or as used herein "tropism" for different tissue types. Examples of AAV serotypes include but are not limited to AAV1, AAV2, AAV3, AAV4, AAV5, AAV6, AAV7, AAV8, AAV9, and AAVrh10. AAV vectors can be produced, for example, by triple transfection of subconfluent HEK293 cells by three plasmids: AAV cis-plasmid containing the gene of interest, AAV trans-plasmid containing AAV rep and cap genes, and an adenovirus helper plasmid, for example, pDF6. For example, the expression vectors described by SEQ ID NOs:1 or 2 or SEQ ID NOs:62-65 can be in the production of recombinant adeno-associated vectors (e.g., viral particles that comprise nucleotide sequences that allow for muscle-specific expression of artificial transcription factors of the invention). Viral particles are described herein by the expression vector used for their production and by the serotype. For example, the viral particle mAAV8-Vp16-Jazz have a capsid serotype 8 and are produced using the mAAV-Vp16-Jazz expression vector.

By "reference" is meant any sample, standard, or level that is used for comparison purposes. A "normal reference sample" can be a sample taken from the same subject prior to the onset of a disorder (e.g., a muscular dystrophy), a sample from a subject not having the disease or disorder, a subject that has been successfully treated for the disease or disorder, or a sample of a purified reference polypeptide at a known normal concentration. By "reference standard or level" is meant a value or number derived from a reference sample. A normal reference standard or level can be a value or number derived from a normal subject that is matched to a sample of a subject by at least one of the following criteria: age, weight, disease stage, and overall health. A "positive reference" sample, standard, or value is a sample, standard, value, or number derived from a subject that is known to have a disorder (e.g., a muscular dystrophy) that is matched to a sample of a subject by at least one of the following criteria: age, weight, disease stage, and overall health.

By "skeletal muscle" is meant the form of striated muscle tissue which is under the control of the somatic nervous system, i.e., it is voluntarily controlled. The term muscle refers to multiple bundles of muscle fibers held together by connective tissue. Skeletal muscles may be attached to bones by tendons. Skeletal muscles may be attached to bones by tendons. Non-limiting examples of skeletal muscles include, for example, the diaphragm, extensor digitorum longus, tibialis anterior, gastrocnemius, soleus, plantaris, biceps, triceps, deltoids, pectoralis major, pectoralis minor, rhomboids, trapezius, sartorius, knee flexors and extensors, elbow flexors and extensors, shoulder abductors, and abdominal muscles.

By "specifically binds" or "binds" is meant a molecule (e.g., an artificial transcription factor) which recognizes and binds another molecule (e.g., a polynucleotide), but that does not substantially recognize and bind other molecules. In one example, an artificial transcription factor specifically binds a DNA sequence in the utrophin "A" promoter but not other polynucleotide sequences. The binding affinity of a molecule X for its partner Y can generally be represented by the dissociation constant (Kd). The term "specific binding," "specifically binds to," or is "specific for" a particular molecule (e.g., a polynucleotide or a polypeptide), as used herein, can be exhibited, for example, by a molecule having a $K_d$ for the molecule to which it binds of at least about $10^{-3}$, $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater. "Binding affinity" generally refers to the strength of the sum total of noncovalent interactions between a single binding site of a molecule (e.g., a fusion protein) and its binding partner (e.g., a polynucleotide sequence).

The term "substantially the same" when used herein with respect to the comparison of a sequence to a reference sequence is applicable to sequences that have at least about 70%, at least about 75%, at least about 80%, at least about 85%, at least about 90%, at least about 95%, at least about 98%, and at least about 99% sequence identity to the reference sequence. The determination of percent identity between two sequences can be determined using standard methods and algorithms including, e.g., BLASTN (NCBI; Schaffer et al., *Nucleic Acids Res.* 29:2994-3005, 2001), BLASTX (NCBI; Schaffer et al., *Nucleic Acids Res.* 29:2994-3005, 2001), ALIGN (GCG, Accelrys), and FASTA (Pearson et al., *Proc. Natl. Acad. Sci. U.S.A.* 85:2444-2448, 1988) programs, which may employ default settings. In various specific examples, as described herein, amino acid sequences of the invention include those having, e.g., 5, 7, 10, 20, 30, 40, 50, 75, or 100 consecutive amino acids that are 100% identical to the reference sequences.

A "substitution", as used herein, refers to the replacement of one or more amino acids or nucleotides by different amino acids or nucleotides, respectively.

By "transcriptional activation element" is meant a polypeptide that is capable of inducing transcription, i.e., the process of making an RNA transcript (e.g., an mRNA) from a DNA template by RNA polymerase. For example, a transcriptional activation element may comprise a trans-activation domain of a transcription factor protein or other domains that can directly or indirectly promote transcription. Transcriptional activation elements can also include polypeptides or fragments thereof that can recruit components of the transcriptional machinery, which includes transcriptional coregulators, transcriptional coactivators (e.g., TAF9, MED15, Gcn5, and CBP/p300), chromatin remodelers (e.g., histone acetylases, histone de-acetylases, or histone methylases), kinases, or DNA methylases, in order to promote transcription. Transcriptional activation elements may function by recruiting proteins that promote transcription or by removing transcriptional inhibitors. A transcriptional activation element typically requires an accompanying DNA binding element to bring it into proximity to DNA. Exemplary transcriptional activation elements include but are not limited to: acidic or hydrophobic activation domains (e.g., from Gal4 or Gcn4, respectively), nine-amino-acid transactivation domains (9aaTAD, e.g., from p53, Vp16, MLL, E2A, HSF1, NF-IL6, and NF-κB), Vp64, p65, SP1, Zif268, and the trans-activation domain CJ7 derived from human Che-1/AATF (see, e.g., Onori et al., *BMC Mol. Biol.* 14:3, 2013). See, for example, US Patent Application Publication No. 2007/0020627and Blancafort et al., *Mol. Pharmacol.* 66(8): 1361-137, 2004. Transcriptional activation elements can also include or be derived from physiological regulators of utrophin expression, including NFAT, GABPα, and GABPβ. An exemplary amino acid sequence of Vp16 is shown in SEQ ID NO:37, and an exemplary amino acid sequence of CJ7 is shown in SEQ ID NO:75.

By "transcription factor" is meant a protein that binds to specific DNA sequences, thereby controlling transcription of DNA into messenger RNA (mRNA). Transcription factors can perform this activity alone or with other proteins in a complex by promoting or blocking the recruitment of RNA polymerase. By "artificial transcription factor" is meant any transcription factor that does not occur in nature. An artificial transcription factor as described herein can be a fusion protein or a modified transcription factor.

By "treating" is meant administering a pharmaceutical composition of the invention for prophylactic and/or therapeutic purposes. Prophylactic treatment may be administered, for example, to a subject who is not yet ill, but who is susceptible to, or otherwise at risk of, a particular muscle disease or defect, e.g., DMD (e.g., the subject may have mutations that cause DMD but is still young and hence, asymptomatic or the status of mutations that cause DMD is unknown. Therapeutic treatment may be administered, for example, to a subject already suffering from DMD in order to improve or stabilize the subject's condition (e.g., a patient already presenting symptoms of DMD). Thus, in the claims and embodiments described herein, treating is the administration to a subject either for therapeutic or prophylactic purposes. In some instances, as compared with an equivalent untreated control, treatment may ameliorate a disorder (e.g., DMD) or a symptom of the disorder, or reduce the progression, severity, or frequency of one or more symptoms of the disorder by, e.g., 1%, 2%, 5%, 10%, 20%, 30%, 40%, 50%, 60%, 70%, 80%, 90%, 95%, or 100% as measured by any standard technique. For example, for measuring symptoms of DMD, one may use, e.g., electromyography (EMG), genetic tests, muscle biopsy, serum Creatine Kinase (CK) levels, muscular strength tests (e.g., manual muscle testing), or range-of-motion (ROM) tests such as the six minute walk test. Symptoms of muscular dystrophy including DMD, which may vary from mild to severe and may depend on what part of the body is affected, the causative mutation, and the age and overall health of the affected person, include, e.g., fatigue, learning difficulties, intellectual disability, muscle weakness (e.g., in the legs, pelvis, arms, neck, diaphragm, heart, or other areas of the body), difficulty with motor skills (e.g., running, hopping, or jumping), frequent falls, trouble getting up from a lying position or climbing stairs, progressive difficulty walking, breathing difficulties, heart disease, abnormal heart muscle (e.g., cardiomyopathy), congestive heart failure, irregular heart rhythm (e.g., arrhythmias), deformities of the chest or back (scoliosis), enlarged muscles of the calves, buttocks, or shoulders, pseudohypertrophy, muscle deformities, respiratory disorders (e.g., pneumonia or poor swallowing). Detecting an improvement in, or the absence of, one or more symptoms of muscular dystrophy, indicates successful treatment.

By "utrophin "A" promoter" or "utrophin promoter "A"" is meant the promoter region located at the 5' upstream region of the utrophin gene. The utrophin "A" promoter lies in an unmethylated CpG island and is active in muscle cells. This is in contrast to the utrophin "B" promoter which is immediately upstream of the large second exon of utrophin and is active in endothelial cells. An exemplary sequence of the human utrophin "A" promoter is defined by SEQ ID NO:20 or can include the sequences having SEQ ID NOs: 9,10,12, or 14. An exemplary sequence of the mouse utrophin "A" promoter is defined by SEQ ID NO:33 or can include the sequences having SEQ ID NOs:11,13, or 15.

By "zinc finger motif" is meant a type of protein structural motif. Typically, zinc finger motifs coordinate one or more zinc ions in order to stabilize the fold. A zinc finger DNA binding domain may comprise 1, 2, 3, 4, 5, 6, 7, 8, 9, or more zinc finger motifs arranged in a tandem array which can bind in the major groove of DNA. $Cys_2.His_2$ type zinc fingers are a well-known example of a zinc finger motif that consists of approximately 28-31 amino acids that fold into a ββα structure. The $Cys_2.His_2$ type zinc fingers motif typically has a sequence of the form $X_3$-Cys-$X_{2-4}$-Cys-$X_{12}$-His-$X_{3-5}$-His-$X_4$, wherein X is any amino acid (e.g. $X_{2-4}$ indicates an oligopeptide 2-4 amino acids in length). There is generally a wide range of sequence variation in the 28-31 amino acids of the known zinc finger polypeptide. Only the two consensus histidine residues and two consensus cysteine residues bound to the central zinc atom are invariant. Of the remaining residues, three to five are highly conserved, while there is significant variation among the other residues. The alpha-helix of each motif (often called the "recognition helix") can make sequence-specific contacts to DNA bases; residues from a single recognition helix typically contact 3 base pairs of DNA. Changes in the key amino acid positions (e.g., positions −1, +3, and +6) of the zinc finger alpha-helix can modify the DNA binding target specificity of a zinc finger motif. See, for example, Corbi et al., *Biochem. Cell. Biol.* 82:428-436, 2004; Klug, Q. *Rev. Biophys.* 43:1-21, 2010; Choo et al., *Curr. Opin. Struct. Biol.* 7:117-125, 1997; Pabo et al., *Annu. Rev. Biochem.* 70:313-340, 2001; and Segal et al., *Curr. Opin. Biotechnol.* 12:632-637, 2001; and Sera, *Adv. Drug Deliv. Rev.* 61:513-526, 2009. Lists of human $Cys_2$-$His_2$ type zinc finger proteins can be found, e.g., from the HUGO Gene Nomenclature Committee (HGNC). Cys2-His2 type zinc finger proteins often contain an effector domain located N-terminally to the zinc finger region, such as the KRAB (Kruppel-Associated-Box), SCAN (SRE-ZBP, CTfin51, AW-1 and Number18 cDNA) and BTB (Broad-Complex, Tramtrack and Bric-a-bric) effector domains. Other exemplary zinc finger motifs include Gag knuckle, Treble clef, zinc ribbon, $Zn_2/Cys_6$, and TAZ2-domain like zinc finger motifs.

Other features and advantages of the invention will be apparent from the following detailed description, and from the claims.

BRIEF DESCRIPTION OF THE DRAWINGS

FIGS. 1A-1D show construction and validation of mAAV vectors. (A) Schematic representation of the engineered mAAV-EGFP and mAAV-Vp16-Jazz vectors under the control of the muscle-specific human alpha-actin promoter. (B) Time course titration curve obtained by qPCRs performed with growth medium fractions containing viral particles from AAV-293 transfected cells. (C) top: EGFP expression in skeletal muscles (abdomen, diaphragm and quadriceps) and cardiac muscle. mAAV8-EGFP-treated and untreated (Ctr) mdx mice were injected intraperitoneally at 5 days of age. Injections were performed with 150 µl of mAAV8-EGFP virus suspension at the concentration of $5 \times 10^{12}$ v.p./ml, or with the same volume of saline solution. At different times after injection mice were analyzed and cryostatic sections were examined for direct EGFP fluorescence. Nuclei were stained with DAPI. All the images were taken at 10× magnification. Bottom left: Graph showing the percentage of EGFP-positive fibers in the indicated muscular tissue at 15 days and 2 months of age. Bottom right: absence of fluorescence signal in the liver from mAAV8-EGFP-infected mdx mice both at 15 days and 2 months of age confirms the muscle-specific expression of the mAAV8-EGFP vector. (D) Evaluation of EGFP protein expression by Western blot analysis in abdominal and diaphragm skeletal muscle, cardiac muscle and liver tissues. Five-day-old mdx mice were injected as above and examined 15 days after injection using the polyclonal antibody against EGFP. Detection of α-tubulin was used to normalize the amount of proteins. Vp16-Jazz is abbreviated as "Jazz" in FIGS. 1A-1D.

FIGS. 12A-12C show schematic depictions of wild type Zif268 and modified transcription factors JZif1 and JZif2. (A) Top: On the left side is a schematic representation of the natural human three zinc finger motif transcription factor Zif268, followed by a representation of the two novel artificial three zinc finger motif transcription factors named "JZif1" and "JZif2". Zif268, JZif1 and JZif2 genes have been cloned and are shown here in the mAAV vector under the control of the muscle-specific human alpha-actin promoter. On the right side the corresponding DNA target sequences for each protein is shown. Bottom: Amino acid sequences of Zif268, JZif1, and JZif2 zinc finger motifs are shown and aligned. Amino acid positions −1, +3, and +6 of the alpha helix, crucial for DNA binding specificity, are indicated and the amino acids are represented in bold. Underlined amino acid positions represent variations in JZif1 and JZif2 from the Zif268 prototype zinc finger motif. Note that zinc finger/DNA recognition involves an anti-parallel arrangement of the protein: the amino-terminal region is involved in 3' DNA contact, while the carboxyl-terminal region is involved in 5' DNA recognition (indicated by crossed lines between residues in the amino acid sequence of the zinc finger motifs and base pairs of the target DNA sequences). (B) shows the amino acid sequence of JZif1 (SEQ ID NO:38). The three zinc finger motifs (ZF1, ZF2, and ZF3) are highlighted in grey. The amino acid positions of the zinc finger motif alpha-helix are indicated above the corresponding amino acid residues (positions −1, 1, 2, 3, 4, 5, 6, 7, 8, and 9). Amino acid positions 1, +3, and +6 of the zinc finger motif alpha-helix are represented in bold. Underlined amino acid residues represent variations in JZif1 from the Zif268 prototype zinc finger motif. (C) shows the amino acid sequence of JZif2 (SEQ ID NO:39). The three zinc finger motifs (ZF1, ZF2, and ZF3) are highlighted in grey. The amino acid positions of each zinc finger motif alpha-helix are indicated above the corresponding amino acid residues (positions −1, 1, 2, 3, 4, 5, 6, 7, 8, and 9). Amino acid positions 1, +3, and +6 of the zinc finger motif alpha-helix are represented in bold. Underlined amino acid residues represent variations in JZif2 from the Zif268 prototype zinc finger motif.

FIG. 13 shows a sequence comparison of a region of the human and mouse utrophin promoter "A". The N-box core sequence and conserved E-box are indicated. The numbering corresponds to: human utrophin promoter sequence EMBL accession no. X95523 and mouse utrophin promoter sequence: EMBL accession no. X95524. The eighteen base pair DNA target sequence recognized by exemplary artificial transcription factors of the invention is underlined. The first nine base pairs are in bold characters and are recognized by Jazz, JZif1, and Bagly. Bagly in addition to these nine base pairs extends its target sequence on the human sequence three additional base pairs in the 5' direction (shown in Italic characters). The second nine base pairs (shown in underlined, bold Italic characters), are recognized by JZif2. UtroUp binds the entire eighteen base pair. DNA target sequence (underlined and bold characters).

DETAILED DESCRIPTION OF THE INVENTION

Figures 1A, 1B:
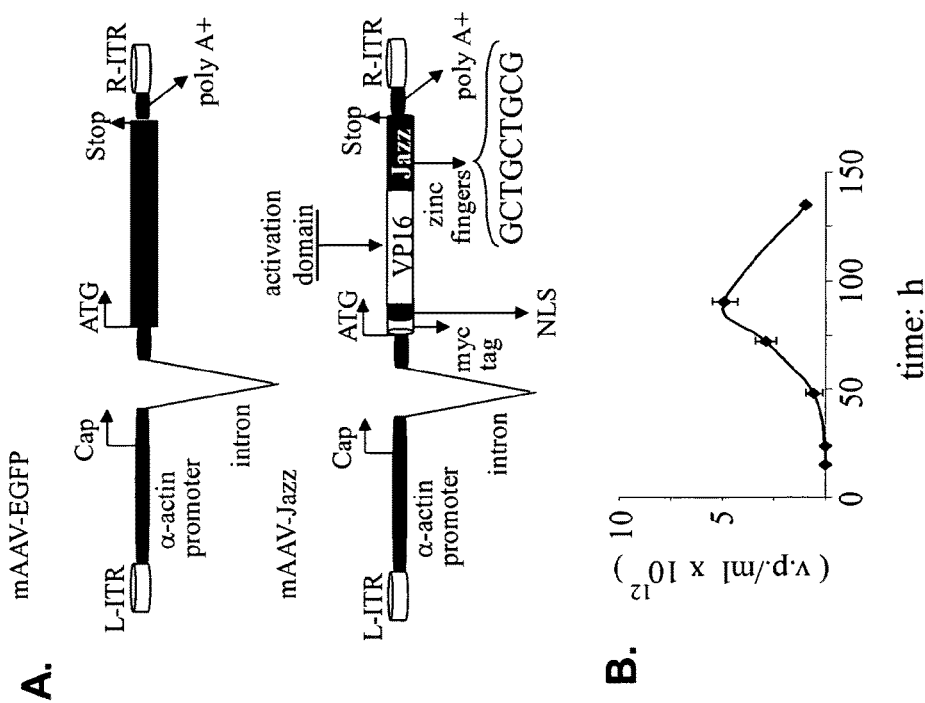
Figure 1D:
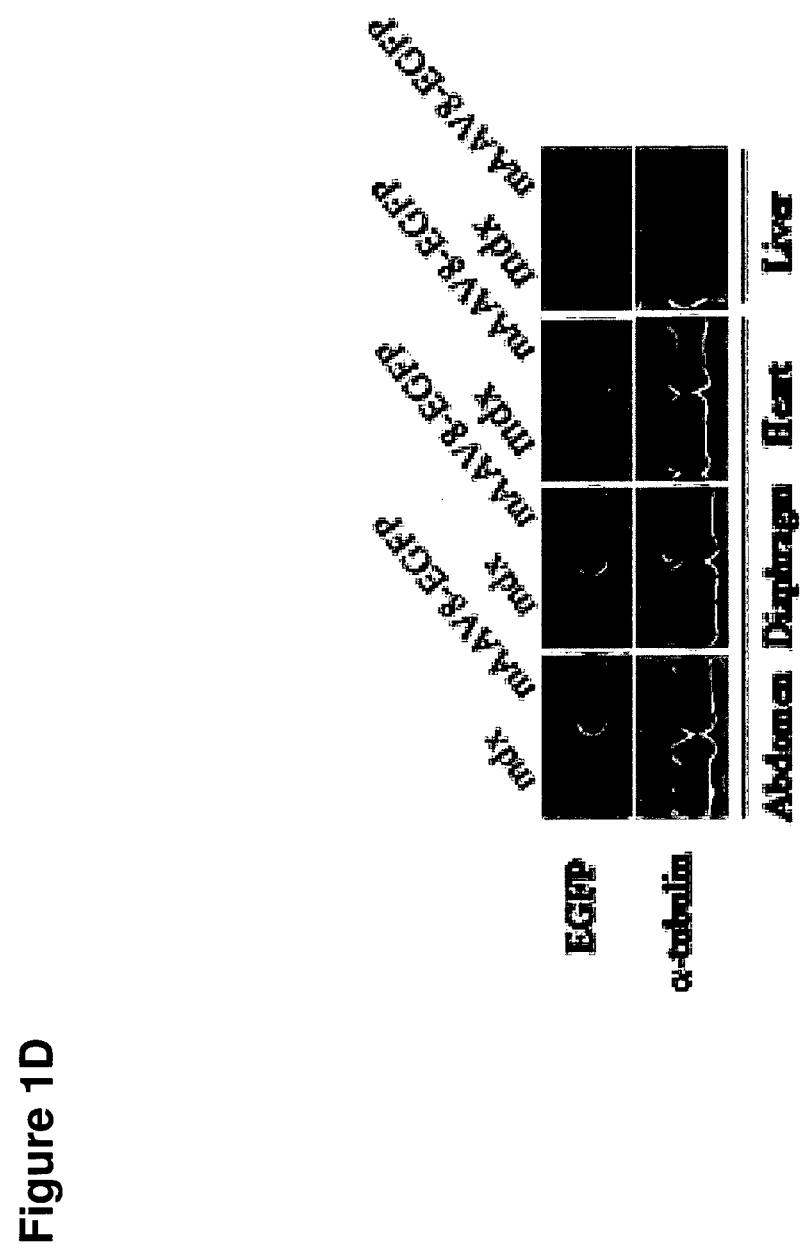

Dystrophinopathies including DMD and BMD are caused by a lack of functional dystrophin protein in muscle cells. Utrophin is considered the autosomal homologue of dystrophin because dystrophin and utrophin share structural and functional motifs across the length of the proteins. Dystrophin and utrophin both function as connecting bridges between cytoskeletal actin, the cell membrane, and the extracellular matrix, via proteins which are collectively called DAPs (dystrophin associated proteins). Utrophin is mainly expressed in the fetus and its expression is reduced post-partum, whereas dystrophin is mainly expressed after birth. In adults the localization of utrophin is limited to the neuromuscular junction, while dystrophin localizes along the entire length of the sarcolemma. Studies carried out on transgenic mdx mice, a well-accepted animal model for DMD that lacks dystrophin, have shown that overexpression of utrophin, which is accompanied by redistribution of the protein across the entire sarcolemma, causes a marked improvement in the dystrophic phenotype of these mice.

To achieve utrophin up-regulation, we engineered artificial zinc finger-based transcription factor (ZF-ATF) fusion proteins capable of binding to the sequences defined by SEQ ID NO:9-14 and activating transcription from the promoter "A" of both the human and mouse utrophin genes. We generated a transgenic mouse model that overexpresses such a fusion protein containing three zinc finger motifs and a transcriptional activation element named "Vp16-Jazz" which recognizes and binds the sequence defined by SEQ ID NO:9. Vp16-Jazz transgenic mice are viable, fertile, and live to adulthood without any health problems. To evaluate the therapeutic potential of the artificial Vp16-Jazz gene, we generated an mdx/Vp16-Jazz mouse model by crossing Vp16-Jazz transgenic mice (Vp16-Jazz mice) with dystrophin-deficient mdx mice. The resulting mdx/Vp16-Jazz mice displayed expression of Vp16-Jazz, significant up-regulation of utrophin mRNA and protein expression and a strong amelioration of the dystrophic phenotype, as described in Italian patent application RM2005A000493.

The approach of the present invention is to up-regulate (i.e., increase) the expression level of the dystrophin-related gene utrophin in the muscles of DMD patients to functionally rescue (i.e., complement) the lack of dystrophin function. This can be done by contacting the utrophin gene promoter with an artificial transcription factor (ATF) of the invention, for example, a fusion protein or modified transcription factor capable of increasing utrophin expression. We have created muscle-specific recombinant adeno-associated vectors capable of promoting the expression of exogenous genes such as the fusion proteins and modified transcription factors of the invention both in skeletal muscle and in cardiac muscle, for use in treating diseases which severely affect both skeletal muscles and cardiac muscles (e.g., DMD). Moreover, the adeno-associated vectors of the present invention have the advantages of greater efficiency in the expression of the exogenous gene (both in slow muscle fibers and in fast muscle fibers), greater stability of the transcript and greater persistence of expression over time. Using the vectors of the present invention, we have discovered that recombinant adeno-associated virus (recombinant AAV) delivery of fusion proteins and modified transcription factors capable of increasing utrophin expression in muscle significantly ameliorates the dystrophic phenotype of mdx dystrophin-deficient mice. Furthermore, the delivery of these artificial transcription factors rescues both the histopathological defects observed in dystrophic mdx muscle tissue as well as in vivo muscle function, both in terms of muscle strength and endurance. Accordingly, the compositions including the vectors and fusion proteins of the present invention can be used to treat muscle defects, particularly DMD.

AAV Vectors and Compositions

In certain embodiments of this invention, a nucleic acid sequence, or fragment thereof, encoding a gene, e.g., an artificial transcription factor (e.g., a fusion protein or modified transcription factor) capable of increasing utrophin expression, is delivered to muscle cells by means of a viral vector, of which many are known and available in the art. In preferred embodiments, the artificial transcription factor is delivered to both skeletal and cardiac muscle. The therapeutic vector is desirably non-toxic, minimally immunogenic (i.e., elicits a very mild immune response, if any), easy to produce, and efficient in protecting and delivering DNA into the target cells. In particular embodiments, the viral vector is a recombinant adeno-associated vector (AAV). In other embodiments, the invention provides a therapeutic composition comprising an AAV comprising an artificial transcription factor (e.g., a fusion protein or a modified transcription factor) under the control of a muscle-specific promoter.

The use of AAVs is a common mode of exogenous delivery of DNA as it is relatively non-toxic, provides efficient gene transfer, and can be easily optimized for specific purposes. More than 30 naturally occurring serotypes of AAV are available. Many natural variants in the AAV capsid exist, allowing identification and use of an AAV with properties specifically suited for muscle cells. AAV viruses may be engineered by conventional molecular biology techniques, making it possible to optimize these particles for cell specific delivery of nucleic acid sequences, for minimizing immunogenicity, for tuning stability and particle lifetime, for efficient degradation, etc. Among the serotypes of AAVs isolated and characterized from human or non-human primates (NHP), human serotype 2 is the first AAV that was developed as a gene transfer vector; it has been widely used for efficient gene transfer experiments in different target tissues and animal models. Other AAV serotypes include, but are not limited to, AAV1, AAV3, AAV4, AAV5, AAV6, AAV7, AAV8, AAV9, and AAVrh10. See, e.g., International Patent Application WO 2005/033321, for a discussion of various AAV serotypes.

In several embodiments, expression of artificial transcription factors of the present invention or other genes can be achieved in muscle cells through delivery by recombinantly engineered AAVs or artificial AAVs that comprise nucleic acid sequences encoding said artificial transcription factors or genes that are operably linked to muscle-specific promoters. In certain preferred embodiments, these AAVs are formulated as pharmaceutical compositions for treatment of muscle defects.

Muscle-specific expression vectors are described in US Patent Application Publication No. 2013/0136729, which describes the combination of AAV9 and muscle-specific CK6 promoter as a particularly efficient system for systemically carrying genes of interest into ischemic skeletal muscle. This publication further describes the combination of AAV9 and cardiac troponin C promoter as a system that is particularly effective in cardiomyocytes and skeletal myocytes with ischemic damage. International Patent Application WO 2005/118611 describes the delivery of microutrophin via adeno-associated vectors in the mdx dystrophic mouse model and incorporation of promoters that are active in muscle such as skeletal β-actin promoters, myosin light chain 2A promoters, dystrophin promoters and muscular creatine kinase promoters.

Expression vectors for the expression of exogenous genes such as zinc finger transcription factors in muscle and non-muscle tissue are also described in, for example, U.S. Pat. No. 8,304,235 (which describes the artificial transcription factor UtroUp (encoding a 6 zinc finger repeat designed to specially bind to utrophin promoter A) fused with the transcriptional activation domain "Vp16" from the Herpes simplex virus under the control of regulatory sequences of cytomegalovirus (CMV)) and the expression thereof via the eukaryotic vector pRK5 (Clontech), Italian Patent Application RM2005A000493, (which describes the artificial transcription factor Vp16-Jazz and the expression thereof via the vector pMEX under the control of the muscle-specific promoter and enhancer region of the murine myosin light chain (MLC) gene). Using these expression vectors, the exogenous gene is expressed mainly in skeletal muscle tissues or in cardiac muscle tissues, but not in both. The present invention advantageously allows for expression of exogenous genes in both skeletal and cardiac muscle tissues.

Desirable AAV fragments for assembly into vectors include the cap proteins, including vp1, vp2, vp3, and hypervariable regions, the rep proteins, including rep78, rep68, rep52, and rep40, and the sequences encoding these proteins. These fragments may be readily utilized in a variety of vector systems and host cells. Such fragments maybe used, alone, in combination with other AAV serotype sequences or fragments, or in combination with elements from other AAV or non-AAV viral sequences. As used herein, artificial AAV serotypes include, e.g., AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV capsid, a chimeric AAV capsid, a recombinant AAV capsid, or a "humanized" AAV capsid. Pseudotyped vectors, wherein the capsid of one AAV is replaced with a heterologous capsid protein, are useful in the invention.

In one embodiment, the vectors useful in compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both MV cap and rep proteins. In vectors in which both AAV rep and cap are provided, the AAV rep and AAV cap sequences can both be of one serotype origin, e.g., all AAV8 origin. In other embodiments, the vectors useful in compositions and methods described herein contain, at a minimum, sequences encoding an AAV6 capsid, or a fragment thereof. In some embodiments, useful vectors contain sequences encoding an AAV6 rep protein, or a fragment thereof. In other embodiments, in vectors in which both AAV rep and cap are provided, the AAV rep and AAV cap sequences can be both of AAV6 origin.

Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein.

A suitable recombinant AAV is generated by culturing a host cell which contains a nucleic acid sequence encoding an AAV serotype capsid protein, or fragment thereof, as defined herein; a functional rep gene; a transgene nucleic acid comprising AAV inverted terminal repeats (ITRs), a muscle-specific promoter sequence, and an artificial transcription factor (e.g., a fusion protein or modified human transcription factor) sequence; and sufficient helper functions to permit packaging of the transgene nucleic acid into the AAV capsid protein. The components required to be cultured in the host cell to package an AAV minigene in an AAV capsid may be provided to the host cell in trans. Alternatively, any one or more of the required components (e.g., transgene nucleic acid sequences, rep sequences, cap sequences, and/or helper functions) may be provided by a stable host cell which has been engineered to contain one or more of the required components using methods known to those of skill in the art. AAV vectors of the present invention can be produced, for example, by triple transfection of subconfluent HEK293 cells by three plasmids: AAV cis-plasmid containing the gene of interest, AAV trans-plasmid containing AAV rep and cap genes, and an adenovirus helper plasmid, for example pDF6.

Such a stable host cell may contain the required component(s) under the control of an inducible promoter. However, the required component(s) may be under the control of a constitutive promoter. Examples of suitable inducible and constitutive promoters are provided herein, in the discussion below of regulatory elements suitable for use with the transgene. In still another alternative, a selected stable host cell may contain selected components under the control of a constitutive promoter and other selected components under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The transgene, rep sequences, cap sequences, and helper functions required for producing the recombinant AAV of the invention may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating recombinant AAV virions are well known and the selection of a suitable method is not a limitation on the present invention. See, e.g., Fisher et al., *J. Virol.* 70:520-532, 1992 and U.S. Pat. No. 5,478,745, among others. These publications are incorporated herein by reference.

Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9, AAV10, or other known and unknown AAV serotypes. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

A transgene of the present invention comprises, for example, an artificial transcription factor (e.g., a fusion protein or modified transcription factor) nucleic acid sequence (e.g., Vp16-Jazz, Vp16-Bagly, Vp16-CJ7-UtroUp, JZif1, or JZif2) or other gene desired to be delivered to muscles, as described above, and its regulatory sequences, and 5' and 3' AAV inverted terminal repeats (ITRs). In one desirable embodiment, the ITRs of AAV serotype 8 are used. However, ITRs from other suitable serotypes may be selected. It is this transgene which is packaged into a capsid protein and delivered to a selected host cell.

The regulatory sequences include conventional control elements which are operably linked to the transgene in a manner which permits its transcription, translation and/or expression in a cell transfected with the vector or infected with the virus produced by the invention. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; sequences that confer nuclear localization (e.g., nuclear localization sequences) and when desired, sequences that enhance secretion of the encoded product. A great number of expression control sequences are known in the art and may be utilized. Poly A sequences may be derived from many suitable species, including, without limitation SV-40, humans, and bovines.

The regulatory sequences useful in the constructs of the present invention may also contain an intron, desirably located between the promoter/enhancer sequence and the gene. One desirable intron sequence is derived from SV-40, and is a 100 bp mini-intron splice donor/splice acceptor referred to as SD-SA. In a preferred embodiment, the intron comprises the first intron of the human alpha-actin gene, including the splice donor site, as well as part of the second intron of the human beta-globin gene and part of the third exon of the human beta-globin gene, including the splice acceptor site.

In other embodiments, the recombinant AAV vectors may include accessory functional elements including cap signals, sequences coding for epitope tags (e.g., haemmaglutinin (HA) tag, myc tag, maltose-binding protein (MBP) tag, green fluorescent protein (GFP) or any other fluorescent protein, etc.), and/or multicloning sites which contain a plurality of restriction enzyme cutting sites that make it possible to insert into the vector any gene coding for a protein of interest. The amino acid sequence of an exemplary myc tag is shown in SEQ ID NO:75.

Another regulatory component of the recombinant AAV useful in the invention is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the FGF-1 internal ribosome entry sequence, which supports transgene expression in skeletal muscle cells. See, e.g., Delluc-Claviéres et al., Gene Ther. 15(15):1090-1098, 2008. Preferably, the IRES is located 3' to the transgene in the recombinant AAV vector.

The selection of the promoter to be employed in the recombinant AAV may be made from among a wide number of constitutive, inducible, cell-type specific, or tissue-type specific promoters that can express the selected transgene in the desired muscle cell. In a preferred embodiment, the promoter is muscle-specific. In particularly preferred embodiments, the promoter is specific for expression of the transgene in skeletal and cardiac muscle cells.

The promoter(s) used in the present invention may be derived from any species. In one embodiment, the promoter is of a small size, under 1000 bp, due to the size limitations of the AAV vector. In another embodiment, the promoter is under 400 bp. Examples of constitutive promoters useful in the invention include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the chicken β-actin (CBA) promoter, the phosphoglycerol kinase (PGK) promoter, the EF1 promoter (Invitrogen), and the immediate early CMV enhancer coupled with the CBA promoter.

Inducible promoters which can be used in the present invention allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Other types of inducible promoters which may be useful in this context are those which are regulated by a specific physiological state, e.g., temperature, acute phase, a particular differentiation state of the cell, or in replicating cells only. Any type of inducible promoter which is tightly regulated and is specific for the particular target cell type may be used.

Other regulatory sequences useful in the invention include enhancer sequences. Enhancer sequences useful in the invention include the IRBP enhancer, immediate early cytomegalovirus enhancer, one derived from an immunoglobulin gene or SV40 enhancer, the cis-acting element identified in the mouse proximal promoter, etc. Other enhancer sequences are also well-known in the art.

In preferred embodiments, the transgene of the invention comprises a muscle-specific promoter. For example, a muscle specific promoter may increase expression of a gene in a muscle at least 2-fold, 3-fold, 4-fold, 5-fold, 10-fold, 15-fold, 20-fold, 30-fold, 50-fold, 100-fold or more compared to a reference non-muscle tissue. Exemplary muscle-specific promoters include but are not limited to: alpha-actin, cardiac troponin C, myosin light chain 2A, skeletal beta-actin, CK6, dystrophin, muscular creatine kinase, dMCK, tMCK, enh348MCK, synthetic C5-12 (Syn), Myf5, MLC1/3f, MyoD1, Myog, and Pax7. See, for example, U.S. Patent Application 2011/0212529, McCarthy et al., *Skeletal Muscle* 2:8, 2012; and Wang et al., *Gene Ther.* 15:1489-1499, 2008.

Selection of these and other common vector and regulatory elements are conventional and many such sequences are available. See, e.g., Sambrook et al., supra and references cited therein, and Ausubel et al., Current Protocols in Molecular Biology, John Wiley & Sons, New York, 1989. Of course, not all vectors and expression control sequences will function equally well to express all of the transgenes of this invention. However, one of skill in the art may make a selection among these, and other, expression control sequences without departing from the scope of this invention, Expression Vectors for Production of Muscle-Specific Recombinant AAV The invention provides expression vectors for the production of recombinant AAV that are muscle-specific (e.g., viral particles that comprise a polynucleotide sequence comprising a muscle-specific promoter and an artificial transcription factor (e.g., a fusion protein or a modified transcription factor)). For example, in one embodiment, the expression vectors described by SEQ ID NOs:1 or 2 or SEQ ID NOs:62-65 can be used to produce the recombinant AAV). In a particular embodiment, the expression vector comprises the nucleotide sequence called SEQ ID NO:1. The expression vector according to this embodiment is referred to as "muscle AAV" ("mAAV"). The functional elements of mAAV are further described below.

Located at the 5' end is the Left-Inverted Terminal Repeat (L-ITR) sequence of the adeno-associated virus, while located at the 3' end is the Right-Inverted Terminal Repeat (R-ITR) sequence of the adeno-associated virus. These inverted terminal repeat sequences are known per se and are described in the literature. In SEQ ID NO:1 they are respectively located between the nucleotide positions from 1 bp to 141 bp (L-ITR) and from 2899 bp to 3040 bp (R-ITR).

Between nucleotide positions 156 bp and 2219 bp of SEQ ID NO:1 there is also a transcriptional regulatory region which includes the promoter of the human alpha-actin gene, part of the first intron of the human alpha-actin gene, including the splice donor site, as well as part of the second intron of the human beta-globin gene and part of the third exon of the human beta-globin gene, including the splice acceptor site.

Between nucleotide positions 2219 and 2264 bp of SEQ ID NO:1 there is also a polylinker, or multiple cloning site, which contains a plurality of restriction enzyme cutting sites that make it possible to insert into the expression vector any gene coding for a protein of interest.

In addition to the aforementioned essential functional elements, there may also be accessory functional elements such as for example a cap signal, a sequence coding for a tag (for example Myc-tag), a polyadenylation consensus sequence, etc.

The main restriction sites, the polylinker, the regulatory region and the elements of the mAAV expression vector of SEQ ID NO:1 are shown in Table 1 below.

TABLE 1

Functional elements of mAAV expression vector

| Main functional elements | | Position (bp) |
|---|---|---|
| Main restriction sites | 2 NotI sites<br>SEQ ID NO: 27<br>GCGGCCGC | 149<br>2899 |
| | 1 MluI site<br>SEQ ID NO: 28<br>ACGCGT | 155 |
| Polylinker | SEQ ID NO: 7<br>ATCGATGGAATT<br>CCGGGATCCGGTC<br>GACCGTACGTACA<br>AGATCT | 2219-2264 |

TABLE 1-continued

Functional elements of mAAV expression vector

| Main functional elements | | Position (bp) |
|---|---|---|
| Regulatory region | Alpha-actin promoter and part of the intron comprising the beta-globin gene acceptor | 156-2219 |
| | splice donor site: SEQ ID NO: 29 GCCCAGGTAGGG | 1606 |
| | splice acceptor site: SEQ ID NO: 30 CCCACAGCTCCT | 2154 |
| Elements of the AAV vector | Left-ITR Right-ITR | 1-141 2899-3040 |

As indicated above, due to the presence of the multiple cloning site, the expression vector of the invention is able to accommodate a sequence coding for any gene of interest, such as, for example a gene coding for a reporter protein or a gene coding for a protein to be specifically expressed in skeletal and cardiac muscle tissue. Particular proteins to be specifically expressed in skeletal and cardiac muscle tissue are artificial transcription factors capable of increasing expression of the utrophin gene.

The mAAV expression vector described herein can be used to produce recombinant AAV (e.g., viral particles that comprise a polynucleotide comprising a muscle-specific promoter and an artificial transcription factor of the invention). Polynucleotides that are portions of the mAAV expression vectors described herein are packaged into recombinant AAV viral particles. For example, the viral particles can include a polynucleotide sequence defined by SEQ ID NO:83-87, corresponding to portions of mAAV-Vp16-Jazz, mAAV-Vp16-Bagly, mAAV-Vp16-CJ7-UtroUp, mAAV-JZif1, and mAAV-JZif2, respectively. Viral particles are described herein by the expression vector used for their production and by the serotype. For example, the viral particles referred to as mAAV8-Vp16-Jazz and mAAV6-Vp16-Jazz have a capsid serotype 8 and serotype 6, respectively, and can be produced using the mAAV-Vp16-Jazz expression vector and methods described herein or known in the art.

DNA Binding Elements

The fusion proteins or modified transcription factors of the invention comprise DNA binding elements. In preferred embodiments, the DNA binding elements comprise zinc finger motifs that specifically bind to defined DNA sequences. In the most preferred embodiments, the DNA binding elements specifically bind to defined sequences in the utrophin "A" promoter. A DNA binding element of the instant invention may be derived or isolated from zinc finger motifs, which are well known in the art. Preferably, the zinc finger motif is derived from a $Cys_2$-$His_2$ type zinc finger. A zinc finger DNA binding element can be derived or produced from a wild type zinc finger-containing polypeptide by truncation or expansion, or as a variant of a wild type-derived polypeptide by a process of site directed mutagenesis, or by a combination of the procedures. See e.g., U.S. Pat. Nos. 6,242,568; 6,140,466; and 6,140,081. The term "truncated" refers to a zinc finger-nucleotide binding polypeptide that contains less that the full number of zinc finger motifs found in the native zinc finger binding polypeptide or that has been deleted of non-desired sequences. For example, truncation of the zinc finger-nucleotide binding protein TFIIIA, which naturally contains nine zinc finger motifs, might be a polypeptide with only zinc fingers one through three. Expansion refers to a zinc finger polypeptide to which additional zinc finger motifs have been added. For example, TFIIIA may be extended to 12 fingers by adding 3 zinc finger motifs.

In addition, a zinc finger DNA binding element may include zinc finger motifs from more than one wild type polypeptide, thus resulting in a "hybrid" zinc finger polypeptide. The term "mutagenized" refers to a zinc finger polypeptide that has been obtained by performing any of the known methods for accomplishing random or site-directed mutagenesis of the DNA encoding the protein. Examples of known zinc finger proteins that can be truncated, expanded, and/or mutagenized according to the present invention in order to alter the function of a zinc finger-nucleotide binding motif include TFIIIA and Zif268. Other zinc finger-containing nucleotide binding polypeptides are well known to those of skill in the art.

A DNA binding element of the present invention typically comprises a plurality of DNA binding domains. Preferably, the DNA binding domains are zinc-finger motifs. Preferably, the DNA binding element contains from 2, 3, 4, 5, 6, 7, 8, 9, or 10 such motifs, more preferably from 2 to 6 such motifs and, most preferably, 3 such motifs. The DNA binding domains are operably linked to each other. In one embodiment, the DNA binding domains are directly linked or bonded together via well known peptide linkages. In another embodiment, the DNA binding domains are operatively linked using a peptide linker containing from 5 to 50 amino acid residues. Preferably, the linker contains from 5 to 40 amino acid residues, more preferably from 5 to 30 amino acid residues and, even more preferably from 5 to 15 amino acid residues. The linkers are preferably flexible. Exemplary linkers are set forth, for example, in US Patent Application Publication No. 2007/0020627.

DNA binding elements used in the invention can be naturally-occurring or non-naturally occurring. Naturally-occurring zinc finger DNA binding domains are well known in the art. In a preferred embodiment, at least one DNA binding domain of a present DNA binding element is non-naturally occurring. Each of the DNA binding zinc finger motifs is preferably designed and made to specifically bind nucleotide target sequences corresponding to the formula 5'-NNN-3', where N is any nucleotide (i.e., A, C, G or T). Such DNA binding domains are well known in the art. See, e.g., U.S. Pat. Nos. 6,242,568, 6,140,466 and 6,140,081. A known "recognition code" that relates the amino acids of a single zinc finger motif to its associated DNA target can be utilized as a guide for the design of the DNA binding elements of the present invention. See, for example, Corbi et al., *Biochem Cell Biol.* 82:428-36, 2004; Klug, Q. *Rev. Biophys.* 31(1):1-21, 2010; Pabo et al., *Annu. Rev. Biochem.* 70:313-340, 2001; Segal et al., *Curr. Opin. Biotechnol.* 12(6):632-637, 2001; Klug, *Annu. Rev. Biochem.* 79:213-231, 2010; and Bhakta et al., *Methods Mol. Biol.* 649:3-30, 2010. This code can be used for modular assembly of DNA binding elements, for example, by combining three separate zinc finger motifs that can each recognize a 3 bp DNA sequence to generate a three zinc-finger DNA binding element that can specifically recognize a 9 bp target site. Alternatively, screening methods or selection strategies can be used to identify zinc finger sequences that specifically bind to a desired DNA sequence. These methods include, for example, phage display, yeast one-hybrid systems, and bacterial one-hybrid and two-hybrid systems and other methods known to one of skill in the art (see, e.g., Maeder et al., *Mol. Cell.* 31:294-301, 2008). Combinations of zinc finger motifs that bind to specific DNA sequences can be obtained from commercial sources or using tools provided by the Zinc Finger Consortium.

Structural information about known zinc finger motifs can be used to guide the design of DNA binding elements that bind to a desired target sequence. For example, the structure of a three finger polypeptide-DNA complex derived from the mouse immediate early protein Zif268 (also known as Krox-24) has been solved by X-ray crystallography (see, e.g., Pavletich et al., Science, 252:809-817, 1991). Each finger contains an anti-parallel beta-turn, a finger tip region, and a short amphipathic alpha-helix which, in the case of the zinc finger motifs of Zif268, binds in the major groove of DNA. In addition, the conserved hydrophobic amino acids and zinc coordination by the cysteine and histidine residues stabilize the structure of the individual finger domain. The crystal structure of Zif268 indicates that specific histidine (non-zinc coordinating His residues) and arginine residues on the surface of the alpha-helix participate in DNA recognition. Specifically, the charged amino acids immediately preceding the alpha-helix and at helix positions 2, 3, and 6 (immediately preceding the conserved histidine) participate in hydrogen bonding to DNA guanines. In general, modifications in or near the alpha-helix are more likely to affect DNA binding specificity, whereas modifications in framework regions (e.g., beta turns or linker regions) are less likely to affect DNA binding specificity, while they may or may not affect structural integrity (e.g. proper folding) of the protein.

A zinc finger DNA binding motif of this invention typically comprises a unique heptamer (contiguous sequence of 7 amino acid residues) within the alpha-helix of the motif, which largely determines binding specificity to a target nucleotide. The heptameric sequence can be located anywhere within the α-helical domain but it is preferred that the heptamer extend from position −1 to position 6 as the residues are conventionally numbered in the art. In some embodiments, one or more modifications in the key amino acid positions (−1, +3, and +6) of the zinc finger alpha-helix can enable it to bind the desired DNA target sequence. In some embodiments, one or more modifications in other amino acid positions of the zinc finger alpha-helix can be used to enable it to bind the desired DNA target sequence (e.g., positions +1, +2, +4, or +5). In other embodiments, changes to residues outside of the heptamer can also be introduced to enable the protein to bind to the desired DNA target sequence. A zinc finger motif can include any β-sheet and framework sequences known in the art to function as part of a zinc finger motif. In some embodiments, the β-sheet and/or framework sequences are not substantially modified during the process of modifying a zinc finger domain to bind to a desired target sequence. Therefore, a zinc finger motif of a DNA binding element of the invention (e.g., in a fusion protein or a modified human transcription factor) may have 50%, 55%, 60%, 65%, 70%, 75%, 80%, 85%, 90%, 91%, 92%, 93%, 94%, 95%, 96%, 97%, 98%, 99%, or more sequence identity to a known zinc finger motif, with only a few different amino acid residues, e.g., 1, 2, 3, 4, 5, 6, 7, or 8 amino acid residues modified from the known zinc finger motif. These modifications are typically located in the alpha-helix or in amino acid residues surrounding the alpha-helix. Residues that are involved structural integrity or proper 3 dimensional protein folding, e.g., in zinc coordination, are disfavored for modification. Methods to determine whether a DNA binding element can bind to a particular DNA sequence are well known to those skilled in the art, and include, e.g., electrophoretic mobility shift assays (EMSA), chromatin immunoprecipitation (ChIP), and DNase I protection assays.

Shown in Table 2 is a comparison of the zinc finger motif sequences for the Jazz, Bagly, and UtroUp DNA binding elements. In some embodiments, the zinc finger motifs of the invention have at least 50% sequence identity to any of the zinc finger motifs described in Table 2 or in SEQ ID NOs:54-60; e.g., 50%, 55%, 60%, 70%, 75%, 80%, 85%, 90%, 95%, 97%, 98%, or 99% sequence identity. In certain embodiments, the zinc finger motifs of the invention have less than 15 amino acid substitutions compared to any of the zinc finger motifs described in Table 2 or in SEQ ID NOs:54-60; e.g., less than 15, 14, 13, 12, 11, 10, 9, 8, 7, 6, 5, 4, 3, 2, or 1 substitution(s).

TABLE 2

Comparison of zinc finger (ZF) motif sequences of selected DNA binding elements

| DNA Binding Element | # ZF Motifs | ZF Motif Sequences | DNA target sequence |
|---|---|---|---|
| Jazz | 3 | ZF1: CPVESCDRRFSRSDELT RHIRIH (SEQ ID NO: 54) ZF2: CRICMRNFSSRDVLRRH NRTH (SEQ ID NO: 55) ZF3: CDICGRKFASRDVLRRH NRIH (SEQ ID NO: 56) | GCTGCTGC G (SEQ ID NO: 9) |
| Bagly | 4 | ZF1: CPVESCDRRFSRSDELT RHIRIH (SEQ ID NO: 54) ZF2: CRICMRNFSSRDVLRRH NRTH SEQ ID NO: 55) ZF3: CDICGRKFASRDVLRRH NRIH (SEQ ID NO: 56) ZF4: CAECGKAFVESSKLKRH QLVH (SEQ ID NO: 57) | CGGGCTGC TGCG (SEQ ID NO: 12) (human) CCGGCTGC TGCG (SEQ ID NO: 13) (mouse) |
| UtroUp | 6 | ZF1: CPVESCDRRFSRSDNLV RHIRIH (SEQ ID NO: 58) ZF2: CRICMRNFSRSDHLTTH NRTH (SEQ ID NO: 59) ZF3: CDICGRKFADPGHLVRH NRIH (SEQ ID NO: 60) ZF4: CPVESCDRRFSRSDELT RHIRIH (SEQ ID NO: 61) ZF5: CRICMRNFSSRDVLRRH NRTH (SEQ ID NO: 55) ZF6: CDICGRKFASRDVLRRH NRIH (SEQ ID NO: 56) | GCTGCTGC GGGCTGGG AG (SEQ ID NO: 14) |

Fusion Proteins

The fusion proteins described herein generally contain from about e.g., 30, 40, 50, 60, 70, 80, 90, 100, 200, 300, 400, 500, 600, 700, 800, 900, 1000 or more amino acid residues. It will be understood by those of ordinary skill in the art that the polypeptides can also be prepared by other means including, for example, recombinant techniques, or by synthesis. Examples of appropriate cloning and sequencing techniques, and instructions sufficient to direct persons of skill through many cloning exercises are found in Sambrook et al., supra. Product information from manufacturers of biological reagents and experimental equipment, such as the SIGMA Chemical Company (Saint Louis, Mo.), and New England BioLabs (Ipswich, Mass.) also provide information useful in known biological methods. The following description briefly provides an overview of various recombinant polypeptide production methodologies applicable to certain embodiments of the present invention.

The polypeptides described herein are derived from transcriptional activation elements and DNA binding elements. The nucleotide sequence of many transcriptional activator elements and DNA binding elements are known. Accordingly, the known nucleic acid sequence can be used to make the polypeptides recombinantly or a nucleic acid encoding the desired polypeptide can be derived from the amino acid sequence. In certain embodiments, the transcriptional activation element of the fusion protein is selected from a group including but not limited to acidic or hydrophobic activation domains (e.g., from Gal4 or Gcn4, respectively), nine-amino-acid transactivation domains (9aaTAD, e.g., from p53, Vp16, MLL, E2A, HSF1, NF-IL6, and NF-κB), Vp64, p65, SP1, Zif268, and the trans-activation domain CJ7 derived from human Che-1/AATF. In some embodiments transcriptional activation element is derived from physiological regulators of utrophin expression, including NFAT, GABPα, and GABPβ. In some embodiments, a fusion protein has multiple transcriptional activation elements, for example, both Vp16 and CJ7.

In some embodiments, the DNA binding element of a fusion protein is a zinc finger domain, helix-turn-helix motif, leucine zipper domain, winged helix domain, winged helix turn helix domain, helix-loop-helix domain, HMG box domain, Wor3 domain, immunoglobulin domain, B3 domain, TAL effector DNA-binding domain, RNA-guided DNA-binding domain, or any DNA binding element described herein (e.g., Jazz, UtroUp, Bagly, and ZFP51 or an element having the sequence of SEQ ID NO:16-19, or having at least 50% (e.g., 50%, 55%, 60%, 70%, 72%, 75%, 80%, 81%, 85%, 90%, 95%, or 99%) identity to that of SEQ ID NO:16-19, or any of the zinc finger motifs described, e.g., in Tables 2 and 6.

Generally, this involves creating a nucleic acid sequence that encodes the polypeptide, placing the nucleic acid in an expression cassette under the control of a particular promoter, expressing the polypeptide in a host, isolating the expressed polypeptide and, if required, renaturing the polypeptide. Techniques sufficient to guide one of skill through such procedures are found in Sambrook et al., supra.

Provided with the polypeptide sequences described herein, one of skill will recognize a variety of equivalent nucleic acids that encode the polypeptide. This is because the genetic code requires that each amino acid residue in a peptide is specified by at least one triplet of nucleotides in a nucleic acid which encodes the peptide. Due to the degeneracy of the genetic code, many amino acids are equivalently coded by more than one triplet of nucleotides. For instance, the triplets CGU, CGC, CGA, CGG, AGA, and AGG all encode the amino acid arginine. Thus, at every position where an arginine is to be encoded by a nucleic acid triplet, the nucleic acid has any of the triplets which encode arginine. One of skill is thoroughly familiar with the genetic code and its use. An introduction to the subject is found in, for example, Chapter 15 of Watson et al., Molecular Biology, of the Gene (Fourth Edition, The Benjamin/Cummings Company, Inc., Menlo Park, Calif. (1987)), and the references cited therein.

Although any nucleic acid triplet or codon which encodes an amino acid can be used to specify the position of the amino acid in a peptide, certain codons are preferred. It is desirable to select codons for elevated expression of an encoded peptide, for example, when the peptide is purified for use as an immunogenic reagent. Codons are selected by reference to species codon bias tables, which show which codons are most typically used by the organism in which the peptide is to be expressed. The codons used frequently by an organism are translated by the more abundant tRNAs in the cells of the organism. Because the tRNAs are abundant, translation of the nucleic acid into a peptide by the cellular translation machinery is facilitated. Codon bias tables are available for most organisms. For an introduction to codon bias tables, see, e.g., Watson et al., supra.

In addition, it will be readily apparent to those of ordinary skill in the art that the fusion proteins described herein and the nucleic acid molecules encoding such fusion proteins can be subject to various changes, such as insertions, deletions, and substitutions, either conservative or non conservative, where such changes might provide for certain advantages in their use, e.g., to increase biological activity.

One of skill will appreciate that many conservative variations of nucleic acid constructs yield a functionally identical construct. For example, due to the degeneracy of the genetic code, silent substitutions (i.e., substitutions of a nucleic acid sequence which do not result in an alteration in an encoded peptide) are an acceptable feature of every nucleic acid sequence which encodes an amino acid. In addition, one of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Sambrook et al., supra.

Modifications to nucleic acids are evaluated by routine screening techniques in suitable assays for the desired characteristic. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Similarly, conservative amino acid substitutions, in one or a few amino acids in an amino acid sequence of a protein are substituted with different amino acids with highly similar properties (see the definitions section, supra), are also readily identified as being highly similar to a disclosed construct.

In one preferred embodiment, the muscle-specific recombinant adeno-associated vector mAAV described above comprises, inserted in the polylinker or multiple cloning site, an exogenous gene which codes for a fusion protein comprising a DNA binding element of the zinc finger type and a transcriptional activation element. Exogenous genes which are preferred for this purpose are those which are capable of increasing utrophin expression. Among these, preference is given to the exogenous gene coding for the fusion protein known as "Vp16-Jazz" described in the Italian patent application RM2005A000493, which codes for a DNA binding domain with three zinc fingers (Jazz) fused with the strong transcriptional activation domain Vp16 of the Herpes simplex virus (the amino acid sequence of Vp16-Jazz is represented by SEQ ID NO:37). In other embodiments, genes encoding for other proteins, such as "Vp16-Bagly" or "Vp16-CJ7-UtroUp" are inserted into the multicloning site of the mAAV expression vector described above.

An exemplary mAAV expression vector of the invention including, inserted in the multiple cloning site, the sequence coding for the artificial transcription factor fusion protein "Vp16-Jazz", is represented by SEQ ID NO:2. The main restriction sites, the regulatory region and the elements of the mAAV expression vector of SEQ ID NO:2 are shown in Table 3 below. It is to be understood that one or more of the elements contained in the vector described below can be replaced or modified. For example, different ITRs, promoter regions, splice acceptors, splice donors, epitope tags, nuclear localization sequences, etc., can be incorporated into vectors of the invention.

TABLE 3

Description of mAAV-Vp16-Jazz expression vector

| Main functional elements | | Position (bp) |
|---|---|---|
| Main restriction sites | 2 NotI sites SEQ ID NO: 27 GCGGCCGC | 149 3658 |
| | 1 MluI site SEQ ID NO: 28 ACGCGT | 155 |
| | ClaI SEQ ID NO: 31 ATCGAT | 2225 |
| | BglII | 3023 |

TABLE 3-continued

Description of mAAV-Vp16-Jazz expression vector

| Main functional elements | | Position (bp) |
|---|---|---|
| | SEQ ID NO: 32 AGATCT | |
| Regulatory region | Alpha-actin promoter and part of the intron comprising the beta-globin gene acceptor | 156-2219 |
| | splice donor: SEQ ID NO: 29 GCCCAGGTAGGG | 1606 |
| | splice acceptor: SEQ ID NO: 30 CCCACAGCTCCT | 2154 |
| Vp16-Jazz Fusion Protein | MT-Vp16Jazz Myc-Tag Nuclear Localization Signal | 2233-3139 2233-2428 2452-2476 |

TABLE 3-continued

Description of mAAV-Vp16-Jazz expression vector

| Main functional elements | | Position (bp) |
|---|---|---|
| | SEQ ID NO: 8 TGGGCCCTAAAAAGA AGCGTAAA | |
| | Vp16 (transcriptional activation domain) | 2476-2727 |
| | Jazz (zinc finger DNA binding domain) | 2727-3139 |
| Elements of the AAV vector | Left-ITR Right-ITR | 1-141 3658-3799 |

In other embodiments of the invention, an mAAV expression vector can comprise a fusion protein that is different from Vp16-Jazz (e.g., fusion proteins that contain the DNA binding elements Bagly or UtroUp. Table 4 shows exemplary mAAV expression vectors including genes encoding for different fusion proteins of the invention.

TABLE 4

Exemplary mAAV-Fusion Protein Expression Vectors

| Vector Name | SEQ ID NO: | Promoter | Splice Donor | Splice Acceptor | Fusion Protein (include myc-NLS) |
|---|---|---|---|---|---|
| mAAV-Vp16-Jazz | 2 | Human alpha-actin promoter | Human alpha-actin (SEQ ID NO: 29) | Human beta-globin (SEQ ID NO: 30) | Vp16-Jazz (SEQ ID NO: 66) |
| mAAV-Vp16-Bagly | 62 | Human alpha-actin promoter | Human alpha-actin (SEQ ID NO: 29) | Human beta-globin (SEQ ID NO: 30) | Vp16-Bagly (SEQ ID NO: 67) |
| mAAV-Vp16-CJ7-UtroUp | 63 | Human alpha-actin promoter | Human alpha-actin (SEQ ID NO: 29) | Human beta-globin (SEQ ID NO: 30) | Vp16-CJ7-UtroUp (SEQ ID NO: 68) |

Table 5 describes exemplary fusion proteins that can be used in the present invention along with their known target DNA sequence. The general human target sequence and general mouse target sequence for the fusion proteins described in Table 5 are shown below. As shown in Table 5, the target sequences of these fusion proteins are located at different sites in the general human and mouse target sequences.

```
(Human target sequence)
                                   SEQ ID NO: 10
CGG-GCT-GCT-GCG-GGC-TGG-GAG (Mouse target sequence)
                                   SEQ ID NO: 11
CCG-GCT-GCT-GCG-GGC-TGG-GAG
```

Other fusion proteins that are substantially the same, or derivatives of these examples, can also be used in the present invention. Any of the fusion proteins described in Table 5 below can be incorporated into a mAAV expression vector as described above. In some embodiments, the fusion proteins described below can include one or more additional elements, such as epitope tags or nuclear localization sequences.

TABLE 5

Exemplary Fusion Proteins and Target Sequences

| DNA Binding Element | Number of Zinc Fingers | Transcriptional Activation Element | DNA target sequence |
|---|---|---|---|
| Jazz | 3 | Vp16, CJ7, Gal4, SP1 | SEQ ID NO: 9 GCT-GCT-GCG |
| Bagly | 4 | Vp16 | SEQ ID NO: 12 CGG-GCT-GCT-GCG (human) SEQ ID NO: 13: CCG-GCT-GCT-GCG (mouse) |
| UtroUp | 6 | Vp16, CJ7 | SEQ ID NO: 14 GCT-GCT-GCG-GGC-TGG-GAG |

It is to be understood that the fusion proteins can consist essentially of a transcriptional activation element and a DNA binding element, for example, without other elements such as epitope tags or nuclear localization sequences. The amino acid sequences of exemplary "minimal" fusion proteins are described in, e.g., SEQ ID NO:71 (Vp16-Jazz); SEQ ID NO:72 (Vp16-Bagly); and SEQ ID NO:73 (Vp16-CJ7-UtroUp). In other embodiments, additional elements such as epitope tags or nuclear localization sequences are included in the fusion protein sequence. The amino acid sequences of exemplary fusion proteins that include epitope tags and nuclear localization sequences are described in, e.g., SEQ ID NO: 34 (myc-NLS-Vp16-Jazz); SEQ ID NO:35 (myc-NLS-Vp16-CJ7-UtroUp); and SEQ ID NO:36 (myc-NLS-Vp16-Bagly). In certain embodiments, the fusion proteins of the invention have at least 50% identity to SEQ ID NOs:71-73 or SEQ ID Nos:34-36, e.g., at least 50%, 55%, 60%, 65%, 70%, 75%, 80%, 90%, 95%, 97%, or 99% identity.

Modified Transcription Factors Capable of Increasing Utrophin Expression

In certain embodiments, a genomically-encoded (i.e., endogenous) transcription factor, for example a zinc finger transcription factor, is modified or engineered to change the target sequence that it specifically binds. In preferred embodiments, the modified transcription factor is derived from a human zinc finger transcription factor. In some embodiments, the modified transcription factor is derived from Zif268, also known as EGR-1 or EGR1. In preferred embodiments, the human zinc finger transcription factor is modified to bind to the utrophin "A" promoter, for example to a region of SEQ ID NOs:20 or 33. The DNA-binding element(s) of a human transcription factor can be modified as discussed above in relation to the DNA binding elements of fusion proteins. For example, the DNA sequences encoding for the zinc finger motifs of Zif268 can be replaced with the DNA sequences encoding for the zinc finger motifs of any of the DNA binding elements described herein, including Jazz, Bagly, or UtroUp, or with zinc finger motifs that have about having at least 70% (e.g., 72%, 75%, 80%, 81%, 85%, 90%, 95%, or 99%) identity to these zinc finger motifs. For example, the zinc finger motifs may have at least 70% identity to any of SEQ ID NOs:16-18.

In some embodiments, the DNA sequences of a human zinc finger protein, for example of Zif268, are modified so that they encode different amino acids in one or more of the zinc finger motif alpha-helix, especially at the −1, 3 and 6 positions of the zinc finger alpha-helix which are especially important in conferring binding to specific DNA targets. The methods described in the preceding section, for example, can also be used to modify the DNA binding sequence of an endogenous transcription factor, such that the endogenous transcriptional activation element (e.g., a trans-activation domain) of the modified transcription factor can induce increased utrophin expression relative to a reference.

In some embodiments, one or more of the −1, 3, and 6 positions, or residues within the zinc finger alpha helix, of a zinc finger motif of human Zif268 are modified to enable the modified transcription factor to bind the utrophin "A" promoter. In other embodiments, one or more additional amino acid residues of a zinc finger motif, preferably in the zinc finger alpha-helix that confers DNA recognition, are further modified, e.g., position 1, 2, 4, 5, 7, 8, or 9. In some embodiments zinc finger motif of a modified transcription factor of the invention (e.g., JZif1 or JZif2) may have 80%, 85%, 90%, 91%, 92%, 93%, 94%, 95%, 96%, 97%, 98%, 99%, or more sequence identity to a known zinc finger motif, with only a few different amino acid residues, e.g., 1, 2, 3, 4, 5, 6, 7, or 8 amino acid residues modified from the genomically-encoded transcription factor (e.g. Zif268). Residues that are involved structural integrity or proper three dimensional protein folding, e.g., in zinc coordination, are disfavored for modification. In some embodiments, one or more of the zinc finger motifs of a modified transcription factor are substantially the same as compared to the genomically-encoded wild-type transcription factor, while other zinc finger motifs are modified; this can be preferred if the desired 3 bp target sequence for a given zinc finger motif is the same for both the wild-type and the corresponding modified zinc finger motif. In preferred embodiments, the zinc finger motifs of Zif268 are modified to obtain the zinc finger sequences shown in Table 6 or described in SEQ ID NOs:48-53. In some embodiments, the modified transcription factors of the invention comprise one or more zinc finger motifs that have at least 50% sequence identity to any of the zinc finger sequences shown in Table 6 or described in SEQ ID NOs:48-53, e.g., 50%, 55%, 60%, 65%, 70%, 75%, 80%, 85%, 90%, 95%, 97%, 98%, or 99% sequence identity. In certain embodiments, the zinc finger motifs of the modified transcription factors of the invention have less than 15 amino acid substitutions compared to any of the zinc finger motifs described in Table 6 or in SEQ ID NOs:48-53; e.g., less than 15, 14, 13, 12, 11, 10, 9, 8, 7, 6, 5, 4, 3, 2, or 1 substitution(s).

In preferred embodiments, the modified transcription factors do not have epitope tags or other elements. For example, the JZif1 and JZif2 modified transcription factors described herein do not have an epitope tag. In the absence of an epitope tag, in some embodiments the expression of modified transcription factors is monitored using Western blot or indirect immunofluorescence assays using antibodies that recognize the genomically-encoded transcription factor from which the modified transcription factor of the invention is derived, which can reveal an augmentation or increase in protein levels compared to reference. This increase in protein levels detected by the antibody compared to reference can indicate that the modified transcription factor is being expressed.

Figure 12A:
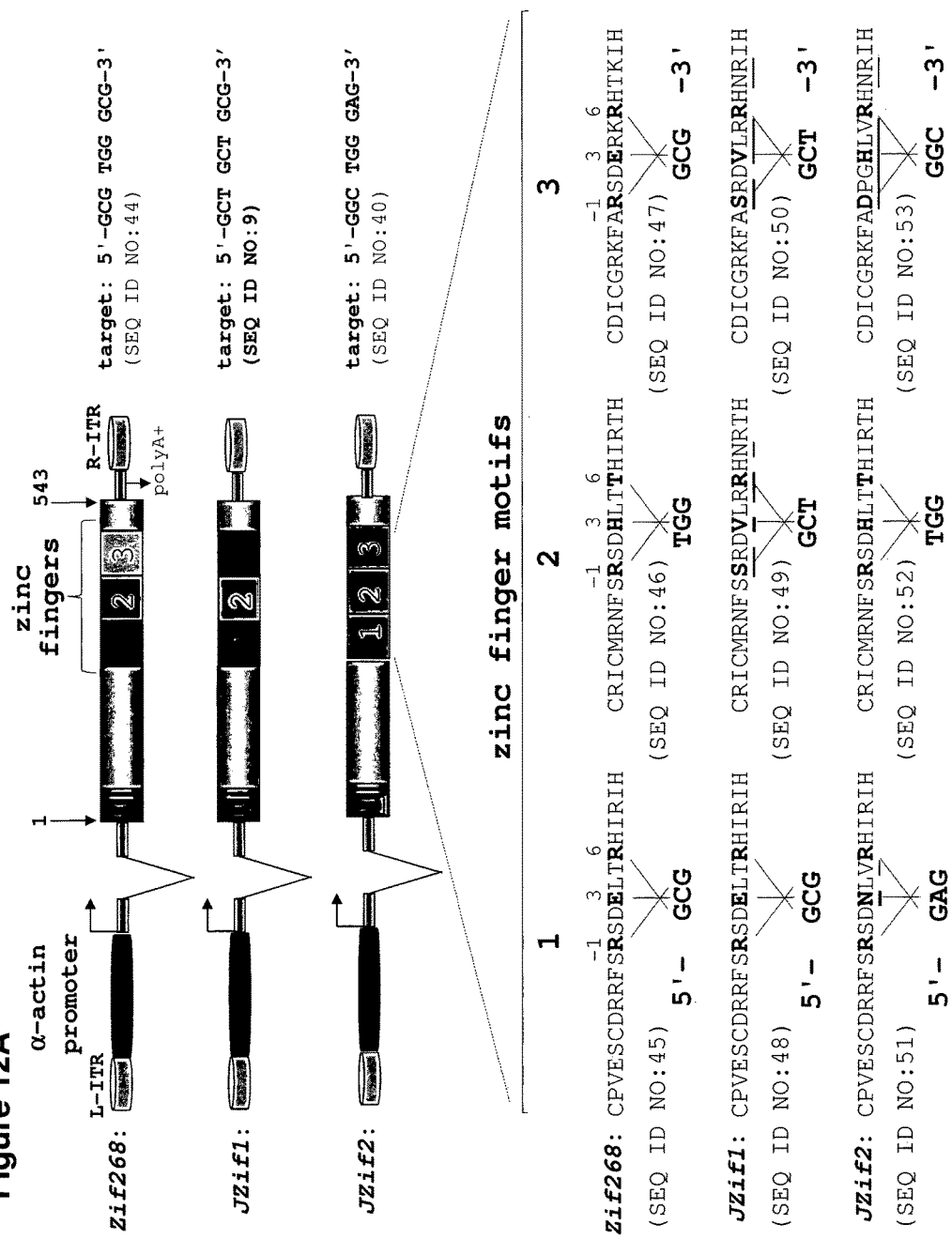

Exemplary modified transcription factors JZif1 and JZif2 of the invention derived from human Zif268 are shown, e.g., in Table 6 and in FIG. 12. As used herein, the terms "Zif1," "Jazz-Zif1," "JZif1," "ZIFJ1," "ZIF1," and "Ziff1" are interchangeable. As used herein, the terms "Zif2," "Jazz-Zif2," "JZif2," "ZIFJ2," "ZIF2," and "Ziff2" are interchangeable.

TABLE 6

Comparison of Zif268 and Modified Transcription Factors JZif1 and JZif2

| Transcription Factor | Number of Zinc Fingers | Zinc Finger (ZF) Motif Sequences (Amino acids in positions -1, 3 and 6 of each ZF motif are underlined and in bold). | DNA target sequence |
|---|---|---|---|
| Zif268 | 3 | ZF1: CPVESCDRRFSRSDELT RHIRIH (SEQ ID NO: 45) ZF2: CRICMRNFSRSDHLTTH IRTH (SEQ ID NO: 46) ZF3: CDICGRKFARSDERKRH TKIH (SEQ ID NO: 47) | SEQ ID NO: 44 GCGTGGG CG |
| JZif1 (SEQ ID NO: 38) | 3 | ZF1: CPVESCDRRFSRSDELT RHIRIH (SEQ ID NO: 48) ZF2: CRICMRNFSSRDVLRRH NRTH (SEQ ID NO: 49) ZF3: CDICGRKFASRDVLRRH NRIH (SEQ ID NO: 50) | SEQ ID NO: 9 GCTGCTG CG |
| JZif2 (SEQ ID NO: 39) | 3 | ZF1: CPVESCDRRFSRSDNLV RHIRIH (SEQ ID NO: 51) ZF2: CRICMRNFSRSDHLTTH IRTH (SEQ ID NO: 52) ZF3: CDICGRKFADPGHLVRH NRIH (SEQ ID NO: 53) | SEQ ID NO: 40 GGC-TGG-GAG |

In some embodiments, the modified transcription factor has an amino acid sequence as defined by SEQ ID NO:38 (JZif1) (see FIG. 12B) or SEQ ID NO:39 (JZif2) (see FIG. 12C). The corresponding DNA sequences that encode these proteins are described in SEQ ID NO:69 (JZif1) or SEQ ID NO:70 (JZif2). The sequences coding for these modified transcription factors can be incorporated into mAAV expression vectors of the invention. For example, the sequence of a mAAV expression vector called mAAV-JZif1 in which JZif1 has been incorporated into the multi-cloning site of mAAV is described in SEQ ID NO:64, and the sequence of a mAAV expression vector called mAAV-JZif2 in which JZif2 has been incorporated into the multi-cloning site of mAAV is described in SEQ ID NO:65. Table 7 shows exemplary mAAV expression vectors including genes encoding for different modified human transcription factors of the invention. In some embodiments, the modified transcription factor has at least 50% sequence identity to any of the sequences described by SEQ ID NOs:38, 39, 69, 70, 64, or 65, e.g., 50%, 55%, 60%, 65%, 70%, 75%, 80%, 85%, 90%, 95%, 97%, 98%, or 99% sequence identity.

TABLE 7

Exemplary mAAV-Modified Transcription Factor Expression Vectors

| Vector Name | SEQ ID NO: | Promoter | Splice Donor | Splice Acceptor | Modified Human Transcription Factor |
|---|---|---|---|---|---|
| mAAV-JZif1 | 64 | Human alpha-actin promoter | Human alpha-actin (SEQ ID NO: 29) | Human beta-globin (SEQ ID NO: 30) | JZif1 (SEQ ID NO: 69) |
| mAAV-JZif2 | 65 | Human alpha-actin promoter | Human alpha-actin (SEQ ID NO: 29) | Human beta-globin (SEQ ID NO: 30) | JZif2 (SEQ ID NO: 70) |

Recombinant AAV of the invention (e.g., recombinant AAV comprising a muscle-specific promoter and a gene encoding an artificial transcription factor (e.g., a fusion protein or modified transcription factor) can be produced, for example, using the mAAV expression vectors described, e.g., in Table 4 and Table 7 using methods known in the art or as described herein. For example, recombinant AAVs of the invention can be produced by the triple-plasmid transfection method, which can include use of the mAAV expression vectors and AAV capsid expression plasmids (e.g., AAV8 or AAV6 capsid expression plasmids). As shown in Table 8, recombinant AAV can comprise, for example, polynucleotides defined by SEQ ID NOs:83-87, which comprise a muscle specific promoter and a gene encoding an artificial transcription factor. Polynucleotides defined by SEQ ID NOs:83-87 can be incorporated into recombinant AAV, for example, during viral packaging. Recombinant AAV comprising polynucleotides having the sequence defined by, e.g., SEQ ID NOs:83-87 can be administered to a subject, e.g., during treatment of a muscle defect. In some embodiments, the invention provides for a use for recombinant AAVs of the invention as a medicament. In other embodiments, the invention provides a use for recombinant AAVs of the invention in a method of treatment, e.g., for a muscle disease including DMD or BMD.

TABLE 8

Exemplary Polynucleotides Incorporated into Recombinant AAV

| SEQ ID NO: | Promoter | Artificial Transcription Factor |
|---|---|---|
| 83 | Human alpha-actin promoter | Vp16-Jazz |
| 84 | Human alpha-actin promoter | Vp16-Bagly |
| 85 | Human alpha-actin promoter | Vp16-CJ7-UtroUp |
| 86 | Human alpha-actin promoter | JZif1 |
| 87 | Human alpha-actin promoter | JZif2 |

Immunogenicity

The invention provides for methods of determining the immunogenicity of a fusion protein or a modified transcription factor of the invention. In some embodiments, the level of antibodies that bind the fusion protein or modified transcription factor (referred to herein as anti-drug antibodies) are measured, e.g., by antigen-binding tests, sandwich ELISA, bridging ELISA, or surface plasmon resonance. In some embodiments, a loss of efficacy of treatment over time or adverse immunological reactions can indicate immunogenicity of the fusion protein or modified transcription factor. Other methods for measuring immunogenicity are described, e.g., in De Groot et al., *Clin. Immunol.* 131:189-201, 2009.

The fusion proteins and modified transcription factors of the invention can be modified to reduce immunogenicity by any method known in the art. For example, in some embodiments a fusion protein or modified transcription factor of the invention is modified by specific deletion of human T cell epitopes or "deimmunization" by the methods disclosed in international patent applications WO 98/52976 and WO 00/34317. Briefly, the sequence of the fusion protein or modified transcription factor can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the fusion protein or modified transcription factor sequences, as described in international Patent Applications WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the fusion protein, or preferably, by single amino acid substitutions. Typically, conservative substitutions are made. Other methods for engineering fusion proteins with reduced immunogenicity are described, e.g., in De Groot et al., *Clin. Immunol.* 131: 189-201, 2009.

In some embodiments, the amino acid changes introduced into a genomically-encoded human transcription factor, e.g., Zif268, to produce a modified transcription factor of the invention are not substantially recognized by the host immune system. Without being bound by theory, this could be due to the fact that the novel zinc finger motifs are in the pool of the thousands of natural zinc finger proteins expressed in humans that vary in the zinc finger alpha-helix in order to bind different DNA targets. In some embodiments, modified human transcription factors capable of increasing utrophin expression are less immunogenic than fusion proteins containing proteins from viral or other sources, such as Vp16.

Pharmaceutical Compositions

The recombinant AAVs of the invention as detailed above are preferably assessed for contamination by conventional methods and then formulated into a pharmaceutical composition. In preferred embodiments, the pharmaceutical composition is intended for injection. Such formulation involves the use of a pharmaceutically and/or physiologically acceptable vehicle or carrier, particularly one suitable for injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322. In one embodiment, the carrier is an isotonic sodium chloride solution. In another embodiment, the carrier is balanced salt solution. In one embodiment, the carrier includes Tween. If the virus is to be stored long-term, it may be frozen in the presence of glycerol or Tween20.

A pharmaceutical composition of this invention can be administered parenterally, orally, nasally, rectally, topically, or buccally. They can also be administered locally or systemically. In preferred embodiments, the pharmaceutical composition is administered parentally. In other preferred embodiments, the pharmaceutical composition is administered systemically. The pharmaceutical compositions can be administered once, or multiple times, at the same or at different sites. The volume and viral titer of each injection is determined individually, as further described below, and may be the same or different from other injections performed during the course of administration. In one embodiment, a particular muscle is selected for intramuscular administration. For example, in the case of mAAV8-Vp16-Jazz and mAAV6-Vp16-Jazz, local infection can be achieved by intramuscular (i.m) injection, for example, by injection of a viral suspension into quadriceps or tibialis anterioris (TA), which can be performed on either limb.

The composition may be delivered in a volume of from about 50 µl to about 2 L, e.g., 50 µL, 100 µL, 150 µL, 200 µL, 250 µL, 500 µL, 1 mL, 2 mL, 5 mL, 10 mL, 20 mL, 25 mL, 50 mL, 100 mL, 150 mL, 200 mL, 250 mL, 300 mL, 400 mL, 500 mL, 600 mL, 700 mL, 800 mL, 900 mL, 1 L, 1.2 L, 1.3 L, 1.4 L, 1.5 L, 1.6 L, 1.7 L, 1.8 L, or 2 L, including all numbers within the range, depending on the size of the patient to be treated, the viral titer used, the route of administration, and the desired effect of the method. Other volumes may be useful as determined by a physician or other person skilled in the art. An effective concentration of a recombinant adeno-associated virus carrying a nucleic acid sequence encoding the desired fusion protein under the control of the muscle-specific promoter desirably ranges between about $10^8$ and $10^{13}$ vector particles per milliliter (v.p./mL), e.g., $10^8$ v.p./mL, $10^9$ v.p./mL, $10^{10}$ v.p./mL, $10^{11}$ v.p./mL, $10^{12}$ v.p./mL, or $10^{13}$ v.p./mL. The recombinant AAV infectious units can be measured, for example, as described in McLaughlin et al., *J. Virol.* 62:1963-1973, 1988. It is desirable that the lowest effective concentration of virus be utilized in order to reduce the risk of undesirable effects, such as toxicity. Still other dosages in these ranges may be selected by the attending physician, taking into account the physical state of the subject, preferably human, being treated, the age of the subject, the particular muscle defect, and the degree to which the disorder, if progressive, has developed.

In some embodiments, the invention provides a pharmaceutical composition comprising a recombinant AAV of the invention for use as a medicament. In other embodiments, the invention provides a pharmaceutical composition comprising a recombinant AAV of the invention for use in a method of treatment, e.g., treatment of a muscular defect. In one such embodiment, the method comprises administering to a subject an effective amount of the pharmaceutical composition of the recombinant AAV. In a further aspect, the invention provides for the use of a pharmaceutical composition of the invention for the manufacture of a medicament. In one embodiment, the medicament is for treatment of a muscle disease, e.g., DMD or BMD.

Increasing Utrophin Expression to Treat Muscle Defects

The present invention provides compositions and methods for increasing utrophin expression, preferably for the treatment of muscle defects, most preferably dystrophinopathies. The approach of the present invention is to increase utrophin expression by contacting the utrophin gene with fusion proteins or modified human transcription factors of the invention, thereby functionally rescuing the muscle defects caused by loss of dystrophin protein function. In preferred embodiments, contacting the utrophin "A" promoter of the utrophin gene with the fusion proteins of the invention leads to increased expression of utrophin.

The compositions and methods of the present invention can be used to increase the expression of the utrophin gene of any species that possesses the gene, e.g., mice, dogs, or primates including humans. The human utrophin gene is described, e.g., in NCBI Entrez Gene ID: 7402. The mRNA sequence of the human utrophin gene can be found, e.g., under NCBI accession number NM_007124. The sequence of the human utrophin protein can be found, e.g., under UniProtKB accession number P46939 or NCBI accession number NP_009055. The mouse utrophin gene is described, e.g., in NCBI Entrez Gene ID: 22288. The mRNA sequence of the mouse utrophin gene can be found, e.g., under NCBI accession number NM_011682. The sequence of the mouse utrophin protein can be found, e.g., under UniProt KB accession number E9Q6R7 or NCBI accession number NP_035812.

In certain embodiments, fusion proteins of the invention, e.g., those having the amino acid sequence of SEQ ID NO:34-38, specifically bind to the utrophin "A" promoter. The utrophin "A" promoter can comprise the DNA sequence of SEQ ID NO:20 (human) or SEQ ID NO:33 (mouse). The target DNA sequence bound by the fusion protein can comprise the DNA sequence of any of SEQ ID NOs 9-14, 40. Binding of the fusion proteins to the utrophin "A" promoter can subsequently lead to an increase in utrophin transcription due to the presence of the transcriptional activation element near the transcriptional start site of the utrophin gene. Alternatively, the target sequence of the fusion proteins can be in the utrophin gene itself or in other utrophin regulatory regions known in the art, e.g., the utrophin "B" promoter. In other embodiments, modified transcription factors, including modified human transcription factors of the invention, for example those having the amino acid sequence of SEQ ID NOs 38 or 39, specifically bind to the utrophin "A" promoter. The target DNA sequence bound by the modified human transcription factor can comprise the DNA sequence of SEQ ID NOs 9 or 40. Binding of the modified human transcription factor to the utrophin "A" promoter will subsequently lead to an increase in utrophin transcription due the presence of the endogenous trans-activation domain of the modified transcription factor near the transcriptional start site of the utrophin gene. Alternatively, the target sequence of the modified transcription factors can be in the utrophin gene itself or in other utrophin regulatory regions known in the art, e.g., the utrophin "B" promoter.

Methods of Treatment

The present invention provides compositions and methods for prophylaxis or treatment of muscle diseases and defects. Non-limiting examples of muscle defects include inherited diseases, such as: myopathy, dystrophy (e.g., DMD, BMD, limb-girdle, congenital, facioscapulohumeral, myotonic, oculopharyngeal, distal, or Emery-Dreifuss muscular dystrophy), myotonia, congenital myopathies (e.g., nemaline, multi/minicore, or centronuclear myopathy), mitochondrial myopathies, familial periodic paralysis, inflammatory myopathies, metabolic myopathies. Muscle defects also include acquired muscle defects, such as: external substance induced myopathy (e.g., drug-induced myopathy, glucocorticoid myopathy, alcoholic myopathy, or other myopathies caused by toxic agents), dermatomyositis, polymyositis, inclusion body myositis, myositis ossificans, rhabdomyolysis, and myoglobinurias.

In preferred embodiments, these diseases are muscular dystrophy. In one embodiment, the muscle disease is BMD. In the most preferred embodiments, the muscle disease is DMD. Generally, the methods include administering to a mammalian subject in need thereof, an effective amount of a composition comprising a recombinant AAV carrying a nucleic acid sequence encoding a fusion protein capable of increasing utrophin expression under the control of a muscle-specific promoter.

Prophylactic treatment may be administered, for example, to a subject who is not yet ill, but who is susceptible to, or otherwise at risk of, a particular biological condition, including DMD (e.g., the subject may have mutations that cause DMD but is asymptomatic or the status of mutations that cause DMD is unknown). Therapeutic treatment may be administered, for example, to a subject already suffering from DMD in order to improve or stabilize the subject's condition (e.g., a patient already presenting symptoms of DMD).

Symptoms of muscular dystrophy including DMD, which may vary from mild to severe and may depend on what part of the body is affected, the causative mutation, and the age and overall health of the affected person, include, e.g., fatigue, learning difficulties, intellectual disability, muscle weakness (e.g., in the legs, pelvis, arms, neck, or other areas of the body), difficulty with motor skills (e.g., running, hopping, or jumping), frequent falls, trouble getting up from a lying position or climbing stairs, progressive difficulty walking, breathing difficulties, heart disease, abnormal heart muscle (e.g., cardiomyopathy), congestive heart failure, irregular heart rhythm (e.g., arrhythmias), deformities of the chest or back (scoliosis), enlarged muscles of the calves, buttocks, or shoulders, pseudohypertrophy, muscle deformities, respiratory disorders (e.g., pneumonia or poor swallowing). Detecting an improvement in, or the absence of, one or more symptoms of muscular dystrophy, indicates successful treatment.

In some embodiments, as compared with an equivalent untreated reference, treatment may ameliorate a disease or disorder (e.g., Duchenne's muscular dystrophy) or a symptom of the disease or disorder, or reduce the progression, severity, or frequency of one or more symptoms of the disease or disorder by, e.g., 1%, 2%, 5%, 10%, 20%, 30%, 40%, 50%, 60%, 70%, 80%, 90%, 95%, or 100% as measured by any standard technique. For measuring symptoms of Duchenne's muscular dystrophy, one may use, e.g., electromyography (EMG), genetic tests, muscle biopsy, serum Creatine Kinase (CK) levels, muscular strength tests (e.g., manual muscle testing), or range-of-motion (ROM) tests, for example, the six-minute walk test, or by other methods known to skilled practitioners. Detecting an improvement in, or the absence of, one or more symptoms of muscular dystrophy, indicates successful treatment.

Assessment of Muscle Function

The effects of the compositions and methods of the invention on muscle function of a subject can be assessed by any assay known to one of skill in the art. For example, muscle strength, endurance, or range-of-motion of any desired muscle or group of muscles can be assessed. Some assays primarily assess muscle strength or muscle endurance, while other assays assess a combination of strength, endurance, or other muscle properties. In certain embodiments, treatment with the compositions and methods of the present invention lead to an improvement in one or more parameters of muscle function in a subject. An improvement can indicate an increase in the parameter (e.g., increased muscle strength or endurance). In muscle diseases characterized by degeneration including DMD, improvement can also indicate maintenance or a reduction in the rate of decline in a parameter over time. In preferred embodiments, the muscle function of a subject having a muscle disease (e.g., muscular dystrophy) being treated with the compositions and methods of the invention is assessed by these assays. In particularly preferred embodiments, treatment with the compositions and methods of the invention lead to an improvement in multiple parameters of muscle function.

The assessment of muscle function can occur prior to the start of treatment with the methods and compositions of the invention, and/or at any time following treatment to determine the response of the subject to the treatment. Assessment of muscle function can occur at fixed periods of time following treatment, for example, every day, every week, every two weeks, every month, every 6 weeks, every 6 months, every year, or any period of time in a range spanning any of these periods of times. Alternatively, assessment can occur at a time of choosing of a skilled practitioner including a researcher or a physician. The assay used for assessing muscle function can be chosen depending upon the condition of the patient; for example, ambulatory patients can be subjected to 6-minute walk tests (6MWT), whereas other assays may be performed on wheelchair-bound or otherwise immobilized patients. Because the loss of muscle function in muscle diseases, including DMD, can occur in the context of normal childhood growth and development, which are associated with, for example, increases in stride length or muscle size, the results obtained from these assays can be compared to age-matched references.

Administration of compositions and methods of the invention can result in improved function of skeletal and/or cardiac muscle of a subject. The function of any muscle (e.g., heart, diaphragm, extensor digitorum longus, tibialis anterior, gastrocnemius, soleus, plantaris, biceps, triceps, deltoids, pectoralis major, pectoralis minor, rhomboids, trapezius, sartorius, knee flexors and extensors, elbow flexors and extensors, shoulder abductors, etc.) or group of muscles in the body (e.g., muscles of the head, neck, torso, chest, abdomen, pelvis, perineum, upper limbs, lower limbs, etc.), can be improved by treatment using the claimed compositions and methods. The movements or actions assessed in these assays may involve cooperation of several groups of muscles or the whole body.

The compositions and methods of the invention can result in an improvement in muscle strength or force generation of a muscle or group of muscles of a subject. The force generated by a muscle can be measured by any assay known in the art. The assays can in vivo, in situ, or ex vivo assays, for example ex vivo or in situ analysis of the contractile profile of a single intact limb muscle (e.g. the extensor digitorum longus for an ex vivo assay and the tibialis anterior muscle for an in situ assay), grip force analysis, downhill treadmill exercise, manual muscle testing, myometry (e.g. assessing upper and lower extremity strength using a myometer, including evaluation of knee flexors and extensors, elbow flexors and extensors, and shoulder abductors), sustained maximum voluntary contraction (MVC) assays or in any of the assays described in Hakim et al., *Methods Mol. Biol.* 709: 75-89, 2011; Sharma et al., *Neurology* 45: 306-310, 1995; and McDonald et al., *Muscle Nerve* 48: 3430356, 2013.

In certain embodiments, administration of compositions comprising the recombinant AAV of the invention to a subject can lead to an improvement in muscle strength or force generation of one or more muscles of a subject as assessed by the assays described above by at least 5%, 10%, 15%, 20%, 25%, 30%, 40%, 50%, 60%, 70%, 80%, 90%, 100%, 150%, or by 3-fold, 4-fold, 5-fold, or more, compared to reference. In other embodiments, treatment maintains muscle strength within about 25% of a reference value. In other embodiments treatment reduces the rate of decrease in muscle strength that occurs over time in muscle diseases, including DMD, by at least 5%, 10%, 15%, 20%, 25%, 30%, 40%, 50%, 60%, 70%, 80%, 90%, 100%, 150%, or by 3-fold, 4-fold, 5-fold, or more, compared to reference. In preferred embodiments, treatment of subjects having muscular dystrophy with the compositions and methods of the invention leads to an increase, maintenance of muscle strength, or reduction in the rate of decline in muscle strength or force of one or more muscles as assessed by any assay known in the art or described herein. In particularly preferred embodiments, treatment of subjects having muscular dystrophy causes an increase in muscle strength, maintenance, or a reduction in the rate of loss of muscle strength over time as measured by myometry. For example, treatment with the compositions and methods of the invention can increase the force (measured by a myometer) exerted by the knee flexors or extensors, elbow flexors or extensors, or shoulder abductors by a patient with DMD by at least 5%, 10%, 15%, 20%, 25%, 30%, 40%, 50%, 60%, 70%, 80%, 90%, 100%, 150%, or by 3-fold, 4-fold, 5-fold, or more compared to reference.

Treatment with the compositions and methods of the invention can also improve muscle endurance of a muscle or group of muscles of a subject. Muscle endurance may be measured by assays including but not limited to treadmill exercise, 6-minute walk test (6MWT), timed function tests, (e.g., time taken to stand from a supine position, time taken to run/walk 10 m, or time taken to climb/descend 4 standard-sized stairs), by any of the tests suitable for testing muscular strength or endurance in mice including but not limited to enforced treadmill exercise, either at constant speed (e.g., any assay described in Radley-Crabb et al., *Neuromuscul. Disord.* 22(2):170-182, 2012) or at accelerated speed (see, e.g., Di Certo et al., *Hum. Mol. Genet.* 19:752-760, 2010 or Strimpakos et al., *J. Cell. Phys.* 229:1283-1291, 2014), voluntary wheel exercise, grip strength test, the hang wire test, the inverted grid test, and the rotarod test, or by any of the assays described in McDonald et al., *Muscle Nerve* 48: 343-356, 2013.

In certain embodiments, treatment with the compositions and methods of the invention increases the subject's muscle endurance by at least 5%, 10%, 15%, 20%, 25%, 30%, 40%, 50%, 60%, 70%, 80%, 90%, 100%, 150%, 2-fold, 3-fold, 4-fold, 5-fold, 6-fold, 7-fold, 8-fold, 9-fold, 10-fold, or more compared to reference) over a specified amount of time. In other embodiments treatment maintains muscle endurance or reduces the rate of decrease in muscle endurance that occurs over time in muscle diseases including DMD by at least 5%, 10%, 15%, 20%, 25%, 30%, 40%, 50%, 60%, 70%, 80%, 90%, 100%, 150%, or by 3-fold, 4-fold, 5-fold, or more compared to reference. For example, treatment with the compositions and methods of the invention can increase the distance that a subject can walk in the time period of 6 minutes as measured by the 6MWT, reduce the number of falls that occur during the 6MWT, maintain the distance a patient can walk as measured by the 6MWT over time, or reduce the rate of decrease in the distance a patient can walk as measured by the 6MWT over time. For example, prior to treatment a patient may have a 6MWT distance in the range of about 0 m to 400 m, but treatment with the compositions and methods of the invention may increase this value by 5 m, 10 m, 20 m, 30 m, 40 m, 50 m, 60 m, 70 m, 80 m, 90 m, 100 m, 200 m, 300 m, 400 m, or any distance in a range spanning these numbers over 1 week, 6 weeks, 12 weeks, 18 weeks, 24 weeks, 30 weeks, 36 weeks, 42 weeks, 48 weeks, 52 weeks, or more of treatment. In other embodiments, treatment may maintain the 6MWT distance within about 25% of the baseline value over 1 week, 6 weeks, 12 weeks, 18 weeks, 24 weeks, 30 weeks, 36 weeks, 42 weeks, 48 weeks, 52 weeks, or more of treatment. In other embodiments, treatment may reduce the rate of decline in the 6MWT distance by 5%, 10%, 15%, 20%, 25%, 30%, 40%, 50%, 60%, 70%, 80%, 90%, 100%, 150%, 2-fold, 3-fold, 4-fold, 5-fold, or more over 1 week, 6 weeks, 12 weeks, 18 weeks, 24 weeks, 30 weeks, 36 weeks, 42 weeks, 48 weeks, 52 weeks, or more of treatment.

The compositions and methods of the invention can also improve serum creatine kinase (CK) levels of a subject. Serum CK levels can be measured by any assay known in the art, including in a coupled enzyme reaction where the rate of NADPH formation is measured photometrically and is directly proportional to the CK activity. In one example, samples can be centrifuged for 5 min (12,000 g) at 4° C., and serum free of hemolysis can be removed. Serum CK activity can be evaluated using the CK-NAC kit (Greiner) and analyzed kinetically by a spectrophotometer (multi-label counter Victor 3; Wallac), by setting the wavelength at 340 nm and the temperature at 37° C. For subjects with DMD, the serum CK levels are typically strongly elevated compared to normal reference controls. After exercise, the serum CK levels of subjects with DMD can increase further, for example, by about 10%, 15%, 20%, 25%, 30%, 35%, 40%, 45%, 50%, 55%, 60%, 65%, 70%, 75%, 80%, 85%, 90%, 95%, 100%, or more compared to before exercise. In certain embodiments, treatment with the compositions and methods of the invention can reduce the subject's serum CK levels, for example prior to or following exercise, by about 5%, 10%, 15%, 20%, 25%, 30%, 35%, 40%, 45%, 50%, 55%, 60%, 65%, 70%, 75%, 80%, 85%, 90%, 95%, or 99% or more compared to reference. In some embodiments, an improvement in serum CK levels following treatment is correlated with improvements in muscle endurance and/or muscle contractile force.

Improvement in muscle function can also be determined as an alleviation of symptoms of muscle disorders. Symptoms of muscle disorders can include, e.g., fatigue, learning difficulties, intellectual disability, muscle weakness (e.g., in the legs, pelvis, arms, neck, diaphragm, heart, or other areas of the body), difficulty with motor skills (e.g., running, hopping, or jumping), frequent falls, trouble getting up from a lying position or climbing stairs, progressive difficulty walking, breathing difficulties, heart disease, abnormal heart muscle (e.g., cardiomyopathy), congestive heart failure, irregular heart rhythm (e.g., arrhythmias), deformities of the chest or back (scoliosis), enlarged muscles of the calves, buttocks, or shoulders, pseudohypertrophy, muscle deformities, respiratory disorders (e.g., pneumonia or poor swallowing). Detecting an improvement in, or the absence of, one or more symptoms of muscular dystrophy, can indicate an improvement in muscle function.

Combination Therapy

The compositions and methods of the invention can also be used in conjunction with other remedies known in the art that are used to treat muscular dystrophy or its complications, including but not limited to: corticosteroids (e.g., cortisol, hydrocortisone, prednisone, prednisolone, deflazacort, triamcinolone, methylprednisolone, dexamethasone, betamethasone, aldosterone, and fludrocortisone); β2-adrenergic agonists (e.g., albuterol, salbutamol, levosalbutamol, terbutaline, pirbuterol, procaterol, clenbuterol, metaproterenol, fenoterol, bitolterol mesylate, ritodrine, isoprenaline, salmeterol, formoterol, bambuterol, and indicaterol); immunosuppressants (e.g., cyclosporine); anti-fibrotic drugs (e.g., peginterferon, IL-10, pioglitazone, pentoxifylline, atanercept); exon-skipping drugs (e.g., antisense oligonucleotides that target exon 51, exon 45, or exon 53 including drisapersen, eteplirsen, PRO044, PRO45, PRO051, and PRO053); stop-codon skipping drugs, (e.g., gentamycin or other aminoglycoside antibiotics and Ataluren (PTC124)); synthetic anabolic steroids (e.g., oxandrolone); osteoporosis remedies (e.g., vitamin D and calcium); constipation remedies including laxatives; cardiomyopathy remedies including angiotensin-converting enzyme (ACE) inhibitors (e.g., benazepril, captopril, enalapril, fosinopril, lisinopril, moexipril, perindopril, quinapril, ramipril, and trandolapril), diuretics, beta-blockers (e.g., bisoprolol or carvedilol), anti-arrhythmic medications (e.g., amiodarone); insulin-like growth factor (IGF-1); myostatin inhibitors (e.g., follistatin, ACE-031, and neutralizing antibodies including MYO-029); drugs that increase nitric oxide levels and/or nNOS protein levels or activity (e.g., L-arginine; phosphodiesterase inhibitors including sildenafil, tadalafil, and pentoxifylline); class II histone deacetylase (HDAC) inhibitors; small molecules that increase utrophin expression (e.g., SMT C1100); nutritional supplements (e.g., glutamine, creatine monohydrate, conjugated linoleic acid, alpha-lipoic acid, and beta-hydroxy-beta-methylbutyrate); anti-histamines (e.g. fexofenadine, loratadine, phenindamine, dexchlorpheniramine, terfenadine, cetirizine, etc.); mast cell stabilizers (e.g., sodium cromoglicate, nedocromil sodium, etc., which can be in a form of aerosols, inhalations, eye drops, etc.); coenzyme $Q_{10}$ (also known as ubiquinone or ubidecarenone); idebenone or other synthetic derivatives of ubidecarenone, (e.g., RAXONE®/CATENA®); omega 3; resveratrol; phytosterols/stanols; anticoagulants (e.g., warfarin); and anticholinergic agents (e.g., anti-muscarinic agents (e.g., atropine, benztropine (COGENTIN®), biperiden, chlorpheniramine (CHLOR-TRIMETON), dicyclomine (dicycloverine), dimenhydrinate (DRAMAMINE)), diphenhydramine (BENADRYL®, SOMINEX™, ADVIL®, PM, etc.), doxylamine (UNISOM™), glycopyrrolate (ROBINUL®), ipratropium (ATROVENT®), orphenadrine, oxitropium (OXIVENT®), oxybutynin (DITROPAN®, DRIPTANE®, LYRINEL® XL), tolterodine (DETROL®, DETRUSITOL), tiotropium (SPIRIVA®), trihexyphenidyl, scopolamine, solifenacin, and tropicamide), and anti-nicotinic agents (e.g., ganglion blockers including bupropion (ZYBAN®, WELLBUTRIN®) and hexamethonium, cough suppressants and ganglion blockers (e.g., dextromethorphan), nondepolarizing skeletal muscular relaxants (e.g., doxacurium and tubocurarine), ganglion blockers and occasional smoking cessation aids (e.g., mecamylamine)), which can be in a form of inhalers, nebulizer solutions, tablets, and can be administered by rectal, oral, transdermal, or parenteral routes). The compositions and methods of the present invention can also be used with, for example, other gene-based therapy approaches (e.g., viral delivery of mini- or micro-dystrophin, mini-utrophin, or trans-splicing recombinant AAV vectors); gene editing, including approaches involving zinc-finger nucleases, transcription activator-like (TAL) type III effector nucleases (TALENs), meganucleases, or clustered regularly interspaced short palindromic repeats (CRISPR), or with cell-based therapies involving transplantation of various types of precursor cells, such as ex vivo-maniupulated muscle side population cells (a lineage of uncommitted cells) into muscle fibers. The compositions and methods can also be used with any of the therapies described in Miura et al., *Trends. Mol. Med.* 12:122-129, 2006; Jarmin et al., *Expert Opin. Biol. Ther.* 14:209-230, 2014; Scully et al., *Expert Opin. Orphan Drugs* 1:33-46, 2013; Fairclough et al., *Exp. Physiol* 96:1101-1113, 2011; and Blankinship et al., *Mol. Therapy.*, 13:241-249, 2006.

The compositions and methods of the invention can also be used in conjunction with other forms of treatment including but not limited to: physical exercise (e.g. physical therapy, range-of-motion exercises); mobility aids, supports or orthotic devices, (e.g. ankle splints, knee-ankle-foot orthosis (KAFO), spinal braces, and wheelchairs); breathing assistance (e.g. ventilators); and surgical remedies (e.g. tendon surgery, scoliosis surgery, installation of a pacemaker, and cardiac transplantation). The choice of specific treatment may vary and will depend upon the severity of the pain, the subject's general health, and the judgment of the attending clinician.

EXAMPLES

The following examples are to illustrate the invention. They are not meant to limit the invention in any way.

Example 1

Materials and Methods

Construction of Artificial Zinc Finger Genes with Specific Binding to Utrophin Promoter "A"
Construction of Jazz Gene
Construction of the Jazz gene was performed as described by Corbi et al., *Gene Therapy* 7:1076-1083, 2000, following as model the three zinc-finger motif backbone of human transcription activation factor Zif268 (Christy et al., *Proc. Natl. Acad. Sci. USA* 85:7857-7861, 1988) to specifically target the 9 base pair Jazz target in the utrophin promoter "A", with the following sequence 5'-GCTGCTGCG-3' (SEQ ID NO:9).
Construction of Bagly Gene
The Bagly four zinc-finger motif gene was constructed as described by Onori et al., *Biochem Cell Biol.* 85:358-365, 2007, to specifically target the 12 base pair Bagly target in the utrophin promoter "A", with the following sequence 5'-CGGGCTGCTGCG-3' (SEQ ID NO:12) or 5'-CCGGCTGCTGCG-3' (SEQ ID NO:13).
Construction of UtroUp Gene
The UtroUp six zinc-finger motif gene was constructed as described by Onori et al., *BMC Molec. Biol.*, 14:3, 2013, to specifically target the 18 base pair UtroUp target in the utrophin promoter "A", with the following sequence 5'-GCTGCTGCGGGCTGGGAG-3' (SEQ ID NO:14).
Construction of Genes Encoding Fusion Proteins with Specific Binding to Utrophin Promoter "A"
Construction of the Gene Encoding Vp16-Jazz Fusion Protein
Fusion of the Jazz gene with the DNA encoding Herpes transcription factor VP16 was performed as described by Mattei et al., *PLoS ONE* 2:e774, 2007.
Construction of the Gene Encoding SP1-Jazz Fusion Protein
Fusion of the Jazz gene with the DNA encoding human transcription factor SP1 (Kadonaga et. al., *Cell* 51:1079-1090, 1987) was performed as described by Corbi et al., *Gene Therapy* 7:1076-1083, 2000.
Construction of the Gene Encoding Gal4-Jazz Fusion Protein
Fusion of the Jazz gene with the DNA encoding transcription activation domain of yeast Gal4 protein (Sadowski, *Genetic Engineering (NY)*, 17:119-148, 1995) was performed as described by Corbi et al., *Gene Therapy* 7:1076-1083, 2000.
Construction of the Gene Encoding Vp16-Bagly Fusion Protein
Fusion of the Bagly gene with the DNA encoding the Herpes transcription activation protein VP16, was performed as described by Onori et al., *Biochem Cell Biol.* 85:358-365, 2007.
Construction of the Gene Encoding Vp16-CJ7-UtroUp Fusion Protein
Fusion of the UtroUp gene with the DNA encoding a 100 amino acid fragment CJ7 of the human transcription activation domain CJ7, derived from the human Che-1/AATF protein (Desantis et al., *Neuromusc. Disord.* 21:158-162, 2009) was performed as described by Onori et al., *BMC Molec. Biol.*, 14:3, 2013.
Design and Construction of Modified Zif268 Genes with Specific Binding to Utrophin Promoter "A"
In order to minimize any possible immune response raised against the ZF-ATF therapeutic gene product, a novel class of ZF-ATFs was developed. In this new generation of ZF-ATFs, called "modified human transcription factors", few amino acid modifications are hidden in the natural context of a resident human gene. To this end the well characterized Zif268/EGR1 gene (FIG. 12) was selected as a starting template. Varying only few appropriate amino acids in the Zif268 alpha-helix zinc finger motifs, two novel artificial genes named: "JZif1" and "JZif2" were produced (FIG. 12). JZif1 and JZif2 bind two DNA contiguous target sequences present in both mouse and human utrophin gene promoter "A": 5'-GCTGCTGCG-3' (SEQ ID NO:9) and 5'-GGCTGGGAG-3' (SEQ ID NO: 40), respectively. In particular, JZif1 binds the same DNA target sequence recognized by Jazz, while JZif2 binds the nine base pairs adjacent to the Jazz DNA target sequence. The JZif1 and JZif2 DNA binding sites are coincident with the 18 base pair DNA target sequence recognized by UtroUp (FIG. 13). Importantly, JZif1 and JZif2 can work synergistically in activating transcription, leading to higher levels of utrophin up-regulation compared to expression of one protein alone. The few amino acid changes introduced into Zif268 to obtain JZif1 and JZif2 are difficult to be recognized by the host immune system, since the novel zinc finger domains will be in the pool of the thousands of natural zinc finger proteins that vary in the alpha-helix in order to bind different DNA targets.

Due to the rationale of using modified transcription factor proteins almost identical to the genomically-encoded transcription factor in order to minimize immunogenicity, the in vivo analysis in mdx mice or treatment of human subjects preferably does not involve the use of an epitope tag fused to the JZif1 or JZif2 proteins. To follow the expression of these proteins in the absence of an epitope tag, it is possible to detect the presence of JZif1 and JZif2 mRNAs using RT-PCR and to perform Western blot or indirect immunofluorescence assays using the commercial anti-Zif268 antibody. An increase in signal in the Western blot or indirect immunofluorescence assay relative to reference can be used to detect expression of exogenous JZif1 or JZif2.

The modified human transcription factors JZif1 and JZif2 were chemically synthesized by GENEART® Gene Synthesis service (Life Technologies) which yielded DNA fragments SEQ ID NO:81 (which contains JZif1 and additional sequences for cloning) and SEQ ID NO:82 (which contains JZif2 and additional sequences for cloning), which were inserted into the vector "mAAV" (SEQ ID NO:1) giving rise to: mAAV-JZif1 (SEQ ID NO:64) and mAAV-JZif2 (SEQ ID NO:65). These DNA fragments were also inserted into the vector "pAAV", giving rise to pAAV-JZif1 and pAAV-JZif2.
Construction of Expression Vectors for Production of Muscle-Specific Recombinant AAV
To achieve the highest degree of muscle-specific expression of artificial fusion proteins (including fusion proteins or modified transcription factors), novel muscle recombinant AAV expression vectors were constructed and combined with the use of AAV serotypes with muscle tropism. As detailed below, the Stratagene commercial pAAV vector was modified by substituting the CMV regulatory regions with upstream regulatory regions of either human alpha-actin gene or myosin light chain gene promoters. In the case of alpha-actin, further stabilization of the transcript was enabled by replacing the human alpha-actin splice acceptor site with the beta-globin intron acceptor. These novel muscle-specific pAAV expression vectors were named "mAAV." These vectors, (e.g., the vectors described by SEQ ID NOs:1 or 2 or SEQ ID NOs:62-65) can be used using the methods described below to produce recombinant adeno-associated vectors (e.g., viral particles that comprise nucleotide sequences that allow for muscle-specific expression of artificial transcription factors of the invention). For example, the viral particles can include a polynucleotide sequence defined by SEQ ID NO:83-87, corresponding to portions of mAAV-Vp16-Jazz, mAAV-Vp16-Bagly, mAAV-Vp16-CJ7-UtroUp, mAAV-JZif1, and mAAV-JZif2, respectively.

Construction of mAAV Expression Vector with the Alpha-Actin Promoter and Beta-Globin Splice-Acceptor A human DNA fragment from chromosome 1 (NT_167186.1), 1542 base pairs long containing the alpha-actin enhancer, promoter, and part of the first intron was amplified (from position 23087438-23088980) using the following oligonucleotides:

```
                                   SEQ ID NO: 3
5' ACGCGTCACCAACTGGGTAACCTCTGCTGA-3'
and

SEQ ID NO: 4
5 GCTAGCAAGCTTACCAGGTGAACCGACTGGGTTCTG-3'.
```

The PCR conditions were the following: 30 cycles at 95° C. for 15 sec, 70° C. for 30 sec, 72° C. for 2 min, and a final extension at 72° C. for 10 min. The cytomegalovirus (CMV) transcription regulatory region of pAAV-hrGFP vector (Stratagene, La Jolla, Calif.) was deleted. The 1542 base pairs long DNA fragment containing the alpha-actin enhancer, promoter, and part of the first intron of the alpha-actin gene was inserted into the pAAV-hrGFP vector deleted for the CMV regulatory region.

In order to optimize tissue-specific expression, transcription efficiency, maturation and stability of the transcript expressed by the mAAV vector, a region of the splice acceptor of the first intron of the human alpha-actin was replaced by the splice acceptor of the second intron and part of the third exon of the human beta-globin gene, as follows:

Using specific oligonucleotides, a 2329 bp DNA fragment containing the splicing regulatory regions of the first intron of alpha-actin gene was deleted of its sequence acceptor splicing at the 3' end. The deleted region was replaced with a fragment containing the sequence acceptor of the second intron and part of the third exon of the human beta-globin gene. The main elements of this vector named "mAAV" are shown in Table 1.

Recombinant pAAV Containing the Myosin Light Chain Promoter and Vp16-Jazz:

The pAAV-MLC-Vp16-Jazz vector was obtained by cloning the pMex-Vp16-Jazz construct described by Mattei et al., PloS One 22(8):e774, 2007 into the NotI sites of the pAAV-hrGFP vector (Stratagene), which was deleted of the GFP gene and all regulatory sequences contained between the two NotI sites.

Construction of Recombinant mAAV Expression Vectors Carrying Fusion Proteins and/or Modified Transcription Factors mAAV expression vectors to express individual fusion proteins (Vp16-Jazz, Vp16-Bagly, or Vp16-CJ7-UtroUp) or individual modified human transcription factors (JZif1 or JZif2) were constructed by cloning DNA fragments containing the DNA sequences encoding each of the proteins into the polylinker site of the mAAV vector.

Production and Purification of Recombinant mAAV8 and mAAV6 Stocks

Using mAAV expression vectors that contain the artificial transcription factors of the invention (e.g. vectors described by SEQ ID NOs:2 or SEQ ID NOs:62-65) or EGFP (SEQ ID NO:80), recombinant mAAV8 and mAAV6 were generated by the triple-plasmid transfection method "AAV Helper-Free System" (Stratagene) according to the manufacturer's instructions by using AAV8 and AAV6 capsid expression plasmids, respectively. Viral particles were purified from DMEM growth medium 72 h after the triple transfection. The transfected cells' growth medium was extensively centrifuged and viral particles were concentrated in a SPECTRA-POR®FLOAT-A-LYZER® G2 Dialysis System (Sigma-Aldrich, St. Louis, Mo.) using Slide-A-Lyzer Concentrating Solution for Dialysis (Thermo Fisher Scientific, St. Waltham, Mass.). 20:1 concentrated viral suspension was dialyzed twice against physiological solution for 5 to 6 h.

Titration of Recombinant mAAV8 and mAAV6 Preparations Using Quantitative Real-Time PCR The titer of recombinant mAAV8 and mAAV6 viral particles present in the growth medium was assessed using a quantitative real-time PCR assay. Growth medium fractions of the triple-transfected cells containing either mAAV8 or mAAV6 viral particles were pre-treated with DNase. For DNase digestion, 5 µl of the viral suspension was incubated with 35 U of DNase I (Roche Molecular Biochemicals, Mannheim, Germany) in a final volume of 90 µl of PCR buffer (50 mM KCl, 10 mM Tris-HCl pH 8, 5 mM $MgCl_2$) (Roche Molecular Biochemicals) at 37° C. for 30 min. DNase I was inactivated by incubation at 70° C. for 10 min. After DNase I treatment viral suspension was incubated with 10 µg Proteinase K (Roche Molecular Biochemicals), at 50° C. for 60 min. A sample of 2.5 µl was used for qPCR. Briefly in each qPCR run a standard curve was generated using serial dilution of the vector mAAV-Jazz containing one α-actin promoter per plasmid molecule (Mayginnes et al., J. Virol. Methods 137:193-204, 2006). The standard curve was generated using the plasmid mAAV-Jazz ranging from $3 \times 10^3$ to $3 \times 10^{13}$ copies. Each dilution step was measured in triplicate per ABI Prism run. PCR was performed using the SYBR Green DNA Master Mix (Life Technologies Corporation, Carlsbad, Calif.). PCR products were subjected to melting curve analysis using the light cycler system to exclude the amplification of unspecific products. Primers were synthesized by Life Technologies Corporation.

The following primers were used: SEQ ID NO:21 5'-CGAGCCGAGAGTAGCAGTTGTAG-3'; SEQ ID NO:22 5-'GCTAGCTAGCAAGCTTACCAGGTGAAC-CGACTGGGTTCTG-3'. The single-stranded nature of the mAAV8 genome as well as the double-stranded plasmid standard curve values were taken into consideration.

Animal Care

Dystrophin-deficient C57BL/10ScSn-DMDmdx/J mice (mdx) were housed under a 12-h light-dark schedule and were fed with fat-enriched rodent chow to ameliorate the low fertility of this strain. C57BL wild type control mice were also bred and housed under a 12-h light-dark schedule and were fed with standard rodent chow. All experiments were carried out in accordance with the Directive 2010/63/EU of the European Community for the care and use of laboratory animals. Housing of the animals meets the behavioral needing of the species and was supervised by the Responsible Veterinarian.

Mice Treatments

Mice were injected with mAAV8-EGFP, mAAV8-Vp16-Jazz, mAAV8-JZif1, mAAV8-JZif2, mAAV8-Vp16-CJ7-UtroUp, or mAAV8-Vp16-Bagly viruses at 5 days of age. Systemic infection was achieved by intraperitoneal (i.p.) injection of 150 µl of viral suspension ($5 \times 10^{12}$ v.p./ml; 75 µl on each side of the lower quadrant of the abdomen) using a 0.3-ml Accu-Fine syringe (Roche Molecular Biochemicals).

RNA Extraction, RT-PCR, and Real-Time PCR

Total RNA was isolated from excised animal tissues and reverse transcribed as previously described (Di Certo et al., *Hum. Mol. Genet.* 19:752-760, 2010). Real-time PCR assays were performed in a 96-well format using the ABI Prism 7000 Sequence Detection System (Applied Biosystems, Foster City, Calif.). To compare the utrophin gene expression rate the amount of target gene was normalized to that of the housekeeping gene β2-microglobulin (β2M). Primers and probes for the target gene (utrophin, UTRN) and for β2M were purchased as TaqMan Gene Expression Assays (Life Technologies Corporation). The PCR reaction was performed as previously described (Mattei et al., *PLos One* 2:e774, 2007). The results were analyzed using Applied Biosystems analysis software. The data are expressed as the ratio between UTRN and β2M mRNA expression. A minimal number of two mice were analyzed for each category. The expression of the fusion protein or modified transcription factor mRNA in different tissues was studied with RT-PCR using the following primers:

Primers for Jazz:

```
                                          SEQ ID NO: 23
5'-GTCGCCCCCCCGACCGATGTCAGC-3';
and

SEQ ID NO: 24
5'-GGGCGATCCAGGATCCCCGGGAAT-3'
```

Primers for Jazz, Bagly and UtroUp:

```
                                          SEQ ID: 76
5'-CGAGCCGAGAGTAGCA-3';
and

SEQ ID: 77
5'-CATGGTGAGGTCGCCCAAGCTCT-3'
```

Primers for JZif1 and JZif2:

```
                                          SEQ ID: 78
5'-CGAGCCGAGAGTAGCA-3';
and

SEQ ID: 79
5'-GAGCTGGAGCTATTGCTTCC-3'
```

Primers for β2M Expression were Used to Control Amplification:

```
                                          SEQ ID NO: 25
5'-TTCTGGTGCTTGTCTCACTGA-3'
and
```

```
                                          SEQ ID NO: 26
5'-CAGTATGTTCGGCTTCCCATTC-3'.
```

PCR Products were Analyzed by Agarose Gel Electrophoresis.

Western Blot Analysis

Protein extracts were obtained as previously described (Di Certo et al., supra). Fifty micrograms of protein extracts was electrophoresed through standard 6% SDS-PAGE or NUPAGE 3-8% (Life Technologies Corporation), according to the manufacturer's instructions. The following antibodies were used: anti-myc monoclonal antibody (9E10 clone, DSHB, Iowa City, IO); anti-GFP polyclonal antibody (Agilent Technologies, Santa Clara, Calif.); anti-utrophin monoclonal antibody (Santa Cruz, Santa Cruz, Calif.); anti α-tubulin monoclonal antibody (Sigma Corporation, St. Louis, Mo.), anti-laminin polyclonal antibody (Sigma Corporation); polyclonal anti-Zif268/Egr-1 (C-19): sc-189 (Santa Cruz, Santa Cruz, Calif.); and polyclonal anti-Utrophin, Abnova A01 (Germany). Immunoreactive bands probed with horseradish peroxidase-conjugated antibodies were visualized by chemiluminescence (ECL; GE Healthcare, Little Chalfont, UK), according to the manufacturer's instructions.

Histological Analysis

Tissues (transverse and cross sections) were excised from control and mAAV-treated mice as previously reported (Di Certo et al., supra). Harvested tissue samples were fixed in either in a solution of CRYO-OCT (Fisher Scientific) or in a 4% paraformaldehyde (PFA) solution in PBS. After fixation, tissue samples were immersed in sucrose 33%, and precipitated tissue was then dried and frozen at −80° C.

Hematoxylin & eosin (Roth, Karlsruhe, Germany; H&E) staining was used for evaluation of degeneration, necrotic foci and lymphocyte infiltration, following the manufacturer's instructions. The entire cross-section, taken at midbelly, was analyzed by microscope (Olympus BX51; Tokyo, Japan). Images were captured using a digital camera at 10× magnification.

Sections were analyzed by a pathologist using a microscope (Olympus BX51; Tokyo, Japan). Images were captured using a digital camera at 10× magnification.

Measure of Cross-sectional Area

Quantification of cross-sectional area (CSA) of single muscle fibers, in various skeletal muscles from 8-week-old control or mAAV8-Vp16-Jazz, mAAV8-EGFP, or saline-injected mdx mice, was expressed in µm². Six mice per group were analyzed and at least 200 myofibers were counted in each section; data are expressed as means±SEM.

EGFP Detection

At the age of 15 days, 2 months and 8 months, mAAV8-EGFP-injected and control mdx mice were sacrificed and perfused with 4% paraformaldehyde in PBS. Cryostatic sections from muscles and other organs were observed for direct EGFP fluorescence by conventional epifluorescence microscope (Olympus BX51). Images were captured using a digital camera at 10× magnification and merged using the IAS2000 software.

Immunohistochemistry

Skeletal muscle cross-sections were subjected to indirect immunofluorescence as previously described (Di Certo et al., supra). The following primary antibodies were used: anti-laminin polyclonal antibody (Sigma Corporation); anti-CD68 monoclonal antibody (Lifespan Biosciences, Seattle, Wash.), and anti-utrophin monoclonal antibody (BD, Lab Transduction). To visualize myc-tagged protein expression, transversal sections of 6-μm thick were treated as described (Veal et al., *Int. J. Biochem. Cell Biol.* 30:811-821, 1998). Briefly, slides were fixed in ice-cold acetone followed by immersion in 1% H2O2 in methanol at room temperature. Sections were blocked with 10% goat serum in PBS for 30 min and dual-stained with anti-myc monoclonal antibody (9E10 clone) and anti-laminin polyclonal antibody (Sigma Corporation), in 10% goat serum in PBS at 4° C. overnight. The following secondary antibodies were used: Alexa Fluor 594 and 488 conjugated IgG (Life Technologies Corporation). Slides were mounted with ProLong Gold antifade reagent with Dapi (Life Technologies Corporation). Stained specimens were analyzed by conventional epifluorescence microscope (Olympus BX51).

Mechanical Response of Isolated Muscles and Procion Orange Uptake

Contractile activity of muscles from mAAV8-Jazz-treated and control mdx mice was examined in vitro by physiological assessment of the muscle force on isolated extensor digitorum longus (EDL) preparations of both hind limbs and of abdominal longitudinal strips (ABD). Muscle preparations were suspended in a 20-mi bath of oxygenated Krebs solution (120 mM NaCl, 25.1 mM NaHCO$_3$, 2.8 mM KCl, 1.2 mM KH$_2$PO$_4$, 1.2 mM MgSO$_4$, 1.3 mM CaCl$_2$, and 5 mM D-glucose) maintained at 37° C., stretched to a tension of 1.0 g and allowed to equilibrate for 30-60 min, changing the superfusion buffer every 15-20 min. Both EDL muscles, mounted vertically with their tendons intact and ABD muscles were exposed to direct field stimulation via platinum wire electrodes using single stimulations of rectilinear pulses of 0.5 msec duration at 0.05-0.2 Hz (Electric Stimulatore Digit 3 T, Lace Elettronica, Pisa, Italy). Muscle excitability was examined by varying the voltage from 0.5 to 7 V, until the supramaximal voltage was reached. Muscle mechanical activity was recorded isotonically by a strain-gauge transducer (7006 isotonic transducer) and displayed on a recording microdynamometer (Unirecord 7050, Basile, Milano, Italy). At the end of the tension recordings, EDL and ABD muscles were subjected to a period of repetitive stimulation. Muscle contractions were elicited by trains of stimuli at a frequency of 40 Hz for 250 msec every second for 3 min. Following this procedure, able to obtain the muscle fatigue, tissues were removed from the chamber and subjected to Procion Orange staining as previously described (Di Certo et al., supra).

Assays of Mice Performances by Treadmill Running and Evans Blue Dye

Treadmill studies were performed on five-lane motorized treadmill (Treadmill Model LE8710, PanLab, Cornelia, Spain) equipped with an electronic control unit, and an electric shock grid at one end of the treadmill. Shock intensity was set at 0.2-0.4 mA. Inclination of treadmill was set at 0°. Mice were subjected to three or four sessions, separated by 2 to 7 days of rest: one treadmill session was of exercise running followed by three sessions of endurance running.

Standard Protocol:

Exercise studies were performed on a five-lane motorized treadmill equipped with an electronic control unit (Treadmill Model LE8710, PanLab, Cornelia, Barcelona, Spain), and an electric shock grid at one end of the treadmill. Shock intensity was set at 0.4 mA. Inclination of the treadmill was set at 0°. During the first session, mice were familiarized to the treadmill apparatus for 2 min followed by a running with the treadmill belt speed set at 6 m/min. Each mouse was immediately removed from the treadmill after three electric shocks. One day after habituation, mice were subjected to an endurance protocol, repeated once a week for four consecutive weeks, with the treadmill belt running at accelerated speed. Mice were first acclimated to the treadmill for 2 min, followed by a running session with the treadmill belt speed initially set at 12 m/min. At 5 min after the initiation of exercise, the speed was increased by 1 m/min every 2 min and exercise continued until exhaustion. Exhaustion was defined as inability of the mouse to maintain running speed despite repeated contact with the electric grid. The time for removal of a mouse from the treadmill was 5 sec on the shocker plate without the mouse attempting to reengage the treadmill. The time to exhaustion was automatically recorded from the beginning of the running session. After the treadmill performance some mice were injected intraperitoneally with 1% of Evans Blue dye (EBD) solution in saline buffer. Muscle specimens were taken and processed as described above.

Accelerated Protocol:

Groups of 5 mice per session were first familiarized to the treadmill for 2 min with the treadmill belt stationary, followed by acclimatization with gentle walking for 2 min at a treadmill belt speed of 4 m/min, followed immediately by an exercise session for 30 min at 12 m/min. If a mouse fatigued during the 30 min exercise session and could no longer run, the following procedure was used: first, the treadmill was turned off for 2 min to give all mice on the treadmill a rest, after which the treadmill belt speed was increased to 4 m/min for 2 min, followed by an increase in the speed to 12 m/min for the remainder of the 30 min. This process was repeated each time a mouse fatigued. Two to three days after this initial habituation, mice were subjected to an endurance running, repeated three times with two to three days of rest between endurance running sessions, with belt running at accelerated speed. Mice were first acclimated to the treadmill for 2 min with the treadmill belt stationary, followed by a running session with the treadmill belt speed initially set at 12 m/min. At 5 min after the initiation of exercise, the speed was increased by 1 m/min every 2 min and exercise continued until exhaustion. Exhaustion was defined as inability to maintain running speed despite repeated contact with the electric grid. The time for removal of mice from the treadmill was 5 s on the shocker plate without attempting to reengage the treadmill. The time to exhaustion was automatically recorded from the beginning of the running session.

Evans Blue Staining

After the treadmill performance some mice were injected intraperitoneal with 1% of Evans Blue dye (EBD) solution in saline buffer. Muscle specimens were taken and processed as described above.

In Vitro Analysis of Utrophin Up-Regulation

Cells and Cell Lines:

Human HeLa cells and NIH 3T3 mouse fibroblasts were grown in Dulbecco's modified Eagle's medium (DMEM) supplemented with 10% fetal calf serum. Murine myogenic C2C7 cells were grown in 20% fetal calf serum (growth medium GM), up to confluence. Differentiation was induced by switching to differentiation medium (DM) consisting of DMEM containing 2% fetal calf serum (for transient transfection experiments) and 4% serum (for recombinant AAV infection experiments). Differentiated C2C7 cells were infected with mAAV8-EGFP, mAAV8-JZif1, or mAAV8-JZif2 viral particles purified according to the method described above (diluted 1:8 in DM medium) and processed after 10 days for Western blot and fluorescence microscopy.

HeLa cells and C2C7 cells were transiently co-transfected with the indicated plasmids and pXP-Luc, consisting of the luciferase gene under the control of about 318 base pairs of the human utrophin promoter A, as described in Onori et al., *BMC Molec. Biol.*, 14:3, 2013 and Dennis et al., Nucleic Acid Research 24:1646-1652, 1996. Following transfection, HeLa cells were processed after 24 h, while C2C7 cells were cultured in GM for another 24 h, incubated in DM for 48 h, and then processed.

Myogenic conversion was induced in NIH 3T3 mouse fibroblasts and HeLa cells by co-transfection with a plasmid expressing the myogenic master gene MyoD under regulation of the cytomegalovirus (CMV) promoter. Following transfection, cells were incubated in differentiation medium (DM) consisting of DMEM containing 5% fetal calf serum for 72 h, followed by processing. Transient transfections were performed using LIPOFECTAMINE® based reagents (Invitrogen, Life Technologies) according to the manufacturer's instructions.

Immunofluorescence Microscopy of Cell Lines

For EGFP direct fluorescence microscopy, C2C7 cells were fixed with 4% paraformaldehyde for 10 min at room temperature. For indirect immunofluorescence microscopy, C2C7 cells were fixed with 4% paraformaldehyde for 10 min at room temperature, then permeabilized with 0.2% Nonidet P-40 in PBS for 10 minutes and incubated for 1 h with rabbit polyclonal antibody anti-Zif268/EGR-1 (sc-189, Santa Cruz, Calif.). The Alexa Fluor 594 conjugated IgG (Life Technologies Corporation, Carlsbad, Calif., USA) secondary antibody was used. Specimens were mounted with PROLONG® Gold antifade reagent (Life Technologies Corporation, Carlsbad, Calif.). Stained slides were processed using a conventional epifluorescence microscope (Olympus BX51; Tokyo, Japan).

Luciferase Assays

Luciferase was measured as described in Onori et al., *BMC Molec. Biol.*, 14:3, 2013. Briefly, cell extracts were prepared and assayed for luciferase (LUC) activity according to the manufacturer's instructions (Promega, Madison, Wis., USA) using a Berthold LB9506 luminometer.

Example 2

Validation of Muscle-specific Recombinant AAV

As described in Example 1 and shown in FIG. 1A, the mAAV vector was used to produce different constructs expressing either the test EGFP gene (vector mAAV-EGFP, SEQ ID NO:80) or the ZF-ATF VP16-Jazz (referred to as mAAV-Jazz in FIGS. 1-4). The mAAV-EGFP construct was used to develop virus purification protocols and to tune tissue infection conditions (FIG. 1B). The AAV tissue specificity is determined by the capsid serotype, and recombinant AAV vectors can alter their tropism when coupled with different capsid serotypes. In the present example AAV serotype 8 (AAV8), which has been demonstrated to display high tropism for both skeletal and cardiac muscles (see, e.g., Wang et al., *Nat. Biotechnol.* 23:321-328, 2005; Gruntman et al., *Curr. Protoc. Microbiol.* 14: Unit 14D.3, 2013), was used. Efficiency, timing and tissue specificity of the mAAV8 infection in the mdx mice were initially assessed by the EGFP reporter gene expression. In FIG. 1C, fluorescence microscopy performed on muscle cryosections shows that mAAV8-EGFP expression was established in several mdx muscles 15 days after intraperitoneal injection. This expression appeared to be persistent after 2 months and up to 8 months, but it showed a decrease of intensity in the different muscles analyzed. Saline solution was injected as a control. Notably, no EGFP expression was detectable in the liver (FIG. 1C) or in other non-muscular tissues tested (data not shown). These results confirm the AAV8 efficacy in transducing muscles by intraperitoneal diffusion underlining the high muscle specificity of mAAV vectors. In FIG. 1D, the expression of mAAV8-EGFP was also evaluated by Western blot analysis of the indicated tissues. These results confirmed the high muscle-specificity of mAAV vectors.

Example 3

Figures 2A, 2B, 2C, 2D, 2E:
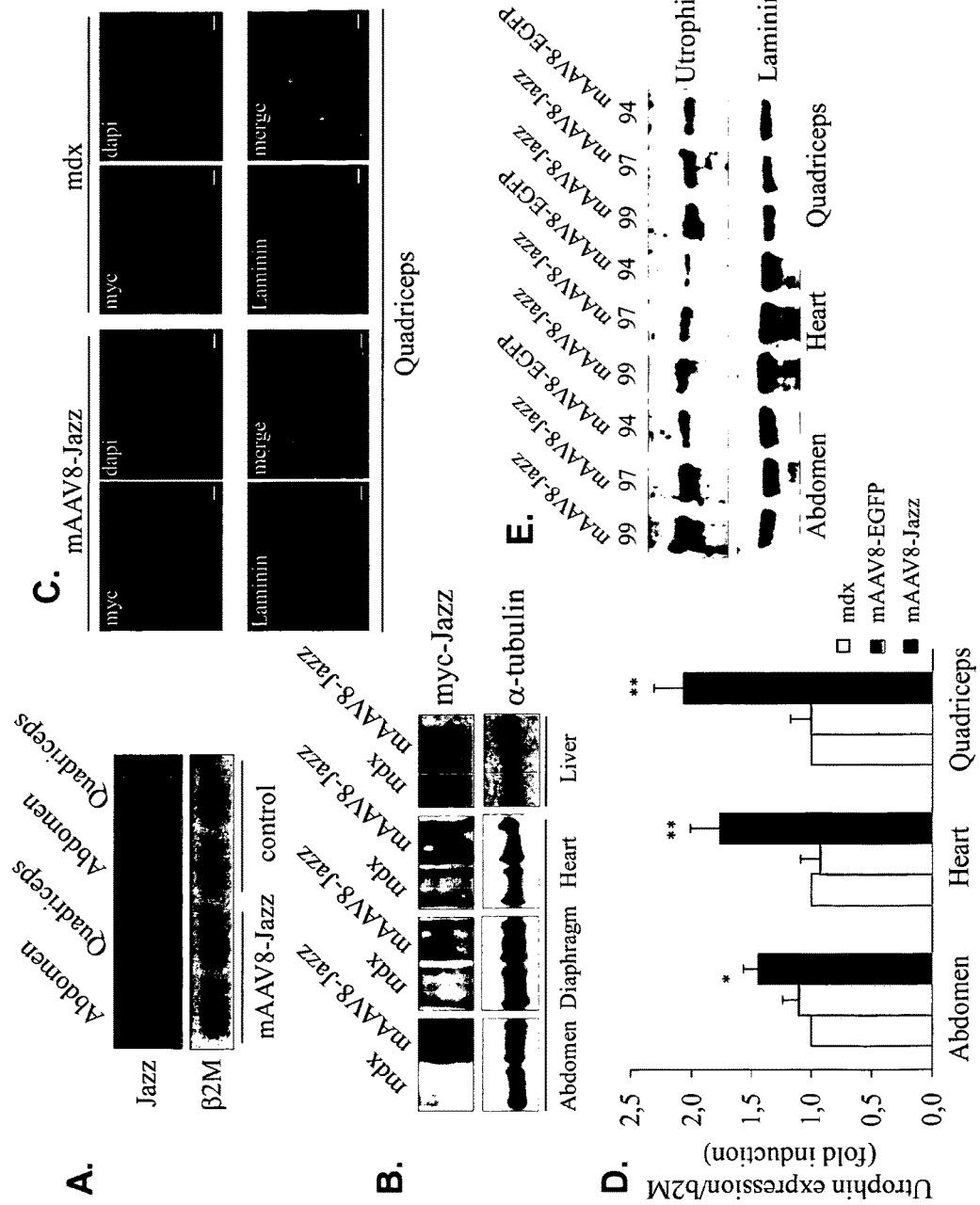
FIGS. 2A-2E show expression of Vp16-Jazz and utrophin up-regulation in mdx mice after intraperitoneal infection at 5 days of age with 150 µl of mAAV8-Vp16-Jazz virus suspension at the concentration of $5\times10^{12}$ v.p./ml, or with the same volume of saline solution. (A) Evaluation of Vp16-Jazz-mRNA expression by RT-PCR of abdominal and quadriceps skeletal muscle mRNA from the mAAV8-Vp16-Jazz-treated and untreated mdx mice, as compared to a 32-microglobulin (b2M) mRNA control from the same samples, shown below. (B) Evaluation of Vp16-Jazz protein expression by Western blot analysis, using the anti-myc tag monoclonal 9E10 antibody, in skeletal (abdomen and quadriceps) muscles, cardiac muscles, and in liver tissues, 15 days post injection. Detection of α-tubulin was used to normalize the amount of proteins. (C) Immunohistochemistry of the quadriceps muscle derived from 2-month-old untreated and mAAV8-Vp16-Jazz-treated mdx mice stained with the anti-myc tag monoclonal 9E10 antibody (red). The extracellular matrix is stained with the anti-laminin polyclonal antibody (green), and nuclei are counterstained with DAPI. Scale bar: 20 µm. (D) Quantification by real-time PCR of utrophin transcripts from skeletal (abdomen and quadriceps) and heart muscles isolated from 2-month-old untreated mdx mice and mAAV8-EGFP-treated or mAAV8-Vp16-Jazz-treated mdx mice. The gene expression ratio between utrophin and β2-microglobulin (132M) is shown as the mean±SEM. from three independent experiments performed in triplicate. *$P<0.05$ and **$P<0.01$ indicate statistical significance by t-test. (E) Western blot analysis of utrophin protein levels in abdominal, heart, and quadriceps muscles isolated from 2-month-old mAAV8-Vp16-Jazz-treated or mAAV8-EGFP-treated mdx mice. Representative individual mice are indicated with numbers. Detection of laminin was used to normalize the amount of proteins. Vp16-Jazz is abbreviated as "Jazz" in FIGS. 2A-2E.

Muscle-specific Delivery of Fusion Protein Vp16-Jazz to Mdx Dystrophic Mice Upregulates Utrophin Levels The expression of the artificial transcription factor fusion protein gene Vp16-Jazz delivered to mdx mice by mAAV8 infection was monitored by different approaches. As shown in FIG. 2A, the presence of Vp16-Jazz transcripts was determined by RT-PCR experiments using RNA extracted from abdominal and quadriceps muscles of mdx mice intraperitoneally injected either with mAAV8-Vp16-Jazz or saline solution (as a control). In FIG. 2B, Western blot analysis of total proteins extracted from skeletal muscles, heart, and liver of mAAV8-Vp16-Jazz-treated, mAAV8-EGFP-treated and control mice (saline injected) confirmed muscle-specific Jazz expression. Finally, immunohistochemical analysis on cryosections of quadriceps muscles, stained with anti-myc tag antibody, revealed the presence of Vp16-Jazz protein in the nuclei of infected myofibers (FIG. 2C).

To determine whether utrophin is up-regulated in the muscles infected by mAAV8-Vp16-Jazz, specimens from skeletal and cardiac muscles were analyzed by both real-time PCR and Western blot experiments. As shown in FIG. 2D, in tissues infected with mAAV8-Vp16-Jazz, the utrophin mRNA expression level was clearly up-regulated (up to two-fold induction). The Western blot presented in FIG. 2E shows that utrophin protein levels was up-regulated (i.e., increased) in the muscles infected with mAAV8-Vp16-Jazz. These data demonstrate that the delivery of mAAV8-Vp16-Jazz by intraperitoneal injection in mdx mice is effective and adequate to re-program utrophin expression in muscle.

Example 4

Figures 3A, 3B, 3C:
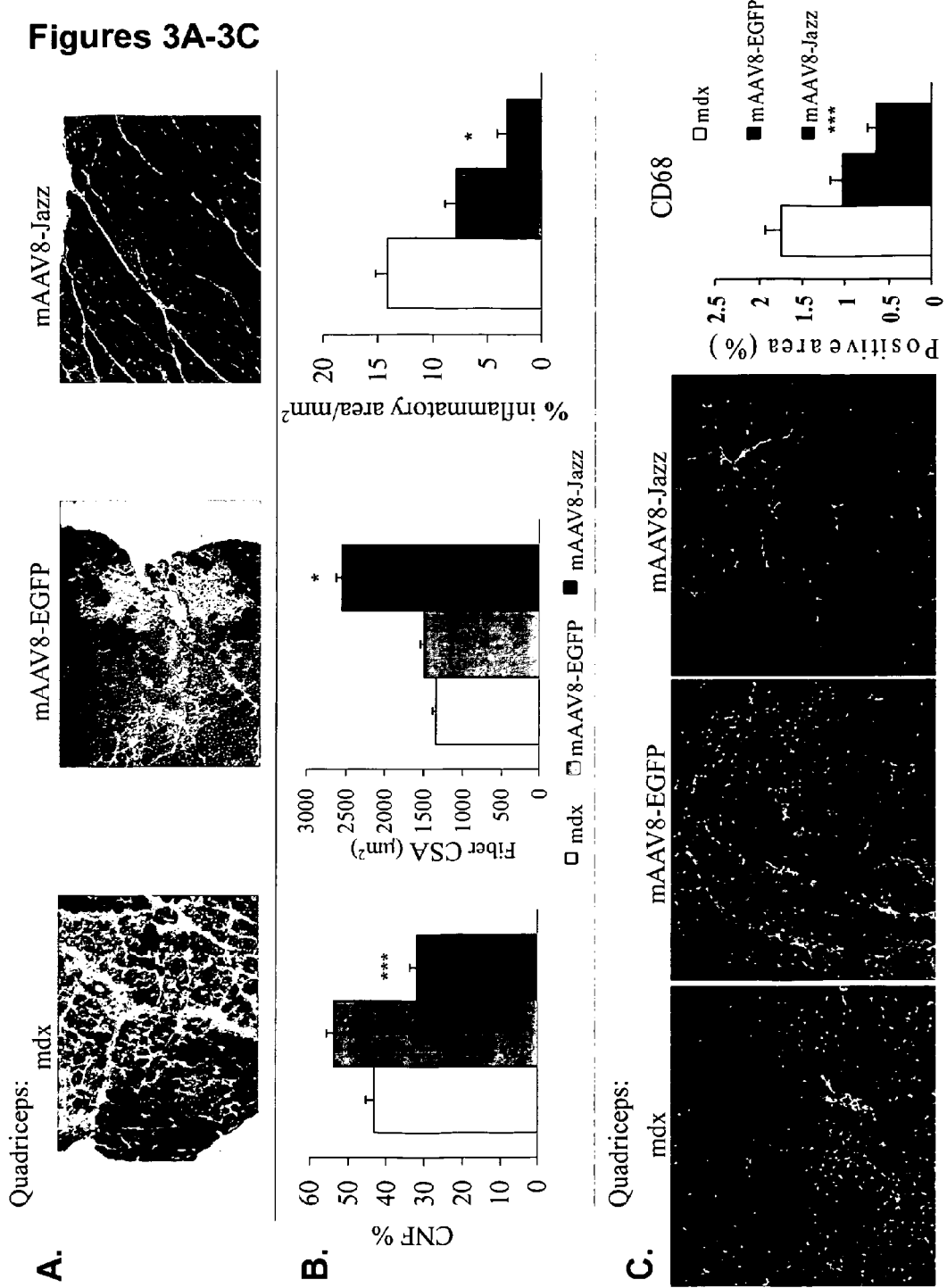
FIGS. 3A-3C show that Vp16-Jazz ameliorates mdx muscle morphology and histopathology. (A) Hematoxylin and eosin (H&E) staining of the quadriceps muscle from 2-month-old untreated, mAAV8-EGFP-treated, and mAAV8-Vp16-Jazz-treated mdx mice. Reduction in degeneration, necrotic foci, and inflammatory cells is observed in mAAV8-Vp16-Jazz-treated myofibers (representative sections out of six mice examined in each group). (B) Quantification of central nucleation (CNF), cross-sectional area (CSA), and inflammatory infiltrates on H&E stained sections of quadriceps muscle from 2-month-old untreated, mAAV8-EGFP-treated, and mAAV8-Vp16-Jazz-treated mdx mice (six mice were analyzed in each group; the number of CNFs was obtained by normalizing to the number of total myofibers per CSA, and at least 200 myofibers per section were counted). (C) Immunohistochemistry of the quadriceps muscle isolated from 2-month-old untreated, mAAV8-Vp16-Jazz-treated, and mAAV-EGFP-treated mdx mice (four mice were analyzed in each group). Quantification of macrophage infiltration was performed by staining with CD68 monoclonal antibody (light shading). The extracellular matrix is counterstained with the anti-laminin polyclonal antibody (reticulated staining). Nuclei are stained with DAPI (not visible in grayscale); see Example 1: Materials and Methods section). Right: Graph shows the quantification of the CD68-positive area (four mice were analyzed in each group). All values are expressed as the mean±SEM. *$P<0.05$ and ***$P<0.001$ indicate statistical significance by t-test. Vp16-Jazz is abbreviated as "Jazz" in FIGS. 3A-3E.
Figure 4:
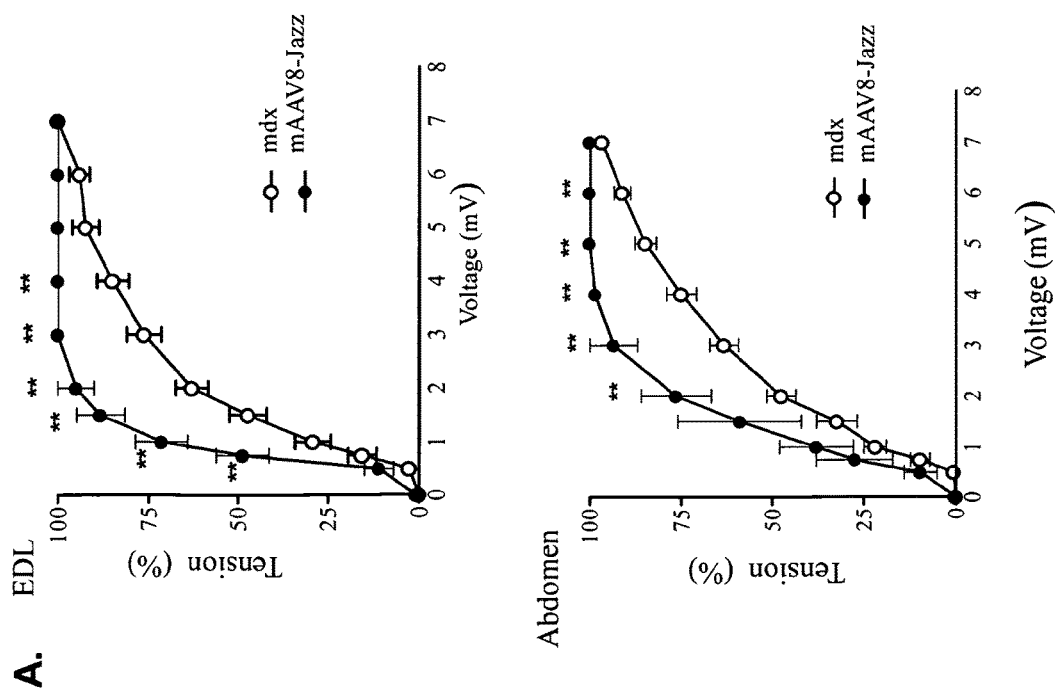
FIGS. 4A-4D show rescue of muscle function in dystrophic mdx mice by mAAV8-Vp16-Jazz treatment. (A) Mechanical response of isolated muscles. Effects of changes in voltage on isotonic contractions in EDL and abdominal muscles, from control and mAAV8-Jazz-treated mdx mice. Muscle contractile force for each voltage was determined and considered as a percentage of maximal contraction. Each point represents the mean of 10 extensor digitorum longus (EDL) muscles (5 animals) and five abdominal muscle strips, with error bars indicating SEM and $P<0.01$ indicating the statistical significance by t-test. (B) Procion Orange dye uptake in sections of abdominal and EDL muscles after force test. Left: Representative images demonstrating the increased ability of mAAV8-Vp16-Jazz-treated mdx mice to exclude dye from stretched fibers. Right: graph shows the mean (±SEM) area of dye-positive fibers expressed as the percentage of the total CSA of muscle sections. (C) Single session performance (left) and total running time (right) relative to four weekly treadmill trials with exhaustive exercise protocol. The mdx mice injected with saline, mAAV8-EGFP, or mAAV8-Vp16-Jazz at day 5 after birth were tested at 3 months of age. For each group, lines indicate the mean duration of running time during each trial (left), and columns indicate the cumulative running time over the four consecutive trials (right). Number of animals was 10 for each experimental group. The mAAV8-Vp16-Jazz-treated mdx mice showed a significant improvement of exercise performance as compared to mdx and to mAAV8-EGFP-treated mdx mice. Statistical analysis with "unpaired t-test" showed a significant main effect of treatment on mice performance indicated by $P<0.01$ and ***$P<0.001$. (D) Evan's blue dye (EBD) uptake was used to compare skeletal muscle membrane integrity after exercise. Top: abdominal muscle and diaphragm muscles from untreated and mAAV8-EGFP-treated (controls) or mAAV8-Vp16-Jazz-treated mdx mice were monitored for EBD uptake by fluorescence microscope. EBD uptake (light shading) was significantly higher in sections of control mdx mice as compared with mAAV8-Vp16-Jazz-treated mdx mice. Bottom: Evans blue uptake was also scored as a percentage of Evans blue positive myofibers. *$P<0.05$ and ***$P<0.001$ indicate statistical significance by t-test. Scale Bar: 50 µm. Vp16-Jazz is abbreviated as "Jazz" in FIGS. 4A-4D.
Figure 4:
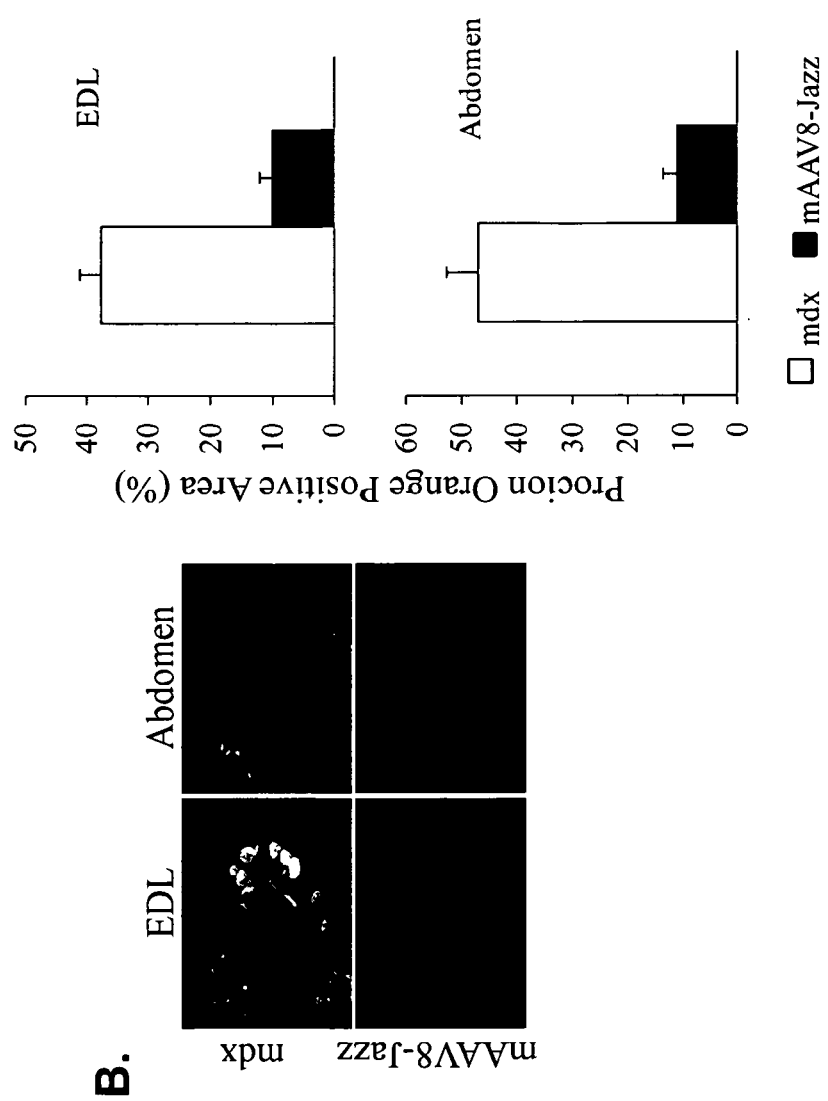
Figure 4:
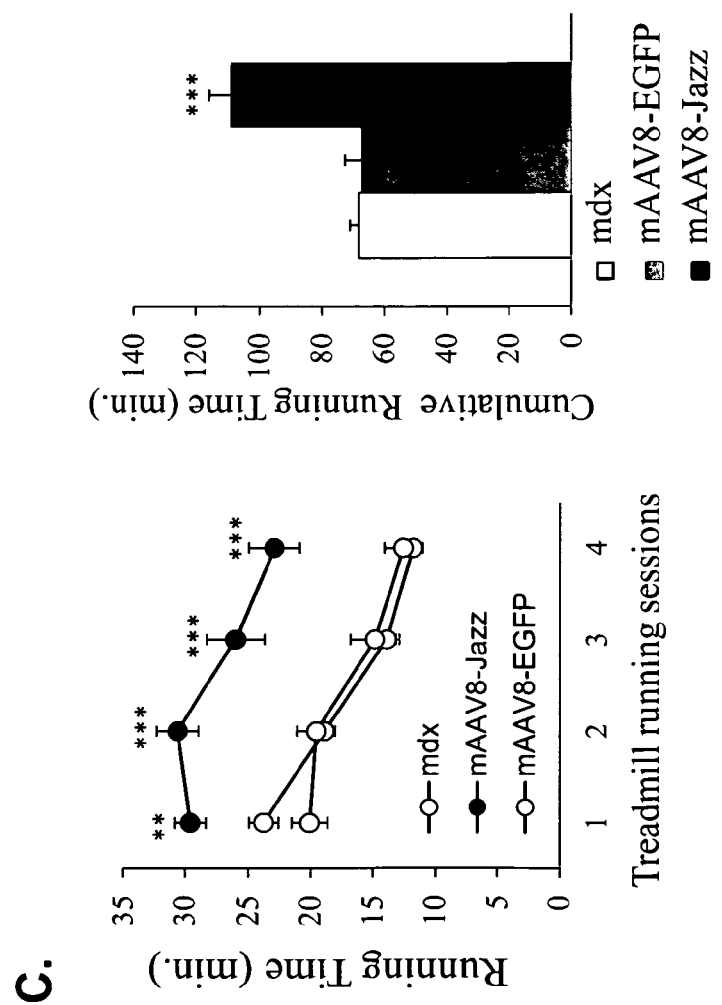
Figure 4:
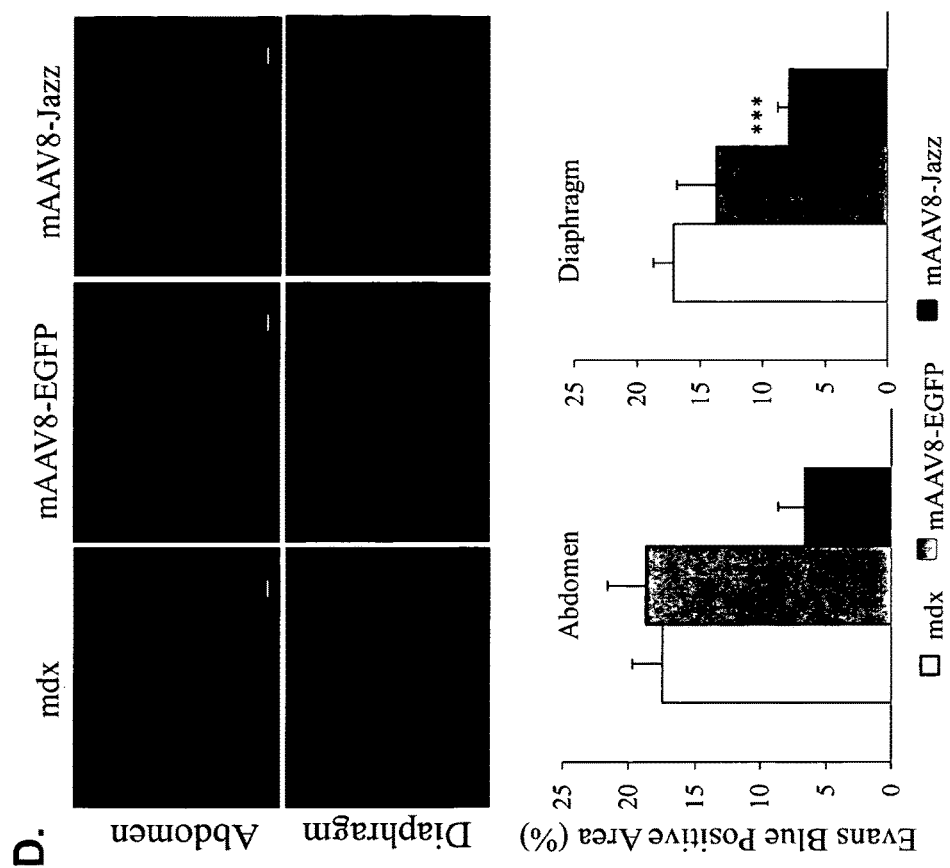

Recombinant AAV Delivery of Vp16-Jazz Improves the Histopathology of Mdx Muscle Tissue The possible therapeutic effects of utrophin up-regulation in the muscle of mdx mice treated with mAAV8-Vp16-Jazz were evaluated by typical DMD diagnostic parameters. Analysis of the slices derived from mAAV8-Vp16-Jazz muscles shows substantial morphology/architecture amelioration in comparison with mAAV8-EGFP and control saline-injected mdx mice (FIG. 3A). The frequency of centrally nucleated myofibers (CNFs), the fiber cross-sectional area (CSA), and the extent of mononuclear inflammatory cell infiltration was also quantified in muscle slices stained with hematoxylin and eosin (H&E), and the results further demonstrated reduced degenerative/regenerative processes in mAAV8-Vp16-Jazz muscles compared to controls (FIG. 3B). Next, as shown in FIG. 3C, a reduction of the muscular inflammatory response was observed in mAAV8-Vp16-Jazz infected mdx mice compared to controls by immunostaining the dystrophic muscle with the macrophage marker CD68.

These data demonstrate that delivery of mAAV8-Vp16-Jazz ameliorates the dystrophic histopathology of mdx muscle tissue.

Example 5

Recombinant AAV Delivery of Vp16-Jazz to Mdx Mice Significantly Ameliorates their Dystrophic Phenotype Dystrophin-deficient muscles are characterized by a severe deficit in contractile force and marked susceptibility to contraction-induced injury (Di Certo et al., supra). To verify whether mAAV8-Vp16-Jazz infection improves the mechanical responses in dystrophic muscle, the contractile activity of muscles from 2-month-old mAAV8-Vp16-Jazz infected and control mdx mice was measured. Isolated abdominal muscle strips and EDL were subjected to ex vivo physiological assessment of muscle force using variable voltages until the supramaximal value was reached. As shown in FIG. 4A, muscles from mAAV8-Vp16-Jazz-treated mdx mice showed a significant increase in strength compared with muscle preparations from control mdx mice. At the end of the force test, contraction-induced injury of the sarcolemma was assessed by staining each muscle with Procion Orange dye. Uptake of this fluorescent dye into individual fibers is an index of membrane integrity loss. As shown in FIG. 4B-left, fluorescence microscopy of both abdominal and EDL muscles cross-sections showed extensive uptake of the Procion Orange dye into non-treated mdx mice compared with mAAV8-Vp16-Jazz injected mdx mice. Quantification of the percentage of dye-positive area in each section confirmed the increased ability of Jazz-expressing muscles to exclude the dye from stressed fibers (FIG. 4B, right). Altogether, these data provide physiological evidence for recovery in both contractile force and sarcolemmal integrity in mdx mice infected with mAAV8-Vp16-Jazz.

In addition to the in vitro testing, the effects of the experimental gene therapy was assessed with mAAV8-Vp16-Jazz on the overall strength of dystrophic muscles in vivo. At 3 months of age mAAV8-Vp16-Jazz mdx-treated mice and control mAAV8-EGFP mdx-treated mice or mdx non-treated mice were subjected to forced physical exercise on an accelerating treadmill. The exercise was repeated once a week for four consecutive weeks and the running time was recorded in each session. As shown in FIG. 4C, mAAV8-Vp16-Jazz mdx-treated mice scored, over the four performances, a cumulative running time of approximately 110 min before reaching exhaustion, compared to the 70 min mean performance of mdx untreated/mAAV8-EGFP-treated mice. Thus, the up-regulation of utrophin achieved by the mAAV8-mediated delivery of ZF-ATF Vp16-Jazz effectively counteracts the symptoms of dystrophic pathology, resulting in an enhanced endurance performance. Furthermore, as already demonstrated in vitro with Procion Orange dye, Vp16-Jazz-mediated utrophin over-expression preserves in vivo sarcolemmal integrity during exercise, as shown by the reduced uptake of Evan's blue dye systemically injected in mice immediately after the end of the treadmill experiments (FIG. 4D). These results demonstrate the remarkable functional recovery of overall muscle strength in mdx mice expressing the artificial transcription factor Vp16-Jazz systemically administered by the mAAV8 vector and provide important insight for the possible future clinical use of ZF-ATFs to up-regulate utrophin expression for DMD gene therapy.

Example 6

Fusion Proteins Vp16-Jazz, Vp16-Bagly, and Vp16-CJ7 UtroUp and Human Modified Transcription Factors JZif1 and JZif2 can Bind to Utrophin Promoter and Increase Downstream Luciferase Reporter Gene Expression To investigate the ability of JZif1, JZif2, Vp16-CJ7-UtroUp, Vp16-Bagly and Vp16-Jazz to upregulate (i.e., increase) expression from the utrophin promoter "A", their ability to drive expression of a luciferase reporter gene placed downstream of a utrophin promoter "A" fragment was tested.

Figure 7:
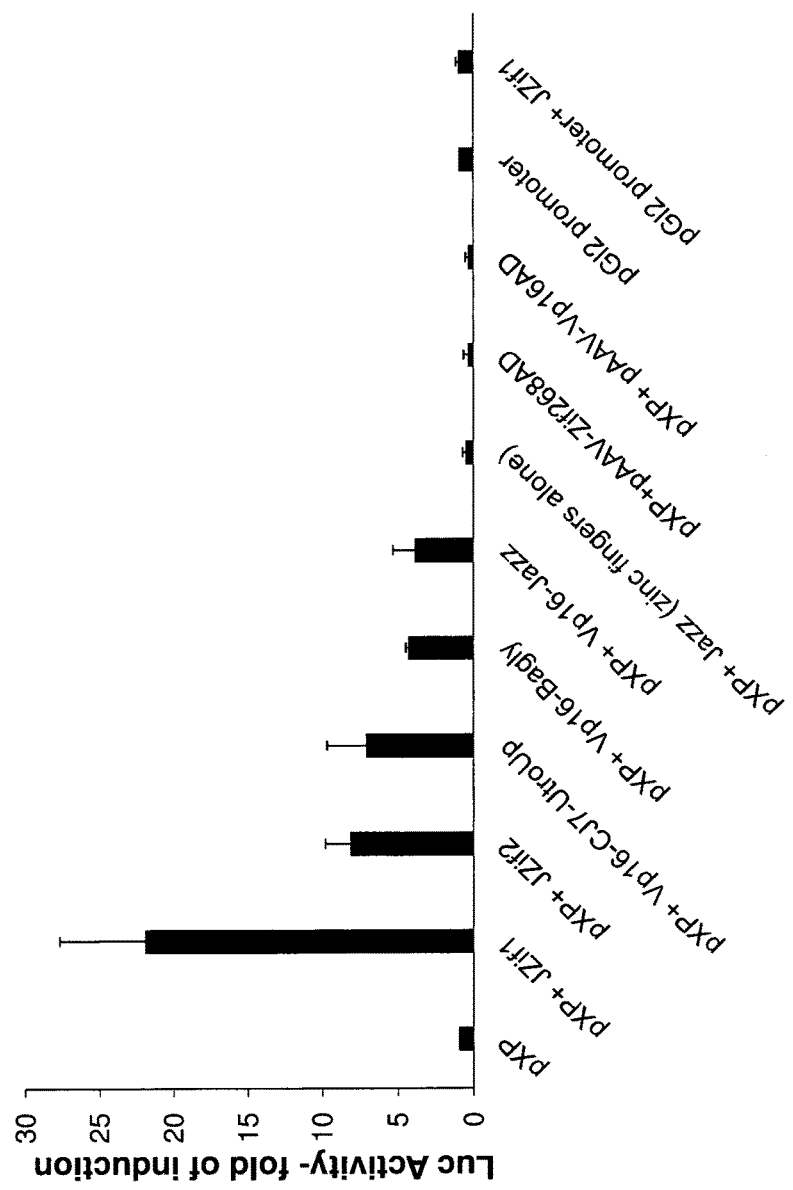
FIG. 7 is a histogram showing the fold-induction of luciferase expression activity (Luc activity) in HeLa cells transfected by the pXP-Luc (pXP) construct, carrying the luciferase gene under regulation of a portion of the utrophin promoter "A". The HeLa cells were co-transfected with pXP and the indicated plasmid carrying JZif1, JZif2, Vp16-CJ7-UtroUp, Vp16-Bagly, Vp16-Jazz, Jazz (zinc fingers alone), the activation domain of Zif268 (Zif268AD), or the activation domain of Vp16 alone (VP16AD), each under regulation of the cytomegalovirus (CMV) promoter. Luciferase induction was compared to that achieved in HeLa cells transfected with the pGL2-Prom construct, carrying the luciferase gene under regulation of the pGL2-SV40 promoter (Promega), alone or co-transfected with JZif1 under control of the CMV promoter. The data are presented as the means±SD of at least three independent experiments that were performed in triplicate.

To test the ability of these artificial transcription factors to increase expression from the utrophin promoter "A" in human cells, HeLa cells were co-transfected with a plasmid carrying JZif1, JZif2, Vp16-CJ7-UtroUp, Vp16-Bagly or Vp16-Jazz under control of the cytomegalovirus (CMV) promoter together with the luciferase reporter construct plasmid pXP-Luc (pXP). JZif1, JZif2, Vp16-CJ7-UtroUp, Vp16-Bagly and Vp16-Jazz were each able to increase luciferase expression relative to controls (FIG. 7). In this assay, JZif1 was identified as the best-performing artificial transcription factor, as co-transfection with a plasmid carrying JZif led to a greater than 20-fold induction of luciferase expression compared to cells transfected with pXP alone (FIG. 7). The modified human transcription factor JZif2, and the fusion proteins Vp16-CJ7-UtroUp, Vp16-Bagly, and Vp16-Jazz were also significantly effective in increasing luciferase expression (FIG. 7). By comparison, no increase in luciferase expression was detected when the pXP plasmid was co-transfected with a plasmid carrying the zinc finger domain of Jazz without a transcriptional activation domain, with a plasmid carrying the genomically-encoded human transcription factor Zif268's transcription activation domain without its zinc finger motifs, or with a plasmid carrying the transcriptional activation domain of Vp16 without a zinc finger DNA binding domain, which served as controls (FIG. 7). Likewise, there was no induction of luciferase activity when a control plasmid carrying the luciferase reporter gene under control of SV40 promoter (pGL2promoter) was used for co-transfection with the JZif1 plasmid (FIG. 7), confirming the specificity of the binding of JZif1 to the utrophin promoter "A". These results indicate that JZif1, JZif2, Vp16-CJ7-UtroUp, Vp16-Bagly, and Vp16-Jazz can each increase expression from the utrophin promoter "A" in human cells.

Figure 8:
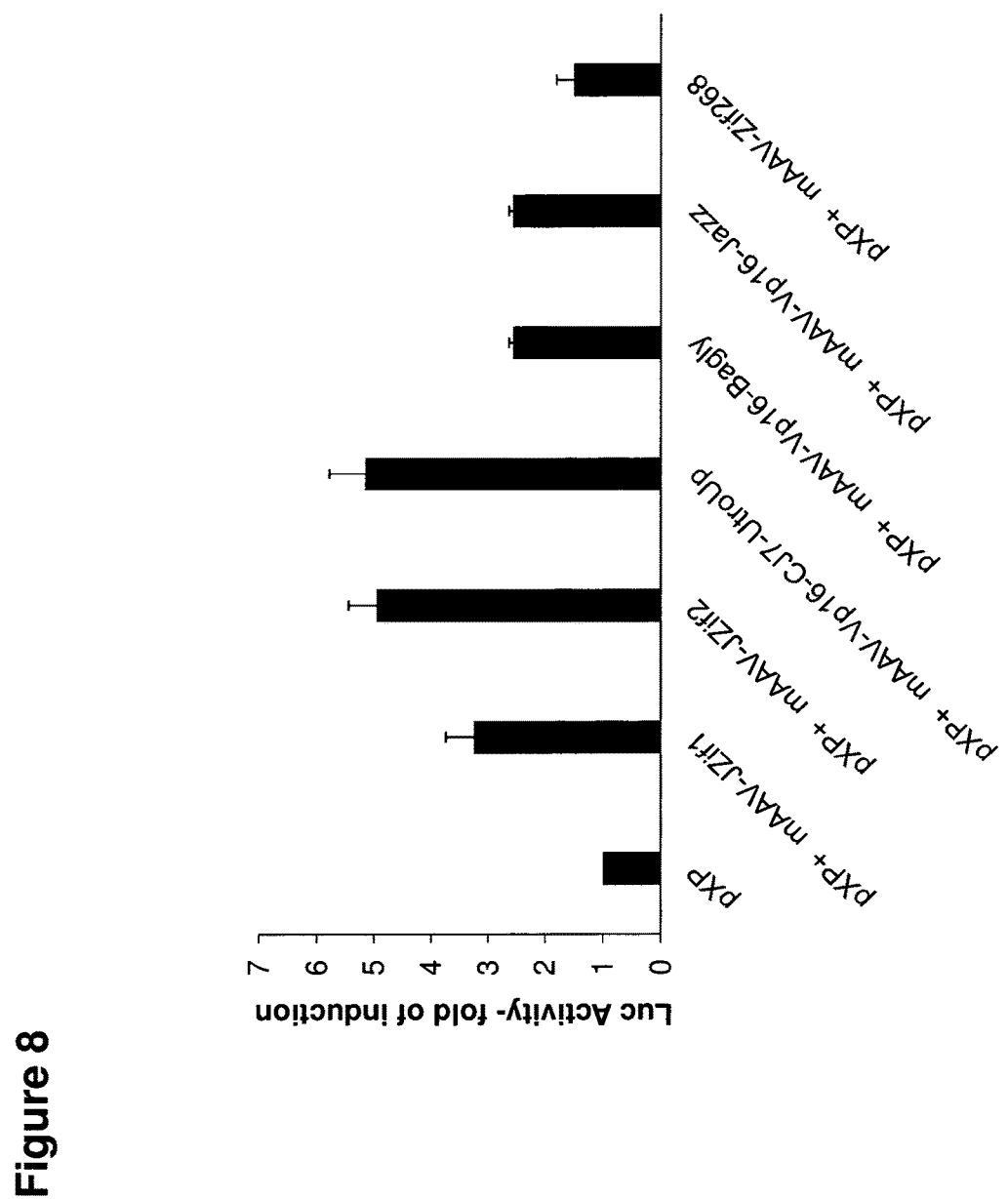
FIG. 8 is a histogram showing the fold of induction of luciferase expression activity in murine C2C7 myogenic cells transfected with the pXP-Luc construct, carrying the luciferase gene under regulation of a portion of the utrophin promoter "A". Myogenic cells were co-transfected with plasmids carrying JZif1, JZif2, Vp16-CJ7-UtroUp, Vp16-Bagly, Vp16-Jazz, or wild type Zif268, all under regulation of the alpha-actin promoter. Luciferase activity was assayed after 2 days of differentiation (in DMEM containing 2% fetal bovine serum). The data are presented as the means±SD of at least two independent experiments that were performed in triplicate.

Similar results were obtained in luciferase reporter assays performed in mouse cells. Murine differentiated myogenic C2C7 cells were co-transfected with pXP and plasmids carrying JZif1, JZif2, Vp16-CJ7-UtroUp, Vp16-Bagly and Vp16-Jazz under the regulation of the muscle-specific alpha-actin promoter. Each of the artificial transcription factors tested showed a significant up-regulation of luciferase expression, ranging from 2.5-fold to 5-fold, compared to the control cells transfected with pXP alone (FIG. 8). As another control, C2C7 cells transfected with a plasmid carrying the genomically-encoded wild type transcription factor Zif268 did not cause a significant increase of luciferase expression, confirming that Zif268 does not specifically bind the utrophin promoter "A". These results indicate that JZif1, JZif2, Vp16-CJ7-UtroUp, Vp16-Bagly, and Vp16-Jazz can each increase expression from the utrophin promoter "A" in mouse cells.

Figure 9:
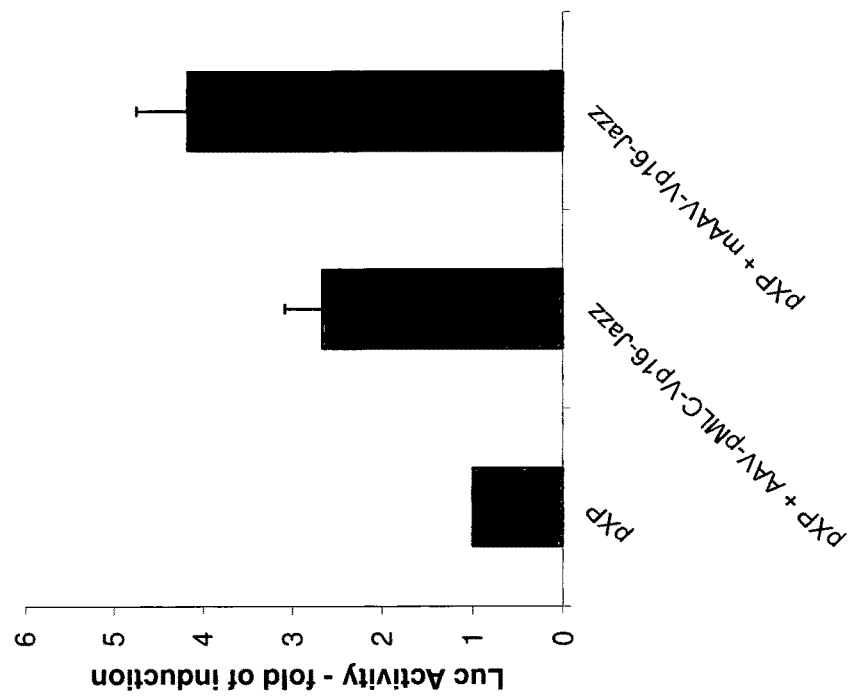
FIG. 9 is a histogram showing the fold-induction of luciferase expression activity (Luc activity) in murine C2C7 myogenic cells transfected with the pXP construct, carrying the luciferase gene under regulation of a portion of the utrophin promoter "A". Myogenic cells were co-transfected with a plasmid carrying Vp16-Jazz under the regulation of the myosin light chain (MLC) promoter or Vp16-Jazz under the regulation of the alpha-actin promoter. Luciferase activity was measured after two days of incubation in differentiation medium (DMEM containing 2% fetal bovine serum). The data are presented as the means±SD of three independent experiments that were performed in triplicate.

In addition to the alpha-actin promoter, other muscle-specific promoters, such as the myosin light chain promoter, can drive muscle-specific expression of an artificial transcription factor. This is evidenced by the significant increase in luciferase expression measured in C2C7 myogenic cells that were co-transfected with pXP and a plasmid carrying Vp16-Jazz under the regulation of either the alpha-actin promoter (mAAV-Vp16-Jazz) or the myosin light chain (MLC) promoter (AAV-pMLC-Vp16-Jazz) (FIG. 9). In this assay, the alpha-actin promoter led to stronger induction of luciferase expression compared to the MLC promoter (FIG. 9).

Example 7

Up-regulation of Utrophin Protein Expression by Modified Human Transcription Factors JZif1 and JZif2

Figures 5A, 5B, 5C, 5D:
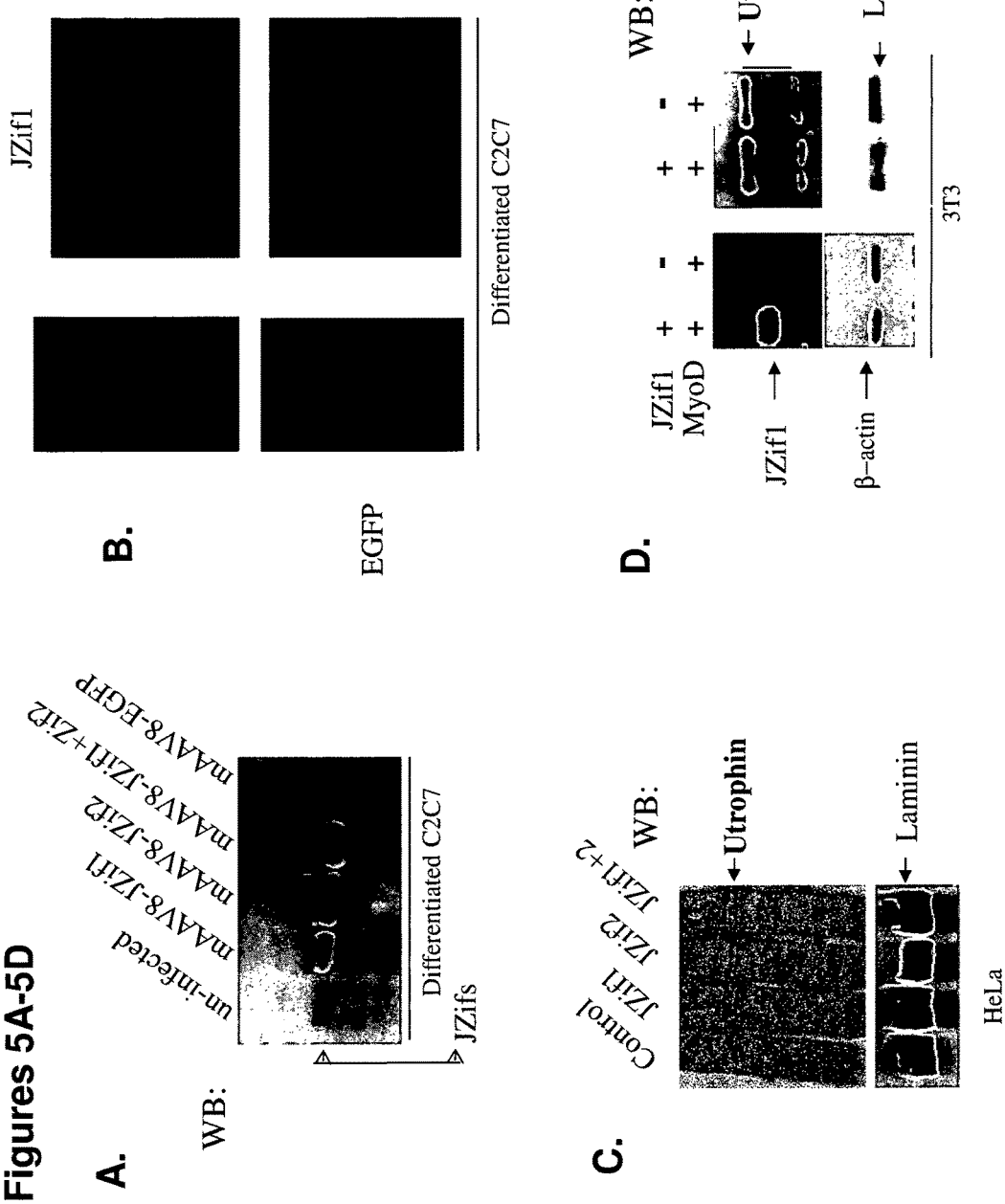
FIGS. 5A-5E show expression of modified human zinc finger proteins JZif1 and JZif2 and up-regulation of utrophin expression by these proteins in mouse and human cells. (A) Western blot analysis of C2C7 mouse myotube cells infected with mAAV8-EGFP, mAAV8-JZif1, mAAV8-JZif2, or combinations thereof. JZif1 and JZif2 proteins were detected with a commercial anti-Zif268 (Egr1) antibody (sc-189, Santa Cruz). Expression of EGFP, JZif1, or JZif2 is under the control of the human alpha-actin promoter. (B) Top left: representative bright field image of differentiated C2C7 cells infected with mAAV8-EGFP. Bottom left: EGFP fluorescence signal of C2C7 cells shown in top left panel. Top right: representative indirect immunofluorescence image of differentiated C2C7 myotubes infected with mAAV8-JZif1 (performed as described in Example 1). Detection was with rabbit polyclonal antibody anti-Zif268/EGR-1. Bottom right: Merge of Zif268 signal shown in top panel with Hoechst-stained nuclei (not visible in grayscale). (C) Western blot analysis of utrophin protein levels in HeLa cells (human) induced to myogenic differentiation by transfection with a plasmid expressing MyoD (control) that were co-transfected with mAAV-JZif1, mAAV-JZif2, or both. Detection of laminin and α-tubulin was used to normalize the amount of proteins. (D) Western blot analysis of mouse 3T3 fibroblasts induced to myogenic differentiation by transfection with a plasmid expressing MyoD, and co-transfected with mAAV-JZif1. Detection was with the indicated antibodies. Left panels: Expression of JZif1 in 3T3 fibroblasts. Detection of β-actin was used to normalize the amount of proteins. Right panels: Western blot analysis of utrophin protein levels. Detection of laminin was use to normalize the amount of proteins. (E) Western blot analysis of utrophin protein levels in heart muscles isolated from 2-month old mAAV8-EGFP, mAAV8-JZif1, or mAAV8-JZif2-treated mdx mice. Detection of laminin was used to normalize the amount of proteins.

To confirm the expression of JZif1 and JZif2 in muscle cells after recombinant AAV infection, murine differentiated myogenic C2C7 cells were infected with mAAV8-JZif1, mAAV8-JZif2, mAAV8-JZif1 and mAAV8-JZif2, or mAAV8-EGFP (control) and subjected to Western blot analysis using the rabbit anti-Zif268 polyclonal antibody. Cells infected with mAAV8-JZif1, mAAV8-JZif2, or both, showed a significantly elevated signal compared to both un-infected controls and cells infected with mAAV8-EGFP, clearly indicating the presence of JZif1 or JZif2 over the signal of the endogenous Zif268 (FIG. 5A). Expression of EGFP or JZif1 after recombinant AAV infection was confirmed using immunofluorescence microscopy analysis of murine differentiated myogenic C2C7 cells that were infected with mAAV8-EGFP or mAAV8-JZif1, respectively (FIG. 5B).

To test whether JZif1 and JZif2 can increase utrophin protein levels, HeLa and 3T3 cells that were induced to myogenic conversion by co-transfection of MyoD were transfected with plasmids carrying JZif1 or JZif2 under regulation of the alpha-actin promoter. Both HeLa (FIG. 5C) and 3T3 (FIG. 5D) cells transfected with plasmids carrying JZif1 or JZif2 showed an increase in utrophin protein levels compared to controls.

Figure 5E:
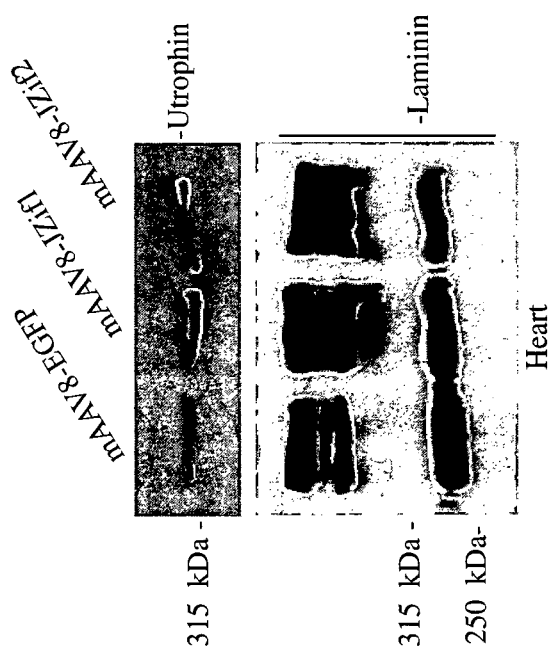
Figure 6:
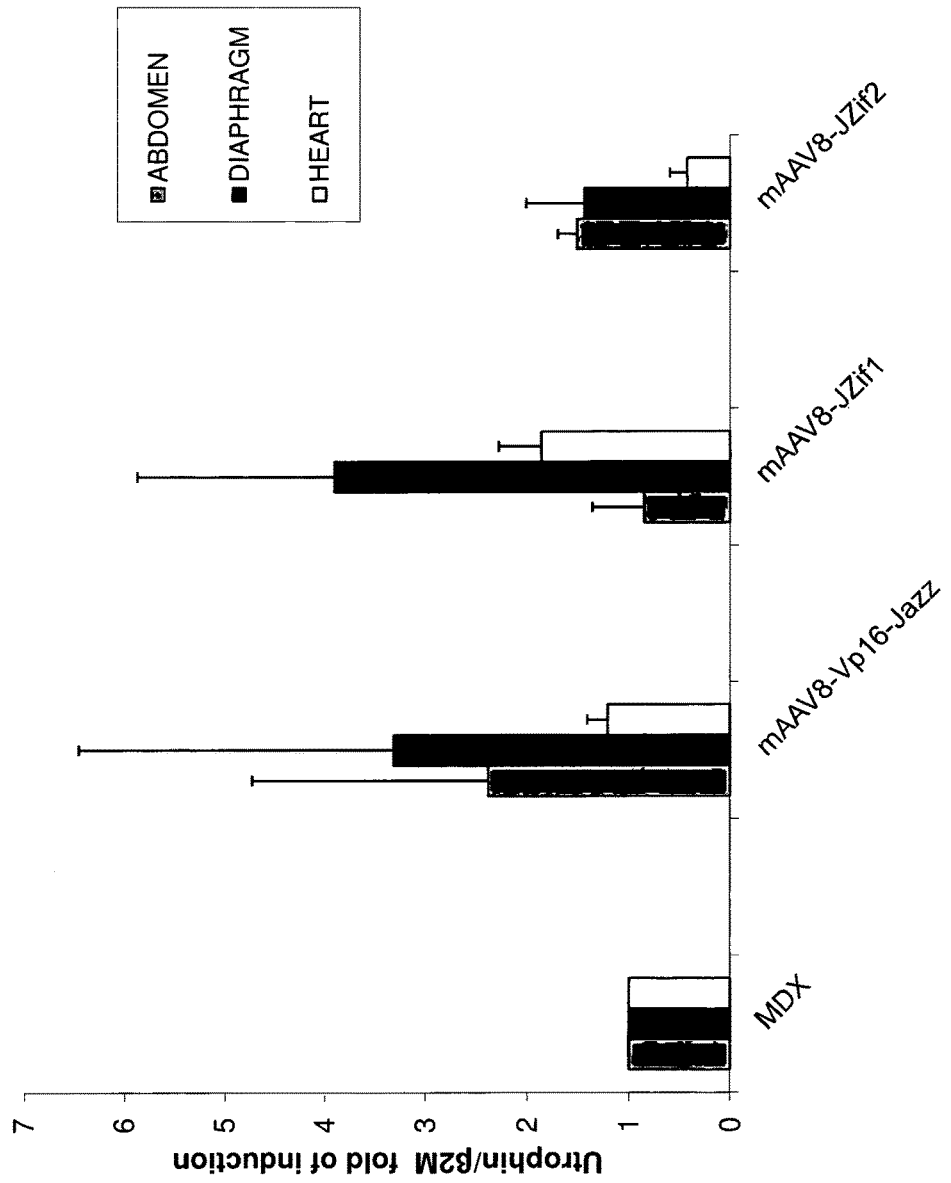
FIG. 6 is a histogram showing the fold increase in utrophin mRNA transcripts, quantified by real-time PCR, in skeletal (abdomen, diaphragm) muscle and cardiac muscle from 6-week old mdx mice untreated or infected with mAAV8-Vp16-Jazz, mAAV8-JZif1, or mAAV8-JZif2. Control β2-microglobulin mRNA transcripts were quantified as a control. Shown is the mean gene expression ratio between utrophin and β2-microglobulin (β2M). Error bars indicate the standard deviation (SD). Vp16-Jazz is abbreviated as "Jazz" in FIG. 6.

To test whether recombinant AAV infection using mAAV8-JZif1 or mAAV8-JZif2 can cause an increase in utrophin protein levels in heart muscle, Western blot analysis of utrophin protein levels was performed on lysates of heart muscles that were isolated from 2-month old mAAV8-EGFP, mAAV8-JZif1, or mAAV8-JZif2-infected mdx mice. Detection of laminin was used to normalize the amount of proteins. Utrophin protein levels were elevated in heart muscles that were isolated from mAAV8-JZif1 or mAAV8-JZif2-infected mdx mice relative to mAAV8-EGFP-infected controls (FIG. 5E).

Figure 14:
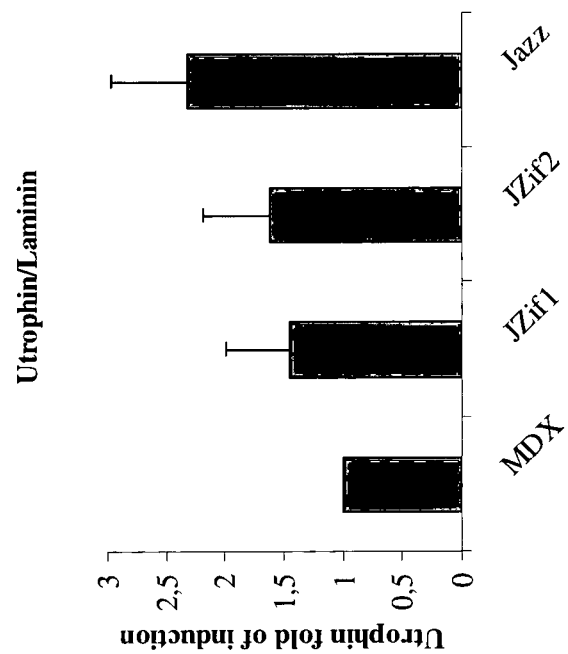
FIG. 14 is a histogram depicting the mean increase in utrophin protein levels in diaphragm muscles isolated from 6-week old mdx mice that were treated with mAAV8-Vp16-Jazz, mAAV8-JZif1, or mAAV8-JZif2 viral vectors, relative to utrophin levels in diaphragm muscles isolated from untreated mdx mice. Utrophin protein expression was assessed by Western blot using the mouse polyclonal anti-utrophin antibody A01 (Abnova). Detection of laminin was used to normalize the amount of proteins. Relative values were measured by densitometric analysis using ImageJ software. At least two animals were tested per group. Vp16-Jazz is abbreviated "Jazz" in FIG. 14.
Figure 15A:
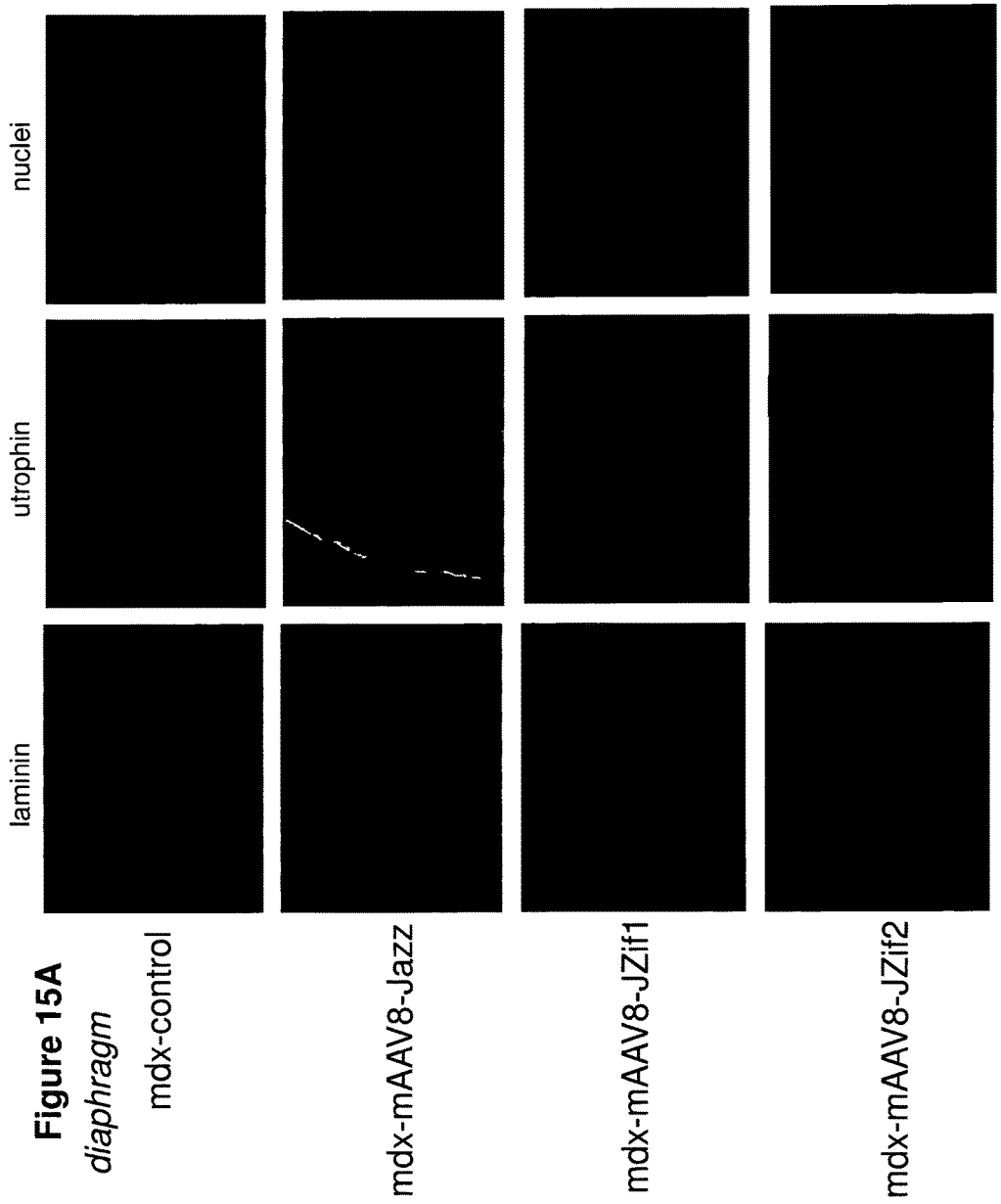
FIGS. 15A-15B show indirect immunofluorescence images of sections of diaphragm (FIG. 15A) and abdomen (FIG. 15B) muscles. Five-day old mdx mice were intraperitoneally injected with PBS (mdx-control) or with mAAV8-Jazz, mAAV8-JZif1, or mAAV8-JZif2 and examined at 6 weeks of age. The sections were immunostained with anti-utrophin monoclonal antibody (BD Lab Transduction, middle panels). The extracellular matrix is counterstained with the anti-laminin polyclonal antibody (left panels). Nuclei are stained with DAPI (right panels). All the images were taken at 20× magnification.
Figure 15B:
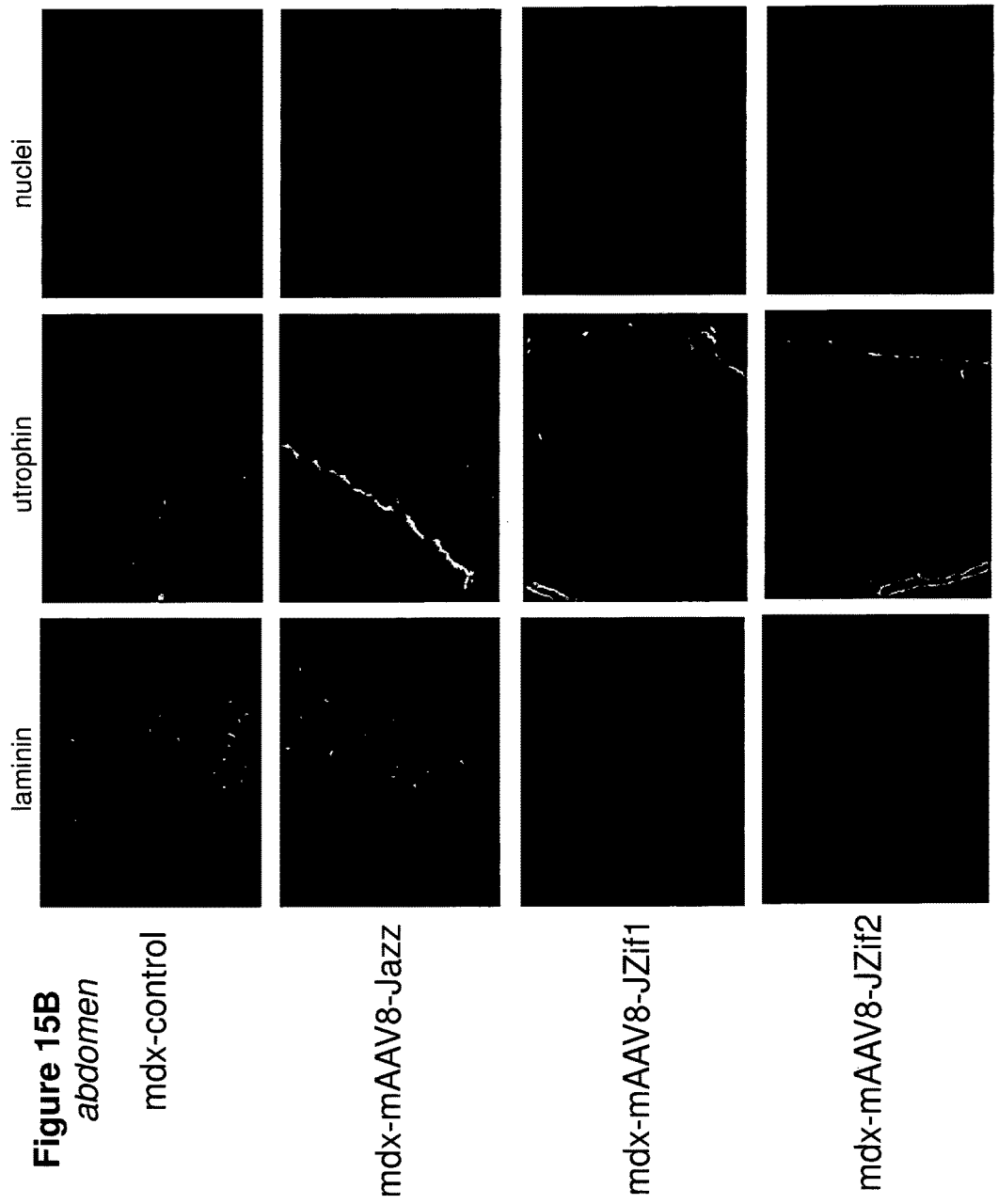
Figure 16A:
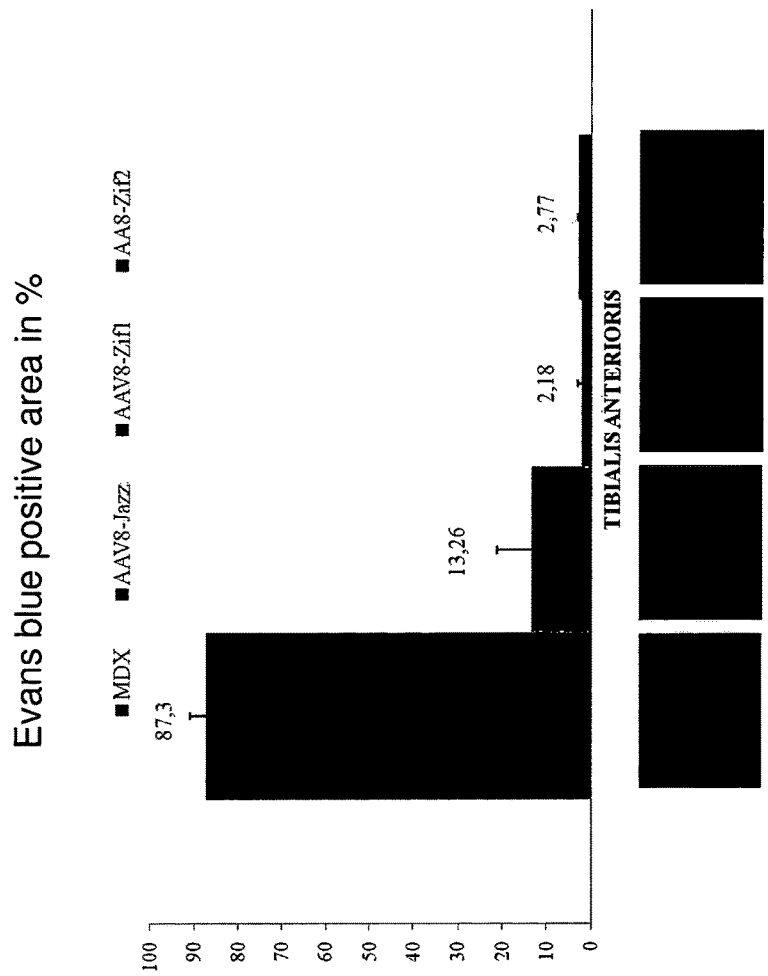
FIGS. 16A-16E shows a histogram of Evan's blue dye (EBD) uptake used to compare skeletal muscle membrane integrity at the end of the third session of treadmill exercise using the accelerated protocol (see Example 1 and FIG. 11). Evan's blue dye uptake was scored as percentage of EBD positive myofibers in tibialis anterioris (FIG. 16A), heart (FIG. 16B), quadriceps (FIG. 16C), abdomen (FIG. 16D), and diaphragm muscles (FIG. 16E) from untreated mdx mice and mdx mice systemically injected with mAAV8-Vp16-Jazz, mAAV8-JZif1, or mAAV8-JZif2 (mean of four slices of each muscle sections counted). Evans' blue dye uptake was detected by fluorescence microscopy. Error bars indicate SEM. Under each column in the histogram are representative images of EBD uptake for each treatment.
Figure 16B:
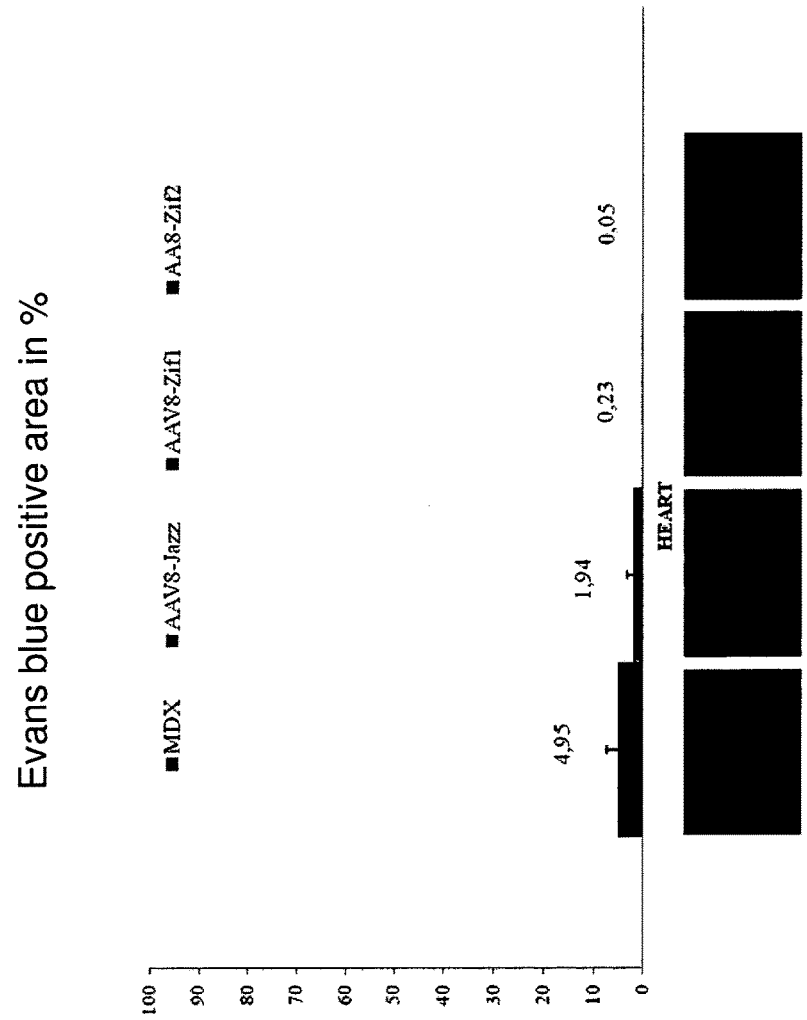
Figure 16C:
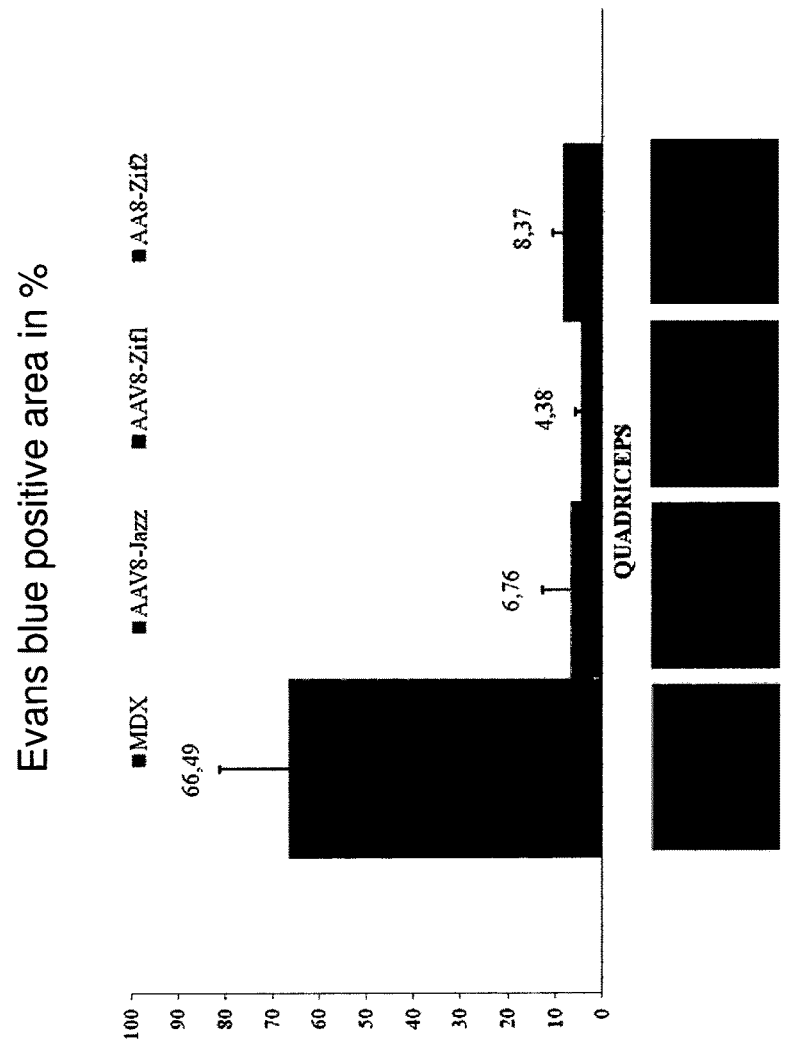
Figure 16D:
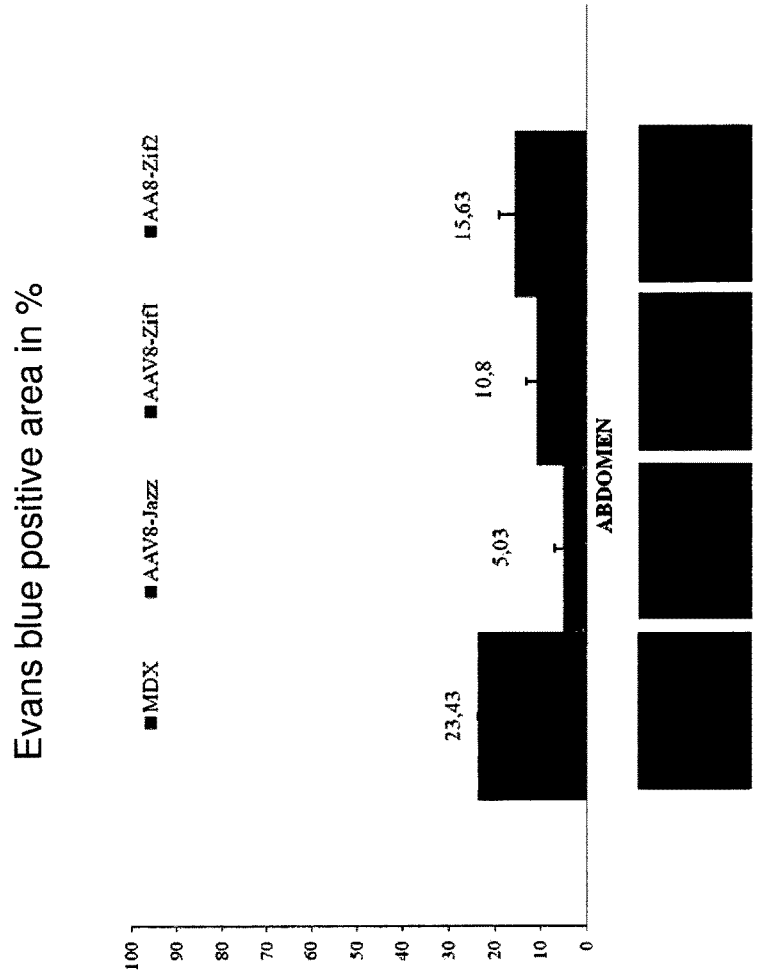
Figure 16E:
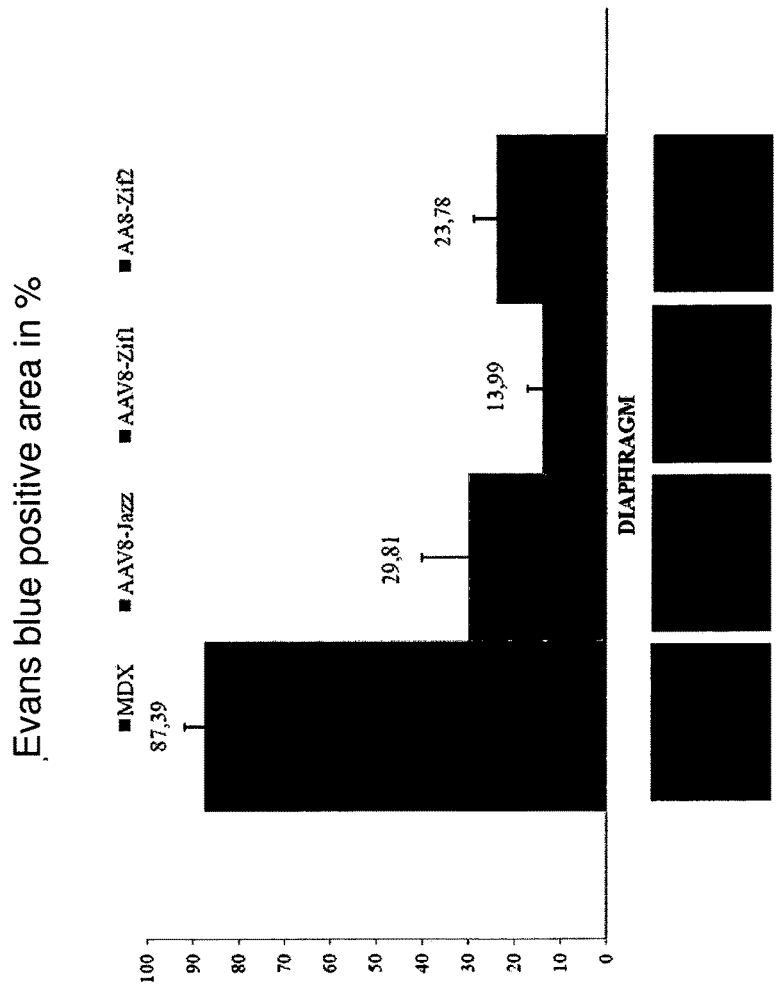

To test whether recombinant AAV infection using mAAV8-JZif1 or mAAV8-JZif2 can cause an increase in utrophin protein levels in skeletal muscle, Western blot analysis of utrophin protein levels was performed on lysates of diaphragm muscles that were isolated from 6-week old mdx mice that were treated with mAAV8-Vp16-Jazz, mAAV8-JZif1, or mAAV8-JZif2 viral vectors, relative to utrophin levels in diaphragm muscles isolated from untreated mdx mice. Utrophin protein expression was assessed by Western blot using the mouse polyclonal anti-utrophin antibody A01 (Abnova). Treatment of mdx mice with mAAV8-Vp16-Jazz, mAAV8-JZif1, or mAAV8-JZif2 each led to increased utrophin protein levels in the diaphragm muscles compared to untreated controls (FIG. 14).

Example 8

Figure 10A:
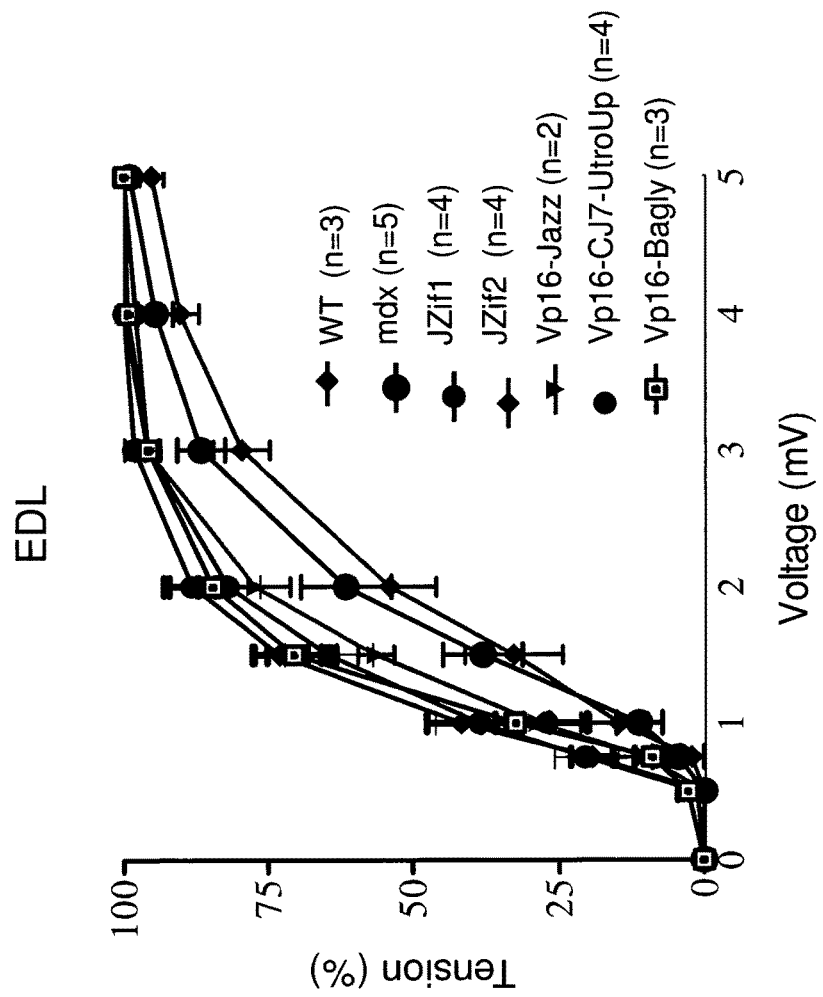
FIGS. 10A-10B are graphs showing the effects of changes in voltage on isotonic contractions in EDL (A) and abdominal muscles (B), from 6 week old control WT C57BL6 mice, mdx-untreated mice, and mdx mice systemically injected with mAAV8-Vp16-Jazz, mAAV8-JZif1, mAAV8-JZif2, mAAV8-CJ7-UtroUp and mAAV8-Vp16-Bagly as described in Example 1. The muscle's contractile force (tension) for each voltage was determined and plotted as a percentage of maximal contraction. Each point represents the mean of two EDL muscles (A) or one abdominal muscle strip (B) for each animal per group as indicated in the legend, with error bars denoting standard error of the mean (SEM). The increased contractile force exerted by EDL or abdominal muscles from wild-type mice or mice infected with mAAV8-Jazz, mAAV8-JZif1, mAAV8-Vp16-CJ7-UtroUp, and mAAV8-Vp16-Bagly compared to untreated mdx mice was statistically significant as calculated by Student's t-test (p<0.05) over a range of voltage values.
Figure 10B:
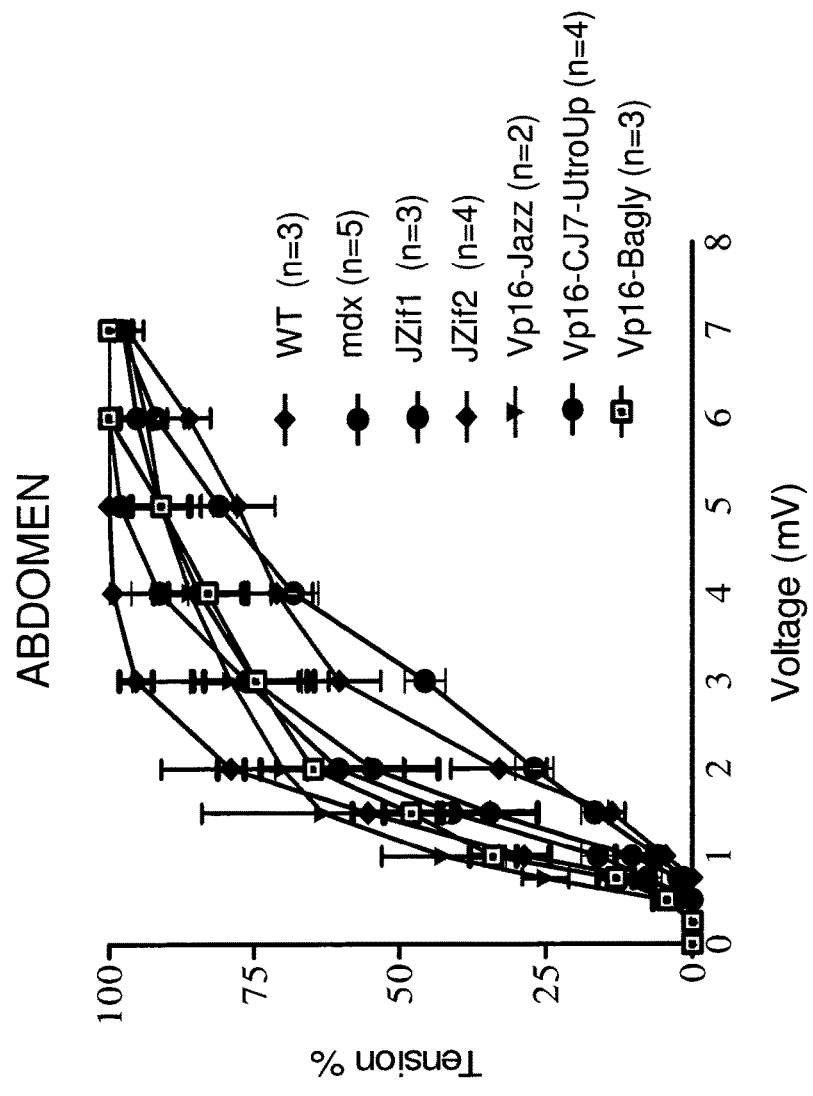

Recombinant AAV Delivery of Vp16-Jazz, Vp16-Bagly, Vp16-CJ7-UtroUp, and Human Modified Transcription Factors JZif1 and JZif2 to Mdx Mice Ameliorates their Dystrophic Phenotype, as Measured by Muscle Function Dystrophin-deficient muscles are characterized by a severe deficit in contractile force and marked susceptibility to contraction-induced injury (Di Certo et al., supra). To test whether mAAV8-Vp16-Jazz, mAAV8-Vp16-Bagly, mAAV8-Vp16-CJ7-UtroUp, mAAV8-JZif1, or mAAV8-JZif2 infection improves the mechanical responses in dystrophic muscle, the contractile force (tension) of muscles from 6 week-old infected and control mdx mice, as well as that of wild type mice was measured. Isolated abdominal muscle strips and EDL were subjected to ex vivo physiological assessment of muscle force using variable voltages until the supramaximal value was reached. As shown in FIGS. 10A-10B, EDL and abdominal muscles from mdx mice treated with mAAV8-JZif1, mAAV8-Vp16-Bagly, mAAV8-Vp16-CJ7-UtroUp showed a statistically significant increase in contractile force (strength) compared with muscle preparations from control mdx mice ($p<0.05$ as determined by Student's t test over a wide range of voltages). Altogether, these data provide physiological evidence for recovery in both contractile force and sarcolemmal integrity in mdx mice infected with mAAV8-JZif1, mAAV8-Vp16-Bagly, mAAV8-Vp16-CJ7-UtroUp.

Figure 11:
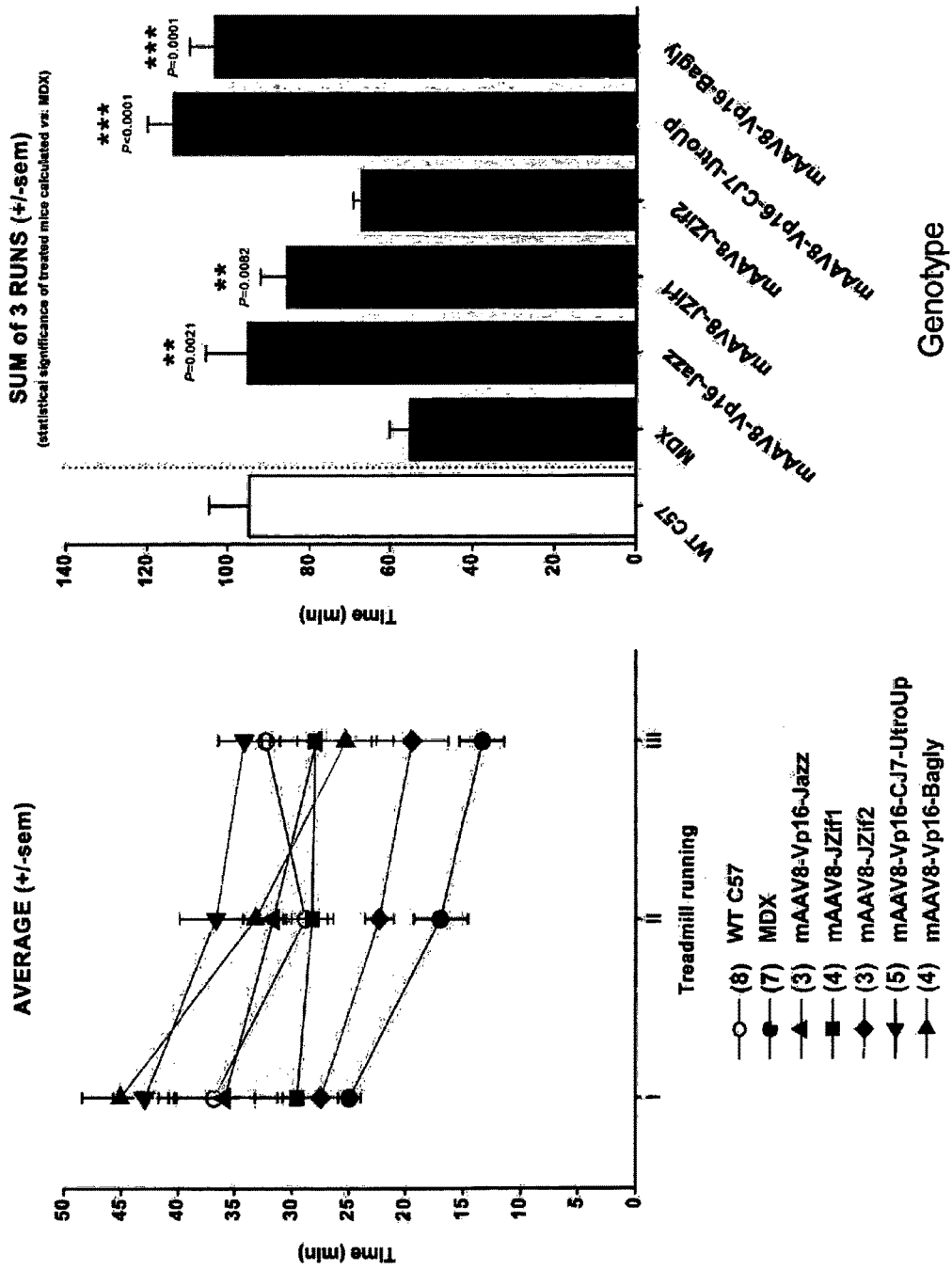
FIG. 11 shows analysis of muscle endurance: 6 week old wild type (WT) C57BL6, mdx, and mdx mice treated at 5 days post birth with mAAV8-Vp16-Jazz, mAAV8-JZif1, mAAV8-JZif2, mAAV8-Vp16-CJ7-UtroUp, and mAAV8-Vp16-Bagly were subjected to treadmill analysis by the Accelerated Method, as described in Example 1. Panel on left depicts the average running time for each of the three treadmill runs post the initial habituation run. The number of animals used for averaging in each category is marked in parentheses. Panel on the right depicts the average total running time for all three runs. The number of animals used for averaging in each category is marked in parentheses. All data are shown as mean±SEM. Data for total time running during treadmill test, were statistically analyzed by one-way analysis of variance (ANOVA) followed by pairwise post-hoc comparisons using Bonferroni-Dunn test. () indicates p<0.01, (*) indicates p<0.001. The mdx mice treated with JZif2 were not significantly different compared to mdx mice. All treated mice that are significantly different compared to mdx mice were not significantly different compared to WT.

In addition to the ex vivo muscle contractile force testing, the effects of the experimental gene therapy on the overall strength and endurance of dystrophic muscles was tested in vivo. At 6 weeks of age, mdx mice treated with mAAV8-Vp16-Jazz, mAAV8-Vp16-Bagly, mAAV8-Vp16-CJ7-UtroUp, mAAV8-JZif1, or mAAV8-JZif2; untreated mdx mice; and wild type C57BL mice were subjected to forced physical exercise on an accelerating treadmill. The exercise was performed via the Accelerated Protocol (see Example 1). As shown in FIG. 11, mdx mice treated with each of the artificial transcription factors had significantly increased mean cumulative running time compared to untreated mdx controls, in some instances having mean cumulative running times that were comparable to wild type mice. For example, mAAV8-Vp16-Jazz-treated mdx mice scored a mean cumulative running time over the 3 running performances of approximately 95 min, while mAAV8-JZif1-treated mdx mice scored a cumulative running time of approximately 85 min, which were both significantly increased ($p<0.01$) compared to the approximately 55 min cumulative running time of untreated mdx mice, and comparable to the approximately 97 min mean cumulative running time of the wild type mice. mAAV8-JZif2-treated mdx mice had a cumulative running time of approximately 69 min, which was also increased compared to untreated mdx mice, although lower than that obtained by treatment with mAAV8-Vp16-Jazz or mAAV8-JZif1. mAAV8-Vp16-CJ7-UtroUp- and mAAV8-VpP16-Bagly-treated mdx mice performed very well, having cumulative running times of approximately 114 min and 104 min, respectively, which was statistically significant compared to the mdx mice ($p<0.001$), but not significantly different from the wild type (WT) C57BL mice.

In parallel, the uptake of Evan's Blue (EBD) was evaluated to compare skeletal muscle membrane integrity after accelerated treadmill exercise in the wild type, untreated mdx mice, and mdx mice treated with the mAAV viral particles carrying the specified artificial transcription factor. As shown in FIG. 16, mdx mice treated with mAAV8-Vp16-Jazz, mAAV8-JZif1, or mAAV8-JZif2 show significantly less EBD uptake, indicating improved membrane stability.

Thus, the up-regulation (i.e., increased expression) of utrophin achieved by the mAAV8 recombinant AAVs that comprise the genes encoding the fusion proteins and modified transcription factors described herein, as shown by Western blots, RT-PCR, and immunofluorescence analyses (FIGS. 6, 14, and 15A-B) counteracts the symptoms of dystrophic pathology, resulting in increased muscle contractile force and enhanced endurance (FIGS. 10A-10B, 11). These results demonstrate the remarkable functional recovery of overall muscle strength in mdx mice expressing the fusion proteins Vp16-Jazz, Vp16-Bagly, Vp16-CJ7-UtroUp, and the modified human transcription factors JZif1 and JZif2 systemically administered by the mAAV8 recombinant AAV, and indicate that treatment with the artificial transcription factors described herein can be used to treat muscle diseases, for example DMD and BMD.

Sequences

The following sequences are used throughout the application.

| SEQ ID NO: | Sequence | Description |
|---|---|---|
| 1 | CCTGCAGGCAGCTGCGCGCTCGCTCGCTCACTGAGGCCGCCCGGGCAAAG<br>CCCGGGCGTCGGGCGACCTTTGGTCGCCCGGCCTCAGTGAGCGAGCGAGC<br>GCGCAGAGAGGGAGTGGCCAACTCCATCACTAGGGGTTCCTGCGGCCGCA<br>CGCGTCACCAACTGGGTAACCTCTGCTGACCCCCACTCTACTTTACCATAAG<br>TAGCTCCAAATCCTTCTAGAAAATCTGAAAGGCATAGCCCCATATATCAGTGA<br>TATAAATAGAACCTGCAGCAGGCTCTGGTAAATGATGACTACAAGGTGGACT<br>GGGAGGCAGCCCGGCCTTGGCAGGCATCATCCTCTAAATATAAAGATGAGT<br>TTGTTCAGCCTTTGCAGAAGGAAAAACTGCCACCCATCCTAGAGTGCCGCGT<br>CCTTGTCCCCCCACCCCCTCCAATTTATTGGGAGGAAGGACCAGCTAAGCC<br>TCATCTAGGAAGAGCCCCTCACCCATCTCCACCTCCACTCCAGGTCTAGCCA<br>GTCCTGGGTTGTGACCCTTGTCTTTCAGCCCCAGGAGAGGGACACACATAG<br>TGCCACCAAAGAGGCTGGGGGAGGGCCTCAGCCCACCAAAACCTGGGGCC<br>AGTGCGTCCTACAGGAGGGGAACCCTCACCCCTTCAATCCCTTTAGGAGAC<br>CCAAGGGCGCTGCGCGTCCCTGAGGCGGACAGCTCCGTGTGCTCAGGCTT<br>TGCGCCTGACAGGCCTATCCCCGGGAGCCCCGCGCCTCCTCCCCGGCGC<br>TCCGCCCTCGCCTCCCCCGCCAGTTGTCTATCCTGCGACAGCTGCGCGCC<br>CTCCGGCCGCCGGTGGCCCTCTGTGCGGTGGGGGAAGGGGTCGACGTGG<br>CTCAGCTTTTTGGATTCAGGGAGCTCGGGGGTGGGAAGAGAGAAATGGAGT<br>TCCAGGGGCGTAAAGGAGAGGGAGTTCGCCTTCCTTCCCTTCCTGAGACTC<br>AGGAGTGACTGCTTCTCCAATCCTCCCAAGCCCACCACTCCACACGACTCC<br>CTCTTCCCGGTAGTCGCAAGTGGGAGTTTGGGGATCTGAGCAAAGAACCCG<br>AAGAGGAGTTGAAATATTGGAAGTCAGCAGTCAGGCACCTTCCCGAGCGCC<br>CAGGGCGCTCAGAGTGGACATGGTTGGGGAGGCCTTTGGGACAGGTGCGG<br>TTCCCGGAGCGCAGGCGCACACATGCACCCACCGGCGAACGCGGTGACCC<br>TCGCCCCACCCCATCCCCTCCGGCGGGCAACTGGGTCGGGTCAGGAGGGG<br>CAAACCCGCTAGGGAGACACTCCATATACGGCCCGGCCCGCGTTACCTGGG<br>ACCGGGCCAACCCGCTCCTTCTTTGGTCAACGCAGGGGACCCGGGCGGGG<br>GCCCAGGCCGCGAACCGGCCGAGGGAGGGGGCTCTAGTGCCCAACACCCA<br>AATATGGCTCGAGAAGGGCAGCGACATTCCTGCGGGGTGGCGCGGAGGGA<br>ATGCCCGCGGGCTATATAAAACCTGAGCAGAGGGACAAGCGGCCACCGCA<br>GCGGACAGCGCCAAGTGAAGCCTCGCTTCCCCTCCGCGGCGACCAGGGCC<br>CGAGCCGAGAGTAGCAGTTGTAGCTACCCGCCCAGGTAGGGCAGGAGTTG<br>GGAGGGGACAGGGGGACAGGGCACTACCGAGGGGAACCTGAAGGACTCC<br>GGGGCAGAACCCAGTCGGTTCACCTGGTAAGCTTGCTAGCTCCGCGGATTC<br>GAATCCCGGCCGGGAACGGTGCATTGGAACGCGGATTCCCCGTGCCAAGA<br>GTGACGTAAGTACCGCCTATAGAGTCTATAGGCCCACAAAAAATGCTTTCTT<br>CTTTTAATATACTTTTTTGTTTATCTTATTTCTAATACTTTCCCTAATCTCTTTCT<br>TTCAGGGCAATAATGATACAATGTATCATGCCTCTTTGCACCATTCTAAAGAA<br>TAACAGTGATAATTTCTGGGTTAAGGCAATAGCAATATTTCTGCATATAAATA<br>TTTCTGCATATAAATTGTAACTGATGTAAGAGGTTTCATATTGCTAATAGCAG<br>CTACAATCCAGCTACCATTCTGCTTTTATTTTATGGTTGGGATAAGGCTGGAT<br>TATTCTGAGTCCAAGCTAGGCCCTTTTGCTAATCATGTTCATACCTCTTATCT<br>TCCTCCCACAGCTCCTGGGCAACGTGCTGGTCTGTGTGCTGGCCCATCACT<br>TTGGCAAAGAATTGGGATTCGAACATCGATGGGAATTCCGGGATCCGGTCG<br>ACCGTACGTACAAGATCTACGGGTGGCATCCCTGTGACCCCTCCCCAGTGC<br>CTCTCCTGGCCCTGGAAGTTGCCACTCCAGTGCCCACCAGCCTTGTCCTAAT<br>AAAATTAAGTTGCATCATTTTGTCTGACTAGTACGGGTGGCATCCCTGTGAC<br>CCCTCCCCAGTGCCTCTCCTGGCCCTGGAAGTTGCCACTCCAGTGCCCACC<br>AGCCTTGTCCTAATAAAATTAAGTTGCATCATTTTGTCTGACTAGGTGTCCTT<br>CTATAATATTATGGGGTGGAGGGGGGTGGTATGGAGCAAGGGGCAAGTTGG<br>GAAGACAACCTGTAGGGCCTGCGGGGTCTATTGGGAACCAAGCTGGAGTGC<br>AGTGGCACAATCTTGGCTCACTGCAATCTCCGCCTCCTGGGTTCAAGCGATT<br>CTCCTGCCTCAGCCTCCCGAGTTGTTGGGATTCCAGGCATGCATGACCAGG<br>CTCAGCTAATTTTTGTTTTTTTGGTAGAGACGGGGTTTCACCATATTGGCCAG<br>GCTGGTCTCCAACTCCTAATCTCAGGTGATCTACCCACCTTGGCCTCCCAAA<br>TTGCTGGGATTACAGGCGTGAACCACTGCTCCCTTCCCTGTCCTTCTGATTT<br>TGTAGGTAACCACGTGCGGACCGAGCGGCCGCAGGAACCCCTAGTGATGG<br>AGTTGGCCACTCCCTCTCTGCGCGCTCGCTCGCTCACTGAGGCCGGGCGA<br>CCAAAGGTCGCCCGACGCCCGGGCTTTGCCCGGGCGGCCTCAGTGAGCGA<br>GCGAGCGCGCAGCTGCCTGCAGGGGCGCCTGATGCGGTATTTTCTCCTTAC | mAAV vector (complete sequence) |

| SEQ ID NO: | Sequence | Description |
|---|---|---|
| | GCATCTGTGCGGTATTTCACACCGCATACGTCAAAGCAACCATAGTACGCGC<br>CCTGTAGCGGCGCATTAAGCGCGGCGGGTGTGGTGGTTACGCGCAGCGTG<br>ACCGCTACACTTGCCAGCGCCCTAGCGCCCGCTCCTTTCGCTTTCTTCCCTT<br>CCTTTCTCGCCACGTTCGCCGGCTTTCCCCGTCAAGCTCTAAATCGGGGGC<br>TCCCTTTAGGGTTCCGATTTAGTGCTTTACGGCACCTCGACCCCAAAAAACT<br>TGATTTGGGTGATGGTTCACGTAGTGGGCCATCGCCCTGATAGACGGTTTTT<br>CGCCCTTTGACGTTGGAGTCCACGTTCTTTAATAGTGGACTCTTGTTCCAAA<br>CTGGAACAACACTCAACCCTATCTCGGGCTATTCTTTTGATTTATAAGGGATT<br>TTGCCGATTTCGGCCTATTGGTTAAAAAATGAGCTGATTTAACAAAAATTTAA<br>CGCGAATTTTAACAAAATATTAACGTTTACAATTTTATGGTGCACTCTCAGTA<br>CAATCTGCTCTGATGCCGCATAGTTAAGCCAGCCCGACACCCGCCAACAC<br>CCGCTGACGCGCCCTGACGGGCTTGTCTGCTCCCGGCATCCGCTTACAGAC<br>AAGCTGTGACCGTCTCCGGGAGCTGCATGTGTCAGAGGTTTTCACCGTCAT<br>CACCGAAACGCGCGAGACGAAAGGGCCTCGTGATACGCCTATTTTTATAGG<br>TTAATGTCATGATAATAATGGTTTCTTAGACGTCAGGTGGCACTTTTCGGGGA<br>AATGTGCGCGGAACCCCTATTTGTTTATTTTTCTAAATACATTCAAATATGTAT<br>CCGCTCATGAGACAATAACCCTGATAAATGCTTCAATAATATTGAAAAGGAA<br>GAGTATGAGTATTCAACATTTCCGTGTCGCCCTTATTCCCTTTTTTGCGGCAT<br>TTTGCCTTCCTGTTTTTGCTCACCCAGAAACGCTGGTGAAAGTAAAAGATGC<br>TGAAGATCAGTTGGGTGCACGAGTGGGTTACATCGAACTGGATCTCAACAG<br>CGGTAAGATCCTTGAGAGTTTTCGCCCCGAAGAACGTTTTCCAATGATGAGC<br>ACTTTTAAAGTTCTGCTATGTGGCGCGGTATTATCCCGTATTGACGCCGGGC<br>AAGAGCAACTCGGTCGCCGCATACACTATTCTCAGAATGACTTGGTTGAGTA<br>CTCACCAGTCACAGAAAAGCATCTTACGGATGGCATGACAGTAAGAGAATTA<br>TGCAGTGCTGCCATAACCATGAGTGATAACACTGCGGCCAACTTACTTCTGA<br>CAACGATCGGAGGACCGAAGGAGCTAACCGCTTTTTTGCACAACATGGGGG<br>ATCATGTAACTCGCCTTGATCGTTGGGAACCGGAGCTGAATGAAGCCATACC<br>AAACGACGAGCGTGACACCACGATGCCTGTAGCAATGGCAACAACGTTGCG<br>CAAACTATTAACTGGCGAACTACTTACTCTAGCTTCCCGGCAACAATTAATAG<br>ACTGGATGGAGGCGGATAAAGTTGCAGGACCACTTCTGCGCTCGGCCCTTC<br>CGGCTGGCTGGTTTATTGCTGATAAATCTGGAGCCGGTGAGCGTGGGTCTC<br>GCGGTATCATTGCAGCACTGGGGCCAGATGGTAAGCCCTCCCGTATCGTAG<br>TTATCTACACGACGGGGAGTCAGGCAACTATGGATGAACGAAATAGACAGAT<br>CGCTGAGATAGGTGCCTCACTGATTAAGCATTGGTAACTGTCAGACCAAGTT<br>TACTCATATATACTTTAGATTGATTTAAAACTTCATTTTTAATTTAAAAGGATCT<br>AGGTGAAGATCCTTTTTGATAATCTCATGACCAAAATCCCTTAACGTGAGTTT<br>TCGTTCCACTGAGCGTCAGACCCCGTAGAAAAGATCAAAGGATCTTCTTGAG<br>ATCCTTTTTTTCTGCGCGTAATCTGCTGCTTGCAAACAAAAAAACCACCGCTA<br>CCAGCGGTGGTTTGTTTGCCGGATCAAGAGCTACCAACTCTTTTTCCGAAGG<br>TAACTGGCTTCAGCAGAGCGCAGATACCAAATACTGTCCTTCTAGTGTAGCC<br>GTAGTTAGGCCACCACTTCAAGAACTCTGTAGCACCGCCTACATACCTCGCT<br>CTGCTAATCCTGTTACCAGTGGCTGCTGCCAGTGGCGATAAGTCGTGTCTTA<br>CCGGGTTGGACTCAAGACGATAGTTACCGGATAAGGCGCAGCGGTCGGGC<br>TGAACGGGGGGTTCGTGCACACAGCCCAGCTTGGAGCGAACGACCTACAC<br>CGAACTGAGATACCTACAGCGTGAGCTATGAGAAAGCGCCACGCTTCCCGA<br>AGGGAGAAAGGCGGACAGGTATCCGGTAAGCGGCAGGGTCGGAACAGGAG<br>AGCGCACGAGGGAGCTTCCAGGGGGAAACGCCTGGTATCTTTATAGTCCTG<br>TCGGGTTTCGCCACCTCTGACTTGAGCGTCGATTTTTGTGATGCTCGTCAGG<br>GGGGCGGAGCCTATGGAAAAACGCCAGCAACGCGGCCTTTTTACGGTTCCT<br>GGCCTTTTGCTGGCCTTTTGCTCACATGT | |
| 2 | CCTGCAGGCAGCTGCGCGCTCGCTCGCTCACTGAGGCCGCCCGGGCAAAG<br>CCCGGGCGTCGGGCGACCTTTGGTCGCCCGGCCTCAGTGAGCGAGCGAGC<br>GCGCAGAGAGGGAGTGGCCAACTCCATCACTAGGGGTTCCTGCGGCCGCA<br>CGCGTCACCAACTGGGTAACCTCTGCTGACCCCCACTCTACTTTACCATAAG<br>TAGCTCCAAATCCTTCTAGAAAATCTGAAAGGCATAGCCCCATATATCAGTGA<br>TATAAATAGAACCTGCAGCAGGCTCTGGTAAATGATGACTACAAGGTGGACT<br>GGGAGGCAGCCCGGCCTTGGCAGGCATCATCCTCTAAATATAAAGATGAGT<br>TTGTTCAGCCTTTGCAGAAGGAAAAACTGCCACCCATCCTAGAGTGCCGCGT<br>CCTTGTCCCCCCACCCCCTCCAATTTATTGGGAGGAAGGACCAGCTAAGCC<br>TCATCTAGGAAGAGCCCCTCACCCATCTCCACCTCCACTCCAGGTCTAGCCA<br>GTCCTGGGTTGTGACCCTTGTCTTTCAGCCCCAGGAGAGGGACACACATAG<br>TGCCACCAAAGAGGCTGGGGAGGGCCTCAGCCCACCAAAACCTGGGGCC<br>AGTGCGTCCTACAGGAGGGGAACCCTCACCCCTTCAATCCCTTTAGGAGAC<br>CCAAGGGCGCTGCGCGTCCCTGAGGCGGACAGCTCCGTGTGCTCAGGCTT<br>TGCGCCTGACAGGCCTATCCCCGGGAGCCCCCGCGCCTCCTCCCCGGCGC<br>TCCGCCCTCGCCTCCCCCGCCAGTTGTCTATCCTGCGACAGCTGCGCGCC<br>CTCCGGCCGCCGGTGGCCCTCTGTGCGGTGGGGAAGGGGTCGACGTGG<br>CTCAGCTTTTTGGATTCAGGGAGCTCGGGGTGGGAAGAGAAATGGAGT<br>TCCAGGGGCGTAAAGGAGAGGGAGTTCGCCTTCCTTCCCTTCCTGAGACTC<br>AGGAGTGACTGCTTCTCAATCCTCCCAAGCCCACCACTCCACACGACTCC<br>CTCTTCCCGGTAGTCGCAAGTGGGAGTTTGGGGATCTGAGCAAAGAACCCG<br>AAGAGGAGTTGAAATATTGGAAGTCAGCAGTCAGGCACCTTCCCGAGCGCC<br>CAGGGCGCTCAGAGTGGACATGGTTGGGGAGGCCTTTGGGACAGGTGCGG<br>TTCCCGGAGCGCAGGCGCACACATGCACCCACCGGCGAACGCGGTGACCC | mAAV-<br>Vp16-Jazz<br>vector<br>(complete<br>sequence) |

| SEQ ID NO: | Sequence | Description |
|---|---|---|
| | TCGCCCCACCCCATCCCCTCCGGCGGGCAACTGGGTCGGGTCAGGAGGGG | |
| | CAAACCCGCTAGGGAGACACTCCATATACGGCCCGGCCCGCGTTACCTGGG | |
| | ACCGGGCCAACCCGCTCCTTCTTTGGTCAACGCAGGGGACCCGGGCGGGG | |
| | GCCCAGGCCGCGAACCGGCCGAGGGAGGGGGCTCTAGTGCCCAACACCCA | |
| | AATATGGCTCGAGAAGGGCAGCGACATTCCTGCGGGGTGGCGCGGAGGGA | |
| | ATGCCCGCGGGCTATATAAAACCTGAGCAGAGGGACAAGCGGCCACCGCA | |
| | GCGGACAGCGCCAAGTGAAGCCTCGCTTCCCCTCCGCGGCGACCAGGGCC | |
| | CGAGCCGAGAGTAGCAGTTGTAGCTACCCGCCCAGGTAGGGCAGGAGTTG | |
| | GGAGGGGACAGGGGGACAGGGCACTACCGAGGGGAACCTGAAGGACTCC | |
| | GGGGCAGAACCCAGTCGGTTCACCTGGTAAGCTTGCTAGCTCCGCGGATTC | |
| | GAATCCCGGCCGGGAACGGTGCATTGGAACGCGGATTCCCCGTGCCAAGA | |
| | GTGACGTAAGTACCGCCTATAGAGTCTATAGGCCCACAAAAAATGCTTTCTT | |
| | CTTTTAATATACTTTTTTGTTTATCTTATTTCTAATACTTTCCCTAATCTCTTTCT | |
| | TTCAGGGCAATAATGATACAATGTATCATGCCTCTTTGCACCATTCTAAAGAA | |
| | TAACAGTGATAATTTCTGGGTTAAGGCAATAGCAATATTTCTGCATATAAATA | |
| | TTTCTGCATATAAATTGTAACTGATGTAAGAGGTTTCATATTGCTAATAGCAG | |
| | CTACAATCCAGCTACCATTCTGCTTTTATTTTATGGTTGGGATAAGGCTGGAT | |
| | TATTCTGAGTCCAAGCTAGGCCCTTTTGCTAATCATGTTCATACCTCTTATCT | |
| | TCCTCCCACAGCTCCTGGGCAACGTGCTGGTCTGTGTGCTGGCCCATCACT | |
| | TTGGCAAAGAATTGGGATTCGAACATCGATTTAAAGCTATGGAGCAAAAGCT | |
| | CATTTCTGAAGAGGACTTGAATGAAATGGAGCAAAAGCTCATTTCTGAAGAG | |
| | GACTTGAATGAAATGGAGCAAAAGCTCATTTCTGAAGAGGACTTGAATGAAA | |
| | TGGAGCAAAAGCTCATTTCTGAAGAGGACTTGAATGAAATGGAGCAAAAGCT | |
| | CATTTCTGAAGAGGACTTGAATGAAATGGAGAGCTTGGGCGACCTCACCATG | |
| | GGCCCTAAAAGAAGCGTAAAGTCGCCCCCCCGACCGATGTCAGCCTGGG | |
| | GGACGAGCTCCACTTAGACGGCGAGGACGTGGCGATGGCGCATGCCGACG | |
| | CGCTAGACGATTTCGATCTGGACATGTTGGGGGACGGGGATTCCCCGGGTC | |
| | CGGGATTTACCCCCCACGACTCCGCCCCTACGGCGCTCTGGATATGGCCG | |
| | ACTTCGAGTTTGAGCAGATGTTTACCGATGCCCTTGGAATTGACGAGTACGG | |
| | TGGGGAATTCCCGGGGATCCTCGATGACAGACCCTATGCTTGCCCAGTGGA | |
| | AAGCTGCGACCGCCGCTTTTCTAGATCGGATGAGCTTACCCGCCATATCCG | |
| | CATCCACACCGGCCAAAAACCCTTTCAATGCCGTATCTGCATGAGGAATTTC | |
| | AGCAGCCGCGATGTCCTGAGGCGCCATAACAGGACCCACACAGGGGAAAA | |
| | GCCATTCGCATGTGACATCTGCGGTCGAAAGTTTGCAAGCCGCGATGTCCT | |
| | GAGGCGCCATAACAGGATACATTTGAGGCAAAATGATCTCGACCGTACGTAC | |
| | AAGATCCGTTAGCATATGCTAACAGATCCACGGGTGGCATCCCTGTGACCC | |
| | CTCCCCAGTGCCTCTCCTGGCCCTGGAAGTTGCCACTCCAGTGCCCACCAG | |
| | CCTTGTCCTAATAAAATTAAGTTGCATCATTTTGTCTGACTAGTACGGGTGGC | |
| | ATCCCTGTGACCCCTCCCCAGTGCCTCTCCTGGCCCTGGAAGTTGCCACTC | |
| | CAGTGCCCACCAGCCTTGTCCTAATAAAATTAAGTTGCATCATTTTGTCTGAC | |
| | TAGGTGTCCTTCTATAATATTATGGGGTGGAGGGGGGTGGTATGGAGCAAG | |
| | GGGCAAGTTGGGAAGACAACCTGTAGGGCCTGCGGGGTCTATTGGGAACC | |
| | AAGCTGGAGTGCAGTGGCACAATCTTGGCTCACTGCAATCTCCGCCTCCTG | |
| | GGTTCAAGCGATTCTCCTGCCTCAGCCTCCCGAGTTGTTGGGATTCCAGGC | |
| | ATGCATGACCAGGCTCAGCTAATTTTTGTTTTTTTGGTAGAGACGGGGTTTCA | |
| | CCATATTGGCCAGGCTGGTCTCCAACTCCTAATCTCAGGTGATCTACCCACC | |
| | TTGGCCTCCCAAATTGCTGGGATTACAGGCGTGAACCACTGCTCCCTTCCCT | |
| | GTCCTTCTGATTTTGTAGGTAACCACGTGCGGACCGAGCGGCCGCAGGAAC | |
| | CCCTAGTGATGGAGTTGGCCACTCCCTCTCTGCGCGCTCGCTCGCTCACTG | |
| | AGGCCGGGCGACCAAAGGTCGCCCGACGCCCGGGCTTTGCCCGGGCGGC | |
| | CTCAGTGAGCGAGCGAGCGCGCAGCTGCCTGCAGGGGCGCCTGATGCGGT | |
| | ATTTTCTCCTTACGCATCTGTGCGGTATTTCACACCGCATACGTCAAAGCAAC | |
| | CATAGTACGCGCCCTGTAGCGGCGCATTAAGCGCGGCGGGTGTGGTGGTT | |
| | ACGCGCAGCGTGACCGCTACACTTGCCAGCGCCCTAGCGCCCGCTCCTTTC | |
| | GCTTTCTTCCCTTCCTTTCTCGCCACGTTCGCCGGCTTTCCCCGTCAAGCTC | |
| | TAAATCGGGGGCTCCCTTTAGGGTTCCGATTTAGTGCTTTACGGCACCTCGA | |
| | CCCCAAAAAACTTGATTTGGGTGATGGTTCACGTAGTGGGCCATCGCCCTGA | |
| | TAGACGGTTTTTCGCCCTTTGACGTTGGAGTCCACGTTCTTTAATAGTGGAC | |
| | TCTTGTTCCAAACTGGAACAACACTCAACCCTATCTCGGGCTATTCTTTTGAT | |
| | TTATAAGGGATTTTGCCGATTTCGGCCTATTGGTTAAAAAATGAGCTGATTTA | |
| | ACAAAAATTTAACGCGAATTTTAACAAAATATTAACGTTTACAATTTATGGTG | |
| | CACTCTCAGTACAATCTGCTCTGATGCCGCATAGTTAAGCCAGCCCCGACAC | |
| | CCGCCAACACCCGCTGACGCGCCCTGACGGGCTTGTCTGCTCCCGGCATC | |
| | CGCTTACAGACAAGCTGTGACCGTCTCCGGGAGCTGCATGTGTCAGAGGTT | |
| | TTCACCGTCATCACCGAAACGCGCGAGACGAAAGGGCCTCGTGATACGCCT | |
| | ATTTTTATAGGTTAATGTCATGATAATAATGGTTTCTTAGACGTCAGGTGGCA | |
| | CTTTTCGGGGAAATGTGCGCGGAACCCCTATTTGTTTATTTTTCTAAATACAT | |
| | TCAAATATGTATCCGCTCATGAGACAATAACCCTGATAAATGCTTCAATAATA | |
| | TTGAAAAAGGAAGAGTATGAGTATTCAACATTTCCGTGTCGCCCTTATTCCCT | |
| | TTTTTGCGGCATTTTGCCTTCCTGTTTTTGCTCACCCAGAAACGCTGGTGAAA | |
| | GTAAAAGATGCTGAAGATCAGTTGGGTGCACGAGTGGGTTACATCGAACTG | |
| | GATCTCAACAGCGGTAAGATCCTTGAGAGTTTTCGCCCCGAAGAACGTTTTC | |
| | CAATGATGAGCACTTTTAAAGTTCTGCTATGTGGCGCGGTATTATCCCGTATT | |
| | GACGCCGGGCAAGAGCAACTCGGTCGCCGCATACACTATTCTCAGAATGAC | |
| | TTGGTTGAGTACTCACCAGTCACAGAAAAGCATCTTACGGATGGCATGACAG | |

-continued

| SEQ ID NO: | Sequence | Description |
|---|---|---|
|  | TAAGAGAATTATGCAGTGCTGCCATAACCATGAGTGATAACACTGCGGCCAA CTTACTTCTGACAACGATCGGAGGACCGAAGGAGCTAACCGCTTTTTTGCAC AACATGGGGATCATGTAACTCGCCTTGATCGTTGGGAACCGGAGCTGAAT GAAGCCATACCAAACGACGAGCGTGACACCACGATGCCTGTAGCAATGGCA ACAACGTTGCGCAAACTATTAACTGGCGAACTACTTACTCTAGCTTCCCGGC AACAATTAATAGACTGGATGGAGGCGGATAAAGTTGCAGGACCACTTCTGCG CTCGGCCCTTCCGGCTGGCTGGTTTATTGCTGATAAATCTGGAGCCGGTGA GCGTGGGTCTCGCGGTATCATTGCAGCACTGGGGCCAGATGGTAAGCCCTC CCGTATCGTAGTTATCTACACGACGGGGAGTCAGGCAACTATGGATGAACG AAATAGACAGATCGCTGAGATAGGTGCCTCACTGATTAAGCATTGGTAACTG TCAGACCAAGTTTACTCATATATACTTTAGATTGATTTAAAACTTCATTTTTAAT TTAAAAGGATCTAGGTGAAGATCCTTTTTGATAATCTCATGACCAAAATCCCT TAACGTGAGTTTTCGTTCCACTGAGCGTCAGACCCCGTAGAAAAGATCAAAG GATCTTCTTGAGATCCTTTTTTTCTGCGCGTAATCTGCTGCTTGCAAACAAAA AAACCACCGCTACCAGCGGTGGTTTGTTTGCCGGATCAAGAGCTACCAACT CTTTTTCCGAAGGTAACTGGCTTCAGCAGAGCGCAGATACCAAATACTGTCC TTCTAGTGTAGCCGTAGTTAGGCCACCACTTCAAGAACTCTGTAGCACCGCC TACATACCTCGCTCTGCTAATCCTGTTACCAGTGGCTGCTGCCAGTGGCGAT AAGTCGTGTCTTACCGGGTTGGACTCAAGACGATAGTTACCGGATAAGGCG CAGCGGTCGGGCTGAACGGGGGGTTCGTGCACACAGCCCAGCTTGGAGCG AACGACCTACACCGAACTGAGATACCTACAGCGTGAGCTATGAGAAAGCGC CACGCTTCCCGAAGGGAGAAAGGCGGACAGGTATCCGGTAAGCGGCAGGG TCGGAACAGGAGAGCGCACGAGGGAGCTTCCAGGGGAAACGCCTGGTAT CTTTATAGTCCTGTCGGGTTTCGCCACCTCTGACTTGAGCGTCGATTTTTGT GATGCTCGTCAGGGGGCGGAGCCTATGGAAAAACGCCAGCAACGCGGCC TTTTTTACGGTTCCTGGCCTTTTGCTGGCCTTTTGCTCACATGT |  |
| 3 | ACGCGTCACCAACTGGGTAACCTCTGCTGA | Oligo |
| 4 | GCTAGCAAGCTTACCAGGTGAACCGACTGGGTTCTG | Oligo |
| 5 | CGATGGGAATTCCGGGATCCGGTCGACCGTACGTACAA | Oligo |
| 6 | GATCTTGTACGTACGGTCGACCGGATCCCGGAATTCCCAT | Oligo |
| 7 | ATCGATGGGAATTCCGGGATCCGGTCGACCGTACGTACAAGATCT | Polylinker |
| 8 | TGGGCCCTAAAAAGAAGCGTAAA | Nuclear localization sequence DNA |
| 9 | GCTGCTGCG | Jazz, JZif1 target seq |
| 10 | CGGGCTGCTGCGGGCTGGGAG | human target sequence for all of Jazz, Bagly, and UtroUp |
| 11 | CCGGCTGCTGCGGGCTGGGAG | mouse target sequence for all of Jazz, Bagly, and UtroUp |
| 12 | CGGGCTGCTGCG | human target sequence for Bagly |
| 13 | CCGGCTGCTGCG | mouse target sequence for Bagly |
| 14 | GCTGCTGCGGGCTGGGAG | target sequence for UtroUp |

| SEQ ID NO: | Sequence | Description |
|---|---|---|
| 15 | GGAGCCGGA | Target seq for Zip51; described in background |
| 16 | CPVESCDRRFSRSDELTRHIRIHTGQKPFQCRICMRNFSSRDVLRRHNRTHTGE KPFACDICGRKFASRDVLRRHNRIH | Zinc finger region Jazz |
| 17 | CPVESCDRRFSRSDNLVRHIRIHTGQKPFQCRICMRNFSRSDHLTTHNRTHTGE KPFACDICGRKFADPGHLVRHNRIHTGEKPFACPVESCDRRFSRSDELTRHIRIH TGQKPFQCRICMRNFSSRDVLRRHNRTHTGEKPFACDICGRKFASRDVLRRHN RIH | Zinc finger region UtroUp |
| 18 | CPVESCDRRFSRSDELTRHIRIHTGQKPFQCRICMRNFSSRDVLRRHNRTHTGE KPFACDICGRKFASRDVLRRHNRIHLRQGPRSHVCAECGKAFVESSKLKRHQLV H | Zinc Finger region Bagly |
| 19 | GCGCAGAACTTGGGGAGCCGCCGCCGCCATCCGCCGCCGCAGCCAGCTTC CGCCGCCGCAGGACCGGCCCCTGCCCCAGCCTCCGCAGCCGCGGCGCGT CCACGCCCGCCCGCGCCCAGGGCGAGTCGGGGTCGCCGCCTGCACGCTT CTCAGTGTTCCCGCCCCGCATGTAACCCGGCCAGGCCCCGCAACTGT GTCCCCTGCAGCTCCAGCCCCGGGCTGCACCCCCCGCCCCGACACCAGC TCTCCAGCCTGCTCGTCAGGATGGCCGCGGCCAAGGCCGAGATGCAGCT GATGTCCCCGCTGCAGATCTCTGACCCGTTCGGATCCTTTCCTCACTCGCC CACCCATGGACAACTACCCTAAGCTGGAGGAGATGATGCTGCTGAGCAACGG GGCTCCCCAGTTCCTCGGCGCCGCCGGGGCCCCAGAGGGCAGCGGCAGC AACAGCAGCAGCAGCAGCAGCGGGGGCGGTGGAGGCGGCGGGGGCGGCA GCAACAGCAGCAGCAGCAGCACCTTCAACCCTCAGGCGGACACGGGC GAGCAGCCCTACGAGCACCTGACCGCAGAGTCTTTTCCTGACATCTCTCTGA ACAACGAGAAGGTGCTGGTGGAGACCAGTTACCCCAGCCAAACCACTCGAC TGCCCCCCATCACCTATACTGGCCGCTTTTCCCTGGAGCCTGCACCCAACA GTGGCAACACCTTGTGGCCCGAGCCCCTCTTCAGCTTGGTCAGTGGCCTAG TGAGCATGACCAACCCACCGGCCTCCTCGTCCTCAGCACCATCTCCAGCGG CCTCCTCCGCCTCCGCCTCCCAGAGCCCACCCCTGAGCTGCGCAGTGCCAT CCAACGACAGCAGTCCCATTTACTCAGCGGCACCCACCTTCCCCACGCCGA ACACTGACATTTTCCCTGAGCCACAAAGCCAGGCCTTCCCGGGCTCGGCAG GGACAGCGCTCCAGTACCCGCCTCCTGCCTACCCTGCCGCCAAGGGTGGC TTCCAGGTTCCCATGATCCCCGACTACCTGTTTCCACAGCAGCAGGGGAT CTGGGCCTGGGCACCCCAGACCAGAAGCCCTTCCAGGGCCTGGAGAGCCG CACCCAGCAGCCTTCGCTAACCCCTCTGTCTACTATTAAGGCCTTTGCCACT CAGTCGGGCTCCCAGGACCTGAAGGCCCTCAATACCAGCTACCAGTCCCAG CTCATCAAACCCAGCCGCATGCGCAAGTACCCCAACCGGCCACAGCAAGACG CCCCCCCACGAACGCCCTTACGCTTGCCCAGTGGAGTCCTGTGATCGCCGC TTCTCCCGCTCCGACGAGCTCACCCGCCACATCCGCATCCACACAGGCCAG AAGCCCTTCCAGTGCCGCATCTGCATGCGCAACTTCAGCCGCAGCGACCAC CTCACCACCCACATCCGCACCCACACAGGCGAAAAGCCCTTCGCCTGCGAC ATCTGTGGAAGAAAGTTTGCCAGGAGCGATGAACGCAAGAGGCATACCAAG ATCCACTTGCGGCAGAAGGACAAGAAAGCAGACAAAAGTGTTGTGGCCTCT TCGGCCACCTCCTCTCTCTTCCTACCCGTCCCCGGTTGCTACCTCTTACC CGTCCCCGGTTACTACCTCTTATCCATCCCGGCCACCACCTCATACCCATC CCCTGTGCCCACCTCCTTCTCCTCTCCCGGCTCCTCGACCTACCCATCCCCT GTGCACAGTGGCTTCCCCTCCCCGTCGGTGGCCACCACGTACTCCTCTGTT CCCCCTGCTTTCCCGGCCCAGGTCAGCAGCTTCCCTTCCTCAGCTGTCACC AACTCCTTCAGCGCCTCCACAGGGCTTTCGGACATGACAGCAACCTTTTCTC CCAGGACAATTGAAATTTGCTAAAGGGAAAGGGGAAAGAAAGGGAAAGGG AGAAAAGAAACACAAGAGACTTAAAGGACAGGAGGAGGAGATGGCCATAG GAGAGGAGGGTTCCTCTTAGGTCAGATGGAGGTTCTCAGAGCCAAGTCCTC CCTCTCTACTGGAGTGGAAGGTCTATTGGCCAACAATCCTTTCTGCCCACTT CCCCTTCCCCAATTACTATTCCCTTTGACTTCAGCTGCCTGAAACAGCCATGT CCAAGTTCTTCACCTCTATCCAAAGAACTTGATTTGCATGGATTTTGGATAAA TCATTTCAGTATCATCTCCATCATATGCCTGACCCCTTGCTCCCTTCAATGCT AGAAAATCGAGTTGGCAAATGGGGTTTGGGCCCCTCAGAGCCCTGCCCTG CACCCCTTGTACAGTGTCTGTGCCATGGATTTCGTTTTTCTTGGGGTACTCTTG ATGTGAAGATAATTTGCATATTCTATTGTATTATTTGGAGTTAGGTCCTCACTT GGGGGAAAAAAAAAAAGAAAAGCCAAGCAAACCAATGGTGATCCTCTATTT TGTGATGATGCTGTGACAATAAGTTTGAACCTTTTTTTTTGAAACAGCAGTCC CAGTATTCTCAGAGCATGTGTCAGAGTGTTGTTCCGTTAACCTTTTTGTAAAT ACTGCTTGACCGTACTCTCACATGTGGCAAAATATGGTTTGGTTTTTCTTTTT TTTTTTTTTGAAAGTGTTTTTTCTTCGTCCTTTTGGTTTAAAAAGTTTCACGTC TTGGTGCCTTTTGTGTGATGCGCCTTGCTGATGGCTTGACATGTGCAATTGT GAGGGACATGCTCACCTCTAGCCTTAAGGGGGCAGGGAGTGATGATTGG GGGAGGCTTTGGGAGCAAAATAAGGAAGAGGGCTGAGCTGAGCTTCGGTTC TCCAGAATGTAAGAAAACAAAATCTAAAACAAAATCTGAACTCTCAAAAGTCT ATTTTTTTAACTGAAAATGTAAATTTATAAATATATTCAGGAGTTGGAATGTTG | Zif268 mRNA sequence |

| SEQ ID NO: | Sequence | Description |
|---|---|---|
| | TAGTTACCTACTGAGTAGGCGGCGATTTTTGTATGTTATGAACATGCAGTTCA TTATTTTGTGGTTCTATTTTACTTTGTACTTGTGTTTGCTTAAACAAAGTGACT GTTTGGCTTATAAACACATTGAATGCGCTTTATTGCCCATGGGATATGTGGT GTATATCCTTCCAAAAAATTAAAACGAAAATAAAGTAGCTGCGATTGGG | |
| 20 | AGAGACCTGTTTTGCCTAAGGGGACGTGACTCACATTTTCGGATAATCTGAA TAAGGGGAATTGTGTCTGCTCGAGGCATCCATTCTGGTTCGGTCTCCGGACT CCCGGCTCCCGGCACGCACGGTTCACTCTGGAGCGCGCGCCCCAGGCCAG CCAAGCGCCGAGCCGGGCTGCTGCGGGCTGGGAGGGCGCGCAGGGCCGG CGCTGATTGACGGGCGCGCAGTCAGGTGACTTGGGGCGCCAAGTTCCCG ACGCGGTGGCCGGTGACCGCCGAGGCCCGGCAGACGCTGACCCGGGA ACGTAGTGGGGCTGATCTTCCGGAACAAAGTTGCTGGGCCGGCGGCGGCG GGGCGAGAGCGCCGAG | Entire Utrophin promoter "A" human DNA sequence |
| 21 | CGAGCCGAGAGTAGCAGTTGTAG | Oligo for qPCR |
| 22 | GCTAGCTAGCAAGCTTACCAGGTGAACCGACTGGGTTCTG | Oligo for qPCR |
| 23 | GTCGCCCCCCCGACCGATGTCAGC | Oligo |
| 24 | TTCTGGTGCTTGTCTCACTGA | Oligo |
| 25 | TTCTGGTGCTTGTCTCACTGA | RT PCR oligo |
| 26 | CAGTATGTTCGGCTTCCCATTC | RT PCR oligo |
| 27 | GCGGCCGC | NotI |
| 28 | ACGCGT | MluI |
| 29 | GCCCAGGTAGGG | Splice donor |
| 30 | CCCACAGCTCCT | Splice acceptor |
| 31 | ATCGAT | ClaI |
| 32 | AGATCT | BglII |
| 33 | AGAGACCTAGTGTGCCTAGAGGGGTGTGACACACATTTTCGGACAATTTGAA TAAAGGGCACGGTGCGTGCGCGGTGACTATTCCAGCTTCTGGCTTCCAG CACGCACGACTGGTTCCGGGATTCTCGCACCGCGCACCGCACGGAGCCGG GCTGCTGCGGGCTGGGAGGGCGCCTAGGGCTAGCGCTGATTGACCGGGC GCGCGGTCAGGTGACCCGAAGCGCCACGTTCTGGGAGCCCGGCCCGCGGT GGCTTCCCAGGCCGGGGCAGGACCGAACCCGGAGCCGAGGGGGACTGGT CTCCCCGGGAGAACAAAGTTGCCCGGCCTGGGGCCCCGGGGCGCGCGAG CGGCGAG | Entire Utrophin promoter "A" mouse DNA sequence |
| 34 | MEQKLISEEDLNEMEQKLISEEDLNEMEQKLISEEDLNEMEQKLISEEDLNEMEQ KLISEEDLNEMESLGDLTMGPKKKRKVAPPTDVSLGDELHLDGEDVAMAHADAL DDFDLDMLGDGDSPGPGFTPHDSAPYGALDMADFEFEQMFTDALGIDEYGGEF PGILDDRPYACPVESCDRRFSRSDELTRHIRIHTGQKPFQCRICMRNFSSRDVL RRHNRTHTGEKPFACDICGRKFASRDVLRRHNRIHLRQNDLDRTYKIR | VP16-Jazz protein with myc tag, NLS, VP16, zinc fingers |
| 35 | MEQKLISEEDLNEMEQKLISEEDLNEMEQKLISEEDLNEMEQKLISEEDLNEMEQ KLISEEDLNEMESLGDLTMGPKKKRKVAPPTDVSLGDELHLDGEDVAMAHADAL DDFDLDMLGDGDSPGPGFTPHDSAPYGALDMADFEFEQMFTDALGIDEYGGEF PGILAKRFADFTVYRNRTLQKWHDKTKLASGKLGKGFGAFERSILTQIDHILMDK ERLLRRTQTKRSVYRVLGKPEPAAQPVPESLPGEPEILPQAPANAHLKDLDEEIF DDDDFYHQLLRELIERKTSSLGILDRPYACPVESCDRRFSRSDNLVRHIRIHTGQ KPFQCRICMRNFSRSDHLTTHNRTHTGEKPFACDICGRKFADPGHLVRHNRIHT GEKPFACPVESCDRRFSRSDELTRHIRIHTGQKPFQCRICMRNFSSRDVLRRHN RTHTGEKPFACDICGRKFASRDVLRRHNRIHLRQNDLERSTGGIPVTPPQCLSW PWKLPLQCPPALS | UtroUp protein (myc tag, NLS, VP16, CJ7, zinc fingers) |
| 36 | MEQKLISEEDLNEMEQKLISEEDLNEMEQKLISEEDLNEMEQKLISEEDLNEMEQ KLISEEDLNEMESLGDLTMGPKKKRKVAPPTDVSLGDELHLDGEDVAMAHADAL DDFDLDMLGDGDSPGPGFTPHDSAPYGALDMADFEFEQMFTDALGIDEYGGEF PGILDDRPYACPVESCDRRFSRSDELTRHIRIHTGQKPFQCRICMRNFSSRDVR RHNRTHTGEKPFACDICGRKFASRDVLRRHNRIHLRQGPRSHVCAECGKAFVE SSKLKRHQLVHELERSPFSSRDLRVASL | VP16-Bagly protein (myc, NLS, VP16, 4 zinc fingers) |

-continued

| SEQ ID NO: | Sequence | Description |
|---|---|---|
| 37 | APPTDVSLGDELHLDGEDVAMAHADALDDFDLDMLGDGDSPGPGFTPHDSAP YGALDMADFEFEQMFTDALGIDEYGG | Vp16 protein seq |
| 38 | MAAAKAEMQLMSPLQISDPFGSFPHSPTMDNYPKLEEMMLLSNGAPQFLGAAG APEGSGSNSSSSSSGGGGGGGGGSNSSSSSSTFNPQADTGEQPYEHLTAESF PDISLNNEKVLVETSYPSQTTRLPPITYTGRFSLEPAPNSGNTLWPEPLFSLVSG LVSMTNPPASSSSAPSPAASSASASASQSPPLSCAVPSNDSSPIYSAAPTFPTPNT DIFPEPQSQAFPGSAGTALQYPPPAYPAAKGGFQVPMIDYLFPQQQGDLGLG TPDQKPFQGLESRTQQPSLTPLSTIKAFATQSGSQDLKALNTSYQSQLIKPSRM RKYPNRPSKTPPHERPYACPVESCDRRFSRSDELTRHIRIHTGQKPFQCRICMR NFSSRDVLRRHNRTHTGEKPFACDICGRKFASRDVLRRHNRIHLRQKDKKADK SVVASSATSSLSSYPSPVATSYPSPVTTSYPSPATTSYPSPVPTSFSSPGSSTYP SPVHSGFPSPSVATTYSSVPPAFPAQVSSFPSSAVTNSFSASTGLSDMTATFSP RTIEIC | JZif1 protein sequence (artificial protein) |
| 39 | MAAAKAEMQLMSPLQISDPFGSFPHSPTMDNYPKLEEMMLLSNGAPQFLGAAG APEGSGSNSSSSSSGGGGGGGGGSNSSSSSSTFNPQADTGEQPYEHLTAESF PDISLNNEKVLVETSYPSQTTRLPPITYTGRFSLEPAPNSGNTLWPEPLFSLVSG LVSMTNPPASSSSAPSPAASSASASASQSPPLSCAVPSNDSSPIYSAAPTFPTPNT DIFPEPQSQAFPGSAGTALQYPPPAYPAAKGGFQVPMIDYLFPQQQGDLGLG TPDQKPFQGLESRTQQPSLTPLSTIKAFATQSGSQDLKALNTSYQSQLIKPSRM RKYPNRPSKTPPHERPYACPVESCDRRFSRSDNLVRHIRIHTGQKPFQCRICMR NFSRSDHLTTHIRTHTGEKPFACDICGRKFADPGHLVRHNRIHLRQKDKKADKS VVASSATSSLSSYPSPVATSYPSPVTTSYPSPATTSYPSPVPTSFSSPGSSTYPS PVHSGFPSPSVATTYSSVPPAFPAQVSSFPSSAVTNSFSASTGLSDMTATFSPR TIEIC | JZif2 protein sequence (artificial protein) |
| 40 | GGCTGGGAG | JZif2 target sequence |
| 41 | MAAAKAEMQLMSPLQISDPFGSFPHSPTMDNYPKLEEMMLLSNGAPQFLGAAG APEGSGSNSSSSSSGGGGGGGGGSNSSSSSSTFNPQADTGEQPYEHLTAESF PDISLNNEKVLVETSYPSQTTRLPPITYTGRFSLEPAPNSGNTLWPEPLFSLVSG LVSMTNPPASSSSAPSPAASSASASASQSPPLSCAVPSNDSSPIYSAAPTFPTPNT DIFPEPQSQAFPGSAGTALQYPPPAYPAAKGGFQVPMIDYLFPQQQGDLGLG TPDQKPFQGLESRTQQPSLTPLSTIKAFATQSGSQDLKALNTSYQSQLIKPSRM RKYPNRPSKTPPHERPYACPVESCDRRFSRSDELTRHIRIHTGQKPFQCRICMR NFSRSDHLTTHIRTHTGEKPFACDICGRKFARSDERKRHTKIHLRQKDKKADKS VVASSATSSLSSYPSPVATSYPSPVTTSYPSPATTSYPSPVPTSFSSPGSSTYPS PVHSGFPSPSVATTYSSVPPAFPAQVSSFPSSAVTNSFSASTGLSDMTATFSPR TIEIC | Zif268 protein human a.a. sequence |
| 42 | CPVESCDRRFSRSDELTRHIRIHTGQKPFQCRICMRNFSSRDVLRRHNRTHTGE KPFACDICGRKFASRDVLRRHNRIH | Jzif1 zinc finger motifs a.a. seq |
| 43 | CPVESCDRRFSRSDNLVRHIRIHTGQKPFQCRICMRNFSRSDHLTTHIRTHTGE KPFACDICGRKFADPGHLVRHNRIH | JZif2 zinc finger motifs a.a. seq |
| 44 | GCGTGGGCG | Zif268 target sequence |
| 45 | CPVESCDRRFSRSDELTRHIRIH | Zif268 ZF1 a.a. seq |
| 46 | CRICMRNFSRSDHLTTHIRTH | Zif268 ZF2 a.a. seq |
| 47 | CDICGRKFARSDERKRHTKIH | JZif268 ZF3 a.a. seq |
| 48 | CPVESCDRRFSRSDELTRHIRIH | JZif1 ZF1 a.a. seq |
| 49 | CRICMRNFSSRDVLRRHNRTH | JZif1 ZF2 a.a. seq |
| 50 | CDICGRKFASRDVLRRHNRIH | JZif1 ZF3 a.a. seq |
| 51 | CPVESCDRRFSRSDNLVRHIRIH | JZif2 ZF1 a.a. seq |

| SEQ ID NO: | Sequence | Description |
|---|---|---|
| 52 | CRICMRNFSRSDHLTTHIRTH | JZif2 ZF2 a.a. seq |
| 53 | CDICGRKFADPGHLVRHNRIH | JZif2 ZF3 a.a. seq |
| 54 | CPVESCDRRFSRSDELTRHIRIH | Jazz, Bagly ZF1 a.a. seq |
| 55 | CRICMRNFSSRDVLRRHNRTH | Jazz, Bagly, ZF2 a.a. seq; UtroUP ZF5 |
| 56 | CDICGRKFASRDVLRRHNRIH | Jazz, Bagly ZF3 a.a. seq; UtroUP ZF6 |
| 57 | CAECGKAFVESSKLKRHQLVH | Bagly ZF4 a.a. seq |
| 58 | CPVESCDRRFSRSDNLVRHIRIH | UtroUp ZF1 a.a. seq |
| 59 | CRICMRNFSRSDHLTTHNRTH | UtroUp ZF2 a.a. seq |
| 60 | CDICGRKFADPGHLVRHNRIH | UtroUp ZF3 a.a. seq |
| 61 | CPVESCDRRFSRSDELTRHIRIH | UtroUp ZF4 a.a. seq |
| 62 | CCTGCAGGCAGCTGCGCGCTCGCTCGCTCACTGAGGCCGCCCGGGCAAAG CCCGGGCGTCGGGCGACCTTTGGTCGCCCGGCCTCAGTGAGCGAGCGAGC GCGCAGAGAGGGAGTGGCCAACTCCATCACTAGGGGTTCCTGCGGCCGCA CGCGTCACCAACTGGGTAACCTCTGCTGACCCCCACTCTACTTTACCATAAG TAGCTCCAAATCCTTCTAGAAAATCTGAAAGGCATAGCCCCATATATCAGTGA TATAAATAGAACCTGCAGCAGGCTCTGGTAAATGATGACTACAAGGTGGACT GGGAGGCAGCCCGGCCTTGGCAGGCATCATCCTCTAAATATAAAGATGAGT TTGTTCAGCCTTTGCAGAAGGAAAAACTGCCACCCATCCTAGAGTGCCGCGT CCTTGTCCCCCACCCCCTCCAATTTATTGGGAGGAAGGACCAGCTAAGCC TCATCTAGGAAGAGCCCCTCACCCATCTCCACCTCCACTCCAGGTCTAGCCA GTCCTGGGTTGTGACCCTTGTCTTTCAGCCCCAGGAGAGGGACACACATAG TGCCACCAAAGAGGCTGGGGGAGGGCCTCAGCCCACCAAAACCTGGGGCC AGTGCGTCCTACAGGAGGGGAACCCTCACCCCTTCAATCCCTTTAGGAGAC CCAAGGGCGCTGCGCGTCCTGAGGCGGACAGCTCCGTGTGCTCAGGCTT TGCGCCTGACAGGCCTATCCCCGGGAGCCCCCGCGCCTCCTCCCCGGCGC TCCGCCCTCGCCTCCCCCGCCAGTTGTCTATCCTGCGACAGCTGCGCGCC CTCCGGCCGCCGGTGGCCCTCTGTGCGGTGGGGGAAGGGGTCGACGTGG CTCAGCTTTTTGGATTCAGGGAGCTCGGGGGTGGGAAGAGAGAAATGGAGT TCCAGGGGCGTAAAGGAGAGGGAGTTCGCCTTCCTTCCCTTCCTGAGACTC AGGAGTGACTGCTTCTCCAATCCTCCCAAGCCCACCACTCCACACGACTCC CTCTTCCCGGTAGTCGCAAGTGGGAGTTTGGGGATCTGAGCAAAGAACCCG AAGAGGAGTTGAAATATTGGAAGTCAGCAGTCAGGCACCTTCCCGAGCGCC CAGGGCGCTCAGAGTGGACATGGTTGGGGAGGCCTTTGGGACAGGTGCGG TTCCCGGAGCGCAGGCGCACACATGCACCCACCGGCGAACGCGGTGACCC TCGCCCCACCCCATCCCCTCCGGCGGGCAACTGGGTCGGGTCAGGAGGGG CAAACCCGCTAGGGAGACACTCCATATACGGCCCGGCCCGCGTTACCTGGG ACCGGGCCAACCCGCTCCTTCTTTGGTCAACGCAGGGGACCCGGGCGGGG GCCCAGGCCGCGAACCGGCCGAGGGAGGGGGCTCTAGTGCCCAACACCCA AATATGGCTCGAGAAGGGCAGCGACATTCCTGCGGGGTGGCGCGGAGGGA ATGCCCGGGGCTATATAAAACCTGAGCAGAGGGACAAGCGGCCACCGCA GCGGACAGCGCCAAGTGAAGCCTCGCTTCCCCTCCGCGGCGACCAGGGCC CGAGCCGAGAGTAGCAGTTGTAGCTACCCGCCCAGGTAGGGCAGGAGTTG GGAGGGGACAGGGGACAGGGCACTACCGAGGGGAACCTGAAGGACTCC GGGGCAGAACCCAGTCGGTTCACCTGGTAAGCTTGCTAGCTCCGCGGATTC GAATCCCGGCCGGGAACGGTGCATTGGAACGCGGATTCCCCGTGCCAAGA GTGACGTAAGTACCGCCTATAGAGTCTATAGGCCCACAAAAAATGCTTTCTT CTTTTAATATACTTTTTTGTTTATCTTATTTCTAATACTTTCCCTAATCTCTTTCT TTCAGGGCAATAATGATACAATGTATCATGCCTCTTTGCACCATTCTAAAGAA TAACAGTGATAATTTCTGGGTTAAGGCAATAGCAATATTTCTGCATATAAATA TTTCTGCATATAAATTGTAACTGATGTAAGAGGTTTCATATTGCTAATAGCAG CTACAATCCAGCTACCATTCTGCTTTTATTTTATGGTTGGGATAAGGCTGGAT | mAAV-Bagly (complete sequence) |

| SEQ ID NO: | Sequence | Description |
|---|---|---|
| | TATTCTGAGTCCAAGCTAGGCCCTTTTGCTAATCATGTTCATACCTCTTATCT | |
| | TCCTCCCACAGCTCCTGGGCAACGTGCTGGTCTGTGTGCTGGCCCATCACT | |
| | TTGGCAAAGAATTGGGATTCGAACATCGATTTAAAGCTATGGAGCAAAAGCT | |
| | CATTTCTGAAGAGGACTTGAATGAAATGGAGCAAAAGCTCATTTCTGAAGAG | |
| | GACTTGAATGAAATGGAGCAAAAGCTCATTTCTGAAGAGGACTTGAATGAAA | |
| | TGGAGCAAAAGCTCATTTCTGAAGAGGACTTGAATGAAATGGAGCAAAAGCT | |
| | CATTTCTGAAGAGGACTTGAATGAAATGGAGAGCTTGGGCGACCTCACCATG | |
| | GGCCCTAAAAAGAAGCGTAAAGTCGCCCCCCCGACCGATGTCAGCCTGGG | |
| | GGACGAGCTCCACTTAGACGGCGAGGACGTGGCGATGGCGCATGCCGACG | |
| | CGCTAGACGATTTCGATCTGGACATGTTGGGGGACGGGGATTCCCCGGGTC | |
| | CGGGATTTACCCCCCACGACTCCGCCCCCTACGGCGCTCTGGATATGGCCG | |
| | ACTTCGAGTTTGAGCAGATGTTTACCGATGCCCTTGGAATTGACGAGTACGG | |
| | TGGGGAATTCCCGGGGATCCTCGATGACAGACCCTATGCTTGCCCAGTGGA | |
| | AAGCTGCGACCGCCGCTTTTCTAGATCGGATGAGCTTACCCGCCATATCCG | |
| | CATCCACACCGGCCAAAAACCCTTTCAATGCCGTATCTGCATGAGGAATTTC | |
| | AGCAGCCGCGATGTCCTGAGGCGCCATAACAGGACCCACACAGGGGAAAA | |
| | GCCATTCGCATGTGACATCTGCGGTCGAAAGTTTGCAAGCCGCGATGTCCT | |
| | GAGGCGCCATAACAGGATACATTTGAGGCAAGGTCCCAGATCTCACGTCTG | |
| | TGCAGAATGTGGCAAAGCGTTCGTTGAGAGCTCAAAGCTAAAACGACACCA | |
| | GCTGGTTCATGAGCTGGAGAGAAGCCCTTTTAGCTCGAGAGATCTACGGGT | |
| | GGCATCCCTGTGACCCTCCCCAGTGCCTCTCCTGGCCCTGGAAGTTGCCA | |
| | CTCCAGTGCCCACCAGCCTTGTCCTAATAAAATTAAGTTGCATCATTTTGTCT | |
| | GACTAGGTGTCCTTCTATAATATTATGGGGTGGAGGGGGGTGGTATGGAGC | |
| | AAGGGGCAAGTTGGGAAGACAACCTGTAGGGCCTGCGGGGTCTATTGGGA | |
| | ACCAAGCTGGAGTGCAGTGGCACAATCTTGGCTCACTGCAATCTCCGCCTC | |
| | CTGGGTTCAAGCGATTCTCCTGCCTCAGCCTCCCGAGTTGTTGGGATTCCA | |
| | GGCATGCATGACCAGGCTCAGCTAATTTTTGTTTTTTTGGTAGAGACGGGGT | |
| | TTCACCATATTGGCCAGGCTGGTCTCCAACTCCTAATCTCAGGTGATCTACC | |
| | CACCTTGGCCTCCCAAATTGCTGGGATTACAGGCGTGAACCACTGCTCCCTT | |
| | CCCTGTCCTTCTGATTTTGTAGGTAACCACGTGCGGACCGAGCGGCCGCAG | |
| | GAACCCCTAGTGATGGAGTTGGCCACTCCCTCTCTGCGCGCTCGCTCGCTC | |
| | ACTGAGGCCGGGCGACCAAAGGTCGCCCGACGCCCGGGCTTTGCCCGGGC | |
| | GGCCTCAGTGAGCGAGCGAGCGCGCAGCTGCCTGCAGGGGCGCCTGATGC | |
| | GGTATTTTCTCCTTACGCATCTGTGCGGTATTTCACACCGCATACGTCAAAG | |
| | CAACCATAGTACGCGCCCTGTAGCGGCGCATTAAGCGCGGCGGGTGTGGT | |
| | GGTTACGCGCAGCGTGACCGCTACACTTGCCAGCGCCCTAGCGCCCGCTC | |
| | CTTTCGCTTTCTTCCCTTCCTTTCTCGCCACGTTCGCCGGCTTTCCCCGTCA | |
| | AGCTCTAAATCGGGGGCTCCCTTTAGGGTTCCGATTTAGTGCTTTACGGCAC | |
| | CTCGACCCCAAAAAACTTGATTTGGGTGATGGTTCACGTAGTGGGCCATCGC | |
| | CCTGATAGACGGTTTTTCGCCCTTTGACGTTGGAGTCCACGTTCTTTAATAGT | |
| | GGACTCTTGTTCCAAACTGGAACAACACTCAACCCTATCTCGGGCTATTCTTT | |
| | TGATTTATAAGGGATTTTGCCGATTTCGGCCTATTGGTTAAAAAATGAGCTGA | |
| | TTTAACAAAAATTTAACGCGAATTTTAACAAAATATTAACGTTTACAATTTTAT | |
| | GGTGCACTCTCAGTACAATCTGCTCTGATGCCGCATAGTTAAGCCAGCCCC | |
| | GACACCCGCCAACACCCGCTGACGCGCCCTGACGGGCTTGTCTGCTCCCG | |
| | GCATCCGCTTACAGACAAGCTGTGACCGTCTCCGGGAGCTGCATGTGTCAG | |
| | AGGTTTTCACCGTCATCACCGAAACGCGCGAGACGAAAGGGCCTCGTGATA | |
| | CGCCTATTTTTATAGGTTAATGTCATGATAATAATGGTTTCTTAGACGTCAGG | |
| | TGGCACTTTTCGGGGAAATGTGCGCGGAACCCCTATTTGTTTATTTTTCTAAA | |
| | TACATTCAAATATGTATCCGCTCATGAGACAATAACCCTGATAAATGCTTCAA | |
| | TAATATTGAAAAAGGAAGAGTATGAGTATTCAACATTTCCGTGTCGCCCTTAT | |
| | TCCCTTTTTTGCGGCATTTTGCCTTCCTGTTTTTGCTCACCCAGAAACGCTGG | |
| | TGAAAGTAAAAGATGCTGAAGATCAGTTGGGTGCACGAGTGGGTTACATCGA | |
| | ACTGGATCTCAACAGCGGTAAGATCCTTGAGAGTTTTCGCCCCGAAGAACGT | |
| | TTTCCAATGATGAGCACTTTTAAAGTTCTGCTATGTGGCGCGGTATTATCCCG | |
| | TATTGACGCCGGGCAAGAGCAACTCGGTCGCCGCATACACTATTCTCAGAAT | |
| | GACTTGGTTGAGTACTCACCAGTCACAGAAAAGCATCTTACGGATGGCATGA | |
| | CAGTAAGAGAATTATGCAGTGCTGCCATAACCATGAGTGATAACACTGCGGC | |
| | CAACTTACTTCTGACAACGATCGGAGGACCGAAGGAGCTAACCGCTTTTTTG | |
| | CACAACATGGGGGATCATGTAACTCGCCTTGATCGTTGGGAACCGGAGCTG | |
| | AATGAAGCCATACCAAACGACGAGCGTGACACCACGATGCCTGTAGCAATG | |
| | GCAACAACGTTGCGCAAACTATTAACTGGCGAACTACTTACTCTAGCTTCCC | |
| | GGCAACAATTAATAGACTGGATGGAGGCGGATAAAGTTGCAGGACCACTTCT | |
| | GCGCTCGGCCCTTCCGGCTGGCTGGTTTATTGCTGATAAATCTGGAGCCGG | |
| | TGAGCGTGGGTCTCGCGGTATCATTGCAGCACTGGGGCCAGATGGTAAGCC | |
| | CTCCCGTATCGTAGTTATCTACACGACGGGGAGTCAGGCAACTATGGATGAA | |
| | CGAAATAGACAGATCGCTGAGATAGGTGCCTCACTGATTAAGCATTGGTAAC | |
| | TGTCAGACCAAGTTTACTCATATATACTTTAGATTGATTTAAAACTTCATTTTT | |
| | AATTTAAAAGGATCTAGGTGAAGATCCTTTTTGATAATCTCATGACCAAAATC | |
| | CCTTAACGTGAGTTTTCGTTCCACTGAGCGTCAGACCCCGTAGAAAAGATCA | |
| | AAGGATCTTCTTGAGATCCTTTTTTTCTGCGCGTAATCTGCTGCTTGCAAACA | |
| | AAAAAACCACCGCTACCAGCGGTGGTTTGTTTGCCGGATCAAGAGCTACCAA | |
| | CTCTTTTTCCGAAGGTAACTGGCTTCAGCAGAGCGCAGATACCAAATACTGT | |
| | CCTTCTAGTGTAGCCGTAGTTAGGCCACCACTTCAAGAACTCTGTAGCACCG | |
| | CCTACATACCTCGCTCTGCTAATCCTGTTACCAGTGGCTGCTGCCAGTGGCG | |

| SEQ ID NO: | Sequence | Description |
|---|---|---|
|  | ATAAGTCGTGTCTTACCGGGTTGGACTCAAGACGATAGTTACCGGATAAGGC<br>GCAGCGGTCGGGCTGAACGGGGGGTTCGTGCACACAGCCCAGCTTGGAGC<br>GAACGACCTACACCGAACTGAGATACCTACAGCGTGAGCTATGAGAAAGCG<br>CCACGCTTCCCGAAGGGAGAAAGGCGGACAGGTATCCGGTAAGCGGCAGG<br>GTCGGAACAGGAGAGCGCACGAGGGAGCTTCCAGGGGGAAACGCCTGGTA<br>TCTTTATAGTCCTGTCGGGTTTCGCCACCTCTGACTTGAGCGTCGATTTTTGT<br>GATGCTCGTCAGGGGGGCGGAGCCTATGGAAAAACGCCAGCAACGCGGCC<br>TTTTTACGGTTCCTGGCCTTTTGCTGGCCTTTTGCTCACATGT |  |
| 63 | CCTGCAGGCAGCTGCGCGCTCGCTCGCTCACTGAGGCCGCCCGGGCAAAG<br>CCCGGGCGTCGGGCGACCTTTGGTCGCCCGGCCTCAGTGAGCGAGCGAGC<br>GCGCAGAGAGGGAGTGGCCAACTCCATCACTAGGGGTTCCTGCGGCCGCA<br>CGCGTCACCAACTGGGTAACCTCTGCTGACCCCCACTCTACTTTACCATAAG<br>TAGCTCCAAATCCTTCTAGAAAATCTGAAAGGCATAGCCCACATATATCAGTGA<br>TATAAATAGAACCTGCAGCAGGCTCTGGTAAATGATGACTACAAGGTGGACT<br>GGGAGGCAGCCCGGCCTTGGCAGGCATCATCCTCTAAATATAAAGATGAGT<br>TTGTTCAGCCTTTGCAGAAGGAAAAACTGCCACCCATCCTAGAGTGCCGCGT<br>CCTTGTCCCCCCACCCCCTCCAATTTATTGGGAGGAAGGACCAGCTAAGCC<br>TCATCTAGGAAGAGCCCCTCACCCATCTCCACCTCCACTCCAGGTCTAGCCA<br>GTCCTGGGTTGTGACCCTTGTCTTTCAGCCCCAGGAGAGGGACACACATAG<br>TGCCACCAAAGAGGCTGGGGAGGGCCTCAGCCCACCAAAACCTGGGGCC<br>AGTGCGTCCTACAGGAGGGGAACCCTCACCCCTTCAATCCCTTTAGGAGAC<br>CCAAGGGCGCTGCGCGTCCCTGAGGCGGACAGCTCCGTGTGCTCAGGCTT<br>TGCGCCTGACAGGCCTATCCCCGGGAGCCCCCGCGCCTCCTCCCCGGCGC<br>TCCGCCCTCGCCTCCCCCGCCAGTTGTCTATCCTGCGACAGCTGCGCGCC<br>CTCCGGCCGCCGGTGGCCCTCTGTGCGGTGGGGAAGGGGTCGACGTGG<br>CTCAGCTTTTTGGATTCAGGGAGCTCGGGGGTGGGAAGAGAGAAATGGAGT<br>TCCAGGGGCGTAAAGGAGAGGGAGTTCGCCTTCCTTCCCTTCCTGAGACTC<br>AGGAGTGACTGCTTCTCCAATCCTCCCAAGCCCACCACTCCACACGACTCC<br>CTCTTCCCGGTAGTCGCAAGTGGGAGTTTGGGGATCTGAGCAAAGAACCCG<br>AAGAGGAGTTGAAATATTGAAGTCAGCAGTCAGGCACCTTCCCGAGCGCC<br>CAGGGCGCTCAGAGTGGACATGGTTGGGGAGGCCTTTGGGACAGGTGCGG<br>TTCCCGGAGCGCAGGCGCACACATGCACCCACCGGCGAACGCGGTGACCC<br>TCGCCCCACCCCATCCCCTCCGGCGGGCAACTGGGTCGGGTCAGGAGGGG<br>CAAACCCGCTAGGGAGACACTCCATATACGGCCCGGCCCGCGTTACCTGGG<br>ACCGGGCCAACCCGCTCCTTCTTTGGTCAACGCAGGGGACCCGGGCGGGG<br>GCCCAGGCCGCGAACCGGCCGAGGGAGGGGGCTCTAGTGCCCAACACCCA<br>AATATGGCTCGAGAAGGGCAGCGACATTCCTGCGGGGTGGCGCGGAGGGA<br>ATGCCCGCGGGCTATATAAAACCTGAGCAGAGGGACAAGCGGCCACCGCA<br>GCGGACAGCGCCAAGTGAAGCCTCGCTTCCCCTCCGCGGCGACCAGGGCC<br>CGAGCCGAGAGTAGCAGTTGTAGCTACCCGCCCAGGTAGGGCAGGAGTTG<br>GGAGGGGACAGGGGGACAGGGCACTACCGAGGGGAACCTGAAGGACTCC<br>GGGGCAGAACCCAGTCGGTTCACCTGGTAAGCTTGCTAGCTCCGCGGATTC<br>GAATCCCGGCCGGGAACGGTGCATTGGAACGCGGATTCCCCGTGCCAAGA<br>GTGACGTAAGTACCGCCTATAGAGTCTATAGGCCCACAAAAAATGCTTTCTT<br>CTTTTAATATACTTTTTTGTTTATCTTATTTCTAATACTTTCCCTAATCTCTTTCT<br>TTCAGGGCAATAATGATACAATGTATCATGCCTCTTTGCACCATTCTAAAGAA<br>TAACAGTGATAATTTCTGGGTTAAGGCAATAGCAATATTTCTGCATATAAATA<br>TTTCTGCATATAAATTGTAACTGATGTAAGAGGTTTCATATTGCTAATAGCAG<br>CTACAATCCAGCTACCATTCTGCTTTTATTTTATGGTTGGGATAAGGCTGGAT<br>TATTCTGAGTCCAAGCTAGGCCCTTTTGCTAATCATGTTCATACCTCTTATCT<br>TCCTCCCACAGCTCCTGGGCAACGTGCTGGTCTGTGTGCTGGCCCATCACT<br>TTGGCAAAGAATTGGGATTCGAACATCGATTTAAAGCTATGGAGCAAAAGCT<br>CATTTCTGAAGAGGACTTGAATGAAATGGAGCAAAAGCTCATTTCTGAAGAG<br>GACTTGAATGAAATGGAGCAAAAGCTCATTTCTGAAGAGGACTTGAATGAAA<br>TGGAGCAAAAGCTCATTTCTGAAGAGGACTTGAATGAAATGGAGCAAAAGCT<br>CATTTCTGAAGAGGACTTGAATGAAATGGAGAGCTTGGGCGACCTCACCATG<br>GGCCCTAAAAAGAAGCGTAAAGTCGCCCCCCCGACCGATGTCAGCCTGGG<br>GGACGAGCTCCACTTAGACGGCGAGGACGTGGCGATGGCGCATGCCGACG<br>CGCTAGACGATTTCGATCTGGACATGTTGGGGGACGGGGATTCCCCGGGTC<br>CGGGATTTACCCCCCACGACTCCGCCCCCTACGGCGCTCTGGATATGGCCG<br>ACTTCGAGTTTGAGCAGATGTTTACCGATGCCCTTGGAATTGACGAGTACGG<br>TGGGGAATTCCCGGGGATCTTGGCAAAGCGCTTTGCCGACTTTACAGTCTA<br>CAGGAACCGCACACTTCAGAAATGGCACGATAAGACCAAACTGGCTTCTGG<br>AAAACTGGGGAAGGGTTTTGGTGCCTTTGAACGCTCAATCTTGACTCAGATC<br>GACCTATATTCTGATGGACAAAGAGAGATTACTTCGAAGGACACAGACCAAGC<br>GCTCTGTCTATCGAGTTCTTGGCAAACCTGAGCCAGCAGCTCAGCCTGTCC<br>CAGAGAGTTTGCCAGGGGAACCGGAGATCCTTCCTCAAGCCCCTGCTAATG<br>CTCATCTGAAGGACTTGGATGAAGAAATCTTTGATGATGATGACTTTTACCAC<br>CAGCTCCTTCGAGAACTCATAGAACGGAAGACCAGCTCCTTGGGGATCCTG<br>GATCGCCCTTACGCCTGCCCTGTGGAATCTTGCGACCGCCGGTTCTCCCGC<br>AGCGATAACCTGGTGCGGCACATCCGGATTCACACCGGCCAGAAACCTTTC<br>CAGTGCAGGATCTGCATGAGAAATTTCTCCCGGTCCGACCACCTGACCACC<br>CACAATAGGACCCACACCGGCGAGAAACCCTTTGCCTGCGACATCTGCGGG<br>AGAAAGTTCGCCGACCCCGGCCACCTGGTGAGACACAATAGAATCCACACC | mAAV-<br>UtroUp<br>(complete<br>sequence) |

| SEQ ID NO: | Sequence | Description |
|---|---|---|
| | GGTGAAAAGCCCTTCGCCTGTCCCGTGGAGAGCTGCGATCGCAGATTCAGC<br>CGCAGCGACGAGCTGACAAGGCACATCAGAATCCACACCGGGCAGAAGCC.<br>TTTTCAGTGCCGGATCTGCATGAGGAACTTCAGCTCCCGGACGTGCTGAG<br>ACGCCACAATCGCACACACACCGGCGAAAAGCCCTTCGCCTGTGATATTTG<br>CGGGCGGAAATTTGCCTCCAGAGATGTGCTGCGCCGCCACAACCGCATTCA<br>CCTGAGACAGAACGATCTCGAGAGATCTACGGGTGGCATCCCTGTGACCCC<br>TCCCCAGTGCCTCTCCTGGCCCTGGAAGTTGCCACTCCAGTGCCCACCAGC<br>CTTGTCCTAATAAAATTAAGTTGCATCATTTTGTCTGACTAGGTGTCCTTCTAT<br>AATATTATGGGGTGGAGGGGGGTGGTATGGAGCAAGGGGCAAGTTGGGAA<br>GACAACCTGTAGGGCCTGCGGGGTCTATTGGGAACCAAGCTGGAGTGCAGT<br>GGCACAATCTTGGCTCACTGCAATCTCCGCCTCCTGGGTTCAAGCGATTCTC<br>CTGCCTCAGCCTCCCGAGTTGTTGGGATTCCAGGCATGCATGACCAGGCTC<br>AGCTAATTTTTGTTTTTTGGTAGAGACGGGGTTTCACCATATTGGCCAGGCT<br>GGTCTCCAACTCCTAATCTCAGGTGATCTACCCACCTTGGCCTCCCAAATTG<br>CTGGGATTACAGGCGTGAACCACTGCTCCCTTCCCTGTCCTTCTGATTTTGT<br>AGGTAACCACGTGCGGACCGAGCGGCCGCAGGAACCCCTAGTGATGGAGT<br>TGGCCACTCCCTCTCTGCGCGCTCGCTCGCTCACTGAGGCCGGGCGACCA<br>AAGGTCGCCCGACGCCCGGGCTTTGCCCGGGCGGCCTCAGTGAGCGAGCG<br>AGCGCGCAGCTGCCTGCAGGGGCGCCTGATGCGGTATTTTCTCCTTACGCA<br>TCTGTGCGGTATTTCACACCGCATACGTCAAAGCAACCATAGTACGCGCCCT<br>GTAGCGGCGCATTAAGCGCGGCGGGTGTGGTGGTTACGCGCAGCGTGACC<br>GCTACACTTGCCAGCGCCCTAGCGCCCGCTCCTTTCGCTTTCTTCCCTTCCT<br>TTCTCGCCACGTTCGCCGGCTTTCCCCGTCAAGCTCTAAATCGGGGGCTCC<br>CTTTAGGGTTCCGATTTAGTGCTTTACGGCACCTCGACCCCAAAAAACTTGA<br>TTTGGGTGATGGTTCACGTAGTGGGCCATCGCCCTGATAGACGGTTTTCGC<br>CCTTTGACGTTGGAGTCCACGTTCTTTAATAGTGGACTCTTGTTCCAAACTG<br>GAACAACACTCAACCCTATCTCGGGCTATTCTTTTGATTTATAAGGGATTTTG<br>CCGATTTCGGCCTATTGGTTAAAAAATGAGCTGATTTAACAAAAATTTAACGC<br>GAATTTTAACAAAATATTAACGTTTACAATTTTATGGTGCACTCTCAGTACAAT<br>CTGCTCTGATGCCGCATAGTTAAGCCAGCCCCGACACCCGCCAACACCCGC<br>TGACGCGCCCTGACGGGCTTGTCTGCTCCCGGCATCCGCTTACAGACAAGC<br>TGTGACCGTCTCCGGGAGCTGCATGTGTCAGAGGTTTTCACCGTCATCACC<br>GAAACGCGCGAGACGAAAGGGCCTCGTGATACGCCTATTTTTATAGGTTAAT<br>GTCATGATAATAATGGTTTCTTAGACGTCAGGTGGCACTTTTCGGGGAAATG<br>TGCGCGGAACCCCTATTTGTTTATTTTTCTAAATACATTCAAATATGTATCCG<br>CTCATGAGACAATAACCCTGATAAATGCTTCAATAATATTGAAAAAGGAAGAG<br>TATGAGTATTCAACATTTCCGTGTCGCCCTTATTCCCTTTTTTGCGGCATTTT<br>GCCTTCCTGTTTTTGCTCACCCAGAAACGCTGGTGAAAGTAAAAGATGCTGA<br>AGATCAGTTGGGTGCACGAGTGGGTTACATCGAACTGGATCTCAACAGCGG<br>TAAGATCCTTGAGAGTTTTCGCCCCGAAGAACGTTTTCCAATGATGAGCACT<br>TTTAAAGTTCTGCTATGTGGCGCGGTATTATCCCGTATTGACGCCGGGCAAG<br>AGCAACTCGGTCGCCGCATACACTATTCTCAGAATGACTTGGTTGAGTACTC<br>ACCAGTCACAGAAAAGCATCTTACGGATGGCATGACAGTAAGAGAATTATGC<br>AGTGCTGCCATAACCATGAGTGATAACACTGCGGCCAACTTACTTCTGACAA<br>CGATCGGAGGACCGAAGGAGCTAACCGCTTTTTTGCACAACATGGGGGATC<br>ATGTAACTCGCCTTGATCGTTGGGAACCGGAGCTGAATGAAGCCATACCAAA<br>CGACGAGCGTGACACCACGATGCCTGTAGCAATGGCAACAACGTTGCGCAA<br>ACTATTAACTGGCGAACTACTTACTCTAGCTTCCCGGCAACAATTAATAGACT<br>GGATGGAGGCGGATAAAGTTGCAGGACCACTTCTGCGCTCGGCCCTTCCGG<br>CTGGCTGGTTTATTGCTGATAAATCTGGAGCCGGTGAGCGTGGGTCTCGCG<br>GTATCATTGCAGCACTGGGGCCAGATGGTAAGCCCTCCCGTATCGTAGTTAT<br>CTACACGACGGGGAGTCAGGCAACTATGGATGAACGAAATAGACAGATCGC<br>TGAGATAGGTGCCTCACTGATTAAGCATTGGTAACTGTCAGACCAAGTTTAC<br>TCATATATACTTTAGATTGATTTAAAACTTCATTTTTAATTTAAAAGGATCTAG<br>GTGAAGATCCTTTTTGATAATCTCATGACCAAAATCCCTTAACGTGAGTTTTC<br>GTTCCACTGAGCGTCAGACCCCGTAGAAAAGATCAAAGGATCTTCTTGAGAT<br>CCTTTTTTTCTGCGCGTAATCTGCTGCTTGCAAACAAAAAAACCACCGCTACC<br>AGCGGTGGTTTGTTTGCCGGATCAAGAGCTACCAACTCTTTTTCCGAAGGTA<br>ACTGGCTTCAGCAGAGCGCAGATACCAAATACTGTCCTTCTAGTGTAGCCGT<br>AGTTAGGCCACCACTTCAAGAACTCTGTAGCACCGCCTACATACCTCGCTCT<br>GCTAATCCTGTTACCAGTGGCTGCTGCCAGTGGCGATAAGTCGTGTCTTACC<br>GGGTTGGACTCAAGACGATAGTTACCGGATAAGGCGCAGCGGTCGGGCTG<br>AACGGGGGGTTCGTGCACACAGCCCAGCTTGGAGCGAACGACCTACACCG<br>AACTGAGATACCTACAGCGTGAGCTATGAGAAAGCGCCACGCTTCCCGAAG<br>GGAGAAAGGCGGACAGGTATCCGGTAAGCGGCAGGGTCGGAACAGGAGAG<br>CGCACGAGGGAGCTTCCAGGGGAAACGCCTGGTATCTTTATAGTCCTGTC<br>GGGTTTCGCCACCTCTGACTTGAGCGTCGATTTTTGTGATGCTCGTCAGGG<br>GGGCGGAGCCTATGGAAAAACGCCAGCAACGCGGCCTTTTTACGGTTCCTG<br>GCCTTTTGCTGGCCTTTTGCTCACATGT | |
| 64 | CCTGCAGGCAGCTGCGCGCTCGCTCGCTCACTGAGGCCGCCCGGGCAAAG<br>CCCGGGCGTCGGGCGACCTTTGGTCGCCCGGCCTCAGTGAGCGAGCGAGC<br>GCGCAGAGAGGGAGTGGCCAACTCCATCACTAGGGGTTCCTGCGGCCGCA<br>CGCGTCACCAACTGGGTAACCTCTGCTGACCCCACTCTACTTTACCATAAG<br>TAGCTCCAAATCCTTCTAGAAAATCTGAAAGGCATAGCCCCATATATCAGTGA | mAAV-JZif1<br>(complete<br>sequence) |

| SEQ ID NO: | Sequence | Description |
|---|---|---|
| | TATAAATAGAACCTGCAGCAGGCTCTGGTAAATGATGACTACAAGGTGGACT | |
| | GGGAGGCAGCCCGGCCTTGGCAGGCATCATCCTCTAAATATAAAGATGAGT | |
| | TTGTTCAGCCTTTGCAGAAGGAAAAACTGCCACCCATCCTAGAGTGCCGCGT | |
| | CCTTGTCCCCCACCCCCTCCAATTTATTGGGAGGAAGGACCAGCTAAGCC | |
| | TCATCTAGGAAGAGCCCCTCACCCATCTCCACCTCCACTCCAGGTCTAGCCA | |
| | GTCCTGGGTTGTGACCCTTGTCTTTCAGCCCCAGGAGAGGGACACACATAG | |
| | TGCCACCAAAGAGGCTGGGGGAGGGCCTCAGCCCACCAAAACCTGGGGCC | |
| | AGTGCGTCCTACAGGAGGGGAACCCTCACCCCTTCAATCCCTTTAGGAGAC | |
| | CCAAGGGCGCTGCGCGTCCCTGAGGCGGACAGCTCCGTGTGCTCAGGCTT | |
| | TGCGCCTGACAGGCCTATCCCCGGGAGCCCCGCGCCTCCTCCCCGGCGC | |
| | TCCGCCCTCGCCTCCCCCGCCAGTTGTCTATCCTGCGACAGCTGCGCGCC | |
| | CTCCGGCCGCCGGTGGCCCTCTGTGCGGTGGGGAAGGGGTCGACGTGG | |
| | CTCAGCTTTTTGGATTCAGGGAGCTCGGGGGTGGGAAGAGAGAAATGGAGT | |
| | TCCAGGGGCGTAAGGAGAGGGAGTTCGCCTTCCTTCCCTTCCTGAGACTC | |
| | AGGAGTGACTGCTTCTCAATCCTCCCAAGCCCACCACTCCACACGACTCC | |
| | CTCTTCCCGGTAGTCGCAAGTGGGAGTTTGGGGATCTGAGCAAAGAACCCG | |
| | AAGAGGAGTTGAAATATTGGAAGTCAGCAGTCAGGCACCTTCCCGAGCGCC | |
| | CAGGGCGCTCAGAGTGGACATGGTTGGGGAGGCCTTTGGGACAGGTGCGG | |
| | TTCCCGGAGCGCAGGCGCACACATGCACCCACCGGCGAACGCGGTGACCC | |
| | TCGCCCCACCCCATCCCCTCCGGCGGGCAACTGGGTCGGGTCAGGAGGGG | |
| | CAAACCCGCTAGGGAGACACTCCATATACGGCCCGGCCCGCGTTACCTGGG | |
| | ACCGGGCCAACCCGCTCCTTCTTTGGTCAACGCAGGGGACCCGGGCGGGG | |
| | GCCCAGGCCGCGAACCGGCCGAGGGAGGGGGCTCTAGTGCCCAACACCCA | |
| | AATATGGCTCGAGAAGGGCAGCGACATTCCTGCGGGGTGGCGCGGAGGGA | |
| | ATGCCCGCGGGCTATATAAACCTGAGCAGAGGGACAAGCGGCCACCGCA | |
| | GCGGACAGCGCCAAGTGAAGCCTCGCTTCCCCTCCGCGGCGACCAGGGCC | |
| | CGAGCCGAGAGTAGCAGTTGTAGCTACCCGCCCAGGTAGGGCAGGAGTTG | |
| | GGAGGGGACAGGGGGACAGGGCACTACCGAGGGGAACCTGAAGGACTCC | |
| | GGGGCAGAACCCAGTCGGTTCACCTGGTAAGCTTGCTAGCTCCGCGGATTC | |
| | GAATCCCGGCCGGGAACGGTGCATTGGAACGCGGATTCCCCGTGCCAAGA | |
| | GTGACGTAAGTACCGCCTATAGAGTCTATAGGCCCACAAAAAATGCTTTCTT | |
| | CTTTTAATATACTTTTTTGTTTATCTTATTTCTAATACTTTCCCTAATCTCTTTCT | |
| | TTCAGGGCAATAATGATACAATGTATCATGCCTCTTTGCACCATTCTAAAGAA | |
| | TAACAGTGATAAATTTCTGGGTTAAGGCAATAGCAATATTTCTGCATATAAATA | |
| | TTTCTGCATATAAATTGTAACTGATGTAAGAGGTTTCATATTGCTAATAGCAG | |
| | CTACAATCCAGCTACCATTCTGCTTTTATTTTATGGTTGGGATAAGGCTGGAT | |
| | TATTCTGAGTCCAAGCTAGGCCCTTTTGCTAATCATGTTCATACCTCTTATCT | |
| | TCCTCCCACAGCTCCTGGGCAACGTGCTGGTCTGTGTGCTGGCCCATCACT | |
| | TTGGCAAAGAATTGGGATTCGAACATCGATGGTACCGAATTCAATGGCCGCT | |
| | GCCAAGGCCGAGATGCAGCTGATGAGCCCCCTGCAGATCAGCGACCCCTTC | |
| | GGCAGCTTCCCCCACAGCCCCACCATGGACAACTACCCCAAGCTGGAAGAG | |
| | ATGATGCTGCTGAGCAATGGCGCTCCTCAGTTCCTGGGAGCCGCTGGCGCC | |
| | CCTGAGGGCAGCGGCAGCAATAGCAGCAGCAGCTCTAGCGGAGGCGG | |
| | AGGGGGAGGCGGCGGAAGCAATAGCTCCAGCTCCAGCAGCACATTCAATC | |
| | CACAAGCCGACACCGGCGAGCAGCCCTATGAGCACCTGACCGCCGAGAGC | |
| | TTCCCCGACATCAGCCTGAACAACGAGAAGGTGCTGGTGGAAACCAGCTAC | |
| | CCCAGCCAGACCACCCGGCTGCCCCCTATCACCTACACAGGCCGGTTCAGC | |
| | CTGGAACCCGCCCCTAACAGCGGCAACACCCTGTGGCCCGAGCCCCTGTTT | |
| | AGCCTGGTGTCCGGCCTGGTGTCTATGACCAACCCCCCTGCCAGCAGCTCC | |
| | TCTGCCCCAAGCCCTGCCGCCAGCTCTGCCTCTGCCAGCCAGAGCCCTCCA | |
| | CTGAGCTGCGCCGTGCCCAGCAACGACAGCAGCCCCATCTACAGCGCCGC | |
| | TCCCACCTTCCCCACCCCCAACACCGACATCTTCCCCGAGCCTCAGAGCCA | |
| | GGCCTTTCCTGGATCTGCCGGCACCGCCCTGCAGTACCCACCTCCTGCCTA | |
| | TCCTGCCGCCAAGGGCGGCTTCCAGGTGCCCATGATCCCCGACTACCTGTT | |
| | CCCCCAGCAGCAGGGCGATCTGGGCCTGGGCACCCCCGACCAGAAGCCTT | |
| | TCCAGGGCCTCGAAAGCCGGACCCAGCAGCCAAGCCTGACCCCCCTGAGC | |
| | ACCATCAAGGCCTTCGCCACCCAGAGCGGCAGCCAGGACCTGAAGGCCCT | |
| | GAACACCAGCTACCAGAGCCAGCTGATCAAGCCCAGCCGGATGCGGAAGTA | |
| | CCCCAACCGGCCCAGCAAGACCCCCCCACACGAGAGGCCTTACGCCTGCC | |
| | CCGTGGAAAGCTGCGACAGACGGTTCAGCAGAAGCGACGAGCTGACCCGG | |
| | CACATCCGGATCCACACCGGCCAGAAACCCTTCCAGTGCCGGATCTGCATG | |
| | CGGAACTTCAGCAGCCGGGACGTGCTGCGGCGGCACAATAGAACCCACAC | |
| | AGGCGAGAAGCCCTTCGCCTGCGACATCTGCGGCCGGAAGTTCGCCAGCA | |
| | GAGATGTGCTGCGGAGACACAACAGGATCCACCTGAGACAGAAGGACAAGA | |
| | AAGCCGACAAGAGCGTGGTCGCCAGCAGCGCTACCAGCAGCCTGAGCAGC | |
| | TACCCTTCTCCTGTGGCCACCTCCTACCCAAGCCCAGTGACCACAAGCTACC | |
| | CATCCCCCGCCACCACCTCTTATCCCAGCCCCGTGCCTACCAGCTTCAGCT | |
| | CTCCCGGCAGCTCCACATACCCCAGCCCTGTGCATAGCGGCTTCCCTAGCC | |
| | CTAGCGTGGCCACCACATACAGCAGCGTGCCCCCTGCCTTCCCAGCTCAAG | |
| | TGTCCAGCTTCCCCAGCTCCGCGTGACCAACAGCTTCAGCGCCAGCACCG | |
| | GCCTGAGCGACATGACCGCCACCTTCAGCCCCCGGACCATCGAGATCTGCT | |
| | GACTCGAGAGATCTACGGGTGGCATCCCTGTGACCCCTCCCCAGTGCCTCT | |
| | CCTGGCCCTGGAAGTTGCCACTCCAGTGCCCACCAGCCTTGTCCTAATAAAA | |
| | TTAAGTTGCATCATTTTGTCTGACTAGGTGTCCTTCTATAATATTATGGGGTG | |
| | GAGGGGGGTGGTATGGAGCAAGGGGCAAGTTGGGAAGACAACCTGTAGGG | |

| SEQ ID NO: | Sequence | Description |
|---|---|---|
| | CCTGCGGGGTCTATTGGGAACCAAGCTGGAGTGCAGTGGCACAATCTTGGC<br>TCACTGCAATCTCCGCCTCCTGGGTTCAAGCGATTCTCCTGCCTCAGCCTCC<br>CGAGTTGTTGGGATTCCAGGCATGCATGACCAGGCTCAGCTAATTTTTGTTT<br>TTTTGGTAGAGACGGGGTTTCACCATATTGGCCAGGCTGGTCTCCAACTCCT<br>AATCTCAGGTGATCTACCCACCTTGGCCTCCCAAATTGCTGGGATTACAGGC<br>GTGAACCACTGCTCCCTTCCCTGTCCTTCTGATTTTGTAGGTAACCACGTGC<br>GGACCGAGCGGCCGCAGGAACCCCTAGTGATGGAGTTGGCCACTCCCTCT<br>CTGCGCGCTCGCTCGCTCACTGAGGCCGGGCGACCAAAGGTCGCCCGACG<br>CCCGGGCTTTGCCCGGGCGGCCTCAGTGAGCGAGCGAGCGCGCAGCTGC<br>CTGCAGGGGCGCCTGATGCGGTATTTTCTCCTTACGCATCTGTGCGGTATTT<br>CACACCGCATACGTCAAAGCAACCATAGTACGCGCCCTGTAGCGGCGCATT<br>AAGCGCGGCGGGTGTGGTGGTTACGCGCAGCGTGACCGCTACACTTGCCA<br>GCGCCCTAGCGCCCGCTCCTTTCGCTTTCTTCCCTTCCTTTCTCGCCACGTT<br>CGCCGGCTTTCCCCGTCAAGCTCTAAATCGGGGGCTCCCTTTAGGGTTCCG<br>ATTTAGTGCTTTACGGCACCTCGACCCCAAAAAACTTGATTTGGGTGATGGT<br>TCACGTAGTGGGCCATCGCCCTGATAGACGGTTTTTCGCCCTTTGACGTTGG<br>AGTCCACGTTCTTTAATAGTGGACTCTTGTTCCAAACTGGAACAACACTCAAC<br>CCTATCTCGGGCTATTCTTTTGATTTATAAGGGATTTTGCCGATTTCGGCCTA<br>TTGGTTAAAAAATGAGCTGATTTAACAAAAATTTAACGCGAATTTTAACAAAAT<br>ATTAACGTTTACAATTTTATGGTGCACTCTCAGTACAATCTGCTCTGATGCCG<br>CATAGTTAAGCCAGCCCCGACACCCGCCAACACCCGCTGACGCGCCCTGAC<br>GGGCTTGTCTGCTCCCGGCATCCGCTTACAGACAAGCTGTGACCGTCTCCG<br>GGAGCTGCATGTGTCAGAGGTTTTCACCGTCATCACCGAAACGCGCGAGAC<br>GAAAGGGCCTCGTGATACGCCTATTTTTATAGGTTAATGTCATGATAATAATG<br>GTTTCTTAGACGTCAGGTGGCACTTTTCGGGGAAATGTGCGCGGAACCCCT<br>ATTTGTTTATTTTTCTAAATACATTCAAATATGTATCCGCTCATGAGACAATAA<br>CCCTGATAAATGCTTCAATAATATTGAAAAAGGAAGAGTATGAGTATTCAACA<br>TTTCCGTGTCGCCCTTATTCCCTTTTTTGCGGCATTTTGCCTTCCTGTTTTTG<br>CTCACCCAGAAACGCTGGTGAAAGTAAAAGATGCTGAAGATCAGTTGGGTG<br>CACGAGTGGGTTACATCGAACTGGATCTCAACAGCGGTAAGATCCTTGAGA<br>GTTTTCGCCCCGAAGAACGTTTTCCAATGATGAGCACTTTTAAAGTTCTGCTA<br>TGTGGCGCGGTATTATCCCGTATTGACGCCGGGCAAGAGCAACTCGGTCGC<br>CGCATACACTATTCTCAGAATGACTTGGTTGAGTACTCACCAGTCACAGAAA<br>AGCATCTTACGGATGGCATGACAGTAAGAGAATTATGCAGTGCTGCCATAAC<br>CATGAGTGATAACACTGCGGCCAACTTACTTCTGACAACGATCGGAGGACC<br>GAAGGAGCTAACCGCTTTTTTGCACAACATGGGGGATCATGTAACTCGCCTT<br>GATCGTTGGGAACCGGAGCTGAATGAAGCCATACCAAACGACGAGCGTGAC<br>ACCACGATGCCTGTAGCAATGGCAACAACGTTGCGCAAACTATTAACTGGCG<br>AACTACTTACTCTAGCTTCCCGGCAACAATTAATAGACTGGATGGAGGCGA<br>TAAAGTTGCAGGACCACTTCTGCGCTCGGCCCTTCCGGCTGGCTGGTTTATT<br>GCTGATAAATCTGGAGCCGGTGAGCGTGGGTCTCGCGGTATCATTGCAGCA<br>CTGGGGCCAGATGGTAAGCCCTCCCGTATCGTAGTTATCTACACGACGGGG<br>AGTCAGGCAACTATGGATGAACGAAATAGACAGATCGCTGAGATAGGTGCC<br>TCACTGATTAAGCATTGGTAACTGTCAGACCAAGTTTACTCATATATACTTTA<br>GATTGATTTAAAACTTCATTTTTAATTTAAAAGGATCTAGGTGAAGATCCTTTT<br>TGATAATCTCATGACCAAAATCCCTTAACGTGAGTTTTCGTTCCACTGAGCGT<br>CAGACCCCGTAGAAAAGATCAAAGGATCTTCTTGAGATCCTTTTTTTCTGCG<br>CGTAATCTGCTGCTTGCAAACAAAAAAACCACCGCTACCAGCGGTGGTTTGT<br>TTGCCGGATCAAGAGCTACCAACTCTTTTTCCGAAGGTAACTGGCTTCAGCA<br>GAGCGCAGATACCAAATACTGTCCTTCTAGTGTAGCCGTAGTTAGGCCACCA<br>CTTCAAGAACTCTGTAGCACCGCCTACATACCTCGCTCTGCTAATCCTGTTA<br>CCAGTGGCTGCTGCCAGTGGCGATAAGTCGTGTCTTACCGGGTTGGACTCA<br>AGACGATAGTTACCGGATAAGGCGCAGCGGTCGGGCTGAACGGGGGGTTC<br>GTGCACACAGCCCAGCTTGGAGCGAACGACCTACACCGAACTGAGATACCT<br>ACAGCGTGAGCTATGAGAAAGCGCCACGCTTCCCGAAGGGAGAAAGGCGG<br>ACAGGTATCCGGTAAGCGGCAGGGTCGGAACAGGAGAGCGCACGAGGGAG<br>CTTCCAGGGGGAAACGCCTGGTATCTTTATAGTCCTGTCGGGTTTCGCCACC<br>TCTGACTTGAGCGTCGATTTTTGTGATGCTCGTCAGGGGGCGGAGCCTAT<br>GGAAAAACGCCAGCAACGCGGCCTTTTTACGGTTCCTGGCCTTTTGCTGGC<br>CTTTTGCTCACATGT | |
| 65 | CCTGCAGGCAGCTGCGCGCTCGCTCGCTCACTGAGGCCGCCCGGGCAAAG<br>CCCGGGCGTCGGGCGACCTTTGGTCGCCCGGCCTCAGTGAGCGAGCGAGC<br>GCGCAGAGAGGGAGTGGCCAACTCCATCACTAGGGGTTCCTGCGGCCGCA<br>CGCGTCACCAACTGGGTAACCTCTGCTGACCCCCACTCTACTTTACCATAAG<br>TAGCTCCAAATCCTTCTAGAAAATCTGAAAGGCATAGCCCCATATATCAGTGA<br>TATAAATAGAACCTGCAGCAGGCTCTGGTAAATGATGACTACAAGGTGGACT<br>GGGAGGCAGCCCGGCCTTGGCAGGCATCATCCTCTAAATATAAAGATGAGT<br>TTGTTCAGCCTTTGCAGAAGGAAAAACTGCCACCCATCCTAGAGTGCCGCGT<br>CCTTGTCCCCCCACCCCCTCCAATTTATTGGGAGGAAGGACCAGCTAAGCC<br>TCATCTAGGAAGAGCCCCTCACCCATCTCCACCTCCACTCCAGGTCTAGCCA<br>GTCCTGGGTTGTGACCCTTGTCTTTCAGCCCCAGGAGAGGGACACACATAG<br>TGCCACCAAAGAGGCTGGGGAGGGCCTCAGCCCACCAAAACCTGGGGCC<br>AGTGCGTCCTACAGGAGGGGAACCCTCACCCCTTCAATCCCTTTAGGAGAC<br>CCAAGGGCGCTGCGCGTCCCTGAGGCGGACAGCTCCGTGTGCTCAGGCTT | mAAV-JZif2 complete sequence |

| SEQ ID NO: | Sequence | Description |
|---|---|---|
| | TGCGCCTGACAGGCCTATCCCCGGGAGCCCCCGCGCCTCCTCCCCGGCGC | |
| | TCCGCCCTCGCCTCCCCCCGCCAGTTGTCTATCCTGCGACAGCTGCGCGCC | |
| | CTCCGGCCGCCGGTGGCCCTCTGTGCGGTGGGGGAAGGGGTCGACGTGG | |
| | CTCAGCTTTTTGGATTCAGGGAGCTCGGGGGTGGGAAGAGAGAAATGGAGT | |
| | TCCAGGGGCGTAAAGGAGAGGGAGTTCGCCTTCCTTCCCTTCCTGAGACTC | |
| | AGGAGTGACTGCTTCTCCAATCCTCCCAAGCCCACCACTCCACACGACTCC | |
| | CTCTTCCCGGTAGTCGCAAGTGGGAGTTTGGGGATCTGAGCAAAGAACCCG | |
| | AAGAGGAGTTGAAATATTGGAAGTCAGCAGTCAGGCACCTTCCCGAGCGCC | |
| | CAGGGCGCTCAGAGTGGACATGGTTGGGGAGGCCTTTGGGACAGGTGCGG | |
| | TTCCCGGAGCGCAGGCGCACACATGCACCCACCGGCGAACGCGGTGACCC | |
| | TCGCCCCACCCCATCCCCTCCGGCGGGCAACTGGGTCGGGTCAGGAGGGG | |
| | CAAACCCGCTAGGGAGACACTCCATATACGGCCCGGCCCGCGTTACCTGGG | |
| | ACCGGGCCAACCCGCTCCTTCTTTGGTCAACGCAGGGGACCCGGGCGGGG | |
| | GCCCAGGCCGCGAACCGGCCGAGGGAGGGGGCTCTAGTGCCCAACACCCA | |
| | AATATGGCTCGAGAAGGGCAGCGACATTCCTGCGGGGTGGCGCGGAGGGA | |
| | ATGCCCGCGGGCTATATAAAACCTGAGCAGAGGGACAAGCGGCCACCGCA | |
| | GCGGACAGCGCCAAGTGAAGCCTCGCTTCCCCTCCGCGGCGACCAGGGCC | |
| | CGAGCCGAGAGTAGCAGTTGTAGCTACCCGCCCAGGTAGGGCAGGAGTTG | |
| | GGAGGGGACAGGGGGACAGGGCACTACCGAGGGGAACCTGAAGGACTCC | |
| | GGGGCAGAACCCAGTCGGTTCACCTGGTAAGCTTGCTAGCTCCGCGGATTC | |
| | GAATCCCGGCCGGGAACGGTGCATTGGAACGCGGATTCCCCGTGCCAAGA | |
| | GTGACGTAAGTACCGCCTATAGAGTCTATAGGCCCACAAAAAATGCTTTCTT | |
| | CTTTTAATATACTTTTTTGTTTATCTTATTTCTAATACTTTCCCTAATCTCTTTCT | |
| | TTCAGGGCAATAATGATACAATGTATCATGCCTCTTTGCACCATTCTAAAGAA | |
| | TAACAGTGATAATTTCTGGGTTAAGGCAATAGCAATATTTCTGCATATAAATA | |
| | TTTCTGCATATAAATTGTAACTGATGTAAGAGGTTTCATATTGCTAATAGCAG | |
| | CTACAATCCAGCTACCATTCTGCTTTTATTTTATGGTTGGGATAAGGCTGGAT | |
| | TATTCTGAGTCCAAGCTAGGCCCTTTTGCTAATCATGTTCATACCTCTTATCT | |
| | TCCTCCCACAGCTCCTGGGCAACGTGCTGGTCTGTGTGCTGGCCCATCACT | |
| | TTGGCAAAGAATTGGGATTCGAACATCGATGGTACCGAATTCAATGGCCGCT | |
| | GCCAAGGCCGAGATGCAGCTGATGAGCCCCTGCAGATCAGCGACCCCTTC | |
| | GGCAGCTTCCCCCACAGCCCCACCATGGACAACTACCCCAAGCTGGAAGAG | |
| | ATGATGCTGCTGAGCAATGGCGCTCCTCAGTTCCTGGGAGCCGCTGGCGCC | |
| | CCTGAGGGCAGCGGCAGCAATAGCAGCAGCAGCTCTAGCGGCGAGGCGG | |
| | AGGGGGAGGCGGCGAAGCAATAGCTCCAGCTCCAGCAGCACATTCAATC | |
| | CACAAGCCGACACCGGCGAGCAGCCCTATGAGCACCTGACCGCCGAGAGC | |
| | TTCCCCGACATCAGCCTGAACAACGAGAAGGTGCTGGTGGAAACCAGCTAC | |
| | CCCAGCCAGACCACCCGGCTGCCCCCTATCACCTACACAGGCCGGTTCAGC | |
| | CTGGAACCCGCCCCTAACAGCGGCAACACCCTGTGGCCCGAGCCCCTGTTT | |
| | AGCCTGGTGTCCGGCCTGGTGTCTATGACCAACCCCCCTGCCAGCAGCTCC | |
| | TCTGCCCCAAGCCCTGCCGCCAGCTCTGCCTCTGCCAGCCAGAGCCCTCCA | |
| | CTGAGCTGCGCCGTGCCCAGCAACGACAGCAGCCCCATCTACAGCGCCGC | |
| | TCCCACCTTCCCCACCCCCAACACCGACATCTTCCCCGAGCCTCAGAGCCA | |
| | GGCCTTTCCTGGATCTGCCGGCACCGCCCTGCAGTACCCACCTCCTGCCTA | |
| | TCCTGCCGCCAAGGGCGGCTTCCAGGTGCCCATGATCCCCGACTACCTGTT | |
| | CCCCCAGCAGCAGGGCGATCTGGGCCTGGGCACCCCCGACCAGAAGCCTT | |
| | TCCAGGGCCTCGAAAGCCGGACCCAGCAGCCAAGCCTGACCCCCCTGAGC | |
| | ACCATCAAGGCCTTCGCCACCCAGAGCGGCAGCCAGGACCTGAAGGCCCT | |
| | GAACACCAGCTACCAGAGCCAGCTGATCAAGCCCAGCCGGATGCGGAAGTA | |
| | CCCCAACCGGCCCAGCAAGACCCCCCCACACGAGAGGCCTTACGCCTGCC | |
| | CCGTGGAAAGCTGCGACAGACGGTTCAGCAGAAGCGACAACCTGGTCCGG | |
| | CACATCCGGATCCACACCGGCCAGAAACCCTTCCAGTGCCGGATCTGCATG | |
| | CGGAACTTCTCTCGGAGCGACCACCTGACCACCCACATCAGAACCCACACA | |
| | GGCGAGAAGCCCTTCGCCTGCGACATCTGCGGCCGGAAGTTCGCCGACCC | |
| | CGGCCACCTCGTCAGACACAACAGGATTCACCTGAGACAGAAGGACAAGAA | |
| | AGCCGACAAGAGCGTGGTCGCCAGCAGCGCTACCAGCAGCCTGAGCAGCT | |
| | ACCCTTCTCCTGTGGCCACCTCCTACCCAAGCCCAGTGACCACAAGCTACC | |
| | CATCCCCCGCCACCACCTCTTATCCCAGCCCCGTGCCTACCAGCTTCAGCT | |
| | CTCCCGGCAGCTCCACATACCCCAGCCCTGTGCATAGCGGCTTCCCTAGCC | |
| | CTAGCGTGGCCACCACATACAGCAGCGTGCCCCCTGCCTTCCCAGCTCAAG | |
| | TGTCCAGCTTCCCCAGCTCCGCCGTGACCAACAGCTTCAGCGCCAGCACCG | |
| | GCCTGAGCGACATGACCGCCACCTTCAGCCCCGGACCATCGAGATCTGCT | |
| | GACTCGAGAGATCTACGGGTGGCATCCCTGTGACCCCTCCCCAGTGCCTCT | |
| | CCTGGCCCTGGAAGTTGCCACTCCAGTGCCCACCAGCCTTGTCCTAATAAAA | |
| | TTAAGTTGCATCATTTTGTCTGACTAGGTGTCCTTCTATAATATTATGGGGTG | |
| | GAGGGGGGTGGTATGGAGCAAGGGGCAAGTTGGGAAGACAACCTGTAGGG | |
| | CCTGCGGGGTCTATTGGGAACCAAGCTGGAGTGCAGTGGCACAATCTTGGC | |
| | TCACTGCAATCTCCGCCTCCTGGGTCAAGCGATTCTCCTGCCTCAGCCTCC | |
| | CGAGTTGTTGGGATTCCAGGCATGCATGACCAGGCTCAGCTAATTTTTGTTT | |
| | TTTTGGTAGAGACGGGGTTTCACCATATTGGCCAGGCTGGTCTCCAACTCCT | |
| | AATCTCAGGTGATCTACCCACCTTGGCCTCCCAAATTGCTGGGATTACAGGC | |
| | GTGAACCACTGCTCCCTTCCCTGTCCTTCTGATTTTGTAGGTAACCACGTGC | |
| | GGACCGAGCGGCCGCAGGAACCCCTAGTGATGGAGTTGGCCACTCCCTCT | |
| | CTGCGCGCTCGCTCGCTCACTGAGGCCGGGCGACCAAAGGTCGCCCGACG | |
| | CCCGGGCTTTGCCCGGGCGGCCTCAGTGAGCGAGCGAGCGCGCAGCTGC | |

| SEQ ID NO: | Sequence | Description |
|---|---|---|
| | CTGCAGGGGCGCCTGATGCGGTATTTTCTCCTTACGCATCTGTGCGGTATTT<br>CACACCGCATACGTCAAAGCAACCATAGTACGCGCCCTGTAGCGGCGCATT<br>AAGCGCGGCGGGTGTGGTGGTTACGCGCAGCGTGACCGCTACACTTGCCA<br>GCGCCCTAGCGCCCGCTCCTTTCGCTTTCTTCCCTTCCTTTCTCGCCACGTT<br>CGCCGGCTTTCCCCGTCAAGCTCTAAATCGGGGGCTCCCTTTAGGGTTCCG<br>ATTTAGTGCTTTACGGCACCTCGACCCCAAAAAACTTGATTTGGGTGATGGT<br>TCACGTAGTGGGCCATCGCCCTGATAGACGGTTTTTCGCCCTTTGACGTTGG<br>AGTCCACGTTCTTTAATAGTGGACTCTTGTTCCAAACTGGAACAACACTCAAC<br>CCTATCTCGGGCTATTCTTTTGATTTATAAGGGATTTTGCCGATTTCGGCCTA<br>TTGGTTAAAAAATGAGCTGATTTAACAAAAATTTAACGCGAATTTTAACAAAAT<br>ATTAACGTTTACAATTTTATGGTGCACTCTCAGTACAATCTGCTCTGATGCCG<br>CATAGTTAAGCCAGCCCCGACACCCGCCAACACCCGCTGACGCGCCCTGAC<br>GGGCTTGTCTGCTCCCGGCATCCGCTTACAGACAAGCTGTGACCGTCTCCG<br>GGAGCTGCATGTGTCAGAGGTTTTCACCGTCATCACCGAAACGCGCGAGAC<br>GAAAGGGCCTCGTGATACGCCTATTTTTATAGGTTAATGTCATGATAATAATG<br>GTTTCTTAGACGTCAGGTGGCACTTTTCGGGGAAATGTGCGCGGAACCCCT<br>ATTTGTTTATTTTTCTAAATACATTCAAATATGTATCCGCTCATGAGACAATAA<br>CCCTGATAAATGCTTCAATAATATTGAAAAAGGAAGAGTATGAGTATTCAACA<br>TTTCCGTGTCGCCCTTATTCCCTTTTTTGCGGCATTTTGCCTTCCTGTTTTTG<br>CTCACCCAGAAACGCTGGTGAAAGTAAAAGATGCTGAAGATCAGTTGGGTG<br>CACGAGTGGGTTACATCGAACTGGATCTCAACAGCGGTAAGATCCTTGAGA<br>GTTTTCGCCCCGAAGAACGTTTTCCAATGATGAGCACTTTTAAAGTTCTGCTA<br>TGTGGCGCGGTATTATCCCGTATTGACGCCGGGCAAGAGCAACTCGGTCGC<br>CGCATACACTATTCTCAGAATGACTTGGTTGAGTACTCACCAGTCACAGAAA<br>AGCATCTTACGGATGGCATGACAGTAAGAGAATTATGCAGTGCTGCCATAAC<br>CATGAGTGATAACACTGCGGCCAACTTACTTCTGACAACGATCGGAGGACC<br>GAAGGAGCTAACCGCTTTTTTGCACAACATGGGGGATCATGTAACTCGCCTT<br>GATCGTTGGGAACCGGAGCTGAATGAAGCCATACCAAACGACGAGCGTGAC<br>ACCACGATGCCTGTAGCAATGGCAACAACGTTGCGCAAACTATTAACTGGCG<br>AACTACTTACTCTAGCTTCCCGGCAACAATTAATAGACTGGATGGAGGCGGA<br>TAAAGTTGCAGGACCACTTCTGCGCTCGGCCCTTCCGGCTGGCTGGTTTATT<br>GCTGATAAATCTGGAGCCGGTGAGCGTGGGTCTCGCGGTATCATTGCAGCA<br>CTGGGGCCAGATGGTAAGCCCTCCCGTATCGTAGTTATCTACACGACGGGG<br>AGTCAGGCAACTATGGATGAACGAAATAGACAGATCGCTGAGATAGGTGCC<br>TCACTGATTAAGCATTGGTAACTGTCAGACCAAGTTTACTCATATATACTTTA<br>GATTGATTTAAAACTTCATTTTTAATTTAAAAGGATCTAGGTGAAGATCCTTTT<br>TGATAATCTCATGACCAAAATCCCTTAACGTGAGTTTTCGTTCCACTGAGCGT<br>CAGACCCCGTAGAAAAGATCAAAGGATCTTCTTGAGATCCTTTTTTTCTGCG<br>CGTAATCTGCTGCTTGCAAACAAAAAAACCACCGCTACCAGCGGTGGTTTGT<br>TTGCCGGATCAAGAGCTACCAACTCTTTTTCCGAAGGTAACTGGCTTCAGCA<br>GAGCGCAGATACCAAATACTGTCCTTCTAGTGTAGCCGTAGTTAGGCCACCA<br>CTTCAAGAACTCTGTAGCACCGCCTACATACCTCGCTCTGCTAATCCTGTTA<br>CCAGTGGCTGCTGCCAGTGGCGATAAGTCGTGTCTTACCGGGTTGGACTCA<br>AGACGATAGTTACCGGATAAGGCGCAGCGGTCGGGCTGAACGGGGGGTTC<br>GTGCACACAGCCCAGCTTGGAGCGAACGACCTACACCGAACTGAGATACCT<br>ACAGCGTGAGCTATGAGAAAGCGCCACGCTTCCCGAAGGGAGAAAGGCGG<br>ACAGGTATCCGGTAAGCGGCAGGGTCGGAACAGGAGAGCGCACGAGGGAG<br>CTTCCAGGGGGAAACGCCTGGTATCTTTATAGTCCTGTCGGGTTTCGCCACC<br>TCTGACTTGAGCGTCGATTTTTGTGATGCTCGTCAGGGGGCGGAGCCTAT<br>GGAAAAACGCCAGCAACGCGGCCTTTTTACGGTTCCTGGCCTTTTGCTGGC<br>CTTTTGCTCACATGT | |
| 66 | ATGGAGCAAAAGCTCATTTCTGAAGAGGACTTGAATGAAATGGAGCAAAAGC<br>TCATTTCTGAAGAGGACTTGAATGAAATGGAGCAAAAGCTCATTTCTGAAGA<br>GGACTTGAATGAAATGGAGCAAAAGCTCATTTCTGAAGAGGACTTGAATGAA<br>ATGGAGCAAAAGCTCATTTCTGAAGAGGACTTGAATGAAATGGAGAGCTTGG<br>GCGACCTCACCATGGGCCCTAAAAAGAAGCGTAAAGTCGCCCCCCCGACCG<br>ATGTCAGCCTGGGGGACGAGCTCCACTTAGACGGCGAGGACGTGGCGATG<br>GCGCATGCCGACGCGCTAGACGATTTCGATCTGGACATGTTGGGGGACGG<br>GGATTCCCCGGGTCCGGGATTTACCCCCACGACTCCGCCCCTACGGCG<br>CTCTGGATATGGCCGACTTCGAGTTTGAGCAGATGTTTACCGATGCCCTTGG<br>AATTGACGAGTACGGTGGGGAATTCCCGGGGATCCTCGATGACAGACCCTA<br>TGCTTGCCCAGTGGAAAGCTGCGACCGCCGCTTTTCTAGATCGGATGAGCT<br>TACCCGCCATATCCGCATCCACACCGGCCAAAAACCCTTTCAATGCCGTATC<br>TGCATGAGGAATTTCAGCAGCCGCGATGTCCTGAGGCGCCATAACAGGACC<br>CACACAGGGGAAAAGCCATTCGCATGTGACATCTGCGGTGAAAGTTTGCA<br>AGCCGCGATGTCCTGAGGCGCCATAACAGGATACATTTGAGGCAAAATGAT<br>CTCGACCGTACGTACAAGATCCGTTAG | DNA sequence Vp16-Jazz (includes myc tag, NLS, Vp16, Jazz) |
| 67 | ATGGAGCAAAAGCTCATTTCTGAAGAGGACTTGAATGAAATGGAGCAAAAGC<br>TCATTTCTGAAGAGGACTTGAATGAAATGGAGCAAAAGCTCATTTCTGAAGA<br>GGACTTGAATGAAATGGAGCAAAAGCTCATTTCTGAAGAGGACTTGAATGAA<br>ATGGAGCAAAAGCTCATTTCTGAAGAGGACTTGAATGAAATGGAGAGCTTGG<br>GCGACCTCACCATGGGCCCTAAAAAGAAGCGTAAAGTCGCCCCCCCGACCG | DNA sequence Vp16-Bagly (includes myc tag, |

| SEQ ID NO: | Sequence | Description |
|---|---|---|
| | ATGTCAGCCTGGGGGACGAGCTCCACTTAGACGGCGAGGACGTGGCGATG<br>GCGCATGCCGACGCGCTAGACGATTTCGATCTGGACATGTTGGGGGACGG<br>GGATTCCCCGGGTCCGGGATTTACCCCCCACGACTCCGCCCCCTACGGCG<br>CTCTGGATATGGCCGACTTCGAGTTTGAGCAGATGTTTACCGATGCCCTTGG<br>AATTGACGAGTACGGTGGGGAATTCCCGGGGATCCTCGATGACAGACCCTA<br>TGCTTGCCCAGTGGAAAGCTGCGACCGCCGCTTTTCTAGATCGGATGAGCT<br>TACCCGCCATATCCGCATCCACACCGGCCAAAAACCCTTTCAATGCCGTATC<br>TGCATGAGGAATTTCAGCAGCCGCGATGTCCTGAGGCGCCATAACAGGACC<br>CACACAGGGGAAAAGCCATTCGCATGTGACATCTGCGGTCGAAAGTTTGCA<br>AGCCGCGATGTCCTGAGGCGCCATAACAGGATACATTTGAGGCAAGGTCCC<br>AGATCTCACGTCTGTGCAGAATGTGGCAAAGCGTTCGTTGAGAGCTCAAAG<br>CTAAAACGACACCAGCTGGTTCATGAGCTGGAGAGAAGCCCTTTTAGCTCGA<br>GAGATCTACGGGTGGCATCCCTGTGA | NLS, Vp16, Bagly) |
| 68 | ATGGAGCAAAAGCTCATTTCTGAAGAGGACTTGAATGAAATGGAGCAAAAGC<br>TCATTTCTGAAGAGGACTTGAATGAAATGGAGCAAAAGCTCATTTCTGAAGA<br>GGACTTGAATGAAATGGAGCAAAAGCTCATTTCTGAAGAGGACTTGAATGAA<br>ATGGAGCAAAAGCTCATTTCTGAAGAGGACTTGAATGAGAGCCTTGG<br>GCGACCTCACCATGGGCCCTAAAAAGAAGCGTAAAGTCGCCCCCCCGACCG<br>ATGTCAGCCTGGGGACGAGCTCCACTTAGACGGCGAGGACGTGGCGATG<br>GCGCATGCCGACGCGCTAGACGATTTCGATCTGGACATGTTGGGGGACGG<br>GGATTCCCCGGGTCCGGGATTTACCCCCCACGACTCCGCCCCCTACGGCG<br>CTCTGGATATGGCCGACTTCGAGTTTGAGCAGATGTTTACCGATGCCCTTGG<br>AATTGACGAGTACGGTGGGGAATTCCCGGGGATCTTGGCAAAGCGCTTTGC<br>CGACTTTACAGTCTACAGGAACCGCACACTTCAGAAATGGCACGATAAGACC<br>AAACTGGCTTCTGGAAAACTGGGGAAGGGTTTTGGTGCCTTTGAACGCTCAA<br>TCTTGACTCAGATCGACCATATTCTGATGGACAAAGAGAGATTACTTCGAAG<br>GACACAGACCAAGCGCTCTGTCTATCGAGTTCTTGGCAAACCTGAGCCAGC<br>AGCTCAGCCTGTCCCAGAGAGTTTGCCAGGGGAACCGGAGATCCTTCCTCA<br>AGCCCCTGCTAATGCTCATCTGAAGGACTTGGATGAAGAAATCTTTGATGAT<br>GATGACTTTTACCACCAGCTCCTTCGAGAACTCATAGAACGGAAGACCAGCT<br>CCTTGGGGATCCTGGATCGCCCTTACGCCTGCCCTGTGGAATCTTGCGACC<br>GCCGGTTCTCCCGCAGCGATAACCTGGTGCGGCACATCCGGATTCACACCG<br>GCCAGAAACCTTTTCCAGTGCAGGATCTGCATGAGAAATTTCTCCCGGTCCGA<br>CCACCTGACCACCCACAATAGGACCCACACCGGCGAGAAACCCTTTGCCTG<br>CGACATCTGCGGGAGAAAGTTCGCCGACCCCGGCCACTGGTGAGACACA<br>ATAGAATCCACACCGGTGAAAAGCCCTTCGCCTGTCCCGTGGAGAGCTGCG<br>ATCGCAGATTCAGCCGCAGCGACGAGCTGACAAGGCACATCAGAATCCACA<br>CCGGGCAGAAGCCTTTTCAGTGCCGGATCTGCATGAGGAACTTCAGCTCCC<br>GGGACGTGCTGAGACGCCACAATCGCACACACACCGGCGAAAAGCCCTTC<br>GCCTGTGATATTTGCGGGCGGAAATTTGCCTCCAGAGATGTGCTGCGCCGC<br>CACAACCGCATTCACCTGAGACAGAACGATCTCAGAGATCTACGGGTGGC<br>ATCCCTGTGACCCCTCCCCAGTGCCTCTCCTGGCCCTGGAAGTTGCCACTC<br>CAGTGCCCACCAGCCTTGTCCTAA | DNA sequence VP16-CJ7-UtroUp (includes myc tag, NLS, Vp16,CJ7 UtroUp) |
| 69 | ATGGCCGCTGCCAAGGCCGAGATGCAGCTGATGAGCCCCCTGCAGATCAG<br>CGACCCCTTCGGCAGCTTCCCCCACAGCCCCACCATGGACAACTACCCCAA<br>GCTGGAAGAGATGATGCTGCTGAGCAATGGCGCTCCTCAGTTCCTGGGAGC<br>CGCTGGCGCCCCTGAGGGCAGCGGCAGCAATAGCAGCAGCAGCTCTAGCG<br>GCGGAGGCGGAGGGGAGGCGGCGGAAGCAATAGCTCCAGCTCCAGCAG<br>CACATTCAATCCACAAGCCGACACCGGCGAGCAGCCCTATGCCGCCTGAC<br>CGCCGAGAGCTTCCCCGACATCAGCCTGAACAACGAGAAGGTGCTGGTGGA<br>AACCAGCTACCCCAGCCAGACCACCCGGCTGCCCCCTATCACCTACACAGG<br>CCGGTTCAGCCTGGAACCCGCCCCTAACAGCGGCAACACCCTGTGGCCCG<br>AGCCCCTGTTTAGCCTGGTGTCCGGCCTGGTGTCTATGACCAACCCCCCTG<br>CCAGCAGCTCCTCTGCCCCAAGCCCTGCCGCCAGCTCTGCCTCTGCCAGCC<br>AGAGCCCTCCACTGAGCTGCGCCGTGCCCAGCAACGACAGCAGCCCCATCT<br>ACAGCGCCGCTCCCACCTTCCCCACCCCCAACACCGACATCTTCCCCGAGC<br>CTCAGAGCCAGGCCTTTCCTGGATCTGCCGGCACCGCCCTGCAGTACCCAC<br>CTCCTGCCTATCCTGCCGCCAAGGGCGGCTTCCAGGTGCCCATGATCCCCG<br>ACTACCTGTTCCCCAGCAGCAGGGCGATCTGGGCCTGGGCACCCCCGAC<br>CAGAAGCCTTTCCAGGGCCTCGAAAGCGGACCCAGCAGCCAAGCCTGAC<br>CCCCCTGAGCACCATCAAGGCCTTCGCCACCCAGAGCGGCAGCCAGGACC<br>TGAAGGCCCTGAACACCAGCTACCAGAGCCAGCTGATCAAGCCCAGCCGGA<br>TGCGGAAGTACCCCAACCGGCCCAGCAAGACCCCCCACACGAGAGGCCT<br>TACGCCTGCCCCGTGGAAAGCTGCGACAGACGGTTCAGCAGAAGCGACGA<br>GCTGACCCGGCACATCCGGATCCACACCGGCCAGAAACCCTTCCAGTGCCG<br>GATCTGCATGCGGAACTTCAGCAGCCGGGACGTGCTGCGGCGGCACAATA<br>GAACCCACACAGGCGAGAAGCCCTTCGCCTGCGACATCTGCGGCCGGAAG<br>TTCGCCAGCAGAGATGTGCTGCGGAGACACAACAGGATCCACCTGAGACAG<br>AAGGACAAGAAGCCGACAAGAGCGTGGTCGCCAGCAGCGCTACCAGCAG<br>CCTGAGCAGCTACCCTTCTCCTGTGGCCACCTCCTACCCAAGCCCAGTGAC<br>CACAAGCTACCCATCCCCGCCACCACCTCTTATCCCAGCCCGTGCCTAC<br>CAGCTTCAGCTCTCCCGGCAGCTCCACATACCCAGCCCTGTGCATAGCGG<br>CTTCCCTAGCCCTAGCGTGGCCACCACATACAGCAGCGTGCCCCCTGCCTT | DNA sequence encoding for full length JZif1 |

| SEQ ID NO: | Sequence | Description |
|---|---|---|
| | CCCAGCTCAAGTGTCCAGCTTCCCCAGCTCCGCCGTGACCAACAGCTTCAG CGCCAGCACCGGCCTGAGCGACATGACCGCCACCTTCAGCCCCCGGACCA TCGAGATCTGCTGA | |
| 70 | ATGGCCGCTGCCAAGGCCGAGATGCAGCTGATGAGCCCCCTGCAGATCAG CGACCCCTTCGGCAGCTTCCCCCACAGCCCCACCATGGACAACTACCCCAA GCTGGAAGAGATGATGCTGCTGAGCAATGGCGCTCCTCAGTTCCTGGGAGC CGCTGGCGCCCTGAGGGCAGCGGCAGCAATAGCAGCAGCAGCTCTAGCG GCGGAGGCGGAGGGGGAGGCGGCGGAAGCAATAGCTCCAGCTCCAGCAG CACATTCAATCCACAAGCCGACACCGGCGAGCAGCCCTATGAGCACCTGAC CGCCGAGAGCTTCCCCGACATCAGCCTGAACAACGAGAAGGTGCTGGTGGA AACCAGCTACCCCAGCCAGACCACCCGGCTGCCCCTATCACCTACACAGG CCGGTTCAGCCTGGAACCCGCCCCTAACAGCGGCAACACCCTGTGGCCCG AGCCCCTGTTTAGCCTGGTGTCCGGCCTGGTGTCTATGACCAACCCCCCTG CCAGCAGCTCCTCTGCCCCAAGCCCTGCCGCCAGCTCTGCCTCTGCCAGCC AGAGCCCTCCACTGAGCTGCGCCGTGCCCAGCAACGACAGCAGCCCCATCT ACAGCGCCGCTCCCACCTTCCCCACCCCCAACACCGACATCTTCCCCGAGC CTCAGAGCCAGGCCTTTCCTGGATCTGCCGGCACCGCCCTGCAGTACCCAC CTCCTGCCTATCCTGCCGCCAAGGGCGGCTTCCAGGTGCCCATGATCCCCG ACTACCTGTTCCCCAGCAGCAGGGCGATCTGGGCCTGGGCACCCCCGAC CAGAAGCCTTTCCAGGGCCTCGAAAGCCGGACCCAGCAGCCAAGCCTGAC. CCCCCTGAGCACCATCAAGGCCTTCGCCACCCAGAGCGGCAGCCAGGACC TGAAGGCCCTGAACACCAGCTACCAGAGCCAGCTGATCAAGCCCAGCCGGA TGCGGAAGTACCCCAACCGGCCCAGCAAGACCCCCCCACACGAGAGGCCT TACGCCCTGCCCCGTGGAAAGCTGCGACAGAGGTTCAGCAGAAGCGACAAC CTGGTCCGGCACATCCGGATCCACACCGGCCAGAAACCCTTCCAGTGCCGG ATCTGCATGCGGAACTTCTCTCGGAGCGACCACCTGACCACCCACATCAGA ACCCACACAGGCGAGAAGCCCTTCGCCTGCGACATCTGCGGCCGGAAGTTC GCCGACCCCGGCCACCTCGTCAGACACAACAGGATTCACCTGAGACAGAAG GACAAGAAAGCCGACAAGAGCGTGGTCGCCAGCAGCGCTACCAGCAGCCT GAGCAGCTACCCTTCTCCTGTGGCCACCTCCTACCCAAGCCACCAGTGACCA AAGCTACCCATCCCCCGCCACCACCTCTTATCCCAGCCCCGTGCCTACCAG CTTCAGCTCTCCCGGCAGCTCCACATACCCAGCCCTGTGCATAGCGGCTT CCCTAGCCCTAGCGTGGCCACCACATACAGCAGCGTGCCCCCTGCCTTCCC AGCTCAAGTGTCCAGCTTCCCCAGCTCCGCCGTGACCAACAGCTTCAGCGC CAGCACCGGCCTGAGCGACATGACCGCCACCTTCAGCCCCCGGACCATCG AGATCTGCTGA | DNA sequence encoding for full length JZif2 |
| 71 | APPTDVSLGDELHLDGEDVAMAHADALDDFDLDMLGDGDSPGPGFTPHDSAP YGALDMADFEFEQMFTDALGIDEYGGEFPGILDDRPYACPVESCDRRFSRSDEL TRHIRIHTGQKPFQCRICMRNFSSRDVLRRHNRTHTGEKPFACDICGRKFASRD VLRRHNRIH | Minimal Jazz (Vp16-Jazz, no tag, NLS) protein seq |
| 72 | APPTDVSLGDELHLDGEDVAMAHADALDDFDLDMLGDGDSPGPGFTPHDSAP YGALDMADFEFEQMFTDALGIDEYGGEFPGILDDRPYACPVESCDRRFSRSDEL TRHIRIHTGQKPFQCRICMRNFSSRDVLRRHNRTHTGEKPFACDICGRKFASRD VLRRHNRIHLRQGPRSHVCAECGKAFVESSKLKRHQLVH | Minimal Bagly (Vp16-Bagly) protein seq |
| 73 | APPTDVSLGDELHLDGEDVAMAHADALDDFDLDMLGDGDSPGPGFTPHDSAP YGALDMADFEFEQMFTDALGIDEYGGEFPGILAKRFADPTVYRNRTLQKWHDKT KLASGKLGKGFGAFERSILTQIDHILMDKERLLRRTQTKRSVYRVLGKPEPAAQP VPESLPGEPEILPQAPANAHLKDLDEEIFDDDDFYHQLLRELIERKTSSLGILDRP YACPVESCDRRFSRSDNLVRHIRIHTGQKPFQCRICMRNFSRSDHLTTHNRTHT GEKPFACDICGRKFADPGHLVRHNRIHTGEKPFACPVESCDRRFSRSDELTRHI RIHTGQKPFQCRICMRNFSSRDVLRRHNRTHTGEKPFACDICGRKFASRDVLRR HNRIH | Minimal UtroUp (Vp16-CJ7-UtroUp) protein seq |
| 74 | AKRFADPTVYRNRTLQKWHDKTKLASGKLGKGFGAFERSILTQIDHILMDKERLL RRTQTKRSVYRVLGKPEPAAQPVPESLPGEPEILPQAPANAHLKDLDEEIFDDD DFYHQLLRELIERKTSSL | CJ7 amino acid sequence |
| 75 | MEQKLISEEDLNEMEQKLISEEDLNEMEQKLISEEDLNEMEQKLISEEDLNEMEQ KLISEEDLNEMESLGDLT | Multi myc tag |
| 76 | CGAGCCGAGAGTAGCA | |
| 77 | CATGGTGAGGTCGCCCAAGCTCT | |
| 78 | CGAGCCGAGAGTAGCA | |
| 79 | GAGCTGGAGCTATTGCTTCC | |

| SEQ ID NO: | Sequence | Description |
|---|---|---|
| 80 | CCTGCAGGCAGCTGCGCGCTCGCTCGCTCACTGAGGCCGCCCGGGCAAAG<br>CCCGGGCGTCGGGCGACCTTTGGTCGCCCGGCCTCAGTGAGCGAGCGAGC<br>GCGCAGAGAGGGAGTGGCCAACTCCATCACTAGGGGTTCCTGCGGCCGCA<br>CGCGTCACCAACTGGGTAACCTCTGCTGACCCCCACTCTACTTTACCATAAG<br>TAGCTCCAAATCCTTCTAGAAAATCTGAAAGGCATAGCCCCATATATCAGTGA<br>TATAAATAGAACCTGCAGCAGGCTCTGGTAAATGATGACTACAAGGTGGACT<br>GGGAGGCAGCCCGGCCTTGGCAGGCATCATCCTCTAAATATAAAGATGAGT<br>TTGTTCAGCCTTTGCAGAAGGAAAAACTGCCACCCATCCTAGAGTGCCGCGT<br>CCTTGTCCCCCCACCCCCTCCAATTTATTGGGAGGAAGGACCAGCTAAGCC<br>TCATCTAGGAAGAGCCCCTCACCCATCTCCACCTCCACTCCAGGTCTAGCCA<br>GTCCTGGGTTGTGACCCTTGTCTTTCAGCCCCAGGAGAGGGACACACATAG<br>TGCCACCAAAGAGGCTGGGGAGGGCCTCAGCCCACCAAAACCTGGGGCC<br>AGTGCGTCCTACAGGAGGGGAACCCTCACCCCTTCAATCCCTTTAGGAGAC<br>CCAAGGGCGCTGCGCGTCCTGAGGCGGACAGCTCCGTGTGCTCAGGCTT<br>TGCGCCTGACAGGCCTATCCCCGGGAGCCCCGCGCCTCCTCCCCGGCGC<br>TCCGCCCTCGCCTCCCCCGCCAGTTGTCTATCCTGCGACAGCTGCGCGCC<br>CTCCGGCCGCCGGTGGCCCTCTGTGCGGTGGGGAAGGGGTCGACGTGG<br>CTCAGCTTTTTGGATTCAGGGAGCTCGGGGTGGGAAGAGAGAAATGGAGT<br>TCCAGGGGCGTAAAGGAGAGGGAGTTCGCCTTCCTTCCCTTCCTGAGACTC<br>AGGAGTGACTGCTTCTCCAATCCTCCCAAGCCCACCACTCCACACGACTCC<br>CTCTTCCCGGTAGTCGCAAGTGGGAGTTTGGGGATCTGAGCAAAGAACCCG<br>AAGAGGAGTTGAAATATTGGAAGTCAGCAGTCAGGCACCTTCCCGAGCGCC<br>CAGGGCGCTCAGAGTGGACATGGTTGGGGAGGCCTTTGGGACAGGTGCGG<br>TTCCCGGAGCGCAGGCGCACACATGCACCCACCGGCGAACGCGGTGACCC<br>TCGCCCCACCCCATCCCCTCCGGCGGGCAACTGGGTCGGGTCAGGAGGGG<br>CAAACCCGCTAGGGAGACACTCCATATACGGCCCGGCCCGCGTTACCTGGG<br>ACCGGGCCAACCCGCTCCTTCTTTGGTCAACGCAGGGGACCCGGGCGGGG<br>GCCCAGGCCGCGAACCGGCCGAGGGAGGGGGCTCTAGTGCCCAACACCCA<br>AATATGGCTCGAGAAGGGCAGCGACATTCCTGCGGGGTGGCGCGGAGGGA<br>ATGCCCGCGGGCTATATAAAACCTGAGCAGAGGGACAAGCGGCCACCGCA<br>GCGGACAGCGCCAAGTGAAGCCTCGCTTCCCCTCCGCGGCGACCAGGGCC<br>CGAGCCGAGAGTAGCAGTTGTAGCTACCCGCCCAGGTAGGGCAGGAGTTG<br>GGAGGGGACAGGGGGACAGGGCACTACCGAGGGGAACCTGAAGGACTCC<br>GGGGCAGAACCCAGTCGGTTCACCTGGTAAGCTTGCTAGCTGTTTAGTGAA<br>CCGTCAGATCGCCTGGAGACGCCATCCACGCTGTTTTGACCTCCATAGAAG<br>ACACCGGGACCGATCCAGCCTCCGCGGATTCGAATCCCGGCCGGGAACGG<br>TGCATTGGAACGCGGATTCCCCGTGCCAAGAGTGACGTAAGTACCGCCTAT<br>AGAGTCTATAGGCCCACAAAAAATGCTTTCTTCTTTTAATATACTTTTTTGTTT<br>ATCTTATTTCTAATACTTTCCCTAATCTCTTTCTTTCAGGGCAATAATGATACA<br>ATGTATCATGCCTCTTTGCACCATTCTAAAGAATAACAGTGATAATTTCTGGG<br>TTAAGGCAATAGCAATATTTCTGCATATAAATATTTCTGCATATAAATTGTAAC<br>TGATGTAAGAGGTTTCATATTGCTAATAGCAGCTACAATCCAGCTACCATTCT<br>GCTTTTATTTTATGGTTGGGATAAGGCTGGATTATTCTGAGTCCAAGCTAGG<br>CCCTTTTGCTAATCATGTTCATACCTCTTATCTTCCTCCCACAGCTCCTGGGC<br>AACGTGCTGGTCTGTGTGCTGGCCCATCACTTTGGCAAAGAATTGGGATTCG<br>AACATCGATTTAAAGCTATGGTGAGTAAACAAATATTGAAGAACACTGGATTG<br>CAGGAGATCATGTCGTTTAAAGTGAATCTGGAAGGTGTAGTAAACAATCATG<br>TGTTCACAATGGAAGGTTGTGGAAAAGGAAATATTTTATTCGGAAACCAACT<br>GGTTCAGATTCGTGTCACAAAAGGGGCTCCGCTTCCATTTGCATTTGATATT<br>CTCTCACCCAGCTTTCCAATACGGCAACCGTACATTCACGAAATACCCGGAGG<br>ATATATCAGACTTTTTTATACAATCATTTCCAGCGGGATTTGTATACGAAAGA<br>ACGTTGCGTTACGAAGATGGTGGACTGGTTGAAATCCGTTCAGATATAAATT<br>TAATCGAGGAGATGTTTGTCTACAGAGTGGAATATAAAGGTAGTAACTTCCC<br>GAATGATGGTCCAGTGATGAAGAAGACAATCACAGGATTACAACCTTCGTTC<br>GAAGTTGTGTATATGAACGATGGCGTCTTGGTTGGCCAAGTCATTCTTGTTT<br>ATAGATTAAACTCTGGCAAATTTTATTCGTGTCACATGAGAACACTGATGAAA<br>TCAAAGGGTGTAGTGAAGGATTTTCCCGAATACCATTTCATTCAACATCGTTT<br>AGAGAAGACGTATGTGGAAGACGGAGGTTTTGTTGAGCAACACGAGACGGC<br>CATTGCTCAACTGACATCGCTGGGGAAACCACTTGGATCCTTACACGAATGG<br>GTTTAACTCGAGAGATCTACGGGTGGCATCCCTGTGACCCCTCCCCAGTGC<br>CTCTCCTGGCCCTGGAAGTTGCCACTCCAGTGCCCACCAGCCTTGTCCTAAT<br>AAAATTAAGTTGCATCATTTTGTCTGACTAGGTGTCCTTCTATAATATTATGG<br>GGTGGAGGGGGTGGTATGGAGCAAGGGGCAAGTTGGGAAGACAACCTGT<br>AGGGCCTGCGGGGTCTATTGGGAACCAAGCTGGAGTGCAGTGGCACAATCT<br>TGGCTCACTGCAATCTCCGCCTCCTGGGTTCAAGCGATTCTCCTGCCTCAGC<br>CTCCCGAGTTGTTGGGATTCCAGGCATGCATGACCAGGCTCAGCTAATTTTT<br>GTTTTTTTGGTAGAGACGGGGTTTCACCATATTGGCCAGGCTGGTCTCCAAC<br>TCCTAATCTCAGGTGATCTACCCACCTTGGCCTCCCAAATTGCTGGGATTAC<br>AGGCGTGAACCACTGCTCCCTTCCCTGTCCTTCTGATTTTGTAGGTAACCAC<br>GTGCGGACCGAGCGGCCGCAGGAACCCCTAGTGATGGAGTTGGCCACTCC<br>CTCTCTGCGCGCTCGCTCGCTCACTGAGGCCGGGCGACCAAAGGTCGCCC<br>GACGCCCGGGCTTTGCCCGGCGGCCTCAGTGAGCGAGCGAGCGCGCAG<br>CTGCCTGCAGGGGCGCCTGATGCGGTATTTTCTCCTTACGCATCTGTGCGG<br>TATTTCACACCGCATACGTCAAAGCAACCATAGTACGCGCCCTGTAGCGGC | mAAV-GFP sequence (complete sequence) |

| SEQ ID NO: | Sequence | Description |
|---|---|---|
|  | GCATTAAGCGCGGCGGGTGTGGTGGTTACGCGCAGCGTGACCGCTACACTT<br>GCCAGCGCCCTAGCGCCCGCTCCTTTCGCTTTCTTCCCTTCCTTTCTCGCCA<br>CGTTCGCCGGCTTTCCCCGTCAAGCTCTAAATCGGGGGCTCCCTTTAGGGT<br>TCCGATTTAGTGCTTTACGGCACCTCGACCCCAAAAAACTTGATTTGGGTGA<br>TGGTTCACGTAGTGGGCCATCGCCCTGATAGACGGTTTTTCGCCCTTTGACG<br>TTGGAGTCCACGTTCTTTAATAGTGGACTCTTGTTCCAAACTGGAACAACACT<br>CAACCCTATCTCGGGCTATTCTTTTGATTTATAAGGGATTTTGCCGATTTCGG<br>CCTATTGGTTAAAAAATGAGCTGATTTAACAAAAATTTAACGCGAATTTTAACA<br>AAATATTAACGTTTACAATTTTATGGTGCACTCTCAGTACAATCTGCTCTGAT<br>GCCGCATAGTTAAGCCAGCCCCGACACCCGCCAACACCCGCTGACGCGCC<br>CTGACGGGCTTGTCTGCTCCCGGCATCCGCTTACAGACAAGCTGTGACCGT<br>CTCCGGGAGCTGCATGTGTCAGAGGTTTTCACCGTCATCACCGAAACGCGC<br>GAGACGAAAGGGCCTCGTGATACGCCTATTTTTATAGGTTAATGTCATGATA<br>ATAATGGTTTCTTAGACGTCAGGTGGCACTTTTCGGGGAAATGTGCGCGGAA<br>CCCCTATTTGTTTATTTTTCTAAATACATTCAAATATGTATCCGCTCATGAGAC<br>AATAACCCTGATAAATGCTTCAATAATATTGAAAAAGGAAGAGTATGAGTATT<br>CAACATTTCCGTGTCGCCCTTATTCCCTTTTTTGCGGCATTTTGCCTTCCTGT<br>TTTTGCTCACCCAGAAACGCTGGTGAAAGTAAAAGATGCTGAAGATCAGTTG<br>GGTGCACGAGTGGGTTACATCGAACTGGATCTCAACAGCGGTAAGATCCTT<br>GAGAGTTTTCGCCCCGAAGAACGTTTTCCAATGATGAGCACTTTTAAAGTTCT<br>GCTATGTGGCGCGGTATTATCCCGTATTGACGCCGGGCAAGAGCAACTCGG<br>TCGCCGCATACACTATTCTCAGAATGACTTGGTTGAGTACTCACCAGTCACA<br>GAAAAGCATCTTACGGATGGCATGACAGTAAGAGAATTATGCAGTGCTGCCA<br>TAACCATGAGTGATAACACTGCGGCCAACTTACTTCTGACAACGATCGGAGG<br>ACCGAAGGAGCTAACCGCTTTTTTGCACAACATGGGGGATCATGTAACTCGC<br>CTTGATCGTTGGGAACCGGAGCTGAATGAAGCCATACCAAACGACGAGCGT<br>GACACCACGATGCCTGTAGCAATGGCAACAACGTTGCGCAAACTATTAACTG<br>GCGAACTACTTACTCTAGCTTCCCGGCAACAATTAATAGACTGGATGGAGGC<br>GGATAAAGTTGCAGGACCACTTCTGCGCTCGGCCCTTCCGGCTGGCTGGTT<br>TATTGCTGATAAATCTGGAGCCGGTGAGCGTGGGTCTCGCGGTATCATTGC<br>AGCACTGGGGCCAGATGGTAAGCCCTCCCGTATCGTAGTTATCTACACGAC<br>GGGGAGTCAGGCAACTATGGATGAACGAAATAGACAGATCGCTGAGATAGG<br>TGCCTCACTGATTAAGCATTGGTAACTGTCAGACCAAGTTTACTCATATATAC<br>TTTAGATTGATTTAAAACTTCATTTTTAATTTAAAAGGATCTAGGTGAAGATCC<br>TTTTTGATAATCTCATGACCAAAATCCCTTAACGTGAGTTTTCGTTCCACTGA<br>GCGTCAGACCCCGTAGAAAAGATCAAAGGATCTTCTTGAGATCCTTTTTTTCT<br>GCGCGTAATCTGCTGCTTGCAAACAAAAAAACCACCGCTACCAGCGGTGGT<br>TTGTTTGCCGGATCAAGAGCTACCAACTCTTTTTCCGAAGGTAACTGGCTTC<br>AGCAGAGCGCAGATACCAAATACTGTCCTTCTAGTGTAGCCGTAGTTAGGCC<br>ACCACTTCAAGAACTCTGTAGCACCGCCTACATACCTCGCTCTGCTAATCCT<br>GTTACCAGTGGCTGCTGCCAGTGGCGATAAGTCGTGTCTTACCGGGTTGGA<br>CTCAAGACGATAGTTACCGGATAAGGCGCAGCGGTCGGGCTGAACGGGGG<br>GTTCGTGCACACAGCCCAGCTTGGAGCGAACGACCTACACCGAACTGAGAT<br>ACCTACAGCGTGAGCTATGAGAAAGCGCCACGCTTCCCGAAGGGAGAAAGG<br>CGGACAGGTATCCGGTAAGCGGCAGGGTCGGAACAGGAGAGCGCACGAGG<br>GAGCTTCCAGGGGGAAACGCCTGGTATCTTTATAGTCCTGTCGGGTTTCGC<br>CACCTCTGACTTGAGCGTCGATTTTTGTGATGCTCGTCAGGGGGGCGGAGC<br>CTATGGAAAAACGCCAGCAACGCGGCCTTTTTACGGTTCCTGGCCTTTTGCT<br>GGCCTTTTGCTCACATGT |  |
| 81 | GAATTCAATGGCCGCGGCCAAGGCCGAGATGCAGCTGATGTCCCCGCTGCA<br>GATCTCTGACCCGTTCGGATCCTTTCCTCACTCGCCCACCATGGACAACTAC<br>CCTAAGCTGGAGGAGATGATGCTGCTGAGCAACGGGGCTCCCCAGTTCCTC<br>GGCGCCGCCGGGGCCCCAGAGGGCAGCGGCAGCAACAGCAGCAGCAGCA<br>GCAGCGGGGCGGTGGAGGCGGCGGGGGCGGCAGCAACAGCAGCAGCA<br>GCAGCAGCACCTTCAACCCTCAGGCGGACACGGGCGAGCAGCCCTACGAG<br>CACCTGACCGCAGAGTCTTTTCCTGACATCTCTCTGAACAACGAGAAGGTGC<br>TGGTGGAGACCAGTTACCCCAGCCAAACCACTCGACTGCCCCCATCACCT<br>ATACTGGCCGCTTTTCCCTGGAGCCTGCACCCAACAGTGGCAACACCTTGT<br>GGCCCGAGCCCCTCTTCAGCTTGGTCAGTGGCCTAGTGAGCATGACCAACC<br>CACCGGCCTCCTCGTCCTCAGCACCATCTCCAGCGGCTCCTCCGCCTCCG<br>CCTCCCAGAGCCCACCCCTGAGCTGCGCAGTGCCATCAACGACAGCAGTC<br>CCATTTACTCAGCGGCACCCACCTTCCCCACGCCGAACACTGACATTTTCCC<br>TGAGCCACAAAGCCAGGCCTTCCCGGGCTCGGCAGGGACAGCGCTCCAGT<br>ACCCGCCTCCTGCCTACCCTGCCGCCAAGGGTGGCTTCCAGGTTCCCATGA<br>TCCCCGACTACCTGTTTCCACAGCAGCAGGGGATCTGGGCCTGGGCACCC<br>CAGACCAGAAGCCCTTCCAGGGCCTGGAGAGCGCACCCAGCAGCCTTCG<br>CTAACCCCTCTGTCTACTATTAAGGCCTTTGCCACTCAGTCGGGCTCCCAGG<br>ACCTGAAGGCCCTCAATACCAGCTACCAGTCCCAGCTCATCAAACCCAGCC<br>GCATGCGCAAGTACCCCAACCGGCCCAGCAAGACGCCCCCCACGAACGC<br>CCTTACGCTTGCCCAGTGGAGTCCTGTGATCGCCGCTTCTCCCGCTCCGAC<br>GAGCTCACCCGCCACATCCGCATCCACACAGGCCAGAAGCCCTTCCAGTGC<br>CGCATCTGCATGCGCAACTTCAGCAGCCGCGACGTCCTCAGGCGCCACAAC<br>CGCACCCACACAGGCGAAAAGCCCTTCGCCTGCGACATCTGTGGAAGAAAG<br>TTTGCCAGCAGGGATGTCCTGAGGAGGCATAACAGGATCCACTTGCGGCAG | Synthesized JZif1 construct to insert into mAAV includes cloning sequences |

| SEQ ID NO: | Sequence | Description |
|---|---|---|
| | AAGGACAAGAAAGCAGACAAAAGTGTTGTGGCCTCTTCGGCCACCTCCTCT<br>CTCTCTTCCTACCCGTCCCCGGTTGCTACCTCTTACCCGTCCCCGGTTACTA<br>CCTCTTATCCATCCCGGCCACCACCTCATACCCATCCCCTGTGCCCACCTC<br>CTTCTCCTCTCCCGGCTCCTCGACCTACCCATCCCCTGTGCACAGTGGCTTC<br>CCCTCCCCGTCGGTGGCCACCACGTACTCCTCTGTTCCCCCTGCTTTCCCG<br>GCCCAGGTCAGCAGCTTCCCTTCCTCAGCTGTCACCAACTCCTTCAGCGCC<br>TCCACAGGGCTTTCGGACATGACAGCAACCTTTTCTCCCAGGACAATTGAAA<br>TTTGCTAACTCGAG | |
| 82 | GAATTCAATGGCCGCGGCCAAGGCCGAGATGCAGCTGATGTCCCCGCTGCA<br>GATCTCTGACCCGTTCGGATCCTTTCCTCACTCGCCCACCATGGACAACTAC<br>CCTAAGCTGGAGGAGATGATGCTGCTGAGCAACGGGGCTCCCCAGTTCCTC<br>GGCGCCGCCGGGGCCCCAGAGGGCAGCGGCAGCAACAGCAGCAGCAGCA<br>GCAGCGGGGCGGTGGAGGCGGCGGGGGCGGCAGCAACAGCAGCAGCA<br>GCAGCAGCACCTTCAACCCTCAGGCGGACACGGGCGAGCAGCCCTACGAG<br>CACCTGACCGCAGAGTCTTTTCCTGACATCTCTCTGAACAACGAGAAGGTGC<br>TGGTGGAGACCAGTTACCCCAGCCAAACCACTCGACTGCCCCCCATCACCT<br>ATACTGGCCGCTTTTCCCTGGAGCTGCACCCAACAGTGGCAACACCTTGT<br>GGCCCGAGCCCCTCTTCAGCTTGGTCAGTGGCCTAGTGAGCATGACCAACC<br>CACCGGCCTCCTCGTCCTCAGCACCATCTCCAGCGGCCTCCTCCGCCTCCG<br>CCTCCCAGAGCCCACCCCTGAGCTGCGCAGTGCCATCAACGACAGCAGTC<br>CCATTTACTCAGCGGCACCCACCTTCCCCACGCCGAACACTGACATTTTCCC<br>TGAGCCACAAAGCCAGGCCTTCCCGGGCTCGGCAGGGACAGCGCTCCAGT<br>ACCCGCCTCCTGCCTACCCTGCCGCCAAGGGTGGCTTCCAGGTTCCCATGA<br>TCCCCGACTACCTGTTTCCACAGCAGCAGGGGATCTGGGCCTGGGCACCC<br>CAGACCAGAAGCCCTTCCAGGGCCTGGAGAGCCGCACCCAGCAGCCTTCG<br>CTAACCCCTCTGTCTACTATTAAGGCCTTTGCCACTCAGTCGGGCTCCCAGG<br>ACCTGAAGGCCCTCAATACCAGCTACCAGTCCCAGCTCATCAAACCCAGCC<br>GCATGCGCAAGTACCCCAACCGGCCCAGCAAGACGCCCCCCCACGAACGC<br>CCTTACGCTTGCCCAGTGGAGTCCTGTGATCGCCGCTTCTCCCGCTCCGAC<br>GAGCTCACCCGCCACATCCGCATCCACACAGGCCAGAAGCCCTTCCAGTGC<br>CGCATCTGCATGCGCAACTTCAGCAGCCGCGACGTCCTCAGGCGCCACAAC<br>CGCACCCACACAGGCGAAAAGCCCTTCGCCTGCGACATCTGTGGAAGAAAG<br>TTTGCCAGCAGGGATGTCCTGAGGAGGCATAACAGGATCCACTTGCGGCAG<br>AAGGACAAGAAAGCAGACAAAAGTGTTGTGGCCTCTTCGGCCACCTCCTCT<br>CTCTCTTCCTACCCGTCCCCGGTTGCTACCTCTTACCCGTCCCCGGTTACTA<br>CCTCTTATCCATCCCGGCCACCACCTCATACCCATCCCCTGTGCCCACCTC<br>CTTCTCCTCTCCCGGCTCCTCGACCTACCCATCCCCTGTGCACAGTGGCTTC<br>CCCTCCCCGTCGGTGGCCACCACGTACTCCTCTGTTCCCCCTGCTTTCCCG<br>GCCCAGGTCAGCAGCTTCCCTTCCTCAGCTGTCACCAACTCCTTCAGCGCC<br>TCCACAGGGCTTTCGGACATGACAGCAACCTTTTCTCCCAGGACAATTGAAA<br>TTTGCTAACTCGAG | Synthesized JZif2 construct to insert into mAAV includes cloning sequences |
| 83 | GCGGCCGCACGCGTCACCAACTGGGTAACCTCTGCTGACCCCCACTCTACT<br>TTACCATAAGTAGCTCCAAATCCTTCTAGAAAATCTGAAAGGCATAGCCCCAT<br>ATATCAGTGATATAAATAGAACCTGCAGCAGGCTCTGGTAAATGATGACTAC<br>AAGGTGGACTGGGAGGCAGCCCGGCCTTGGCAGGCATCATCCTCTAAATAT<br>AAAGATGAGTTTGTTCAGCCTTTGCAGAAGGAAAAACTGCCACCCATCCTAG<br>AGTGCCGCGTCCTTGTCCCCCCACCCCCTCCAATTTATTGGGAGGAAGGAC<br>CAGCTAAGCCTCATCTAGGAAGAGCCCCTCACCCATCTCCACCTCCACTCCA<br>GGTCTAGCCAGTCCTGGGTTGTGACCCTTGTCTTTCAGCCCCAGGAGAGGG<br>ACACACATAGTGCCACCAAAGAGGCTGGGGGAGGGCCTCAGCCCACCAAAA<br>CCTGGGGCCAGTGCGTCCTACAGGAGGGGAACCCTCACCCCTTCAATCCCT<br>TTAGGAGACCCAAGGGCGCTGCGCGTCCCTGAGGCGGACAGCTCCGTGTG<br>CTCAGGCTTTGCGCCTGACAGGCCTATCCCCGGGAGCCCCCGCGCCTCCT<br>CCCCGGCGCTCCGCCCTCGCCTCCCCCCGCCAGTTGTCTATCCTGCGACAG<br>CTGCGCGCCCTCCGGCCGCCGGTGGCCCCTCTGTGCGGTGGGGGAAGGGG<br>TCGACGTGGCTCAGCTTTTTGGATTCAGGGAGCTCGGGGGTGGGAAGAGAG<br>AAATGGAGTTCCAGGGGCGTAAAGGAGAGGGAGTTCGCCTTCCTTCCCTTC<br>CTGAGACTCAGGAGTGACTGCTTCTCCAATCCTCCCAAGCCCACCACTCCAC<br>ACGACTCCCTCTTCCCGGTAGTCGCAAGTGGGAGTTTGGGGATCTGAGCAA<br>AGAACCCGAAGAGGAGTTGAAATATTGGAAGTCAGCAGTCAGGCACCTTCC<br>CGAGCGCCCAGGGCGCTCAGAGTGGACATGGTTGGGGAGGCCTTTGGGAC<br>AGGTGCGGTTCCCGGAGCGCAGGCGCACACATGCACCCACCGGCGAACGC<br>GGTGACCCTCGCCCCACCCCATCCCCTCCGGCGGGCAACTGGGTCGGGTC<br>AGGAGGGGCAAACCCGCTAGGGAGACACTCCATATACGGCCCGGCCCGCG<br>TTACCTGGGACCGGGCCAACCCGCTCCTTCTTTGGTCAACGCAGGGGACCC<br>GGGCGGGGCCCAGGCCGCGAACCGGCCGAGGGAGGGGGCTCTAGTGCC<br>CAACACCCAAATATGGCTCGAGAAGGGCAGCGACATTCCTGCGGGGTGGC<br>GCGGAGGGAATGCCCGCGGGCTATATAAAACCTGAGCAGAGGGACAAGCG<br>GCCACCGCAGCGGACAGCGCCAAGTGAAGCCTCGCTTCCCCTCCGCGGCG<br>ACCAGGGCCCGAGCCGAGAGTAGCAGTTGTAGCTACCCGCCCAGGTAGGG<br>CAGGAGTTGGGAGGGGACAGGGGGACAGGGCACTACCGAGGGGAACCTG<br>AAGGACTCCGGGGCAGAACCCAGTCGGITCACCTGGTAAGCTTGCTAGCTC<br>CGCGGATTCGAATCCCGGCCGGGAACGGTGCATTGGAACGCGGATTCCCC | Sequence of mAAV-Vp16-Jazz that is incorporated into viral particle and delivered to humans or mice |

| SEQ ID NO: | Sequence | Description |
|---|---|---|
| | GTGCCAAGAGTGACGTAAGTACCGCCTATAGAGTCTATAGGCCCACAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCA<br>TTCTAAAGAATAACAGTGATAATTTCTGGGTTAAGGCAATAGCAATATTTCTG<br>CATATAAATATTTCTGCATATAAATTGTAACTGATGTAAGAGGTTTCATATTGC<br>TAATAGCAGCTACAATCCAGCTACCATTCTGCTTTTATTTTATGGTTGGGATA<br>AGGCTGGATTATTCTGAGTCCAAGCTAGGCCCTTTTGCTAATCATGTTCATAC<br>CTCTTATCTTCCTCCCACAGCTCCTGGGCAACGTGCTGGTCTGTGTGCTGGC<br>CCATCACTTTGGCAAAGAATTGGGATTCGAACATCGATTTAAAGCTATGGAG<br>CAAAAGCTCATTTCTGAAGAGGACTTGAATGAAATGGAGCAAAAGCTCATTT<br>CTGAAGAGGACTTGAATGAAATGGAGCAAAAGCTCATTTCTGAAGAGGACTT<br>GAATGAAATGGAGCAAAAGCTCATTTCTGAAGAGGACTTGAATGAAATGGAG<br>CAAAAGCTCATTTCTGAAGAGGACTTGAATGAAATGGAGAGCTTGGGCGACC<br>TCACCATGGGCCCTAAAAAGAAGCGTAAAGTCGCCCCCCCGACCGATGTCA<br>GCCTGGGGACGAGCTCCACTTAGACGGCGAGGACGTGGCGATGGCGCAT<br>GCCGACGCGCTAGACGATTTCGATCTGGACATGTTGGGGGACGGGGATTCC<br>CCGGGTCCGGGATTTACCCCCCACGACTCCGCCCCCTACGGCGCTCTGGAT<br>ATGGCCGACTTCGAGTTTGAGCAGATGTTTACCGATGCCCTTGGAATTGACG<br>AGTACGGTGGGGAATTCCCGGGGATCCTCGATGACAGACCCTATGCTTGCC<br>CAGTGGAAAGCTGCGACCGCCGCTTTTCTAGATCGGATGAGCTTACCCGCC<br>ATATCCGCATCCACACCGGCCAAAAACCCTTTCAATGCCGTATCTGCATGAG<br>GAATTTCAGCAGCCGCGATGTCCTGAGGCGCCATAACAGGACCCACACAGG<br>GGAAAAGCCATTCGCATGTGACATCTGCGGTCGAAAGTTTGCAAGCCGCGA<br>TGTCCTGAGGCGCCATAACAGGATACATTTGAGGCAAAATGATCTCGACCGT<br>ACGTACAAGATCCGTTAGCATATGCTAACAGATCCACGGGTGGCATCCCTGT<br>GACCCCTCCCCAGTGCCTCTCCTGGCCCTGGAAGTTGCCACTCCAGTGCCC<br>ACCAGCCTTGTCCTAATAAAATTAAGTTGCATCATTTTGTCTGACTAGTACGG<br>GTGGCATCCCTGTGACCCCTCCCCAGTGCCTCTCCTGGCCCTGGAAGTTGC<br>CACTCCAGTGCCCACCAGCCTTGTCCTAATAAAATTAAGTTGCATCATTTTGT<br>CTGACTAGGTGTCCTTCTATAATATTATGGGGTGGAGGGGGGTGGTATGGA<br>GCAAGGGCAAGTTGGGAAGACAACCTGTAGGGCCTGCGGGTCTATTGG<br>GAACCAAGCTGGAGTGCAGTGGCACAATCTTGGCTCACTGCAATCTCCGCC<br>TCCTGGGTTCAAGCGATTCTCCTGCCTCAGCCTCCCGAGTTGTTGGGATTCC<br>AGGCATGCATGACCAGGCTCAGCTAATTTTTGTTTTTTGGTAGAGACGGGG<br>TTTCACCATATTGGCCAGGCTGGTCTCCAACTCCTAATCTCAGGTGATCTAC<br>CCACCTTGGCCTCCCAAATTGCTGGGATTACAGGCGTGAACCACTGCTCCC<br>TTCCCTGTCCTTCTGATTTTGTAGGTAACCACGTGCGGACCGAGCGGCCGC | |
| 84 | GCGGCCGCACGCGTCACCAACTGGGTAACCTCTGCTGACCCCCACTCTACT<br>TTACCATAAGTAGCTCCAAATCCTTCTAGAAAATCTGAAAGGCATAGCCCCAT<br>ATATCAGTGATATAAATAGAACCTGCAGCAGGCTCTGGTAAATGATGACTAC<br>AAGGTGGACTGGGAGGCAGCCCGGCCTTGGCAGGCATCATCCTCTAAATAT<br>AAAGATGAGTTTGTTCAGCCTTTGCAGAAGGAAAAACTGCCACCCATCCTAG<br>AGTGCCGCGTCCTTGTCCCCCCACCCCCTCCAATTTATTGGGAGGAAGGAC<br>CAGCTAAGCCTCATCTAGGAAGAGCCCCTCACCCATCTCCACCTCCACTCCA<br>GGTCTAGCCAGTCCTGGGTTGTGACCCTTGTCTTTCAGCCCCAGGAGAGGG<br>ACACACATAGTGCCACCAAAGAGGCTGGGGGAGGGCCTCAGCCCACCAAAA<br>CCTGGGGCCAGTGCGTCCTACAGGAGGGGAACCCTCACCCCTTCAATCCCT<br>TTAGGAGACCCAAGGGCGCTGCGCGTCCCTGAGGCGGACAGCTCCGTGTG<br>CTCAGGCTTTGCGCCTGACAGGCCTATCCCCGGGAGCCCCGCGCCTCCT<br>CCCCGGCGCTCCGCCCTCGCCTCCCCCCGCCAGTTGTCTATCCTGCGACAG<br>CTGCGCGCCCTCCGGCCGCCGGTGGCCCTCTGTGCGGTGGGGGAAGGGG<br>TCGACGTGGCTCAGCTTTTTGGATTCAGGGAGCTCGGGGGTGGGAAGAGAG<br>AAATGGAGTTCCAGGGGCGTAAAGGAGAGGGAGTTCGCCTTCCTTCCCTTC<br>CTGAGACTCAGGAGTGACTGCTTCTCCAATCCTCCCAAGCCCACCACTCCAC<br>ACGACTCCCTCTTCCCGGTAGTCGCAAGTGGGAGTTTGGGGATCTGAGCAA<br>AGAACCCGAAGAGGAGTTGAAATATTGGAAGTCAGCAGTCAGGCACCTTCC<br>CGAGCGCCCAGGGCGCTCAGAGTGGACATGGTTGGGGAGGCCTTTGGGAC<br>AGGTGCGGTTCCCGGAGCGCAGGCGCACACATGCACCCACCGGCGAACGC<br>GGTGACCCTCGCCCCACCCCATCCCCTCCGGCGGGCAACTGGGTCGGGTC<br>AGGAGGGGCAAACCCGCTAGGGAGACACTCCATATACGGCCCGGCCCGCG<br>TTACCTGGGACCGGGCCAACCCGCTCCTTCTTTGGTCAACGCAGGGGACCC<br>GGGCGGGGGCCCAGGCCGCGAACCGGCCGAGGGAGGGGGCTCTAGTGCC<br>CAACACCCAAATATGGCTCGAGAAGGGCAGCGACATTCCTGCGGGGTGGC<br>GCGGAGGGAATGCCCGCGGGCTATATAAAACCTGAGCAGAGGGACAAGCG<br>GCCACCGCAGCGGACAGCGCCAAGTGAAGCCTCGCTTCCCCTCCGCGGCG<br>ACCAGGGCCCGAGCCGAGAGTAGCAGTTGTAGCTACCCGCCCAGGTAGGG<br>CAGGAGTTGGGAGGGGACAGGGGACAGGGCACTACCGAGGGGAACCTG<br>AAGGACTCCGGGGCAGAACCCAGTCGGTTCACCTGGTAAGCTTGCTAGCTC<br>CGCGGATTCGAATCCCGGCCGGGAACGGTGCATTGGAACGCGGATTCCCC<br>GTGCCAAGAGTGACGTAAGTACCGCCTATAGAGTCTATAGGCCCACAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCA<br>TTCTAAAGAATAACAGTGATAATTTCTGGGTTAAGGCAATAGCAATATTTCTG<br>CATATAAATATTTCTGCATATAAATTGTAACTGATGTAAGAGGTTTCATATTGC | Sequence of mAAV-Vp16-Bagly that is incorporated into viral particle and delivered to humans or mice |

| SEQ ID NO: | Sequence | Description |
|---|---|---|
| | TAATAGCAGCTACAATCCAGCTACCATTCTGCTTTTATTTTATGGTTGGGATA<br>AGGCTGGATTATTCTGAGTCCAAGCTAGGCCCTTTTGCTAATCATGTTCATAC<br>CTCTTATCTTCCTCCCACAGCTCCTGGGCAACGTGCTGGTCTGTGTGCTGGC<br>CCATCACTTTGGCAAAGAATTGGGATTCGAACATCGATTTAAAGCTATGGAG<br>CAAAAGCTCATTTCTGAAGAGGACTTGAATGAAATGGAGCAAAAGCTCATTT<br>CTGAAGAGGACTTGAATGAAATGGAGCAAAAGCTCATTTCTGAAGAGGACTT<br>GAATGAAATGGAGCAAAAGCTCATTTCTGAAGAGGACTTGAATGAAATGGAG<br>CAAAAGCTCATTTCTGAAGAGGACTTGAATGAAATGGAGCTTGGGCGACC<br>TCACCATGGGCCCTAAAAGAAGCGTAAAGTCGCCCCCCCGACCGATGTCA<br>GCCTGGGGACGAGCTCCACTTAGACGGCGAGGACGTGGCGATGGCGCAT<br>GCCGACGCGCTAGACGATTTCGATCTGGACATGTTGGGGGACGGGGATTCC<br>CCGGGTCCGGGATTTACCCCCACGACTCCGCCCCCTACGGCGCTCTGGAT<br>ATGGCCGACTTCGAGTTTGAGCAGATGTTTACCGATGCCCTTGGAATTGACG<br>AGTACGGTGGGGAATTCCCGGGGATCCTCGATGACAGACCCTATGCTTGCC<br>CAGTGGAAAGCTGCGACCGCCGCTTTTCTAGATCGGATGAGCTTACCCGCC<br>ATATCCGCATCCACACCGGCCAAAAACCCTTTCAATGCCGTATCTGCATGAG<br>GAATTTCAGCAGCCGCGATGTCCTGAGGCGCCATAACAGGACCCACACAGG<br>GGAAAAGCCATTCGCATGTGACATCTGCGGTCGAAAGTTTGCAAGCCGCGA<br>TGTCCTGAGGCGCCATAACAGGATACATTTGAGGCAAGGTCCCAGATCTCA<br>CGTCTGTGCAGAATGTGGCAAAGCGTTCGTTGAGAGCTCAAAGCTAAAACG<br>ACACCAGCTGGTTCATGAGCTGGAGAGAAGCCCTTTTAGCTCGAGAGATCTA<br>CGGGTGGCATCCCTGTGACCCCTCCCCAGTGCCTCTCCTGGCCTGGAAGT<br>TGCCACTCCAGTGCCCACCAGCCTTGTCCTAATAAAATTAAGTTGCATCATTT<br>TGTCTGACTAGGTGTCCTTCTATAATATTATGGGGTGGAGGGGGGTGGTATG<br>GAGCAAGGGGCAAGTTGGGAAGACAACCTGTAGGGCCTGCGGGGTCTATT<br>GGGAACCAAGCTGGAGTGCAGTGGCACAATCTTGGCTCACTGCAATCTCCG<br>CCTCCTGGGTTCAAGCGATTCTCCTGCCTCAGCCTCCCGAGTTGTTGGGATT<br>CCAGGCATGCATGACCAGGCTCAGCTAATTTTTGTTTTTTTGGTAGAGACGG<br>GGTTTCACCATATTGGCCAGGCTGGTCTCCAACTCCTAATCTCAGGTGATCT<br>ACCCACCTTGGCCTCCCAAATTGCTGGGATTACAGGCGTGAACCACTGCTC<br>CCTTCCCTGTCCTTCTGATTTTGTAGGTAACCACGTGCGGACCGAGCGGCC<br>GC | |
| 85 | GCGGCCGCACGCGTCACCAACTGGGTAACCTCTGCTGACCCCCACTCTACT<br>TTACCATAAGTAGCTCCAAATCCTTCTAGAAAATCTGAAAGGCATAGCCCCAT<br>ATATCAGTGATATAAATAGAACCTGCAGCAGGCTCTGGTAAATGATGACTAC<br>AAGGTGGACTGGGAGGCAGCCCGGCCTTGGCAGGCATCATCCTCTAAATAT<br>AAAGATGAGTTTGTTCAGCCTTTGCAGAAGGAAAAACTGCCACCCATCCTAG<br>AGTGCCGCGTCCTTGTCCCCCCACCCCCTCCAATTTATTGGGAGGAAGGAC<br>CAGCTAAGCCTCATCTAGGAAGAGCCCCTCACCCATCTCCACCTCCACTCCA<br>GGTCTAGCCAGTCCTGGGTTGTGACCCTTGTCTTTCAGCCCCAGGAGAGGG<br>ACACACATAGTGCCACCAAAGAGGCTGGGGAGGGCCTCAGCCCACCAAA<br>CCTGGGGCCAGTGCGTCCTACAGGAGGGGAACCCTCACCCCTTCAATCCCT<br>TTAGGAGACCCAAGGGCGCTGCGCGTCCCTGAGGCGGACAGCTCCGTGTG<br>CTCAGGCTTTGCGCCTGACAGGCCTATCCCCGGGAGCCCCCGCGCCTCCT<br>CCCCGGCGCTCCGCCCTCGCCTCCCCCCGCCAGTTGTCTATCCTGCGACAG<br>CTGCGCGCCCTCCGGCCGCCGGTGGCCCTCTGTGCGGTGGGGAAGGGG<br>TCGACGTGGCTCAGCTTTTTGGATTCAGGGAGCTCGGGGTGGGAAGAGAG<br>AAATGGAGTTCCAGGGGCGTAAAGGAGAGGGAGTTCGCCTTCCTTCCCTTC<br>CTGAGACTCAGGAGTGACTGCTTCTCCAATCCTCCCAAGCCCACCACTCCAC<br>ACGACTCCCTCTTCCCGGTAGTCGCAAGTGGGAGTTTGGGGATCTGAGCAA<br>AGAACCCGAAGAGGAGTTGAAATATTGGAAGTCAGCAGTCAGGCACCTTCC<br>CGAGCGCCCAGGGCGCTCAGAGTGGACATGGTTGGGGAGGCCTTTGGGAC<br>AGGTGCGGTTCCCGGAGCGCAGGCGCACACATGCACCCACCGGCGAACGC<br>GGTGACCCTCGCCCCACCCCATCCCCTCCGGCGGGCAACTGGGTCGGGTC<br>AGGAGGGGCAAACCCGCTAGGGAGACACTCCATATACGGCCCGGCCCGCG<br>TTACCTGGGACCGGGCCAACCCGCTCCTTCTTTGGTCAACGCAGGGGACCC<br>GGGCGGGGGCCCAGGCCGCGAACCGGCCGAGGGAGGGGGCTCTAGTGCC<br>CAACACCCAAATATGGCTCGAGAAGGGCAGCGACATTCCTGCGGGGTGGC<br>GCGGAGGGAATGCCCGCGGGCTATATAAAACCTGAGCAGAGGGACAAGCG<br>GCCACCGCAGCGGACAGCGCAAGTGAAGCCTCGCTTCCCCTCCGCGGCG<br>ACCAGGGCCCGAGCCGAGAGTAGCAGTTGTAGCTACCCGCCCAGGTAGGG<br>CAGGAGTTGGGAGGGGACAGGGGACAGGGCACTACCGAGGGGAACCTG<br>AAGGACTCCGGGGCAGAACCCAGTCGGTTCACCTGGTAAGCTTGCTAGCTC<br>CGCGGATTCGAATCCCGGCCGGGAACGGTGCATTGGAACGCGGATTCCCC<br>GTGCCAAGAGTGACGTAAGTACCGCCTATAGAGTCTATAGGCCCACAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCA<br>TTCTAAAGAATAACAGTGATAATTTCTGGGTTAAGGCAATAGCAATATTTCTG<br>CATATAAATATTTCTGCATATAAATTGTAACTGATGTAAGAGGTTTCATATTGC<br>TAATAGCAGCTACAATCCAGCTACCATTCTGCTTTTATTTTATGGTTGGGATA<br>AGGCTGGATTATTCTGAGTCCAAGCTAGGCCCTTTTGCTAATCATGTTCATAC<br>CTCTTATCTTCCTCCCACAGCTCCTGGGCAACGTGCTGGTCTGTGTGCTGGC<br>CCATCACTTTGGCAAAGAATTGGGATTCGAACATCGATTTAAAGCTATGGAG<br>CAAAAGCTCATTTCTGAAGAGGACTTGAATGAAATGGAGCAAAAGCTCATTT | Sequence of mAAV-Vp16-CJ7-UtroUp that is incorporated into viral particle and delivered to humans or mice |

| SEQ ID NO: | Sequence | Description |
|---|---|---|
| | CTGAAGAGGACTTGAATGAAATGGAGCAAAAGCTCATTTCTGAAGAGGACTT<br>GAATGAAATGGAGCAAAAGCTCATTTCTGAAGAGGACTTGAATGAAATGGAG<br>CAAAAGCTCATTTCTGAAGAGGACTTGAATGAAATGGAGAGCTTGGGCGACC<br>TCACCATGGGCCCTAAAAAGAAGCGTAAAGTCGCCCCCCCGACCGATGTCA<br>GCCTGGGGGACGAGCTCCACTTAGACGGCGAGGACGTGGCGATGGCGCAT<br>GCCGACGCGCTAGACGATTTCGATCTGGACATGTTGGGGGACGGGGATTCC<br>CCGGGTCCGGGATTTACCCCCCACGACTCCGCCCCCTACGGCGCTCTGGAT<br>ATGGCCGACTTCGAGTTTGAGCAGATGTTTACCGATGCCCTTGGAATTGACG<br>AGTACGGTGGGGAATTCCCGGGGATCTTGGCAAAGCGCTTTGCCGACTTTA<br>CAGTCTACAGGAACCGCACACTTCAGAAATGGCACGATAAGACCAAACTGG<br>CTTCTGGAAAACTGGGGAAGGGTTTTGGTGCCTTTGAACGCTCAATCTTGAC<br>TCAGATCGACCATATTCTGATGGACAAAGAGAGATTACTTCGAAGGACACAG<br>ACCAAGCGCTCTGTCTATCGAGTTCTTGGCAAACCTGAGCCAGCAGCTCAG<br>CCTGTCCCAGAGAGTTTGCCAGGGGAACCGGAGATCCTTCCTCAAGCCCCT<br>GCTAATGCTCATCTGAAGGACTTGGATGAAGAAATCTTTGATGATGATGACTT<br>TTACCACCAGCTCCTTCGAGAACTCATAGAACGGAAGACCAGCTCCTTGGG<br>GATCCTGGATCGCCCTTACGCCTGCCCTGTGGAATCTTGCGACCGCCGGTT<br>CTCCCGCAGCGATAACCTGGTGCGGCACATCCGGATTCACACCGGCCAGAA<br>ACCTTTCCAGTGCAGGATCTGCATGAGAAATTTCTCCCGGTCCGACCACCTG<br>ACCACCCACAATAGGACCCACACCGGCGAGAAACCCTTTGCCTGCGACATC<br>TGCGGGAGAAAGTTCGCCGACCCCGGCCACCTGGTGAGACACAATAGAATC<br>CACACCGGTGAAAAGCCCTTCGCCTGTCCCGTGGAGAGCTGCGATCGCAGA<br>TTCAGCCGCAGCGACGAGCTGACAAGGCACATCAGAATCCACACCGGGCAG<br>AAGCCTTTTCAGTGCCGGATCTGCATGAGGAACTTCAGCTCCCGGGACGTG<br>CTGAGACGCCACAATCGCACACACACCGGCGAAAAGCCCTTCGCCTGTGAT<br>ATTTGCGGGCGGAAATTTGCCTCCAGAGATGTGCTGCGCCGCCACAACCGC<br>ATTCACCTGAGACAGAACGATCTCGAGAGATCTACGGGTGGCATCCCTGTG<br>ACCCCTCCCCAGTGCCTCTCCTGGCCCTGGAAGTTGCCACTCCAGTGCCCA<br>CCAGCCTTGTCCTAATAAAATTAAGTTGCATCATTTTGTCTGACTAGGTGTCC<br>TTCTATAATATTATGGGGTGGAGGGGGGTGGTATGGAGCAAGGGCAAGTT<br>GGGAAGACAACCTGTAGGGCCTGCGGGGTCTATTGGGAACCAAGCTGGAG<br>TGCAGTGGCACAATCTTGGCTCACTGCAATCTCCGCCTCCTGGGTTCAAGC<br>GATTCTCCTGCCTCAGCCTCCCGAGTTGTTGGGATTCCAGGCATGCATGAC<br>CAGGCTCAGCTAATTTTTGTTTTTTTGGTAGAGACGGGGTTTCACCATATTGG<br>CCAGGCTGGTCTCCAACTCCTAATCTCAGGTGATCTACCCACCTTGGCCTCC<br>CAAATTGCTGGGATTACAGGCGTGAACCACTGCTCCCTTCCCTGTCCTTCTG<br>ATTTTGTAGGTAACCACGTGCGGACCGAGCGGCCGC | |
| 86 | GCGGCCGCACGCGTCACCAACTGGGTAACCTCTGCTGACCCCCACTCTACT<br>TTACCATAAGTAGCTCCAAATCCTTCTAGAAAATCTGAAAGGCATAGCCCCAT<br>ATATCAGTGATATAAATAGAACCTGCAGCAGGCTCTGGTAAATGATGACTAC<br>AAGGTGGACTGGGAGGCAGCCCGGCCTTGGCAGGCATCATCCTCTAAATAT<br>AAAGATGAGTTTGTTCAGCCTTTGCAGAAGGAAAAACTGCCACCCATCCTAG<br>AGTGCCGCGTCCTTGTCCCCCCACCCCCTCCAATTTATTGGGAGGAAGGAC<br>CAGCTAAGCCTCATCTAGGAAGAGCCCCTCACCCATCTCCACCTCCACTCCA<br>GGTCTAGCCAGTCCTGGGTTGTGACCCTTGTCTTTCAGCCCCAGGAGAGGG<br>ACACACATAGTGCCACCAAAGAGGCTGGGGGAGGGCCTCAGCCCACCAAAA<br>CCTGGGGCCAGTGCGTCCTACAGGAGGGGAACCCTCACCCCTTCAATCCCT<br>TTAGGAGACCCAAGGGCGCTGCGCGTCCCTGAGGCGGACAGCTCCGTGTG<br>CTCAGGCTTTGCGCCTGACAGGCCTATCCCGGGAGCCCCCGCGCCTCCT<br>CCCCGGCGCTCCGCCCTCGCCTCCCCCCGCCAGTTGTCTATCCTGCGACAG<br>CTGCGCGCCCTCCGGCCGCCGGTGGCCCTCTGTGCGGTGGGGGAAGGGG<br>TCGACGTGGCTCAGCTTTTTGGATTCAGGGAGCTCGGGGTGGGAAGAGAG<br>AAATGGAGTTCCAGGGGCGTAAAGGAGAGGGAGTTCGCCTTCCTTCCCTTC<br>CTGAGACTCAGGAGTGACTGCTTCTCCAATCCTCCCAAGCCCACCACTCCAC<br>ACGACTCCCTCTTCCCGGTAGTCGCAAGTGGGAGTTTGGGGATCTGAGCAA<br>AGAACCCGAAGAGGAGTTGAAATATTGGAAGTCAGCAGTCAGGCACCTTCC<br>CGAGCGCCCAGGGCGCTCAGAGTGGACATGGTTGGGGAGGCCTTTGGGAC<br>AGGTGCGGTTCCCGGAGCGCAGGCGCACACATGCACCCACCGGCGAACGC<br>GGTGACCCTCGCCCCACCCCATCCCCTCCGGCGGGCAACTGGGTCGGGTC<br>AGGAGGGGCAAACCCGCTAGGGAGACACTCCATATACGGCCCGGCCCGCG<br>TTACCTGGGACCGGGCCAACCCGCTCCTTCTTTGGTCAACGCAGGGACCC<br>GGGCGGGGCCCAGGCCGCGAACCGGCCGAGGGAGGGGGCTCTAGTGCC<br>CAACACCCAAATATGGCTCGAGAAGGGCAGCGACATTCCTGCGGGGTGGC<br>GCGGAGGGAATGCCCGCGGGCTATATAAAACCTGAGCAGAGGGACAAGCG<br>GCCACCGCAGCGGACAGCGCCAAGTGAAGCCTCGCTTCCCCTCCGCGGCG<br>ACCAGGGCCCGAGCCGAGAGTAGCAGTTGTAGCTACCCGCCCAGGTAGGG<br>CAGGAGTTGGAGGGGACAGGGGACAGGGCACTACCGAGGGGAACCTG<br>AAGGACTCCGGGGCAGAACCCAGTCGGTTCACCTGGTAAGCTTGCTAGCTC<br>CGCGGATTCGAATCCCGGCCGGGAACGGTGCATTGGAACGCGGATTCCCC<br>GTGCCAAGAGTGACGTAAGTACCGCCTATAGAGTCTATAGGCCCACAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCA<br>TTCTAAAGAATAACAGTGATAATTTCTGGGTTAAGGCAATAGCAATATTTCTG<br>CATATAAATATTTCTGCATATAAATTGTAACTGATGTAAGAGGTTTCATATTGC | Sequence of mAAV-JZif1 that is incorporated into viral particle and delivered to humans or mice |

| SEQ ID NO: | Sequence | Description |
|---|---|---|
|  | TAATAGCAGCTACAATCCAGCTACCATTCTGCTTTTATTTTATGGTTGGGATA<br>AGGCTGGATTATTCTGAGTCCAAGCTAGGCCCTTTTGCTAATCATGTTCATAC<br>CTCTTATCTTCCTCCCACAGCTCCTGGGCAACGTGCTGGTCTGTGTGCTGGC<br>CCATCACTTTGGCAAAGAATTGGGATTCGAACATCGATGGTACCGAATTCAA<br>TGGCCGCTGCCAAGGCCGAGATGCAGCTGATGAGCCCCCTGCAGATCAGC<br>GACCCCTTCGGCAGCTTCCCCCACAGCCCCACCATGGACAACTACCCCAAG<br>CTGGAAGAGATGATGCTGCTGAGCAATGGCGCTCCTCAGTTCCTGGGAGCC<br>GCTGGCGCCCCTGAGGGCAGCGGCAGCAATAGCAGCAGCAGCTCTAGCGG<br>CGGAGGCGGAGGGGGAGGCGGCGGAAGCAATAGCTCCAGCTCCAGCAGC<br>ACATTCAATCCACAAGCCGACACCGGCGAGCAGCCCTATGAGCACCTGACC<br>GCCGAGAGCTTCCCCGACATCAGCCTGAACAACGAGAAGGTGCTGGTGGAA<br>ACCAGCTACCCCAGCCAGACCACCCGGCTGCCCCCTATCACCTACACAGGC<br>CGGTTCAGCCTGGAACCCGCCCCTAACAGCGGCAACACCCTGTGGCCCGA<br>GCCCCTGTTTAGCCTGGTGTCCGGCCTGGTGTCTATGACCAACCCCCCTGC<br>CAGCAGCTCCTCTGCCCCAAGCCCTGCCGCCAGCTCTGCCTCTGCCAGCCA<br>GAGCCCTCCACTGAGCTGCGCCGTGCCCAGCAACGACAGCAGCCCCATCTA<br>CAGCGCCGCTCCCACCTTCCCCACCCCCAACACCGACATCTTCCCCGAGCC<br>TCAGAGCCAGGCCTTTCCTGGATCTGCCGGCACCGCCCTGCAGTACCCACC<br>TCCTGCCTATCCTGCCGCCAAGGGCGGCTTCCAGGTGCCCATGATCCCCGA<br>CTACCTGTTCCCCCAGCAGCAGGGCGATCTGGGCCTGGGCACCCCCGACC<br>AGAAGCCTTTCCAGGGCCTCGAAAGCCGGACCCAGCAGCCAAGCCTGACC<br>CCCCTGAGCACCATCAAGGCCTTCGCCACCCAGAGCGGCAGCCAGGACCT<br>GAAGGCCCTGAACACCAGCTACCAGAGCCAGCTGATCAAGCCCCAGCCGGAT<br>GCGGAAGTACCCCAACCGGCCCAGCAAGACCCCCCCACACGAGAGGCCTT<br>ACGCCTGCCCCGTGGAAAGCTGCGACAGACGGTTCAGCAGAAGCGACGAG<br>CTGACCCGGCACATCCGGATCCACACCGGCCAGAAACCCTTCCAGTGCCGG<br>ATCTGCATGCGGAACTTCAGCAGCCGGGACGTGCTGCGGCGGCACAATAGA<br>ACCCACACAGGCGAGAAGCCCTTCGCCTGCGACATCTGCGGCCGGAAGTTC<br>GCCAGCAGAGATGTGCTGCGGAGACACAACAGGATCCACCTGAGACAGAAG<br>GACAAGAAAGCCGACAAGAGCGTGGTCGCCAGCAGCGCTACCAGCAGCCT<br>GAGCAGCTACCCTTCTCCTGTGGCCACCTCCTACCCAAGCCCAGTGACCAC<br>AAGCTACCCATCCCCCGCCACCACCTCTTATCCCAGCCCCGTGCCTACCAG<br>CTTCAGCTCTCCCGGCAGCTCCACATACCCCAGCCCTGTGCATAGCGGCTT<br>CCCTAGCCCTAGCGTGGCCACCACATACAGCAGCGTGCCCCCTGCCTTCCC<br>AGCTCAAGTGTCCAGCTTCCCCAGCTCCGCCGTGACCAACAGCTTCAGCGC<br>CAGCACCGGCCTGAGCGACATGACCGCCACCTTCAGCCCCCGGACCATCG<br>AGATCTGCTGACTCGAGAGATCTACGGGTGGCATCCCTGTGACCCCTCCCC<br>AGTGCCTCTCCTGGCCCTGGAAGTTGCCACTCCAGTGCCCACCAGCCTTGT<br>CCTAATAAAATTAAGTTGCATCATTTTGTCTGACTAGGTGTCCTTCTATAATAT<br>TATGGGTGGAGGGGGTGGTATGGAGCAAGGGGCAAGTTGGGAAGACAA<br>CCTGTAGGGCCTGCGGGGTCTATTGGGAACCAAGCTGGAGTGCAGTGGCA<br>CAATCTTGGCTCACTGCAATCTCCGCCTCCTGGGTTCAAGCGATTCTCCTGC<br>CTCAGCCTCCCGAGTTGTTGGGATTCCAGGCATGCATGACCAGGCTCAGCT<br>AATTTTTTGTTTTTTTGGTAGAGACGGGGTTTCACCATATTGGCCAGGCTGGT<br>CTCCAACTCCTAATCTCAGGTGATCTACCCACCTTGGCCTCCCAAATTGCTG<br>GGATTACAGGCGTGAACCACTGCTCCCTTCCCTGTCCTTCTGATTTTGTAGG<br>TAACCACGTGCGGACCGAGCGGCCGC |  |
| 87 | GCGGCCGCACGCGTCACCAACTGGGTAACCTCTGCTGACCCCCACTCTACT<br>TTACCATAAGTAGCTCCAAATCCTTCTAGAAAATCTGAAAGGCATAGCCCCAT<br>ATATCAGTGATATAAATAGAACCTGCAGCAGGCTCTGGTAAATGATGACTAC<br>AAGGTGGACTGGGAGGCAGCCCGGCCTTGGCAGGCATCATCCTCTAAATAT<br>AAAGATGAGTTTGTTCAGCCTTTGCAGAAGGAAAAACTGCCACCCATCCTAG<br>AGTGCCGTCCTTGTCCCCCCACCCCCTCCAATTTATTGGGAGGAAGGAC<br>CAGCTAAGCCTCATCTAGGAAGAGCCCCTCACCCATCTCCACCTCCACTCCA<br>GGTCTAGCCAGTCCTGGGTTGTGACCCTTGTCTTTCAGCCCCAGGAGAGGG<br>ACACACATAGTGCCACCAAAGAGGCTGGGGGAGGGCCTCAGCCCACCAAAA<br>CCTGGGGCCAGTGCGTCCTACAGGAGGGGAACCCTCACCCCTTCAATCCCT<br>TTAGGAGACCCAAGGGCGCTGCGCGTCCCTGAGGCGGACAGCTCCGTGTG<br>CTCAGGCTTTGCGCCTGACAGGCCTATCCCCGGGAGCCCCCGCGCCTCCT<br>CCCCGGCGCTCCGCCCTCGCCTCCCCCCGCCAGTTGTCTATCCTGCGACAG<br>CTGCGCGCCCTCCGGCCGCCGGTGGCCCTCTGTGCGGTGGGGAAGGGG<br>TCGACGTGGCTCAGCTTTTTGGATTCAGGGAGCTCGGGGGTGGGAAGAGAG<br>AAATGGAGTTCCAGGGGCGTAAAGGAGAGGGAGTTCGCCTTCCTTCCCTTC<br>CTGAGACTCAGGAGTGACTGCTTCTCCAATCCTCCCAAGCCCACCACTCCAC<br>ACGACTCCCTCTTCCCGGTAGTCGCAAGTGGGAGTTTGGGGATCTGAGCAA<br>AGAACCCGAAGAGGAGTTGAAATATTGGAAGTCAGCAGTCAGGCACCTTCC<br>CGAGCGCCCAGGGCGCTCAGAGTGGACATGGTTGGGGAGGCCTTTGGGAC<br>AGGTGCGGTTCCGGAGCGCAGGCGCACACATGCACCCACCGGCGAACGC<br>GGTGACCCTCGCCCCACCCCATCCCCTCCGGCGGGCAACTGGGTCGGGTC<br>AGGAGGGGCAAACCCGCTAGGGAGACACTCCATATACGGCCCGGCCCGCG | Sequence of mAAV-JZif2 that is incorporated into viral particle and delivered to humans or mice |

| SEQ ID NO: | Sequence | Description |
|---|---|---|
| | TTACCTGGGACCGGGCCAACCCGCTCCTTCTTTGGTCAACGCAGGGGACCC<br>GGGCGGGGGCCCAGGCCGCGAACCGGCCGAGGGAGGGGGCTCTAGTGCC<br>CAACACCCAAATATGGCTCGAGAAGGGCAGCGACATTCCTGCGGGGTGGC<br>GCGGAGGGAATGCCCGCGGGCTATATAAAACCTGAGCAGAGGGACAAGCG<br>GCCACCGCAGCGGACAGCGCCAAGTGAAGCCTCGCTTCCCCTCCGCGGCG<br>ACCAGGGCCCGAGCCGAGAGTAGCAGTTGTAGCTACCCGCCCAGGTAGGG<br>CAGGAGTTGGGAGGGGACAGGGGGACAGGGCACTACCGAGGGGAACCTG<br>AAGGACTCCGGGGCAGAACCCAGTCGGTTCACCTGGTAAGCTTGCTAGCTC<br>CGCGGATTCGAATCCCGGCCGGGAACGGTGCATTGGAACGCGGATTCCCC<br>GTGCCAAGAGTGACGTAAGTACCGCCTATAGAGTCTATAGGCCCACAAAAAA<br>TGCTTTCTTCTTTTAATATACTTTTTTGTTTATCTTATTTCTAATACTTTCCCTA<br>ATCTCTTTCTTTCAGGGCAATAATGATACAATGTATCATGCCTCTTTGCACCA<br>TTCTAAAGAATAACAGTGATAATTTCTGGGTTAAGGCAATAGCAATATTTCTG<br>CATATAAATATTTCTGCATATAAATTGTAACTGATGTAAGAGGTTTCATATTGC<br>TAATAGCAGCTACAATCCAGCTACCATTCTGCTTTTATTTTATGGTTGGGATA<br>AGGCTGGATTATTCTGAGTCCAAGCTAGGCCCTTTTGCTAATCATGTTCATAC<br>CTCTTATCTTCCTCCCACAGCTCCTGGGCAACGTGCTGGTCTGTGTGCTGGC<br>CCATCACTTTGGCAAAGAATTGGGATTCGAACATCGATGGTACCGAATTCAA<br>TGGCCGCTGCCAAGGCCGAGATGCAGCTGATGAGCCCCCTGCAGATCAGC<br>GACCCCTTCGGCAGCTTCCCCCACAGCCCCACCATGGACAACTACCCCAAG<br>CTGGAAGAGATGATGCTGCTGAGCAATGGCGCTCCTCAGTTCCTGGGAGCC<br>GCTGGCGCCCCTGAGGGCAGCGGCAGCAATAGCAGCAGCAGCTCTAGCGG<br>CGGAGGCGGAGGGGGAGGCGGCGGAAGCAATAGCTCCAGCTCCAGCAGC<br>ACATTCAATCCACAAGCCGACACCGGCGAGCAGCCCTATGAGCACCTGACC<br>GCCGAGAGCTTCCCCGACATCAGCCTGAACAACGAGAAGGTGCTGGTGGAA<br>ACCAGCTACCCCAGCCAGACCACCCGGCTGCCCCCTATCACCTACACAGGC<br>CGGTTCAGCCTGGAACCCGCCCCTAACAGCGGCAACACCCTGTGGCCCGA<br>GCCCCTGTTTAGCCTGGTGTCCGGCCTGGTGTCTATGACCAACCCCCCTGC<br>CAGCAGCTCCTCTGCCCCAAGCCCTGCCGCCAGCTCTGCCTCTGCCAGCCA<br>GAGCCCTCCACTGAGCTGCGCCGTGCCCAGCAACGACAGCAGCCCCATCTA<br>CAGCGCCGCTCCCACCTTCCCCACCCCCAACACCGACATCTTCCCCGAGCC<br>TCAGAGCCAGGCCTTTCCTGGATCTGCCGGCACCGCCCTGCAGTACCCACC<br>TCCTGCCTATCCTGCCGCCAAGGGCGGCTTCCAGGTGCCCATGATCCCCGA<br>CTACCTGTTCCCCCAGCAGCAGGGCGATCTGGGCCTGGGCACCCCCGACC<br>AGAAGCCTTTCCAGGGCCTCGAAAGCCGGACCCAGCAGCCAAGCCTGACC<br>CCCCTGAGCACCATCAAGGCCTTCGCCACCCAGAGCGGCAGCCAGGACCT<br>GAAGGCCCTGAACACCAGCTACCAGAGCCAGCTGATCAAGCCCAGCCGGAT<br>GCGGAAGTACCCCAACCGGCCCAGCAAGACCCCCCCACACGAGAGGCCTT<br>ACGCCTGCCCCGTGGAAAGCTGCGACAGACGGTTCAGCAGAAGCGACAAC<br>CTGGTCCGGCACATCCGGATCCACACCGGCCAGAAACCCTTCCAGTGCCGG<br>ATCTGCATGCGGAACTTCTCTCGGAGCGACCACCTGACCACCCACATCAGA<br>ACCCACACAGGCGAGAAGCCCTTCGCCTGCGACATCTGCGGCCGGAAGTTC<br>GCCGACCCCGGCCACCTCGTCAGACACAACAGGATTCACCTGAGACAGAAG<br>GACAAGAAAGCCGACAAGAGCGTGGTCGCCAGCAGCGCTACCAGCAGCCT<br>GAGCAGCTACCCTTCTCCTGTGGCCACCTCCTACCCAAGCCCAGTGACCAC<br>AAGCTACCCATCCCCCGCCACCACCTCTTATCCCAGCCCCGTGCCTACCAG<br>CTTCAGCTCTCCCGGCAGCTCCACATACCCCAGCCCTGTGCATAGCGGCTT<br>CCCTAGCCCTAGCGTGGCCACCACATACAGCAGCGTGCCCCCTGCCTTCCC<br>AGCTCAAGTGTCCAGCTTCCCCAGCTCCGCCGTGACCAACAGCTTCAGCGC<br>CAGCACCGGCCTGAGCGACATGACCGCCACCTTCAGCCCCCGGACCATCG<br>AGATCTGCTGACTCGAGAGATCTACGGGTGGCATCCCTGTGACCCCTCCCC<br>AGTGCCTCTCCTGGCCCTGGAAGTTGCCACTCCAGTGCCCACCAGCCTTGT<br>CCTAATAAAATTAAGTTGCATCATTTTGTCTGACTAGGTGTCCTTCTATAATAT<br>TATGGGTGGAGGGGGTGGTATGGAGCAAGGGGCAAGTTGGGAAGACAA<br>CCTGTAGGGCCTGCGGGGTCTATTGGGAACCAAGCTGGAGTGCAGTGGCA<br>CAATCTTGGCTCACTGCAATCTCCGCCTCCTGGGTTCAAGCGATTCTCCTGC<br>CTCAGCCTCCCGAGTTGTTGGGATTCCAGGCATGCATGACCAGGCTCAGCT<br>AATTTTTGTTTTTTGGTAGAGACGGGGTTTCACCATATTGGCCAGGCTGGT<br>CTCCAACTCCTAATCTCAGGTGATCTACCCACCTTGGCCTCCAAATTGCTG<br>GGATTACAGGCGTGAACCACTGCTCCCTTCCCTGTCCTTCTGATTTTGTAGG<br>TAACCACGTGCGGACCGAGCGGCCGC | |

OTHER EMBODIMENTS

Various modifications and variations of the described compositions and methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. All publications, patents, and patent applications mentioned in the above specification are hereby incorporated by reference.

What is claimed is:

1. A recombinant adeno-associated vector (AAV) for expression of a gene in skeletal or cardiac muscle tissue comprising a muscle-specific promoter and a gene encoding a fusion protein, wherein said fusion protein comprises:
   a) a transcriptional activation element and
   b) a DNA binding element, wherein said DNA binding element binds to a promoter of the utrophin gene, wherein said utrophin promoter is a mouse or human utrophin "A" promoter,
   wherein said fusion protein, when expressed in said skeletal or cardiac muscle tissue, is capable of increasing utrophin expression, increasing muscle contractile force, or increasing muscle endurance, and
   wherein said vector comprises the sequence of SEQ ID NO:83, 84, or 85.

2. The vector of claim 1, wherein said muscle-specific promoter is alpha-actin.

3. The vector of claim 1, wherein said vector further comprises at least one element selected from a group consisting of an inverted terminal repeat, a cap signal, a multicloning site, an intron splice-donor site, an intron splice-acceptor site, an epitope tag, a nuclear localization sequence, and a polyadenylation consensus sequence.

4. The vector of claim 1, wherein said mouse or human utrophin "A" promoter comprises the sequence of SEQ ID NO:9 or SEQ ID NO:14.

5. The vector of claim 1, wherein said human utrophin "A" promoter comprises the sequence of SEQ ID NO:10 or SEQ ID NO:12 or said mouse utrophin "A" promoter comprises the sequence of SEQ ID NO:11 or SEQ ID NO:13.

6. The vector of claim 1, wherein said muscle-specific promoter is constitutively expressable throughout differentiation.

7. The vector of claim 6, wherein the muscle-specific promoter is selected from the group consisting of alpha-actin, cardiac troponin C, myosin light chain 2 A, skeletal beta-actin, CK 6, dystrophin, muscular creatine kinase, dMCK, tMCK, enh348MCK, synthetic C5-12 (Syn), Myf5, MLC1/3f. MyoD1, Myog, and Pax7.

8. The vector of claim 1, wherein said vector has a serotype selected from the group consisting of AAV1, AAV2, AAV3, AAV4, AAV5, AAV6, AAV7, AAV8, and AAV9.

9. A composition comprising the vector of claim 1 and a pharmaceutically acceptable carrier.

* * * * *

SEQUENCE LISTING

<160> NUMBER OF SEQ ID NOS: 87

<210> SEQ ID NO 1
<211> LENGTH: 5637
<212> TYPE: DNA
<213> ORGANISM: Artificial Sequence
<220> FEATURE:
<223> OTHER INFORMATION: Synthetic Construct

<400> SEQUENCE: 1

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggggttcc | tgcggccgca | cgcgtcacca | actgggtaac | ctctgctgac | 180 |
| ccccactcta | ctttaccata | gtagctccaa | atccttcta | gaaaatctga | aaggcatagc | 240 |
| cccatatatc | agtgatataa | atagaacctg | cagcaggctc | tggtaaatga | tgactacaag | 300 |
| gtggactggg | aggcagcccg | gccttggcag | gcatcatcct | ctaaatataa | agatgagttt | 360 |
| gttcagcctt | tgcagaagga | aaaactgcca | cccatcctag | agtgccgcgt | ccttgtcccc | 420 |
| ccacccccte | caatttattg | ggaggaagga | ccagctaagc | ctcatctagg | aagagcccct | 480 |
| cacccatctc | cacctccact | ccaggtctag | ccagtcctgg | gttgtgaccc | ttgtctttca | 540 |
| gccccaggag | agggacacac | atagtgccac | caaagaggct | gggggagggc | ctcagcccac | 600 |
| caaaacctgg | ggccagtgcg | tcctacagga | ggggaaccct | caccccttca | atcccttag | 660 |
| gagacccaag | ggcgctgcgc | gtccctgagg | cggacagctc | cgtgtgctca | ggctttgcgc | 720 |
| ctgacaggcc | tatccccggg | agccccgcg | cctcctcccc | ggcgctccgc | cctcgcctcc | 780 |
| ccccgccagt | tgtctatcct | gcgacagctg | cgcgccctcc | ggccgccggt | ggccctctgt | 840 |
| gcggtggggg | aaggggtcga | cgtggctcag | ctttttggat | tcagggagct | cggggggtggg | 900 |
| aagagagaaa | tggagttcca | ggggcgtaaa | ggagagggag | ttcgccttcc | ttcccttcct | 960 |
| gagactcagg | agtgactgct | tctccaatcc | tcccaagccc | accactccac | acgactccct | 1020 |
| cttcccggta | gtcgcaagtg | ggagtttggg | gatctgagca | aagaacccga | agaggagttg | 1080 |
| aaatattgga | agtcagcagt | caggcacctt | cccgagcgcc | cagggcgctc | agagtggaca | 1140 |
| tggttgggga | ggcctttggg | acaggtgcgg | ttccccggagc | gcaggcgcac | acatgcaccc | 1200 |
| accggcgaac | gcggtgaccc | tcgccccacc | ccatcccctc | cggcgggcaa | ctgggtcggg | 1260 |
| tcaggagggg | caaacccgct | agggagacac | tccatatacg | gcccggcccg | cgttacctgg | 1320 |
| gaccgggcca | acccgctcct | tctttggtca | acgcagggga | cccgggcggg | ggcccaggcc | 1380 |
| gcgaaccggc | cgagggaggg | ggctctagtg | cccaacaccc | aaatatggct | cgagaagggc | 1440 |
| agcgacattc | ctgcggggtg | gcgcggaggg | aatgcccgcg | ggctatataa | aacctgagca | 1500 |
| gagggacaag | cggccaccgc | agcggacagc | gccaagtgaa | gcctcgcttc | ccctccgcgg | 1560 |
| cgaccagggc | ccgagccgag | agtagcagtt | gtagctaccc | gcccaggtag | ggcaggagtt | 1620 |
| gggaggggac | aggggggacag | ggcactaccg | aggggaacct | gaaggactcc | ggggcagaac | 1680 |
| ccagtcggtt | cacctggtaa | gcttgctagc | tccgcggatt | cgaatcccgg | ccgggaacgg | 1740 |
| tgcattggaa | cgcggattcc | ccgtgccaag | agtgacgtaa | gtaccgccta | tagagtctat | 1800 |
| aggcccacaa | aaaatgctttt | cttctttaa | tatacttttt | tgtttatctt | atttctaata | 1860 |
| ctttccctaa | tctctttctt | tcagggcaat | aatgatacaa | tgtatcatgc | ctctttgcac | 1920 |
| cattctaaag | aataacagtg | ataatttctg | ggttaaggca | atagcaatat | ttctgcatat | 1980 |
| aaatatttct | gcatataaat | tgtaactgat | gtaagaggtt | tcatattgct | aatagcagct | 2040 |

```
acaatccagc taccattctg ctttatttt atggttggga taaggctgga ttattctgag    2100
tccaagctag gcccttttgc taatcatgtt catacctctt atcttcctcc cacagctcct   2160
gggcaacgtg ctggtctgtg tgctggccca tcactttggc aaagaattgg gattcgaaca   2220
tcgatgggaa ttccgggatc cggtcgaccg tacgtacaag atctacgggt ggcatccctg   2280
tgacccctcc ccagtgcctc tcctggccct ggaagttgcc actccagtgc ccaccagcct   2340
tgtcctaata aaattaagtt gcatcatttt gtctgactag tacgggtggc atccctgtga   2400
ccctccccca gtgcctctcc tggccctgga agttgccact ccagtgccca ccagccttgt   2460
cctaataaaa ttaagttgca tcattttgtc tgactaggtg tccttctata atattatggg   2520
gtggaggggg gtggtatgga gcaaggggca agttgggaag acaacctgta gggcctgcgg   2580
ggtctattgg gaaccaagct ggagtgcagt ggcacaatct ggctcactg caatctccgc    2640
ctcctgggtt caagcgattc tcctgcctca gcctcccgag ttgttgggat tccaggcatg   2700
catgaccagg ctcagctaat ttttgttttt tggtagaga cggggtttca ccatattggc    2760
caggctggtc tccaactcct aatctcaggt gatctaccca ccttggcctc ccaaattgct   2820
gggattacag gcgtgaacca ctgctccctt ccctgtcctt ctgattttgt aggtaaccac   2880
gtgcggaccg agcggccgca ggaacccta gtgatggagt tggccactcc ctctctgcgc    2940
gctcgctcgc tcactgaggc cgggcgacca aggtcgccc gacgcccggg ctttgcccgg    3000
gcggcctcag tgagcgagcg agcgcgcagc tgcctgcagg ggcgcctgat gcggtatttt   3060
ctccttacgc atctgtgcgg tatttcacac cgcatacgtc aaagcaacca tagtacgcgc   3120
cctgtagcgg cgcattaagc gcggcgggtg tggtggttac gcgcagcgtg accgctacac   3180
ttgccagcgc cctagcgccc gctcctttcg ctttcttccc ttcctttctc gccacgttcg   3240
ccggctttcc ccgtcaagct ctaaatcggg ggctccctt agggttccga tttagtgctt   3300
tacggcacct cgaccccaaa aaacttgatt tgggtgatgg ttcacgtagt gggccatcgc   3360
cctgatagac ggttttcgc cctttgacgt tggagtccac gttctttaat agtggactct    3420
tgttccaaac tggaacaaca ctcaacccta tctcgggcta ttcttttgat ttataaggga   3480
ttttgccgat ttcggcctat tggttaaaaa atgagctgat ttaacaaaaa tttaacgcga   3540
attttaacaa atattaacg tttacaattt tatggtgcac tctcagtaca atctgctctg    3600
atgccgcata gttaagccag ccccgacacc cgccaacacc cgctgacgcg ccctgacggg   3660
cttgtctgct cccggcatcc gcttacagac aagctgtgac cgtctccggg agctgcatgt   3720
gtcagaggtt ttcaccgtca tcaccgaaac gcgcgagacg aaagggcctc gtgatacgcc   3780
tatttttata ggttaatgtc atgataataa tggtttctta gacgtcaggt ggcacttttc   3840
ggggaaatgt gcgcggaacc cctatttgtt tatttttcta aatacattca aatatgtatc   3900
cgctcatgag acaataaccc tgataaatgc ttcaataata ttgaaaaagg aagagtatga   3960
gtattcaaca tttccgtgtc gcccttattc ccttttttgc ggcattttgc cttcctgttt   4020
ttgctcaccc agaaacgctg gtgaaagtaa aagatgctga agatcagttg ggtgcacgag   4080
tgggttacat cgaactggat ctcaacagcg gtaagatcct tgagagtttt cgccccgaag   4140
aacgttttcc aatgatgagc actttaaag ttctgctatg tggcgcggta ttatcccgta    4200
ttgacgccgg gcaagagcaa ctcggtcgcc gcatacacta ttctcagaat gacttggttg   4260
agtactcacc agtcacagaa aagcatctta cggatggcat gacagtaaga gaattatgca   4320
gtgctgccat aaccatgagt gataacactg cggccaactt acttctgaca acgatcggag   4380
```

|  |  |
|---|---|
| gaccgaagga gctaaccgct tttttgcaca acatgggga tcatgtaact cgccttgatc | 4440 |
| gttgggaacc ggagctgaat gaagccatac caaacgacga gcgtgacacc acgatgcctg | 4500 |
| tagcaatggc aacaacgttg cgcaaactat taactggcga actacttact ctagcttccc | 4560 |
| ggcaacaatt aatagactgg atggaggcgg ataaagttgc aggaccactt ctgcgctcgg | 4620 |
| cccttccggc tggctggttt attgctgata atctggagc cggtgagcgt gggtctcgcg | 4680 |
| gtatcattgc agcactgggg ccagatggta agccctcccg tatcgtagtt atctacacga | 4740 |
| cggggagtca ggcaactatg gatgaacgaa atagacagat cgctgagata ggtgcctcac | 4800 |
| tgattaagca ttggtaactg tcagaccaag tttactcata tatactttag attgatttaa | 4860 |
| aacttcattt ttaatttaaa aggatctagg tgaagatcct ttttgataat ctcatgacca | 4920 |
| aaatccctta acgtgagttt tcgttccact gagcgtcaga ccccgtagaa aagatcaaag | 4980 |
| gatcttcttg agatcctttt tttctgcgcg taatctgctg cttgcaaaca aaaaaaccac | 5040 |
| cgctaccagc ggtggtttgt ttgccggatc aagagctacc aactctttt ccgaaggtaa | 5100 |
| ctggcttcag cagagcgcag ataccaaata ctgtccttct agtgtagccg tagttaggcc | 5160 |
| accacttcaa gaactctgta gcaccgccta catacctcgc tctgctaatc ctgttaccag | 5220 |
| tggctgctgc cagtggcgat aagtcgtgtc ttaccgggtt ggactcaaga cgatagttac | 5280 |
| cggataaggc gcagcggtcg ggctgaacgg ggggttcgtg cacacagccc agcttggagc | 5340 |
| gaacgaccta caccgaactg agatacctac agcgtgagct atgagaaagc gccacgcttc | 5400 |
| ccgaagggag aaaggcggac aggtatccgg taagcggcag gtcggaaca ggagagcgca | 5460 |
| cgagggagct tccaggggga aacgcctggt atctttatag tcctgtcggg tttcgccacc | 5520 |
| tctgacttga gcgtcgattt ttgtgatgct cgtcaggggg gcggagccta tggaaaaacg | 5580 |
| ccagcaacgc ggcctttta cggttcctgg ccttttgctg gccttttgct cacatgt | 5637 |

<210> SEQ ID NO 2
<211> LENGTH: 6418
<212> TYPE: DNA
<213> ORGANISM: Artificial Sequence
<220> FEATURE:
<223> OTHER INFORMATION: Synthetic Construct

<400> SEQUENCE: 2

|  |  |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtcacca actgggtaac ctctgctgac | 180 |
| ccccactcta ctttaccata agtagctcca aatccttcta gaaaatctga aaggcatagc | 240 |
| cccatatatc agtgatataa atagaacctg cagcaggctc tggtaaatga tgactacaag | 300 |
| gtggactggg aggcagcccg gccttggcag gcatcatcct ctaaatataa agatgagttt | 360 |
| gttcagcctt tgcagaagga aaaactgcca cccatcctag agtgccgcgt ccttgtcccc | 420 |
| ccaccccctc caatttattg ggaggaagga ccagctaagc ctcatctagg aagagcccct | 480 |
| cacccatctc cacctccact ccaggtctag ccagtcctgg gttgtgaccc ttgtctttca | 540 |
| gccccaggag agggacacac atagtgccac caaagaggct gggggagggc ctcagcccac | 600 |
| caaaacctgg ggccagtgcg tcctacagga ggggaaccct caccccttca atcccttag | 660 |
| gagacccaag ggcgctgcgc gtccctgagg cggacagctc cgtgtgctca ggctttgcgc | 720 |
| ctgacaggcc tatccccggg agccccgcg cctcctcccc ggcgctccgc cctcgcctcc | 780 |
| ccccgccagt tgtctatcct gcgacagctg cgcgccctcc ggccgccggt ggccctctgt | 840 |

```
gcggtggggg aagggggtcga cgtggctcag cttttttggat tcaggagct cgggggtggg       900
aagagagaaa tggagttcca ggggcgtaaa ggagagggag ttcgccttcc ttcccttcct       960
gagactcagg agtgactgct tctccaatcc tcccaagccc accactccac acgactccct      1020
cttcccggta gtcgcaagtg ggagtttggg gatctgagca aagaacccga agaggagttg      1080
aaatattgga agtcagcagt caggcacctt cccgagcgcc cagggcgctc agagtggaca      1140
tggttgggga ggcctttggg acaggtgcgg ttcccggagc gcaggcgcac acatgcaccc      1200
accggcgaac gcggtgaccc tcgccccacc ccatcccctc cggcgggcaa ctgggtcggg      1260
tcaggagggg caaacccgct agggagacac tccatatacg gccggcccg cgttacctgg       1320
gaccgggcca acccgctcct tctttggtca acgcagggga cccgggcggg ggcccaggcc      1380
gcgaaccggc cgagggaggg ggctctagtg cccaacaccc aaatatggct cgagaagggc      1440
agcgacattc ctgcggggtg gcgcggaggg aatgcccgcg ggctatataa aacctgagca      1500
gagggacaag cggccaccgc agcggacagc gccaagtgaa gcctcgcttc ccctccgcgg      1560
cgaccagggc ccgagccgag agtagcagtt gtagctaccc gcccaggtag ggcaggagtt      1620
gggaggggac aggggggacag ggcactaccg agggggaacct gaaggactcc ggggcagaac    1680
ccagtcggtt cacctggtaa gcttgctagc tccgcggatt cgaatcccgg ccgggaacgg      1740
tgcattggaa cgcggattcc ccgtgccaag agtgacgtaa gtaccgccta tagagtctat      1800
aggcccacaa aaaatgcttt cttctttttaa tatactttt tgtttatctt atttctaata      1860
cttttcccctaa tctctttctt tcagggcaat aatgatacaa tgtatcatgc ctctttgcac     1920
cattctaaag aataacagtg ataatttctg ggttaaggca atagcaatat ttctgcatat      1980
aaatatttct gcatataaat tgtaactgat gtaagaggtt tcatattgct aatagcagct      2040
acaatccagc taccattctg cttttatttt atggttggga taaggctgga ttattctgag      2100
tccaagctag gcccttttgc taatcatgtt catacctctt atcttcctcc cacagctcct      2160
gggcaacgtg ctggtctgtg tgctggccca tcactttggc aaagaattgg gattcgaaca      2220
tcgatttaaa gctatggagc aaaagctcat ttctgaagag acttgaatg aaatggagca       2280
aaagctcatt tctgaagagg acttgaatga atgagcaa aagctcattt ctgaagagga        2340
cttgaatgaa atggagcaaa agctcatttc tgaagaggac ttgaatgaaa tggagcaaaa      2400
gctcatttct gaagaggact tgaatgaaat ggagagcttg ggcgacctca ccatgggccc      2460
taaaaagaag cgtaaagtcg cccccccgac cgatgtcagc ctgggggacg agctccactt      2520
agacggcgaa gacgtggcga tggcgcatgc cgacgcgcta gacgatttcg atctggacat      2580
gttgggggac ggggattccc cgggtccggg atttacccccc cacgactccg ccccctacgg     2640
cgctctggat atggccgact tcgagtttga gcagatgttt accgatgccc ttggaattga      2700
cgagtacggt ggggaattcc cggggatcct cgatgacaga ccctatgctt gcccagtgga     2760
aagctgcgac cgccgctttt ctagatcgga tgagcttacc cgccatatcc gcatccacac      2820
cggccaaaaa cccttttcaat gccgtatctg catgaggaat tcagcagcc gcgatgtcct      2880
gaggcgccat aacaggaccc acacagggga aaagccattc gcatgtgaca tctgcggtcg      2940
aaagtttgca agccgcgatg tcctgaggcg ccataacagg atacatttga ggcaaaatga      3000
tctcgaccgt acgtacaaga tccgttagca tatgctaaca gatccacggg tggcatccct      3060
gtgacccctc cccagtgcct ctcctggccc tggaagttgc cactccagtg cccaccagcc      3120
ttgtcctaat aaaattaagt tgcatcattt tgtctgacta gtacgggtgg catccctgtg      3180
```

```
acccctcccc agtgcctctc ctggccctgg aagttgccac tccagtgccc accagccttg    3240
tcctaataaa attaagttgc atcattttgt ctgactaggt gtccttctat aatattatgg    3300
ggtggagggg ggtggtatgg agcaaggggc aagttgggaa gacaacctgt agggcctgcg    3360
gggtctattg ggaaccaagc tggagtgcag tggcacaatc ttggctcact gcaatctccg    3420
cctcctgggt tcaagcgatt ctcctgcctc agcctcccga gttgttggga ttccaggcat    3480
gcatgaccag gctcagctaa ttttttgtttt tttggtagag acggggtttc accatattgg    3540
ccaggctggt ctccaactcc taatctcagg tgatctaccc accttggcct cccaaattgc    3600
tgggattaca ggcgtgaacc actgctccct tccctgtcct tctgattttg taggtaacca    3660
cgtgcggacc gagcggccgc aggaacccct agtgatggag ttggccactc cctctctgcg    3720
cgctcgctcg ctcactgagg ccgggcgacc aaaggtcgcc cgacgcccgg gctttgcccg    3780
ggcggcctca gtgagcgagc gagcgcgcag ctgcctgcag gggcgcctga tgcggtattt    3840
tctccttacg catctgtgcg gtatttcaca ccgcatacgt caaagcaacc atagtacgcg    3900
ccctgtagcg cgcgcattaag cgcggcgggt gtggtggtta cgcgcagcgt gaccgctaca    3960
cttgccagcg ccctagcgcc cgctccttttc gctttcttcc cttcctttct cgccacgttc    4020
gccggctttc cccgtcaagc tctaaatcgg gggctccctt tagggttccg atttagtgct    4080
ttacggcacc tcgaccccaa aaaacttgat ttgggtgatg gttcacgtag tgggccatcg    4140
ccctgataga cggttttttcg ccctttgacg ttggagtcca cgttctttaa tagtggactc    4200
ttgttccaaa ctggaacaac actcaaccct atctcgggct attctttga tttataaggg    4260 attttgccga tttcggccta ttggttaaaa aatgagctga tttaacaaaa atttaacgcg    4320
aattttaaca aaatattaac gtttacaatt ttatggtgca ctctcagtac aatctgctct    4380
gatgccgcat agttaagcca gccccgacac ccgccaacac ccgctgacgc gccctgacgg    4440
gcttgtctgc tcccggcatc cgcttacaga caagctgtga ccgtctccgg gagctgcatg    4500
tgtcagaggt tttcaccgtc atcaccgaaa cgcgcgagac gaaagggcct cgtgatacgc    4560
ctatttttat aggttaatgt catgataata atggtttctt agacgtcagg tggcacttttt    4620 cggggaaatg tgcgcggaac ccctatttgt ttatttttct aaatacattc aaatatgtat    4680
ccgctcatga gacaataacc ctgataaatg cttcaataat attgaaaaag gaagagtatg    4740
agtattcaac atttccgtgt cgcccttatt ccctttttttg cggcattttg ccttcctgtt    4800
tttgctcacc cagaaacgct ggtgaaagta aaagatgctg aagatcagtt gggtgcacga    4860
gtgggttaca tcgaactgga tctcaacagc ggtaagatcc ttgagagttt tcgccccgaa    4920
gaacgttttc caatgatgag cacttttaaa gttctgctat gtggcgcggt attatcccgt    4980
attgacgccg ggcaagagca actcggtcgc cgcatacact attctcagaa tgacttggtt    5040
gagtactcac cagtcacaga aaagcatctt acggatggca tgacagtaag agaattatgc    5100
agtgctgcca taaccatgag tgataacact gcggccaact tacttctgac aacgatcgga    5160
ggaccgaagg agctaaccgc ttttttgcac aacatggggg atcatgtaac tcgccttgat    5220
cgttgggaac cggagctgaa tgaagccata ccaaacgacg agcgtgacac cacgatgcct    5280
gtagcaatgg caacaacgtt gcgcaaacta ttaactggcg aactacttac tctagcttcc    5340
cggcaacaat taatagactg gatggaggcg gataaagttg caggaccact tctgcgctcg    5400
gcccttccgg ctggctggtt tattgctgat aaatctggag ccggtgagcg tgggtctcgc    5460
ggtatcattg cagcactggg gccagatggt aagccctccc gtatcgtagt tatctacacg    5520
acggggagtc aggcaactat ggatgaacga aatagacaga tcgctgagat aggtgcctca    5580
```

```
ctgattaagc attggtaact gtcagaccaa gtttactcat atatacttta gattgattta    5640
aaacttcatt tttaatttaa aaggatctag gtgaagatcc ttttgataa tctcatgacc    5700 aaaatccctt aacgtgagtt ttcgttccac tgagcgtcag accccgtaga aaagatcaaa    5760
ggatcttctt gagatccttt ttttctgcgc gtaatctgct gcttgcaaac aaaaaaacca    5820
ccgctaccag cggtggtttg tttgccggat caagagctac caactctttt tccgaaggta    5880
actggcttca gcagagcgca gataccaaat actgtccttc tagtgtagcc gtagttaggc    5940
caccacttca agaactctgt agcaccgcct acatacctcg ctctgctaat cctgttacca    6000
gtggctgctg ccagtggcga taagtcgtgt cttaccgggt tggactcaag acgatagtta    6060
ccggataagg cgcagcggtc gggctgaacg gggggttcgt gcacacagcc agcttggag     6120 cgaacgacct acaccgaact gagatacccta cagcgtgagc tatgagaaag cgccacgctt    6180
cccgaaggga gaaaggcgga caggtatccg gtaagcggca gggtcggaac aggagagcgc    6240
acgagggagc ttccagggggg aaacgcctgg tatctttata gtcctgtcgg gtttcgccac    6300
ctctgacttg agcgtcgatt tttgtgatgc tcgtcagggg gcgagcct atggaaaaac     6360 gccagcaacg cggccttttt acggttcctg gccttttgct ggccttttgc tcacatgt     6418
```

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
acgcgtcacc aactgggtaa cctctgctga                                      30

<210> SEQ ID NO 4
<211> LENGTH: 36
<212> TYPE: DNA
<213> ORGANISM: Artificial Sequence
<220> FEATURE:
<223> OTHER INFORMATION: Synthetic Construct

<400> SEQUENCE: 4
gctagcaagc ttaccaggtg aaccgactgg gttctg                               36

<210> SEQ ID NO 5
<211> LENGTH: 38
<212> TYPE: DNA
<213> ORGANISM: Artificial Sequence
<220> FEATURE:
<223> OTHER INFORMATION: Synthetic Construct

<400> SEQUENCE: 5
cgatgggaat tccgggatcc ggtcgaccgt acgtacaa                             38

<210> SEQ ID NO 6
<211> LENGTH: 40
<212> TYPE: DNA
<213> ORGANISM: Artificial Sequence
<220> FEATURE:
<223> OTHER INFORMATION: Synthetic Construct

<400> SEQUENCE: 6
gatcttgtac gtacggtcga ccggatcccg gaattcccat                           40

<210> SEQ ID NO 7

```
<211> LENGTH: 45
<212> TYPE: DNA
<213> ORGANISM: Artificial Sequence
<220> FEATURE:
<223> OTHER INFORMATION: Synthetic Construct

<400> SEQUENCE: 7
atcgatggga attccgggat ccggtcgacc gtacgtacaa gatct          45

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
tgggccctaa aagaagcgt aaa                                    23

<210> SEQ ID NO 9
<211> LENGTH: 9
<212> TYPE: DNA
<213> ORGANISM: Artificial Sequence
<220> FEATURE:
<223> OTHER INFORMATION: Synthetic Construct

<400> SEQUENCE: 9 gctgctgcg                                                    9

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
cgggctgctg cgggctggga g                                     21

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
ccggctgctg cgggctggga g                                     21

<210> SEQ ID NO 12
<211> LENGTH: 12
<212> TYPE: DNA
<213> ORGANISM: Artificial Sequence
<220> FEATURE:
<223> OTHER INFORMATION: Synthetic Construct

<400> SEQUENCE: 12
cgggctgctg cg                                               12

<210> SEQ ID NO 13
<211> LENGTH: 12
<212> TYPE: DNA
<213> ORGANISM: Artificial Sequence
<220> FEATURE:
<223> OTHER INFORMATION: Synthetic Construct

<400> SEQUENCE: 13
```

-continued ccggctgctg cg					12

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
gctgctgcgg gctgggag					18

<210> SEQ ID NO 15
<211> LENGTH: 9
<212> TYPE: DNA
<213> ORGANISM: Artificial Sequence
<220> FEATURE:
<223> OTHER INFORMATION: Synthetic Construct

<400> SEQUENCE: 15 ggagccgga					9

<210> SEQ ID NO 16
<211> LENGTH: 79
<212> TYPE: PRT
<213> ORGANISM: Artificial Sequence
<220> FEATURE:
<223> OTHER INFORMATION: Synthetic Construct

<400> SEQUENCE: 16

Cys Pro Val Glu Ser Cys Asp Arg Arg Phe Ser Arg Ser Asp Glu Leu
1               5                   10                  15

Thr Arg His Ile Arg Ile His Thr Gly Gln Lys Pro Phe Gln Cys Arg
            20                  25                  30

Ile Cys Met Arg Asn Phe Ser Ser Arg Asp Val Leu Arg Arg His Asn
        35                  40                  45

Arg Thr His Thr Gly Glu Lys Pro Phe Ala Cys Asp Ile Cys Gly Arg
    50                  55                  60

Lys Phe Ala Ser Arg Asp Val Leu Arg Arg His Asn Arg Ile His
65                  70                  75

<210> SEQ ID NO 17
<211> LENGTH: 165
<212> TYPE: PRT
<213> ORGANISM: Artificial Sequence
<220> FEATURE:
<223> OTHER INFORMATION: Synthetic Construct

<400> SEQUENCE: 17

Cys Pro Val Glu Ser Cys Asp Arg Arg Phe Ser Arg Ser Asp Asn Leu
1               5                   10                  15

Val Arg His Ile Arg Ile His Thr Gly Gln Lys Pro Phe Gln Cys Arg
            20                  25                  30

Ile Cys Met Arg Asn Phe Ser Arg Ser Asp His Leu Thr Thr His Asn
        35                  40                  45

Arg Thr His Thr Gly Lys Pro Phe Ala Cys Asp Ile Cys Gly Arg
    50                  55                  60

Lys Phe Ala Asp Pro Gly His Leu Val Arg His Asn Arg Ile His Thr
65                  70                  75                  80

Gly Glu Lys Pro Phe Ala Cys Pro Val Glu Ser Cys Asp Arg Arg Phe
                85                  90                  95

Ser Arg Ser Asp Glu Leu Thr Arg His Ile Arg Ile His Thr Gly Gln
            100                 105                 110

Lys Pro Phe Gln Cys Arg Ile Cys Met Arg Asn Phe Ser Arg Ser Asp
        115                 120                 125

Val Leu Arg Arg His Asn Arg Thr His Thr Gly Glu Lys Pro Phe Ala
130                 135                 140

Cys Asp Ile Cys Gly Arg Lys Phe Ala Ser Arg Asp Val Leu Arg Arg
145                 150                 155                 160

His Asn Arg Ile His
                165

<210> SEQ ID NO 18
<211> LENGTH: 109
<212> TYPE: PRT
<213> ORGANISM: Artificial Sequence
<220> FEATURE:
<223> OTHER INFORMATION: Synthetic Construct

<400> SEQUENCE: 18

Cys Pro Val Glu Ser Cys Asp Arg Arg Phe Ser Arg Ser Asp Glu Leu
1               5                   10                  15

Thr Arg His Ile Arg Ile His Thr Gly Gln Lys Pro Phe Gln Cys Arg
            20                  25                  30

Ile Cys Met Arg Asn Phe Ser Arg Ser Asp Val Leu Arg Arg His Asn
        35                  40                  45

Arg Thr His Thr Gly Glu Lys Pro Phe Ala Cys Asp Ile Cys Gly Arg
    50                  55                  60

Lys Phe Ala Ser Arg Asp Val Leu Arg Arg His Asn Arg Ile His Leu
65                  70                  75                  80

Arg Gln Gly Pro Arg Ser His Val Cys Ala Glu Cys Gly Lys Ala Phe
                85                  90                  95

Val Glu Ser Ser Lys Leu Lys Arg His Gln Leu Val His
            100                 105

<210> SEQ ID NO 19
<211> LENGTH: 3136
<212> TYPE: DNA
<213> ORGANISM: Homo sapiens

<400> SEQUENCE: 19
gcgcagaact tggggagccg ccgccgccat ccgccgccgc agccagcttc cgccgccgca      60
ggaccggccc ctgccccagc ctccgcagcc gcggcgcgtc cacgcccgcc cgcgcccagg     120
gcgagtcggg gtcgccgcct gcacgcttct cagtgttccc cgcgccccgc atgtaacccg     180
gccaggcccc cgcaactgtg tccctgcag ctccagcccc gggctgcacc ccccgcccc      240 gacaccagct ctccagcctg ctcgtccagg atggccgcgg ccaaggccga gatgcagctg     300
atgtccccgc tgcagatctc tgaccgcttc ggatcctttc ctcactcgcc caccatggac     360
aactacccta agctggagga gatgatgctg ctgagcaacg gggctcccca gttcctcggc     420
gccgccgggg ccccagaggg cagcggcagc aacagcagca gcagcagcag cggggcggt     480 ggaggcggcg ggggcggcag caacagcagc agcagcagca gcaccttcaa ccctcaggcg     540
gacacgggcg agcagcccta cgagcacctg accgcagagt cttttcctga catctctctg     600
aacaacgaga aggtgctggt ggagaccagt taccccagcc aaaccactcg actgccccc      660 atcacctata ctggccgctt ttccctggag cctgcaccca cagtggcaa caccttgtgg     720

```
cccgagcccc tcttcagctt ggtcagtggc ctagtgagca tgaccaaccc accggcctcc    780
tcgtcctcag caccatctcc agcggcctcc tccgcctccg cctcccagag cccacccctg    840
agctgcgcag tgccatccaa cgacagcagt cccatttact cagcggcacc caccttcccc    900
acgccgaaca ctgacatttt ccctgagcca caaagccagg ccttcccggg ctcggcaggg    960
acagcgctcc agtacccgcc tcctgcctac cctgccgcca agggtggctt ccaggttccc   1020
atgatccccg actacctgtt tccacagcag caggggatc tgggcctggg caccccagac    1080
cagaagccct tccagggcct ggagagccgc acccagcagc cttcgctaac ccctctgtct   1140
actattaagg cctttgccac tcagtcgggc tccaggacc tgaaggccct caataccagc    1200
taccagtccc agctcatcaa acccagccgc atgcgcaagt accccaaccg gcccagcaag   1260
acgccccccc acgaacgccc ttacgcttgc ccagtggagt cctgtgatcg ccgcttctcc   1320
cgctccgacg agctcacccg ccacatccgc atccacacag gccagaagcc cttccagtgc   1380
cgcatctgca tgcgcaactt cagccgcagc gaccacctca ccacccacat ccgcacccac   1440
acaggcgaaa agcccttcgc ctgcgacatc tgtggaagaa agtttgccag gagcgatgaa   1500
cgcaagaggc ataccaagat ccacttgcgg cagaaggaca agaaagcaga caaaagtgtt   1560
gtggcctctt cggccacctc ctctctctct tcctacccgt ccccggttgc tacctcttac   1620
ccgtccccgg ttactacctc ttatccatcc ccggccacca cctcataccc atcccctgtg   1680
cccacctcct tctcctctcc cggctcctcg acctacccat ccctgtgca cagtggcttc   1740
ccctccccgt cggtggccac cacgtactcc tctgttcccc ctgctttccc ggcccaggtc   1800
agcagcttcc cttcctcagc tgtcaccaac tccttcagcg cctccacagg gctttcggac   1860
atgacagcaa ccttttctcc caggacaatt gaaatttgct aaagggaaag gggaagaaa    1920
gggaaagggg agaaaagaa acacaagaga cttaaaggac aggaggagga gatggccata   1980
ggagaggagg gttcctctta ggtcagatgg aggttctcag agccaagtcc tccctctcta   2040
ctggagtgga aggtctattg gccaacaatc ctttctgccc acttcccctt ccccaattac   2100
tattcccttt gacttcagct gcctgaaaca gccatgtcca agttcttcac ctctatccaa   2160
agaacttgat ttgcatggat tttggataaa tcatttcagt atcatctcca tcatatgcct   2220
gacccccttgc tcccttcaat gctagaaaat cgagttggca aaatgggggtt tgggcccctc   2280
agagccctgc cctgcaccct tgtacagtgt ctgtgccatg gatttcgttt tcttggggt   2340
actcttgatg tgaagataat ttgcatattc tattgtatta tttggagtta ggtcctcact   2400
tgggggaaaa aaaaaaaga aaagccaagc aaaccaatgg tgatcctcta ttttgtgatg   2460
atgctgtgac aataagtttg aaccttttttt tttgaaacag cagtcccagt attctcagag   2520
catgtgtcag agtgttgttc cgttaacctt tttgtaaata ctgcttgacc gtactctcac   2580
atgtggcaaa atatggtttg gtttttcttt ttttttttt ttgaaagtgt tttttcttcg   2640
tccttttggt ttaaaagtt tcacgtcttg gtgccttttg tgtgatgcgc cttgctgatg   2700
gcttgacatg tgcaattgtg agggacatgc tcacctctag ccttaagggg ggcagggagt   2760
gatgatttgg gggaggcttt gggagcaaaa taggaagag ggctgagctg agcttcggtt   2820
ctccagaatg taagaaaaca aaatctaaaa caaaatctga actctcaaaa gtctatttt   2880
ttaactgaaa atgtaaattt ataatatat tcaggagttg gaatgttgta gttacctact   2940
gagtaggcgg cgattttgt atgttatgaa catgcagttc attatttgt ggttctattt   3000
tactttgtac ttgtgtttgc ttaaacaaag tgactgttg gcttataaac acattgaatg   3060
cgctttattg cccatgggat atgtggtgta tatccttcca aaaaattaaa acgaaaataa   3120
```

```
<210> SEQ ID NO 20
<211> LENGTH: 368
<212> TYPE: DNA
<213> ORGANISM: Artificial Sequence
<220> FEATURE:
<223> OTHER INFORMATION: Synthetic Construct

<400> SEQUENCE: 20
agagacctgt tttgcctaag gggacgtgac tcacattttc ggataatctg aataagggga    60
attgtgtctg ctcgaggcat ccattctggt tcggtctccg gactcccggc tcccggcacg   120
cacggttcac tctggagcgc gcgccccagg ccagccaagc gccgagccgg gctgctgcgg   180
gctgggaggg cgcgcagggc cggcgctgat tgacggggcg cgcagtcagg tgacttgggg   240
cgccaagttc ccgacgcggt ggccgcggtg accgccgagg cccggcagac gctgacccgg   300
gaacgtagtg gggctgatct tccggaacaa agttgctggg ccggcggcgg cggggcgaga   360
gcgccgag                                                            368

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
cgagccgaga gtagcagttg tag                                            23

<210> SEQ ID NO 22
<211> LENGTH: 40
<212> TYPE: DNA
<213> ORGANISM: Artificial Sequence
<220> FEATURE:
<223> OTHER INFORMATION: Synthetic Construct

<400> SEQUENCE: 22
gctagctagc aagcttacca ggtgaaccga ctgggttctg                          40

<210> SEQ ID NO 23
<211> LENGTH: 24
<212> TYPE: DNA
<213> ORGANISM: Artificial Sequence
<220> FEATURE:
<223> OTHER INFORMATION: Synthetic Construct

<400> SEQUENCE: 23 gtcgccccccc cgaccgatgt cagc                                          24

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
ttctggtgct tgtctcactg a                                              21

<210> SEQ ID NO 25
<211> LENGTH: 21
<212> TYPE: DNA
```

(agtagctgcg attggg — 3136, continued from previous)

```
<213> ORGANISM: Artificial Sequence
<220> FEATURE:
<223> OTHER INFORMATION: Synthetic Construct

<400> SEQUENCE: 25
ttctggtgct tgtctcactg a                                              21

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct

<400> SEQUENCE: 26
cagtatgttc ggcttcccat tc                                             22

<210> SEQ ID NO 27
<211> LENGTH: 8
<212> TYPE: DNA
<213> ORGANISM: Artificial Sequence
<220> FEATURE:
<223> OTHER INFORMATION: Synthetic Construct

<400> SEQUENCE: 27 gcggccgc                                                              8

<210> SEQ ID NO 28
<211> LENGTH: 6
<212> TYPE: DNA
<213> ORGANISM: Artificial Sequence
<220> FEATURE:
<223> OTHER INFORMATION: Synthetic construct

<400> SEQUENCE: 28 acgcgt                                                                6

<210> SEQ ID NO 29
<211> LENGTH: 12
<212> TYPE: DNA
<213> ORGANISM: Artificial Sequence
<220> FEATURE:
<223> OTHER INFORMATION: Synthetic Construct

<400> SEQUENCE: 29
gcccaggtag gg                                                        12

<210> SEQ ID NO 30
<211> LENGTH: 12
<212> TYPE: DNA
<213> ORGANISM: Artificial Sequence
<220> FEATURE:
<223> OTHER INFORMATION: Synthetic Construct

<400> SEQUENCE: 30
cccacagctc ct                                                        12

<210> SEQ ID NO 31
<211> LENGTH: 6
<212> TYPE: DNA
<213> ORGANISM: Artificial Sequence
<220> FEATURE:
<223> OTHER INFORMATION: Synthetic Construct

<400> SEQUENCE: 31 atcgat                                                                6
```

<210> SEQ ID NO 32
<211> LENGTH: 6
<212> TYPE: DNA
<213> ORGANISM: Artificial Sequence
<220> FEATURE:
<223> OTHER INFORMATION: Synthetic Construct

<400> SEQUENCE: 32 agatct                                                                    6

<210> SEQ ID NO 33
<211> LENGTH: 357
<212> TYPE: DNA
<213> ORGANISM: Artificial Sequence
<220> FEATURE:
<223> OTHER INFORMATION: Synthetic Construct

<400> SEQUENCE: 33
agagacctag tgtgcctaga ggggtgtgac acacattttc ggacaatttg aataaagggc     60
acggtgcgtg cgcgcggtga ctattccagc ttctggcttc agcacgcac gactggttcc    120 gggattctcg caccgcgcac cgcacggagc cgggctgctg cgggctggga gggcgcctag    180
ggctagcgct gattgaccgg gcgcgcggtc aggtgacccg aagcgccacg ttctgggagc    240
ccggcccgcg gtggcttccc aggccggggc aggaccgaac ccggagccga gggggactgg    300
tctccccggg agaacaaagt tgcccggcct ggggccccgg ggcgcgcgag cggcgag       357

<210> SEQ ID NO 34
<211> LENGTH: 264
<212> TYPE: PRT
<213> ORGANISM: Artificial Sequence
<220> FEATURE:
<223> OTHER INFORMATION: Synthetic Construct

<400> SEQUENCE: 34

Met Glu Gln Lys Leu Ile Ser Glu Glu Asp Leu Asn Glu Met Glu Gln
1               5                   10                  15

Lys Leu Ile Ser Glu Glu Asp Leu Asn Glu Met Glu Gln Lys Leu Ile
            20                  25                  30

Ser Glu Glu Asp Leu Asn Glu Met Glu Gln Lys Leu Ile Ser Glu Glu
        35                  40                  45

Asp Leu Asn Glu Met Glu Gln Lys Leu Ile Ser Glu Glu Asp Leu Asn
    50                  55                  60

Glu Met Glu Ser Leu Gly Asp Leu Thr Met Gly Pro Lys Lys Arg
65                  70                  75                  80

Lys Val Ala Pro Pro Thr Asp Val Ser Leu Gly Asp Glu Leu His Leu
                85                  90                  95

Asp Gly Glu Asp Val Ala Met Ala His Ala Asp Ala Leu Asp Asp Phe
            100                 105                 110

Asp Leu Asp Met Leu Gly Asp Gly Asp Ser Pro Gly Pro Gly Phe Thr
        115                 120                 125

Pro His Asp Ser Ala Pro Tyr Gly Ala Leu Asp Met Ala Asp Phe Glu
    130                 135                 140

Phe Glu Gln Met Phe Thr Asp Ala Leu Gly Ile Asp Glu Tyr Gly Gly
145                 150                 155                 160

Glu Phe Pro Gly Ile Leu Asp Asp Arg Pro Tyr Ala Cys Pro Val Glu
                165                 170                 175

Ser Cys Asp Arg Arg Phe Ser Arg Ser Asp Glu Leu Thr Arg His Ile

```
                    180                 185                 190
Arg Ile His Thr Gly Gln Lys Pro Phe Gln Cys Arg Ile Cys Met Arg
                195                 200                 205

Asn Phe Ser Ser Arg Asp Val Leu Arg Arg His Asn Arg Thr His Thr
    210                 215                 220

Gly Glu Lys Pro Phe Ala Cys Asp Ile Cys Gly Arg Lys Phe Ala Ser
225                 230                 235                 240

Arg Asp Val Leu Arg Arg His Asn Arg Ile His Leu Arg Gln Asn Asp
                245                 250                 255

Leu Asp Arg Thr Tyr Lys Ile Arg
                260

<210> SEQ ID NO 35
<211> LENGTH: 502
<212> TYPE: PRT
<213> ORGANISM: Artificial Sequence
<220> FEATURE:
<223> OTHER INFORMATION: Synthetic Construct

<400> SEQUENCE: 35

Met Glu Gln Lys Leu Ile Ser Glu Glu Asp Leu Asn Glu Met Glu Gln
1               5                   10                  15

Lys Leu Ile Ser Glu Glu Asp Leu Asn Glu Met Glu Gln Lys Leu Ile
                20                  25                  30

Ser Glu Glu Asp Leu Asn Glu Met Glu Gln Lys Leu Ile Ser Glu Glu
            35                  40                  45

Asp Leu Asn Glu Met Glu Gln Lys Leu Ile Ser Glu Glu Asp Leu Asn
50                  55                  60

Glu Met Glu Ser Leu Gly Asp Leu Thr Met Gly Pro Lys Lys Lys Arg
65                  70                  75                  80

Lys Val Ala Pro Pro Thr Asp Val Ser Leu Gly Asp Glu Leu His Leu
                85                  90                  95

Asp Gly Glu Asp Val Ala Met Ala His Ala Asp Ala Leu Asp Asp Phe
            100                 105                 110

Asp Leu Asp Met Leu Gly Asp Gly Asp Ser Pro Gly Pro Gly Phe Thr
        115                 120                 125

Pro His Asp Ser Ala Pro Tyr Gly Ala Leu Asp Met Ala Asp Phe Glu
    130                 135                 140

Phe Glu Gln Met Phe Thr Asp Ala Leu Gly Ile Asp Glu Tyr Gly Gly
145                 150                 155                 160

Glu Phe Pro Gly Ile Leu Ala Lys Arg Phe Ala Asp Phe Thr Val Tyr
                165                 170                 175

Arg Asn Arg Thr Leu Gln Lys Trp His Asp Lys Thr Lys Leu Ala Ser
            180                 185                 190

Gly Lys Leu Gly Lys Gly Phe Gly Ala Phe Glu Arg Ser Ile Leu Thr
        195                 200                 205

Gln Ile Asp His Ile Leu Met Asp Lys Glu Arg Leu Leu Arg Arg Thr
    210                 215                 220

Gln Thr Lys Arg Ser Val Tyr Arg Val Leu Gly Lys Pro Glu Pro Ala
225                 230                 235                 240

Ala Gln Pro Val Pro Glu Ser Leu Pro Gly Glu Pro Glu Ile Leu Pro
                245                 250                 255

Gln Ala Pro Ala Asn Ala His Leu Lys Asp Leu Asp Glu Glu Ile Phe
            260                 265                 270

Asp Asp Asp Asp Phe Tyr His Gln Leu Leu Arg Glu Leu Ile Glu Arg
```

```
            275                 280                 285
Lys Thr Ser Ser Leu Gly Ile Leu Asp Arg Pro Tyr Ala Cys Pro Val
    290                 295                 300
Glu Ser Cys Asp Arg Arg Phe Ser Arg Ser Asp Asn Leu Val Arg His
305                 310                 315                 320
Ile Arg Ile His Thr Gly Gln Lys Pro Phe Gln Cys Arg Ile Cys Met
                325                 330                 335
Arg Asn Phe Ser Arg Ser Asp His Leu Thr Thr His Asn Arg Thr His
                340                 345                 350
Thr Gly Glu Lys Pro Phe Ala Cys Asp Ile Cys Gly Arg Lys Phe Ala
                355                 360                 365
Asp Pro Gly His Leu Val Arg His Asn Arg Ile His Thr Gly Glu Lys
                370                 375                 380
Pro Phe Ala Cys Pro Val Glu Ser Cys Asp Arg Arg Phe Ser Arg Ser
385                 390                 395                 400
Asp Glu Leu Thr Arg His Ile Arg Ile His Thr Gly Gln Lys Pro Phe
                405                 410                 415
Gln Cys Arg Ile Cys Met Arg Asn Phe Ser Ser Arg Asp Val Leu Arg
                420                 425                 430
Arg His Asn Arg Thr His Thr Gly Glu Lys Pro Phe Ala Cys Asp Ile
                435                 440                 445
Cys Gly Arg Lys Phe Ala Ser Arg Asp Val Leu Arg Arg His Asn Arg
                450                 455                 460
Ile His Leu Arg Gln Asn Asp Leu Glu Arg Ser Thr Gly Gly Ile Pro
465                 470                 475                 480
Val Thr Pro Pro Gln Cys Leu Ser Trp Pro Trp Lys Leu Pro Leu Gln
                485                 490                 495
Cys Pro Pro Ala Leu Ser
                500

<210> SEQ ID NO 36
<211> LENGTH: 297
<212> TYPE: PRT
<213> ORGANISM: Artificial Sequence
<220> FEATURE:
<223> OTHER INFORMATION: Synthetic Construct

<400> SEQUENCE: 36

Met Glu Gln Lys Leu Ile Ser Glu Glu Asp Leu Asn Glu Met Glu Gln
1               5                   10                  15
Lys Leu Ile Ser Glu Glu Asp Leu Asn Glu Met Glu Gln Lys Leu Ile
                20                  25                  30
Ser Glu Glu Asp Leu Asn Glu Met Glu Gln Lys Leu Ile Ser Glu Glu
            35                  40                  45
Asp Leu Asn Glu Met Glu Gln Lys Leu Ile Ser Glu Glu Asp Leu Asn
        50                  55                  60
Glu Met Glu Ser Leu Gly Asp Leu Thr Met Gly Pro Lys Lys Lys Arg
65                  70                  75                  80
Lys Val Ala Pro Pro Thr Asp Val Ser Leu Gly Asp Glu Leu His Leu
                85                  90                  95
Asp Gly Glu Asp Val Ala Met Ala His Ala Asp Ala Leu Asp Asp Phe
                100                 105                 110
Asp Leu Asp Met Leu Gly Asp Gly Asp Ser Pro Gly Pro Gly Phe Thr
            115                 120                 125
Pro His Asp Ser Ala Pro Tyr Gly Ala Leu Asp Met Ala Asp Phe Glu
```

Phe Glu Gln Met Phe Thr Asp Ala Leu Gly Ile Asp Glu Tyr Gly Gly
145                 150                 155                 160

Glu Phe Pro Gly Ile Leu Asp Asp Arg Pro Tyr Ala Cys Pro Val Glu
            165                 170                 175

Ser Cys Asp Arg Arg Phe Ser Arg Ser Asp Glu Leu Thr Arg His Ile
            180                 185                 190

Arg Ile His Thr Gly Gln Lys Pro Phe Gln Cys Arg Ile Cys Met Arg
            195                 200                 205

Asn Phe Ser Ser Arg Asp Val Arg Arg His Asn Arg Thr His Thr Gly
            210                 215                 220

Glu Lys Pro Phe Ala Cys Asp Ile Cys Gly Arg Lys Phe Ala Ser Arg
225                 230                 235                 240

Asp Val Leu Arg His Asn Arg Ile His Leu Arg Gln Gly Pro Arg
            245                 250                 255

Ser His Val Cys Ala Glu Cys Gly Lys Ala Phe Val Glu Ser Ser Lys
            260                 265                 270

Leu Lys Arg His Gln Leu Val His Glu Leu Glu Arg Ser Pro Phe Ser
            275                 280                 285

Ser Arg Asp Leu Arg Val Ala Ser Leu
            290                 295

<210> SEQ ID NO 37
<211> LENGTH: 78
<212> TYPE: PRT
<213> ORGANISM: Artificial Sequence
<220> FEATURE:
<223> OTHER INFORMATION: Synthetic Construct

<400> SEQUENCE: 37

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
            35                  40                  45

Asp Ser Ala Pro Tyr Gly Ala Leu Asp Met Ala Asp Phe Glu Phe Glu
        50                  55                  60

Gln Met Phe Thr Asp Ala Leu Gly Ile Asp Glu Tyr Gly Gly
65                  70                  75

<210> SEQ ID NO 38
<211> LENGTH: 543
<212> TYPE: PRT
<213> ORGANISM: Artificial Sequence
<220> FEATURE:
<223> OTHER INFORMATION: Synthetic Construct

<400> SEQUENCE: 38

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
            35                  40                  45

Leu Gly Ala Ala Gly Ala Pro Glu Gly Ser Gly Ser Asn Ser Ser Ser
        50                  55                  60

```
Ser Ser Ser Gly Gly Gly Gly Gly Gly Gly Ser Asn Ser Ser
 65                  70                  75                  80

Ser Ser Ser Ser Thr Phe Asn Pro Gln Ala Asp Thr Gly Glu Gln Pro
                 85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
            165                 170                 175

Pro Ala Ala Ser Ser Ala Ser Ala Ser Gln Ser Pro Leu Ser Cys
                180                 185                 190

Ala Val Pro Ser Asn Asp Ser Ser Pro Ile Tyr Ser Ala Ala Pro Thr
            195                 200                 205

Phe Pro Thr Pro Asn Thr Asp Ile Phe Pro Glu Pro Gln Ser Gln Ala
210                 215                 220

Phe Pro Gly Ser Ala Gly Thr Ala Leu Gln Tyr Pro Pro Pro Ala Tyr
225                 230                 235                 240

Pro Ala Ala Lys Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
                260                 265                 270

Pro Phe Gln Gly Leu Glu Ser Arg Thr Gln Gln Pro Ser Leu Thr Pro
    275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
                340                 345                 350

Asp Glu Leu Thr Arg His Ile Arg Ile His Thr Gly Gln Lys Pro Phe
            355                 360                 365

Gln Cys Arg Ile Cys Met Arg Asn Phe Ser Ser Arg Asp Val Leu Arg
        370                 375                 380

Arg His Asn Arg Thr His Thr Gly Glu Lys Pro Phe Ala Cys Asp Ile
385                 390                 395                 400

Cys Gly Arg Lys Phe Ala Ser Arg Asp Val Leu Arg Arg His Asn Arg
                405                 410                 415

Ile His Leu Arg Gln Lys Asp Lys Ala Asp Lys Ser Val Val Ala
            420                 425                 430

Ser Ser Ala Thr Ser Ser Leu Ser Ser Tyr Pro Ser Pro Val Ala Thr
            435                 440                 445

Ser Tyr Pro Ser Pro Val Thr Thr Ser Tyr Pro Ser Pro Ala Thr Thr
        450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
```

```
                      485                 490                 495
Thr Thr Tyr Ser Ser Val Pro Ala Phe Pro Ala Gln Val Ser Ser
                500                 505                 510

Phe Pro Ser Ser Ala Val Thr Asn Ser Phe Ser Ala Ser Thr Gly Leu
            515                 520                 525

Ser Asp Met Thr Ala Thr Phe Ser Pro Arg Thr Ile Glu Ile Cys
    530                 535                 540

<210> SEQ ID NO 39
<211> LENGTH: 543
<212> TYPE: PRT
<213> ORGANISM: Artificial Sequence
<220> FEATURE:
<223> OTHER INFORMATION: Synthetic Construct

<400> SEQUENCE: 39

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
```

```
              305                 310                 315                 320
      Met Arg Lys Tyr Pro Asn Arg Pro Ser Lys Thr Pro His Glu Arg
                      325                 330                 335

Pro Tyr Ala Cys Pro Val Glu Ser Cys Asp Arg Arg Phe Ser Arg Ser
                      340                 345                 350

Asp Asn Leu Val Arg His Ile Arg Ile His Thr Gly Gln Lys Pro Phe
                      355                 360                 365

Gln Cys Arg Ile Cys Met Arg Asn Phe Ser Arg Ser Asp His Leu Thr
                      370                 375                 380

Thr His Ile Arg Thr His Thr Gly Glu Lys Pro Phe Ala Cys Asp Ile
      385                 390                 395                 400

Cys Gly Arg Lys Phe Ala Asp Pro Gly His Leu Val Arg His Asn Arg
                      405                 410                 415

Ile His Leu Arg Gln Lys Asp Lys Lys Ala Asp Lys Ser Val Val Ala
                      420                 425                 430

Ser Ser Ala Thr Ser Ser Leu Ser Ser Tyr Pro Ser Pro Val Ala Thr
                      435                 440                 445

Ser Tyr Pro Ser Pro Val Thr Thr Ser Tyr Pro Ser Pro Ala Thr Thr
                      450                 455                 460

Ser Tyr Pro Ser Pro Val Pro Thr Ser Phe Ser Pro Gly Ser Ser
      465                 470                 475                 480

Thr Tyr Pro Ser Pro Val His Ser Gly Phe Pro Ser Pro Ser Val Ala
                      485                 490                 495

Thr Thr Tyr Ser Ser Val Pro Pro Ala Phe Pro Ala Gln Val Ser Ser
                      500                 505                 510

Phe Pro Ser Ser Ala Val Thr Asn Ser Phe Ser Ala Ser Thr Gly Leu
                      515                 520                 525

Ser Asp Met Thr Ala Thr Phe Ser Pro Arg Thr Ile Glu Ile Cys
                      530                 535                 540

<210> SEQ ID NO 40
<211> LENGTH: 9
<212> TYPE: DNA
<213> ORGANISM: Artificial Sequence
<220> FEATURE:
<223> OTHER INFORMATION: Synthetic Construct

<400> SEQUENCE: 40 ggctgggag                                                                 9

<210> SEQ ID NO 41
<211> LENGTH: 543
<212> TYPE: PRT
<213> ORGANISM: Artificial Sequence
<220> FEATURE:
<223> OTHER INFORMATION: Synthetic Construct

<400> SEQUENCE: 41

Met Ala Ala Ala Lys Ala Glu Met Gln Leu Met Ser Pro Leu Gln Ile
      1               5                   10                  15

Ser Asp Pro Phe Gly Ser Phe Pro His Ser Pro Thr Met Asp Asn Tyr
                      20                  25                  30

Pro Lys Leu Glu Glu Met Met Leu Leu Ser Asn Gly Ala Pro Gln Phe
                      35                  40                  45

Leu Gly Ala Ala Gly Ala Pro Glu Gly Ser Gly Ser Asn Ser Ser Ser
                      50                  55                  60

Ser Ser Ser Gly Gly Gly Gly Gly Gly Gly Gly Ser Asn Ser Ser
```

-continued

```
             65                  70                  75                  80
Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Arg Leu
            115                 120                 125

Pro Pro Ile Thr Tyr Thr Gly Arg Phe Ser Leu Glu Pro Ala Pro Asn
            130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Leu Ser Cys
                180                 185                 190

Ala Val Pro Ser Asn Asp Ser Ser Pro Ile Tyr Ser Ala Ala Pro Thr
                195                 200                 205

Phe Pro Thr Pro Asn Thr Asp Ile Phe Pro Glu Pro Gln Ser Gln Ala
                210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
                260                 265                 270

Pro Phe Gln Gly Leu Glu Ser Arg Thr Gln Gln Pro Ser Leu Thr Pro
                275                 280                 285

Leu Ser Thr Ile Lys Ala Phe Ala Thr Gln Ser Gly Ser Gln Asp Leu
                290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
                340                 345                 350

Asp Glu Leu Thr Arg His Ile Arg Ile His Thr Gly Gln Lys Pro Phe
                355                 360                 365

Gln Cys Arg Ile Cys Met Arg Asn Phe Ser Arg Ser Asp His Leu Thr
                370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
                405                 410                 415

Ile His Leu Arg Gln Lys Asp Lys Lys Ala Asp Lys Ser Val Val Ala
                420                 425                 430

Ser Ser Ala Thr Ser Ser Leu Ser Ser Tyr Pro Ser Pro Val Ala Thr
                435                 440                 445

Ser Tyr Pro Ser Pro Val Thr Thr Ser Tyr Pro Ser Pro Ala Thr Thr
                450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
                485                 490                 495
```

Thr Thr Tyr Ser Ser Val Pro Pro Ala Phe Pro Ala Gln Val Ser Ser
            500                 505                 510

Phe Pro Ser Ser Ala Val Thr Asn Ser Phe Ser Ala Ser Thr Gly Leu
        515                 520                 525

Ser Asp Met Thr Ala Thr Phe Ser Pro Arg Thr Ile Glu Ile Cys
    530                 535                 540

<210> SEQ ID NO 42
<211> LENGTH: 79
<212> TYPE: PRT
<213> ORGANISM: Artificial Sequence
<220> FEATURE:
<223> OTHER INFORMATION: Synthetic Construct

<400> SEQUENCE: 42

Cys Pro Val Glu Ser Cys Asp Arg Arg Phe Ser Arg Ser Asp Glu Leu
1               5                   10                  15

Thr Arg His Ile Arg Ile His Thr Gly Gln Lys Pro Phe Gln Cys Arg
            20                  25                  30

Ile Cys Met Arg Asn Phe Ser Ser Arg Asp Val Leu Arg Arg His Asn
        35                  40                  45

Arg Thr His Thr Gly Glu Lys Pro Phe Ala Cys Asp Ile Cys Gly Arg
    50                  55                  60

Lys Phe Ala Ser Arg Asp Val Leu Arg Arg His Asn Arg Ile His
65                  70                  75

<210> SEQ ID NO 43
<211> LENGTH: 79
<212> TYPE: PRT
<213> ORGANISM: Artificial Sequence
<220> FEATURE:
<223> OTHER INFORMATION: Synthetic Construct

<400> SEQUENCE: 43

Cys Pro Val Glu Ser Cys Asp Arg Arg Phe Ser Arg Ser Asp Asn Leu
1               5                   10                  15

Val Arg His Ile Arg Ile His Thr Gly Gln Lys Pro Phe Gln Cys Arg
            20                  25                  30

Ile Cys Met Arg Asn Phe Ser Arg Ser Asp His Leu Thr Thr His Ile
        35                  40                  45

Arg Thr His Thr Gly Glu Lys Pro Phe Ala Cys Asp Ile Cys Gly Arg
    50                  55                  60

Lys Phe Ala Asp Pro Gly His Leu Val Arg His Asn Arg Ile His
65                  70                  75

<210> SEQ ID NO 44
<211> LENGTH: 9
<212> TYPE: DNA
<213> ORGANISM: Artificial Sequence
<220> FEATURE:
<223> OTHER INFORMATION: Synthetic Construct

<400> SEQUENCE: 44 gcgtgggcg                                                                9

<210> SEQ ID NO 45
<211> LENGTH: 23
<212> TYPE: PRT
<213> ORGANISM: Artificial Sequence
<220> FEATURE:
<223> OTHER INFORMATION: Synthetic Construct

```
<400> SEQUENCE: 45

Cys Pro Val Glu Ser Cys Asp Arg Arg Phe Ser Arg Ser Asp Glu Leu
1               5                   10                  15

Thr Arg His Ile Arg Ile His
            20

<210> SEQ ID NO 46
<211> LENGTH: 21
<212> TYPE: PRT
<213> ORGANISM: Artificial Sequence
<220> FEATURE:
<223> OTHER INFORMATION: Synthetic Construct

<400> SEQUENCE: 46

Cys Arg Ile Cys Met Arg Asn Phe Ser Arg Ser Asp His Leu Thr Thr
1               5                   10                  15

His Ile Arg Thr His
            20

<210> SEQ ID NO 47
<211> LENGTH: 21
<212> TYPE: PRT
<213> ORGANISM: Artificial Sequence
<220> FEATURE:
<223> OTHER INFORMATION: Synthetic Construct

<400> SEQUENCE: 47

Cys Asp Ile Cys Gly Arg Lys Phe Ala Arg Ser Asp Glu Arg Lys Arg
1               5                   10                  15

His Thr Lys Ile His
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic Construct

<400> SEQUENCE: 48

Cys Pro Val Glu Ser Cys Asp Arg Arg Phe Ser Arg Ser Asp Glu Leu
1               5                   10                  15

Thr Arg His Ile Arg Ile His
            20

<210> SEQ ID NO 49
<211> LENGTH: 21
<212> TYPE: PRT
<213> ORGANISM: Artificial Sequence
<220> FEATURE:
<223> OTHER INFORMATION: Synthetic Construct

<400> SEQUENCE: 49

Cys Arg Ile Cys Met Arg Asn Phe Ser Ser Arg Asp Val Leu Arg Arg
1               5                   10                  15

His Asn Arg Thr His
            20

<210> SEQ ID NO 50
<211> LENGTH: 21
<212> TYPE: PRT
<213> ORGANISM: Artificial Sequence
<220> FEATURE:
```

```
<223> OTHER INFORMATION: Synthetic Construct

<400> SEQUENCE: 50

Cys Asp Ile Cys Gly Arg Lys Phe Ala Ser Arg Asp Val Leu Arg Arg
1               5                   10                  15

His Asn Arg Ile His
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic Construct

<400> SEQUENCE: 51

Cys Pro Val Glu Ser Cys Asp Arg Arg Phe Ser Arg Ser Asp Asn Leu
1               5                   10                  15

Val Arg His Ile Arg Ile His
            20

<210> SEQ ID NO 52
<211> LENGTH: 21
<212> TYPE: PRT
<213> ORGANISM: Artificial Sequence
<220> FEATURE:
<223> OTHER INFORMATION: Synthetic Construct

<400> SEQUENCE: 52

Cys Arg Ile Cys Met Arg Asn Phe Ser Arg Ser Asp His Leu Thr Thr
1               5                   10                  15

His Ile Arg Thr His
            20

<210> SEQ ID NO 53
<211> LENGTH: 21
<212> TYPE: PRT
<213> ORGANISM: Artificial Sequence
<220> FEATURE:
<223> OTHER INFORMATION: Synthetic Construct

<400> SEQUENCE: 53

Cys Asp Ile Cys Gly Arg Lys Phe Ala Asp Pro Gly His Leu Val Arg
1               5                   10                  15

His Asn Arg Ile His
            20

<210> SEQ ID NO 54
<211> LENGTH: 23
<212> TYPE: PRT
<213> ORGANISM: Artificial Sequence
<220> FEATURE:
<223> OTHER INFORMATION: Synthetic Construct

<400> SEQUENCE: 54

Cys Pro Val Glu Ser Cys Asp Arg Arg Phe Ser Arg Ser Asp Glu Leu
1               5                   10                  15

Thr Arg His Ile Arg Ile His
            20

<210> SEQ ID NO 55
<211> LENGTH: 21
<212> TYPE: PRT
<213> ORGANISM: Artificial Sequence
```

<220> FEATURE:
<223> OTHER INFORMATION: Synthetic Construct

<400> SEQUENCE: 55

Cys Arg Ile Cys Met Arg Asn Phe Ser Ser Arg Asp Val Leu Arg Arg
1               5                   10                  15

His Asn Arg Thr His
            20

<210> SEQ ID NO 56
<211> LENGTH: 21
<212> TYPE: PRT
<213> ORGANISM: Artificial Sequence
<220> FEATURE:
<223> OTHER INFORMATION: Synthetic Construct

<400> SEQUENCE: 56

Cys Asp Ile Cys Gly Arg Lys Phe Ala Ser Arg Asp Val Leu Arg Arg
1               5                   10                  15

His Asn Arg Ile His
            20

<210> SEQ ID NO 57
<211> LENGTH: 21
<212> TYPE: PRT
<213> ORGANISM: Artificial Sequence
<220> FEATURE:
<223> OTHER INFORMATION: Synthetic Construct

<400> SEQUENCE: 57

Cys Ala Glu Cys Gly Lys Ala Phe Val Glu Ser Ser Lys Leu Lys Arg
1               5                   10                  15

His Gln Leu Val His
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic Construct

<400> SEQUENCE: 58

Cys Pro Val Glu Ser Cys Asp Arg Arg Phe Ser Arg Ser Asp Asn Leu
1               5                   10                  15

Val Arg His Ile Arg Ile His
            20

<210> SEQ ID NO 59
<211> LENGTH: 21
<212> TYPE: PRT
<213> ORGANISM: Artificial Sequence
<220> FEATURE:
<223> OTHER INFORMATION: Synthetic Construct

<400> SEQUENCE: 59

Cys Arg Ile Cys Met Arg Asn Phe Ser Arg Ser Asp His Leu Thr Thr
1               5                   10                  15

His Asn Arg Thr His
            20

<210> SEQ ID NO 60
<211> LENGTH: 21
<212> TYPE: PRT

<213> ORGANISM: Artificial Sequence
<220> FEATURE:
<223> OTHER INFORMATION: Synthetic Construct

<400> SEQUENCE: 60

```
Cys Asp Ile Cys Gly Arg Lys Phe Ala Asp Pro Gly His Leu Val Arg
1               5                   10                  15

His Asn Arg Ile His
            20
```

<210> SEQ ID NO 61
<211> LENGTH: 23
<212> TYPE: PRT
<213> ORGANISM: Artificial Sequence
<220> FEATURE:
<223> OTHER INFORMATION: Synthetic Construct

<400> SEQUENCE: 61

```
Cys Pro Val Glu Ser Cys Asp Arg Arg Phe Ser Arg Ser Asp Glu Leu
1               5                   10                  15

Thr Arg His Ile Arg Ile His
            20
```

<210> SEQ ID NO 62
<211> LENGTH: 6367
<212> TYPE: DNA
<213> ORGANISM: Artificial Sequence
<220> FEATURE:
<223> OTHER INFORMATION: Synthetic Construct

<400> SEQUENCE: 62

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtcacca actgggtaac ctctgctgac | 180 |
| ccccactcta ctttaccata agtagctcca aatccttcta gaaaatctga aaggcatagc | 240 |
| cccatatatc agtgatataa atagaacctg cagcaggctc tggtaaatga tgactacaag | 300 |
| gtggactggg aggcagcccg gccttggcag gcatcatcct ctaaatataa agatgagttt | 360 |
| gttcagcctt tgcagaagga aaaactgcca cccatcctag agtgccgcgt ccttgtcccc | 420 |
| ccaccccctc caatttattg ggaggaagga ccagctaagc ctcatctagg aagagcccct | 480 |
| cacccatctc cacctccact ccaggtctag ccagtcctgg gttgtgaccc ttgtctttca | 540 |
| gccccaggag agggacacac atagtgccac caaagaggct gggggagggc ctcagcccac | 600 |
| caaaacctgg ggccagtgcg tcctacagga ggggaaccct cacccttca atcccttag | 660 |
| gagacccaag ggcgctgcgc gtccctgagg cggacagctc cgtgtgctca ggctttgcgc | 720 |
| ctgacaggcc tatccccggg agccccgcg cctcctcccc ggcgctccgc cctcgcctcc | 780 |
| ccccgccagt tgtctatcct gcgacagctg cgcgccctcc ggccgccggt ggccctctgt | 840 |
| gcggtggggg aaggggtcga cgtggctcag cttttggat tcaggagct cggggtgggg | 900 |
| aagagagaaa tggagttcca ggggcgtaaa ggagagggag ttcgccttcc ttcccttcct | 960 |
| gagactcagg agtgactgct tctccaatcc tcccaagccc accactccac acgactccc | 1020 |
| cttcccggta gtcgcaagtg ggagtttggg gatctgagca agaacccga agaggagttg | 1080 |
| aaatattgga agtcagcagt caggcacctt cccgagcgcc cagggcgctc agagtggaca | 1140 |
| tggttgggga ggccttttggg acaggtgcgg ttccgggagc gcaggcgcac acatgcaccc | 1200 |
| accggcgaac gcggtgaccc tcgccccacc ccatcccctc cggcgggcaa ctgggtcggg | 1260 |

```
tcaggagggg caaacccgct agggagacac tccatatacg gcccggcccg cgttacctgg   1320
gaccgggcca acccgctcct tctttggtca acgcagggga cccgggcggg ggcccaggcc   1380
gcgaaccggc cgagggaggg ggctctagtg cccaacaccc aaatatggct cgagaagggc   1440
agcgacattc ctgcggggtg gcgcggaggg aatgcccgcg ggctatataa aacctgagca   1500
gagggacaag cggccaccgc agcggacagc gccaagtgaa gcctcgcttc ccctccgcgg   1560
cgaccagggc ccgagccgag agtagcagtt gtagctaccc gcccaggtag ggcaggagtt   1620
gggaggggac aggggacag ggcactaccg aggggaacct gaaggactcc ggggcagaac    1680
ccagtcggtt cacctggtaa gcttgctagc tccgcggatt cgaatcccgg ccgggaacgg   1740
tgcattggaa cgcggattcc ccgtgccaag agtgacgtaa gtaccgccta tagagtctat   1800
aggcccacaa aaaatgcttt cttcttttaa tatactttt tgtttatctt atttctaata    1860 cttccctaa tctctttctt tcagggcaat aatgatacaa tgtatcatgc ctctttgcac    1920
cattctaaag aataacagtg ataatttctg ggttaaggca atagcaatat ttctgcatat   1980
aaatatttct gcatataaat tgtaactgat gtaagaggtt tcatattgct aatagcagct   2040
acaatccagc taccattctg cttttatttt atggttggga taaggctgga ttattctgag   2100
tccaagctag gccccttttgc taatcatgtt catacctctt atcttcctcc cacagctcct   2160
gggcaacgtg ctggtctgtg tgctggccca tcactttggc aaagaattgg gattcgaaca   2220
tcgatttaaa gctatggagc aaaagctcat ttctgaagag gacttgaatg aaatggagca   2280
aaagctcatt tctgaagagg acttgaatga aatggagcaa aagctcattt ctgaagagga   2340
cttgaatgaa atggagcaaa agctcatttc tgaagaggac ttgaatgaaa tggagcaaaa   2400
gctcatttct gaagaggact tgaatgaaat ggagagcttg ggcgacctca ccatgggccc   2460
taaaaagaag cgtaaagtcg ccccccgac cgatgtcagc ctggggacg agctccactt    2520 agacggcgag gacgtggcga tggcgcatgc cgacgcgcta gacgatttcg atctggacat   2580 gttggggggac ggggattccc cgggtccggg atttaccccc cacgactccg ccccctacgg   2640
cgctctggat atggccgact tcgagtttga gcagatgttt accgatgccc ttggaattga   2700
cgagtacggt ggggaattcc cggggatcct cgatgacaga ccctatgctt gcccagtgga   2760
aagctgcgac cgccgcttt ctagatcgga tgagcttacc cgccatatcc gcatccacac    2820
cggccaaaaa ccctttcaat gccgtatctg catgaggaat tcagcagcc gcgatgtcct   2880 gaggcgccat aacaggaccc acacagggga aaagccattc gcatgtgaca tctgcggtcg   2940
aaagtttgca agccgcgatg tcctgaggcg ccataacagg atacatttga ggcaaggtcc   3000
cagatctcac gtctgtgcag aatgtggcaa agcgttcgtt gagagctcaa agctaaaacg   3060
acaccagctg gttcatgagc tggagagaag ccctttttagc tcgagagatc tacgggtggc   3120
atccctgtga ccctccca gtgcctctcc tggccctgga agttgccact ccagtgccca     3180
ccagccttgt cctaataaaa ttaagttgca tcattttgtc tgactaggtg tccttctata   3240
atattatggg gtgaggggg gtggtatgga gcaagggca agttgggaag acaacctgta     3300
gggcctgcgg ggtctattgg gaaccaagct ggagtgcagt ggcacaatct tggctcactg   3360
caatctccgc ctcctgggtt caagcgattc tcctgcctca gcctcccgag ttgttgggat   3420
tccaggcatg catgaccagg ctcagctaat ttttgttttt ttggtagaga cggggtttca   3480
ccatattggc caggctggtc tccaactcct aatctcaggt gatctaccca ccttggcctc   3540
ccaaattgct gggattacag gcgtgaacca ctgctccctt ccctgtcctt ctgattttgt   3600
```

```
aggtaaccac gtgcggaccg agcggccgca ggaaccccta gtgatggagt tggccactcc   3660
ctctctgcgc gctcgctcgc tcactgaggc cgggcgacca aggtcgccc gacgcccggg    3720
ctttgcccgg gcggcctcag tgagcgagcg agcgcgcagc tgcctgcagg ggcgcctgat   3780
gcggtatttt ctccttacgc atctgtgcgg tatttcacac cgcatacgtc aaagcaacca   3840
tagtacgcgc cctgtagcgg cgcattaagc gcggcgggtg tggtggttac gcgcagcgtg   3900
accgctacac ttgccagcgc cctagcgccc gctcctttcg ctttcttccc ttcctttctc   3960
gccacgttcg ccggctttcc ccgtcaagct ctaaatcggg ggctcccttt agggttccga   4020
tttagtgctt tacggcacct cgaccccaaa aaacttgatt tgggtgatgg ttcacgtagt   4080
gggccatcgc cctgatagac ggttttttcgc cctttgacgt tggagtccac gttctttaat   4140
agtggactct tgttccaaac tggaacaaca ctcaacccta tctcgggcta ttcttttgat   4200
ttataaggga ttttgccgat tcggcctat tggttaaaaa atgagctgat ttaacaaaaa    4260
tttaacgcga attttaacaa atattaacg tttacaattt tatggtgcac tctcagtaca    4320
atctgctctg atgccgcata gttaagccag ccccgacacc cgccaacacc cgctgacgcg   4380
ccctgacggg cttgtctgct cccggcatcc gcttacagac aagctgtgac cgtctccggg   4440
agctgcatgt gtcagaggtt ttcaccgtca tcaccgaaac gcgcgagacg aaagggcctc   4500
gtgatacgcc tatttttata ggttaatgtc atgataataa tggtttctta gacgtcaggt   4560
ggcacttttc ggggaaatgt gcgcggaacc cctatttgtt tatttttcta aatacattca   4620
aatatgtatc cgctcatgag acaataaccc tgataaatgc ttcaataata ttgaaaaagg   4680
aagagtatga gtattcaaca tttccgtgtc gcccttattc ccttttttgc ggcattttgc   4740
cttcctgttt ttgctcaccc agaaacgctg gtgaaagtaa aagatgctga agatcagttg   4800
ggtgcacgag tgggttacat cgaactggat ctcaacagcg gtaagatcct tgagagtttt   4860
cgccccgaag aacgttttcc aatgatgagc acttttaaag ttctgctatg tggcgcggta   4920
ttatcccgta ttgacgccgg gcaagagcaa ctcggtcgcc gcatacacta ttctcagaat   4980
gacttggttg agtactcacc agtcacagaa aagcatctta cggatggcat gacagtaaga   5040
gaattatgca gtgctgccat aaccatgagt gataacactg cggccaactt acttctgaca   5100
acgatcggag gaccgaagga gctaaccgct ttttgcaca acatggggga tcatgtaact   5160
cgccttgatc gttgggaacc ggagctgaat gaagccatac caaacgacga gcgtgacacc   5220
acgatgcctg tagcaatggc aacaacgttg cgcaaactat taactggcga actacttact   5280
ctagcttccc ggcaacaatt aatagactgg atggaggcgg ataaagttgc aggaccactt   5340
ctgcgctcgg cccttccggc tggctggttt attgctgata aatctggagc cggtgagcgt   5400
gggtctcgcg gtatcattgc agcactgggg ccagatggta agccctcccg tatcgtagtt   5460
atctacacga cggggagtca ggcaactatg gatgaacgaa atagacagat cgctgagata   5520
ggtgcctcac tgattaagca ttggtaactg tcagaccaag tttactcata tatactttag   5580
attgatttaa aacttcattt ttaatttaaa aggatctagg tgaagatcct ttttgataat   5640
ctcatgacca aaatccctta acgtgagttt tcgttccact gagcgtcaga ccccgtagaa   5700
aagatcaaag gatcttcttg agatcctttt tttctgcgcg taatctgctg cttgcaaaca   5760
aaaaaccac cgctaccagc ggtggtttgt ttgccggatc aagagctacc aactcttttt   5820
ccgaaggtaa ctggcttcag cagagcgcag ataccaaata ctgtccttct agtgtagccg   5880
tagttaggcc accacttcaa gaactctgta gcaccgccta catacctcgc tctgctaatc   5940
ctgttaccag tggctgctgc cagtggcgat aagtcgtgtc ttaccgggtt ggactcaaga   6000
```

```
cgatagttac cggataaggc gcagcggtcg ggctgaacgg ggggttcgtg cacacagccc    6060
agcttggagc gaacgaccta caccgaactg agatacctac agcgtgagct atgagaaagc    6120
gccacgcttc ccgaagggag aaaggcggac aggtatccgg taagcggcag ggtcggaaca    6180
ggagagcgca cgagggagct ccagggggaa aacgcctggt atctttatag tcctgtcggg    6240
tttcgccacc tctgacttga gcgtcgattt ttgtgatgct cgtcaggggg cggagccta    6300 tggaaaaacg ccagcaacgc ggcctttta cggttcctgg ccttttgctg ccttttgct     6360 cacatgt                                                              6367

<210> SEQ ID NO 63
<211> LENGTH: 6914
<212> TYPE: DNA
<213> ORGANISM: Artificial Sequence
<220> FEATURE:
<223> OTHER INFORMATION: Synthetic Construct

<400> SEQUENCE: 63
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtcacca actgggtaac ctctgctgac     180
ccccactcta ctttaccata agtagctcca aatccttcta gaaaatctga aaggcatagc     240
cccatatatc agtgatataa atagaacctg cagcaggctc tggtaaatga tgactacaag     300
gtggactggg aggcagcccg gccttggcag gcatcatcct ctaaatataa agatgagttt     360
gttcagcctt tgcagaagga aaaactgcca cccatcctag agtgccgcgt ccttgtcccc     420
ccaccccctc caatttattg ggaggaagga ccagctaagc ctcatctagg aagagcccct     480
cacccatctc cacctccact ccaggtctag ccagtcctgg gttgtgaccc ttgtctttca     540
gccccaggag agggacacac atagtgccac caaagaggct gggggagggc ctcagcccac     600
caaaacctgg ggccagtgcg tcctacagga ggggaaccct caccccttca atcccttag      660 gagacccaag ggcgctgcgc gtccctgagg cggacagctc cgtgtgctca ggctttgcgc     720
ctgacaggcc tatccccggg agccccgcg cctcctcccc ggcgctccgc cctcgcctcc      780
ccccgccagt tgtctatcct gcgacagctg cgcgccctcc ggccgccggt ggccctctgt     840
gcggtggggg aaggggtcga cgtggctcag ctttttggat tcaggagct cggggtgggg     900 aagagagaaa tggagttcca ggggcgtaaa ggagagggag ttcgccttcc ttcccttcct     960
gagactcagg agtgactgct tctccaatcc tcccaagccc accactccac acgactccct    1020
cttcccggta gtcgcaagtg ggagtttggg gatctgagca agaacccga agaggagttg     1080 aaatattgga agtcagcagt caggcacctt cccgagcgcc cagggcgctc agagtggaca    1140
tggttgggga ggcctttggg acaggtgcgg ttcccggagc gcaggcgcac acatgcaccc    1200
accggcgaac gcggtgaccc tcgcccacc ccatccctc cggcgggcaa ctgggtcggg      1260
tcaggagggg caaacccgct agggagacac tccatatacg gccggcccg cgttacctgg     1320 gaccgggcca acccgctcct tctttggtca acgcagggga ccgggcggg ggccaggcc      1380 gcgaaccggc cgagggaggg ggctctagtg cccaacaccc aaatatggct cgagaagggc    1440
agcgacattc ctgcggggtg gcgcggaggg aatgcccgcg ggctatataa aacctgagca    1500
gagggacaag cggccaccgc agcggacagc gccaagtgaa gcctcgcttc ccctccgcgg    1560
cgaccagggc ccgagccgag agtagcagtt gtagctaccc gcccaggtag ggcaggagtt    1620
```

```
gggaggggac aggggggacag ggcactaccg aggggaacct gaaggactcc ggggcagaac    1680
ccagtcggtt cacctggtaa gcttgctagc tccgcggatt cgaatcccgg ccgggaacgg    1740
tgcattggaa cgcggattcc ccgtgccaag agtgacgtaa gtaccgccta tagagtctat    1800
aggcccacaa aaaatgcttt cttcttttaa tatacttttt tgtttatctt atttctaata    1860
ctttccctaa tctctttctt tcagggcaat aatgatacaa tgtatcatgc ctctttgcac    1920
cattctaaag aataacagtg ataatttctg ggttaaggca atagcaatat ttctgcatat    1980
aaatatttct gcatataaat tgtaactgat gtaagaggtt tcatattgct aatagcagct    2040
acaatccagc taccattctg cttttatttt atggttggga taaggctgga ttattctgag    2100
tccaagctag gcccttttgc taatcatgtt catacctctt atcttcctcc cacagctcct    2160
gggcaacgtg ctggtctgtg tgctggccca tcactttggc aaagaattgg gattcgaaca    2220
tcgatttaaa gctatggagc aaaagctcat ttctgaagag acttgaatg aaatggagca    2280
aaagctcatt tctgaagagg acttgaatga atggagcaa aagctcattt ctgaagagga    2340
cttgaatgaa atggagcaaa agctcatttc tgaagaggac ttgaatgaaa tggagcaaaa    2400
gctcatttct gaagaggact gaatgaaat ggagagcttg gcgacctca ccatgggccc    2460
taaaaagaag cgtaaagtcg ccccccccgac cgatgtcagc ctgggggacg agctccactt    2520
agacggcgag gacgtggcga tggcgcatgc cgacgcgcta gacgatttcg atctggacat    2580
gttgggggac ggggattccc cgggtccggg atttacccccc cacgactccg cccccctacgg    2640
cgctctggat atggccgact tcgagtttga gcagatgttt accgatgccc ttggaattga    2700
cgagtacggt ggggaattcc cggggatctt ggcaaagcgc tttgccgact ttacagtcta    2760
caggaaccgc acacttcaga atggcacga taagaccaaa ctggcttctg gaaaactggg    2820
gaagggtttt ggtgccttg aacgctcaat cttgactcag atcgaccata ttctgatgga    2880
caaagagaga ttacttcgaa ggacacagac caagcgctct gtctatcgag ttcttggcaa    2940
acctgagcca gcagctcagc ctgtcccaga gagtttgcca ggggaaccgg agatccttcc    3000
tcaagcccct gctaatgctc atctgaagga cttggatgaa gaaatctttg atgatgatga    3060
cttttaccac cagctccttc gagaactcat agaacggaag accagctcct ggggatcct    3120
ggatcgccct tacgcctgcc ctgtggaatc ttgcgaccgc cggttctccc gcagcgataa    3180
cctggtgcgg cacatccgga ttcacaccgg ccagaaacct ttccagtgca ggatctgcat    3240
gagaaatttc tcccggtccg accacctgac cacccacaat aggacccaca ccggcgagaa    3300
accctttgcc tgcgacatct gcgggagaaa gttcgccgac cccggccacc tggtgagaca    3360
caatagaatc cacaccggtg aaaagccctt cgcctgtccc gtggagagct gcgatcgcag    3420
attcagccgc agcgacagc tgacaaggca catcagaatc cacaccgggc agaagccttt    3480
tcagtgccgg atctgcatga ggaacttcag ctcccgggac gtgctgagac gccacaatcg    3540
cacacacacc ggcgaaaagc ccttcgcctg tgatatttgc gggcggaaat ttgcctccag    3600
agatgtgctg cgccgccaca accgcattca cctgagacag aacgatctcg agagatctac    3660
gggtggcatc cctgtgaccc ctccccagtg cctctcctgg ccctggaagt tgccactcca    3720
gtgcccacca gccttgtcct aataaaatta agttgcatca ttttgtctga ctaggtgtcc    3780
ttctataata ttatggggtg agggggggtg gtatggcaag agggcaagt tgggaagaca    3840
acctgtaggg cctgcggggt ctattgggaa ccaagctgga gtgcagtggc acaatcttgg    3900
ctcactgcaa tctccgcctc ctgggttcaa gcgattctcc tgcctcagcc tcccgagttg    3960
ttgggattcc aggcatgcat gaccaggctc agctaatttt tgttttttg gtagagacgg    4020
```

```
ggtttcacca tattggccag gctggtctcc aactcctaat ctcaggtgat ctacccacct    4080
tggcctccca aattgctggg attacaggcg tgaaccactg ctcccttccc tgtccttctg    4140
attttgtagg taaccacgtg cggaccgagc ggccgcagga acccctagtg atggagttgg    4200
ccactccctc tctgcgcgct cgctcgctca ctgaggccgg gcgaccaaag gtcgcccgac    4260
gcccgggctt tgcccgggcg gcctcagtga gcgagcgagc gcgcagctgc ctgcaggggc    4320
gcctgatgcg gtattttctc cttacgcatc tgtgcggtat ttcacaccgc atacgtcaaa    4380
gcaaccatag tacgcgccct gtagcggcgc attaagcgcg gcgggtgtgg tggttacgcg    4440
cagcgtgacc gctacacttg ccagcgccct agcgcccgct cctttcgctt tcttcccttc    4500
ctttctcgcc acgttcgccg gctttccccg tcaagctcta atcgggggc tccctttagg     4560
gttccgattt agtgctttac ggcacctcga ccccaaaaaa cttgatttgg gtgatggttc    4620
acgtagtggg ccatcgccct gatagacggt ttttcgccct tgacgttgg agtccacgtt     4680
ctttaatagt ggactcttgt tccaaactgg aacaacactc aaccctatct cgggctattc    4740
ttttgattta aagggatttt gccgatttcg gcctattgg ttaaaaaatg agctgattta     4800
acaaaaattt aacgcgaatt ttaacaaaat attaacgttt acaatttat ggtgcactct     4860
cagtacaatc tgctctgatg ccgcatagtt aagccagccc cgacacccgc caacacccgc    4920
tgacgcgccc tgacgggctt gtctgctccc ggcatccgct tacagacaag ctgtgaccgt    4980
ctccgggagc tgcatgtgtc agaggttttc accgtcatca ccgaaacgcg cgagacgaaa    5040
gggcctcgtg atacgcctat ttttataggt taatgtcatg ataataatgg tttcttagac    5100
gtcaggtggc acttttcggg gaaatgtgcg cggaacccct atttgtttat ttttctaaat    5160
acattcaaat atgtatccgc tcatgagaca ataaccctga taaatgcttc aataatattg    5220
aaaaaggaag agtatgagta ttcaacattt ccgtgtcgcc cttattccct ttttgcggc     5280
attttgcctt cctgttttg ctcacccaga aacgctggtg aaagtaaaag atgctgaaga    5340
tcagttgggt gcacgagtgg gttacatcga actggatctc aacagcggta agatccttga    5400
gagttttcgc cccgaagaac gttttccaat gatgagcact tttaaagttc tgctatgtgg    5460
cgcggtatta tcccgtattg acgccgggca agagcaactc ggtcgccgca tacactattc    5520
tcagaatgac ttggttgagt actcaccagt cacagaaaag catcttacgg atggcatgac    5580
agtaagagaa ttatgcagtg ctgccataac catgagtgat aacactgcgg ccaacttact    5640
tctgacaacg atcggaggac cgaaggagct aaccgctttt ttgcacaaca tgggggatca    5700
tgtaactcgc cttgatcgtt gggaaccgga gctgaatgaa gccataccaa acgacgagcg    5760
tgacaccacg atgcctgtag caatggcaac aacgttgcgc aaactattaa ctggcgaact    5820
acttactcta gcttcccggc aacaattaat agactggatg gaggcggata agttgcagg     5880
accacttctg cgctcggccc ttccggctgg ctggtttatt gctgataaat ctggagccgg    5940
tgagcgtggg tctcgcggta tcattgcagc actggggcca gatggtaagc cctcccgtat    6000
cgtagttatc tacacgacgg ggagtcaggc aactatggat gaacgaaata gacagatcgc    6060
tgagataggt gcctcactga ttaagcattg gtaactgtca gaccaagttt actcatatat    6120
actttagatt gatttaaaac ttcatttta atttaaaagg atctaggtga agatcctttt    6180
tgataatctc atgaccaaaa tcccttaacg tgagttttcg ttccactgag cgtcagaccc    6240
cgtagaaaag atcaaaggat cttcttgaga tccttttttt ctgcgcgtaa tctgctgctt    6300
gcaaacaaaa aaccaccgc taccagcggt ggtttgtttg ccggatcaag agctaccaac    6360
```

```
tcttttttccg aaggtaactg gcttcagcag agcgcagata ccaaatactg tccttctagt    6420
gtagccgtag ttaggccacc acttcaagaa ctctgtagca ccgcctacat acctcgctct    6480
gctaatcctg ttaccagtgg ctgctgccag tggcgataag tcgtgtctta ccgggttgga    6540
ctcaagacga tagttaccgg ataaggcgca gcggtcgggc tgaacggggg gttcgtgcac    6600
acagcccagc ttggagcgaa cgacctacac cgaactgaga tacctacagc gtgagctatg    6660
agaaagcgcc acgcttcccg aagggagaaa ggcggacagg tatccggtaa gcggcagggt    6720
cggaacagga gagcgcacga gggagcttcc agggggaaac gcctggtatc tttatagtcc    6780
tgtcgggttt cgccacctct gacttgagcg tcgatttttg tgatgctcgt caggggggcg    6840
gagcctatgg aaaaacgcca gcaacgcggc cttttttacgg ttcctggcct tttgctggcc    6900
ttttgctcac atgt                                                       6914
```

```
<210> SEQ ID NO 64
<211> LENGTH: 7138
<212> TYPE: DNA
<213> ORGANISM: Artificial Sequence
<220> FEATURE:
<223> OTHER INFORMATION: Synthetic Construct

<400> SEQUENCE: 64
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtcacca actgggtaac ctctgctgac     180
ccccactcta ctttaccata agtagctcca aatccttcta gaaaatctga aaggcatagc     240
cccatatatc agtgatataa atagaacctg cagcaggctc tggtaaatga tgactacaag     300
gtggactggg aggcagcccg gccttggcag gcatcatcct ctaaatataa agatgagttt     360
gttcagcctt tgcagaagga aaaactgcca cccatcctag agtgccgcgt ccttgtcccc     420
ccaccccctc caatttattg ggaggaagga ccagctaagc ctcatctagg aagagcccct     480
cacccatctc cacctccact ccaggtctag ccagtcctgg gttgtgaccc ttgtctttca     540
gccccaggag agggacacac atagtgccac caaagaggct ggggagggc ctcagcccac     600 caaaacctgg ggccagtgcg tcctacagga ggggaaccct caccccttca atcccttttag     660 gagacccaag ggcgctgcgc gtccctgagg cggacagctc cgtgtgctca ggctttgcgc     720
ctgacaggcc tatccccggg agccccgcg cctcctcccc ggcgctccgc cctcgcctcc     780
ccccgccagt tgtctatcct gcgacagctg cgcgccctcc ggccgccggt ggccctctgt     840
gcggtggggg aaggggtcga cgtggctcag cttttttggat tcagggagct cggggggtggg     900 aagagagaaa tggagttcca ggggcgtaaa ggagagggag ttcgccttcc ttcccttcct     960
gagactcagg agtgactgct tctccaatcc tcccaagccc accactccac acgactccct    1020
cttcccggta gtcgcaagtg ggagtttggg gatctgagca agaacccga agaggagttg    1080 aaatattgga agtcagcagt caggcacctt cccgagcgcc cagggcgctc agagtggaca    1140
tggttgggga ggcctttggg acaggtgcgg ttcccggagc gcaggcgcac acatgcaccc    1200
accggcgaac gcggtgaccc tcgccccacc ccatcccctc cggcgggcaa ctgggtcggg    1260
tcaggagggg caaacccgct agggagacac tccatatacg gcccggcccg cgttacctgg    1320
gaccgggcca acccgctcct tctttggtca acgcagggga cccgggcggg ggcccaggcc    1380
gcgaaccggc cgagggaggg ggctctagtg cccaacaccc aaatatggct cgagaagggc    1440
agcgacattc ctgcggggtg gcgcggaggg aatgcccgcg ggctatataa aacctgagca    1500
```

```
gagggacaag cggccaccgc agcggacagc gccaagtgaa gcctcgcttc ccctccgcgg    1560
cgaccagggc ccgagccgag agtagcagtt gtagctaccc gcccaggtag ggcaggagtt    1620
gggaggggac aggggacag ggcactaccg aggggaacct gaaggactcc ggggcagaac     1680
ccagtcggtt cacctggtaa gcttgctagc tccgcggatt cgaatcccgg ccgggaacgg    1740
tgcattggaa cgcggattcc ccgtgccaag agtgacgtaa gtaccgccta tagagtctat    1800
aggcccacaa aaaatgcttt cttcttttaa tatactttt tgtttatctt atttctaata     1860
ctttccctaa tctctttctt tcagggcaat aatgatacaa tgtatcatgc ctctttgcac    1920
cattctaaag aataacagtg ataatttctg ggttaaggca atagcaatat ttctgcatat    1980
aaatatttct gcatataaat tgtaactgat gtaagaggtt tcatattgct aatagcagct    2040
acaatccagc taccattctg cttttatttt atggttggga taaggctgga ttattctgag    2100
tccaagctag gccttttgc taatcatgtt catacctctt atcttcctcc cacagctcct     2160
gggcaacgtg ctggtctgtg tgctggccca tcactttggc aaagaattgg gattcgaaca    2220
tcgatggtac cgaattcaat ggccgctgcc aaggccgaga tgcagctgat gagcccctg     2280 cagatcagcg accccttcgg cagcttcccc cacagcccca ccatggacaa ctaccccaag    2340
ctggaagaga tgatgctgct gagcaatggc gctcctcagt tcctgggagc cgctggcgcc    2400
cctgagggca gcggcagcaa tagcagcagc agctctagcg gcggaggcgg aggggaggc    2460 ggcggaagca atagctccag ctccagcagc acattcaatc cacaagccga caccggcgag    2520 cagcccctatg agcacctgac cgccgagagc ttccccgaca tcagcctgaa caacgagaag    2580
gtgctggtgg aaaccagcta ccccagccag accacccggc tgcccccctat cacctacaca    2640 ggccggttca gcctggaacc cgcccctaac agcggcaaca ccctgtggcc cgagcccctg    2700
tttagcctgg tgtccggcct ggtgtctatg accaaccccc tgccagcag ctcctctgcc     2760 ccaagccctg ccgccagctc tgcctctgcc agcagagcc ctccactgag ctgcgccgtg     2820
cccagcaacg acagcagccc catctacagc gccgctccca ccttccccac cccaacacc     2880 gacatcttcc ccgagcctca gagccaggcc tttcctggat ctgccggcac cgccctgcag    2940
tacccacctc ctgcctatcc tgccgccaag ggcggcttcc aggtgccat gatccccgac     3000 tacctgttcc cccagcagca gggcgatctg ggcctgggca ccccgacca gaagcctttc    3060 cagggcctcg aaagccggac ccagcagcca agcctgaccc cctgagcac catcaaggcc    3120 ttcgccaccc agagcggcag ccaggacctg aaggccctga acaccagcta ccagagccag    3180
ctgatcaagc ccagccggat gcggaagtac cccaaccggc cagcaagac ccccccacac     3240 gagaggcctt acgcctgccc cgtggaaagc tgcgacagac ggttcagcag aagcgacgag    3300
ctgacccggc acatccggat ccacaccggc cagaaacct tccagtgccg gatctgcatg    3360
cggaacttca gcagccggga cgtgctgcgg cggcacaata gaacccacac aggcgagaag    3420
cccttcgcct gcgacatctg cggcggaag ttcgccagca gagatgtgct gcggagacac     3480
aacaggatcc acctgagaca gaaggacaag aaagccgaca agagcgtggt cgccagcagc    3540
gctaccagca gcctgagcag ctaccttct cctgtggcca cctcctaccc aagcccagtg     3600
accacaagct acccatcccc cgccaccacc tcttatccca gccccgtgcc taccagcttc    3660
agctctcccg gcagctccac ataccccagc cctgtgcata gcggcttccc tagccctagc    3720
gtggccacca catacagcag cgtgccccct gccttcccag ctcaagtgtc cagcttcccc    3780
agctccgccg tgaccaacag cttcagcgcc agcaccggcc tgagcgacat gaccgccacc    3840
```

```
ttcagccccc ggaccatcga gatctgctga ctcgagagat ctacgggtgg catccctgtg    3900
acccctcccc agtgcctctc ctggccctgg aagttgccac tccagtgccc accagccttg    3960
tcctaataaa attaagttgc atcatttttgt ctgactaggt gtccttctat aatattatgg   4020
ggtggagggg ggtggtatgg agcaaggggc aagttgggaa gacaacctgt agggcctgcg    4080
gggtctattg ggaaccaagc tggagtgcag tggcacaatc ttggctcact gcaatctccg    4140
cctcctgggt tcaagcgatt ctcctgcctc agcctcccga gttgtggga ttccaggcat     4200
gcatgaccag gctcagctaa ttttttgtttt tttggtagag acggggtttc accatattgg   4260
ccaggctggt ctccaactcc taatctcagg tgatctaccc accttggcct cccaaattgc    4320
tgggattaca ggcgtgaacc actgctccct tccctgtcct tctgattttg taggtaacca    4380
cgtgcggacc gagcggccgc aggaaccct agtgatggag ttggccactc cctctctgcg     4440
cgctcgctcg ctcactgagg ccgggcgacc aaaggtcgcc cgacgcccgg gctttgcccg    4500
ggcggcctca gtgagcgagc gagcgcgcag ctgcctgcag gggcgcctga tgcggtattt    4560
tctccttacg catctgtgcg gtatttcaca ccgcatacgt caaagcaacc atagtacgcg    4620
ccctgtagcg cgcattaag cgcggcgggt gtggtggtta cgcgcagcgt gaccgctaca     4680
cttgccagcg ccctagcgcc cgctcctttc gctttcttcc cttcctttct cgccacgttc    4740
gccggctttc cccgtcaagc tctaaatcgg gggctccctt tagggttccg atttagtgct    4800
ttacggcacc tcgaccccaa aaaacttgat ttgggtgatg gttcacgtag tgggccatcg    4860
ccctgataga cggtttttcg ccctttgacg ttggagtcca cgttctttaa tagtggactc    4920
ttgttccaaa ctggaacaac actcaaccct atctcgggct attctttga tttataaggg     4980
attttgccga tttcggccta ttggttaaaa aatgagctga tttaacaaaa atttaacgcg    5040
aattttaaca aaatattaac gtttacaatt ttatggtgca ctctcagtac aatctgctct    5100
gatgccgcat agttaagcca gccccgacac ccgccaacac ccgctgacgc gccctgacgg    5160
gcttgtctgc tcccggcatc cgcttacaga caagctgtga ccgtctccgg gagctgcatg    5220
tgtcagaggt tttcaccgtc atcaccgaaa cgcgcgagac gaaagggcct cgtgatacgc    5280
ctatttttat aggttaatgt catgataata atggtttctt agacgtcagg tggcactttt    5340
cggggaaatg tgcgcggaac ccctatttgt ttatttttct aaatacattc aaatatgtat    5400
ccgctcatga caataaacc ctgataaatg cttcaataat attgaaaaag gaagagtatg     5460
agtattcaac atttccgtgt cgcccttatt ccctttttg cggcattttg ccttcctgtt     5520
tttgctcacc cagaaacgct ggtgaaagta aaagatgctg aagatcagtt gggtgcacga    5580
gtgggttaca tcgaactgga tctcaacagc ggtaagatcc ttgagagttt tcgccccgaa    5640
gaacgttttc caatgatgag cacttttaaa gttctgctat gtggcgcggt attatcccgt    5700
attgacgccg ggcaagagca actcggtcgc cgcatacact attctcagaa tgacttggtt    5760
gagtactcac cagtcacaga aaagcatctt acggatggca tgacagtaag agaattatgc    5820
agtgctgcca taaccatgag tgataacact gcggccaact tacttctgac aacgatcgga    5880
ggaccgaagg agctaaccgc ttttttgcac aacatggggg atcatgtaac tcgccttgat    5940
cgttgggaac cggagctgaa tgaagccata ccaaacgacg agcgtgacac cacgatgcct    6000
gtagcaatgg caacaacgtt gcgcaaacta ttaactggcg aactacttac tctagcttcc    6060
cggcaacaat taatagactg gatggaggcg gataaagttg caggaccact tctgcgctcg    6120
gcccttccgg ctggctggtt tattgctgat aaatctggag ccggtgagcg tgggtctcgc    6180
ggtatcattg cagcactggg gccagatggt aagccctccc gtatcgtagt tatctacacg    6240
```

```
acgggagtc aggcaactat ggatgaacga aatagacaga tcgctgagat aggtgcctca    6300
ctgattaagc attggtaact gtcagaccaa gtttactcat atatacttta gattgattta    6360
aaacttcatt tttaatttaa aaggatctag gtgaagatcc ttttgataa tctcatgacc     6420 aaaatcccttt aacgtgagtt ttcgttccac tgagcgtcag accccgtaga aaagatcaaa    6480
ggatcttctt gagatccttt ttttctgcgc gtaatctgct gcttgcaaac aaaaaaacca    6540
ccgctaccag cggtggtttg tttgccggat caagagctac caactctttt tccgaaggta    6600
actggcttca gcagagcgca gataccaaat actgtccttc tagtgtagcc gtagttaggc    6660
caccacttca agaactctgt agcaccgcct acatacctcg ctctgctaat cctgttacca    6720
gtggctgctg ccagtggcga taagtcgtgt cttaccgggt tggactcaag acgatagtta    6780
ccggataagg cgcagcggtc gggctgaacg gggggttcgt gcacacagcc cagcttggag    6840
cgaacgacct acaccgaact gagataccta cagcgtgagc tatgagaaag cgccacgctt    6900
cccgaaggga gaaaggcgga caggtatccg gtaagcggca gggtcggaac aggagagcgc    6960
acgagggagc ttccaggggg aaacgcctgg tatctttata gtcctgtcgg gtttcgccac    7020
ctctgacttg agcgtcgatt tttgtgatgc tcgtcagggg gcggagcct atggaaaaac      7080 gccagcaacg cggccttttt acggttcctg gccttttgct ggccttttgc tcacatgt      7138
```

<210> SEQ ID NO 65
<211> LENGTH: 7138
<212> TYPE: DNA
<213> ORGANISM: Artificial Sequence
<220> FEATURE:
<223> OTHER INFORMATION: Synthetic Construct

<400> SEQUENCE: 65

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgtcacca actgggtaac ctctgctgac    180
ccccactcta ctttaccata gtagctccaa atccttcta gaaaatctga aaggcatagc    240
cccatatatc agtgatataa atagaacctg cagcaggctc tggtaaatga tgactacaag    300
gtggactggg aggcagcccg gccttggcag gcatcatcct ctaaatataa agatgagttt    360
gttcagcctt tgcagaagga aaaactgcca cccatcctag agtgccgcgt ccttgtcccc    420 ccacccctc caatttattg ggaggaagga ccagctaagc ctcatctagg aagagcccct     480
cacccatctc cacctccact ccaggtctag ccagtcctgg gttgtgaccc ttgtctttca    540
gccccaggag agggacacac atagtgccac caaagaggct gggggaggcc ctcagcccac    600 caaaaccctgg ggcagtgcg tcctacagga ggggaaccct cacccctcca atcccttag    660 gagacccaag ggcgctgcgc gtccctgagg cggacagctc cgtgtgctca ggctttgcgc    720
ctgacaggcc tatcccgggg agccccgcg cctcctcccc ggcgctccgc cctcgcctcc     780 cccgccagt tgtctatcct gcgacagctg cgcgccctcc ggccgccggt ggccctctgt     840
gcggtggggg aagggtcga cgtggctcag ctttttggat tcaggagct cggggggtggg    900 aagagagaaa tggagttcca ggggcgtaaa ggagagggag ttcgccttcc ttcccttcct    960
gagactcagg agtgactgct tctccaatcc tcccaagccc accactccac acgactccct   1020
cttcccggta gtcgcaagtg ggagtttggg gatctgagca agaacccga agaggagttg   1080 aaatattgga agtcagcagt caggcacctt cccgagcgcc cagggcgctc agagtggaca   1140
```

```
tggttgggga ggcctttggg acaggtgcgg ttcccggagc gcaggcgcac acatgcaccc    1200
accggcgaac gcggtgaccc tcgccccacc ccatcccctc cggcgggcaa ctgggtcggg    1260
tcaggagggg caaacccgct agggagacac tccatatacg gcccggcccg cgttacctgg    1320
gaccgggcca acccgctcct tctttggtca acgcagggga cccgggcggg ggcccaggcc    1380
gcgaaccggc cgagggaggg ggctctagtg cccaacaccc aaatatggct cgagaagggc    1440
agcgacattc ctgcggggtg gcgcggaggg aatgcccgcg ggctatataa aacctgagca    1500
gagggacaag cggccaccgc agcggacagc gccaagtgaa gcctcgcttc ccctccgcgg    1560
cgaccagggc ccgagccgag agtagcagtt gtagctaccc gcccaggtag ggcaggagtt    1620
gggaggggac aggggggacag ggcactaccg aggggaacct gaaggactcc ggggcagaac    1680
ccagtcggtt cacctggtaa gcttgctagc tccgcggatt cgaatcccgg ccgggaacgg    1740
tgcattggaa cgcggattcc ccgtgccaag agtgacgtaa gtaccgccta tagagtctat    1800
aggcccacaa aaaatgcttt cttcttttaa tatactttt tgtttatctt atttctaata    1860
cttcccctaa tctctttctt tcaggcaat aatgatacaa tgtatcatgc ctctttgcac    1920
cattctaaag aataacagtg ataatttctg ggttaaggca atagcaatat ttctgcatat    1980
aaatatttct gcatataaat tgtaactgat gtaagaggtt tcatattgct aatagcagct    2040
acaatccagc taccattctg ctttatttt atggttggga taaggctgga ttattctgag    2100
tccaagctag gccttttgc taatcatgtt catacctctt atcttcctcc acagctcct    2160 gggcaacgtg ctggtctgtg tgctggccca tcactttggc aaagaattgg gattcgaaca    2220
tcgatggtac cgaattcaat ggccgctgcc aaggccgaga tgcagctgat gagcccctg    2280 cagatcagcg accccttcgg cagcttcccc cacagcccca ccatggacaa ctaccccaag    2340
ctggaagaga tgatgctgct gagcaatggc gctcctcagt tcctgggagc cgctggcgcc    2400
cctgagggca gcggcagcaa tagcagcagc agctctagcg gcggaggcgg aggggaggc    2460 ggcggaagca atagctccag ctccagcagc acattcaatc cacaagccga caccggcgag    2520
cagccctatg agcacctgac cgccgagagc ttccccgaca tcagcctgaa caacgagaag    2580
gtgctggtgg aaaccagcta ccccagccag accaccggc tgcccccctat cacctacaca    2640 ggccggttca gcctggaacc cgcccctaac agcggcaaca ccctgtggcc cgagcccctg    2700 tttagcctg tgtccggcct ggtgtctatg accaaccccc ctgccagcag ctcctctgcc    2760
ccaagccctg ccgccagctc tgcctctgcc agccagagcc ctcactgag ctgcgccgtg    2820 cccagcaacg acagcagccc catctacagc gccgctccca ccttccccac cccaacacc    2880 gacatcttcc ccgagcctca gagccaggcc tttcctggat ctgccggcac cgccctgcag    2940
tacccacctc ctgcctatcc tgccgccaag ggcggcttcc aggtgcccat gatccccgac    3000
tacctgttcc cccagcagca gggcgatctg ggcctgggca cccccgacca gaagcctttc    3060
cagggcctcg aaagcggac ccagcagcca agcctgaccc cctgagcac catcaaggcc    3120 ttcgccaccc agagcggcag ccaggacctg aaggccctga acaccagcta ccagagccag    3180
ctgatcaagc cagccggat gcggaagtac cccaaccggc ccagcaagac cccccacac    3240 gagaggcctt acgcctgccc cgtggaaagc tgcgacagac ggttcagcag aagcgacaac    3300
ctggtccggc acatccggat ccacaccggc cagaaccct tccagtgccg gatctgcatg    3360
cggaacttct ctcggagcga ccacctgacc acccacatca gaacccacac aggcgagaag    3420
cccttcgcct gcgacatctg cggccggaag ttcgccgacc ccggccacct cgtcagacac    3480
aacaggattc acctgagaca gaaggacaag aaagccgaca agagcgtggt cgccagcagc    3540
```

```
gctaccagca gcctgagcag ctacccttct cctgtggcca cctcctaccc aagcccagtg    3600
accacaagct acccatcccc cgccaccacc tcttatccca gccccgtgcc taccagcttc    3660
agctctcccg gcagctccac ataccccagc cctgtgcata gcggcttccc tagccctagc    3720
gtggccacca catacagcag cgtgccccct gccttcccag ctcaagtgtc cagcttcccc    3780
agctccgccg tgaccaacag cttcagcgcc agcaccggcc tgagcgacat gaccgccacc    3840
ttcagccccc ggaccatcga gatctgctga ctcgagagat ctacgggtgg catccctgtg    3900
accctcccc agtgcctctc ctggccctgg aagttgccac tccagtgccc accagccttg    3960
tcctaataaa attaagttgc atcattttgt ctgactaggt gtccttctat aatattatgg    4020
ggtggagggg ggtggtatgg agcaaggggc aagttgggaa gacaacctgt agggcctgcg    4080
gggtctattg gaaccaagc tggagtgcag tggcacaatc ttggctcact gcaatctccg    4140
cctcctgggt tcaagcgatt ctcctgcctc agcctcccga gttgttggga ttccaggcat    4200
gcatgaccag gctcagctaa tttttgtttt tttggtagag acggggtttc accatattgg    4260
ccaggctggt ctccaactcc taatctcagg tgatctaccc accttggcct cccaaattgc    4320
tgggattaca ggcgtgaacc actgctccct tccctgtcct tctgattttg taggtaacca    4380
cgtgcggacc gagcggccgc aggaacccct agtgatggag ttggccactc cctctctgcg    4440
cgctcgctcg ctcactgagg ccgggcgacc aaaggtcgcc cgacgcccgg gctttgcccg    4500
ggcggcctca gtgagcgagc gagcgcgcag ctgcctgcag gggcgcctga tgcggtattt    4560
tctccttacg catctgtgcg gtatttcaca ccgcatacgt caaagcaacc atagtacgcg    4620
ccctgtagcg gcgcattaag cgcggcgggt gtggtggtta cgcgcagcgt gaccgctaca    4680
cttgccagcg ccctagcgcc cgctcctttc gctttcttcc cttcctttct cgccacgttc    4740
gccggctttc cccgtcaagc tctaaatcgg gggctccctt tagggttccg atttagtgct    4800
ttacggcacc tcgaccccaa aaaacttgat ttgggtgatg gttcacgtag tgggccatcg    4860
ccctgataga cggttttttcg ccctttgacg ttggagtcca cgttctttaa tagtggactc    4920
ttgttccaaa ctggaacaac actcaaccct atctcgggct attctttga tttataaggg    4980
attttgccga tttcggccta ttggttaaaa aatgagctga tttaacaaaa atttaacgcg    5040
aattttaaca aaatattaac gtttacaatt ttatggtgca ctctcagtac aatctgctct    5100
gatgccgcat agttaagcca gccccgacac ccgccaacac ccgctgacgc gccctgacgg    5160
gcttgtctgc tcccggcatc cgcttacaga caagctgtga ccgtctccgg agctgcatg    5220
tgtcagaggt tttcaccgtc atcaccgaaa cgcgcgagac gaaagggcct cgtgatacgc    5280
ctatttttat aggttaatgt catgataata atggtttctt agacgtcagg tggcactttt    5340
cggggaaatg tgcgcggaac ccctatttgt ttatttttct aaatacattc aaatatgtat    5400
ccgctcatga caataaacc ctgataaatg cttcaataat attgaaaaag gaagagtatg    5460
agtattcaac atttccgtgt cgcccttatt ccctttttg cggcattttg ccttcctgtt    5520
tttgctcacc cagaaacgct ggtgaaagta aaagatgctg aagatcagtt gggtgcacga    5580
gtgggttaca tcgaactgga tctcaacagc ggtaagatcc ttgagagttt tcgccccgaa    5640
gaacgttttc caatgatgag cacttttaaa gttctgctat gtggcgcggt attatcccgt    5700
attgacgccg ggcaagagca actcggtcgc cgcatacact attctcagaa tgacttggtt    5760
gagtactcac cagtcacaga aaagcatctt acggatggca tgacagtaag agaattatgc    5820
agtgctgcca taaccatgag tgataacact gcggccaact tacttctgac aacgatcgga    5880
```

| | |
|---|---|
| ggaccgaagg agctaaccgc ttttttgcac aacatgggg atcatgtaac tcgccttgat | 5940 |
| cgttgggaac cggagctgaa tgaagccata ccaaacgacg agcgtgacac cacgatgcct | 6000 |
| gtagcaatgg caacaacgtt gcgcaaacta ttaactggcg aactacttac tctagcttcc | 6060 |
| cggcaacaat taatagactg gatggaggcg gataaagttg caggaccact tctgcgctcg | 6120 |
| gcccttccgg ctggctggtt tattgctgat aaatctggag ccggtgagcg tgggtctcgc | 6180 |
| ggtatcattg cagcactggg gccagatggt aagcccctcc gtatcgtagt tatctacacg | 6240 |
| acggggagtc aggcaactat ggatgaacga atagacaga tcgctgagat aggtgcctca | 6300 |
| ctgattaagc attggtaact gtcagaccaa gtttactcat atatacttta gattgattta | 6360 |
| aaacttcatt tttaatttaa aaggatctag gtgaagatcc ttttgataa tctcatgacc | 6420 |
| aaaatccctt aacgtgagtt ttcgttccac tgagcgtcag accccgtaga aaagatcaaa | 6480 |
| ggatcttctt gagatccttt ttttctgcgc gtaatctgct gcttgcaaac aaaaaaacca | 6540 |
| ccgctaccag cggtggtttg tttgccggat caagagctac caactctttt tccgaaggta | 6600 |
| actggcttca gcagagcgca gataccaaat actgtcctc tagtgtagcc gtagttaggc | 6660 |
| caccacttca agaactctgt agcaccgcct acatacctcg ctctgctaat cctgttacca | 6720 |
| gtggctgctg ccagtggcga taagtcgtgt cttaccgggt tggactcaag acgatagtta | 6780 |
| ccggataagg cgcagcggtc gggctgaacg gggggttcgt gcacacagcc cagcttggag | 6840 |
| cgaacgacct acaccgaact gagatacccta cagcgtgagc tatgagaaag cgccacgctt | 6900 |
| cccgaaggga gaaaggcgga caggtatccg gtaagcggca gggtcggaac aggagagcgc | 6960 |
| acgagggagc ttccaggggg aaacgcctgg tatctttata gtcctgtcgg gtttcgccac | 7020 |
| ctctgacttg agcgtcgatt tttgtgatgc tcgtcagggg gcggagcct atggaaaaac | 7080 |
| gccagcaacg cggcctttttt acggttcctg gccttttgct ggccttttgc tcacatgt | 7138 |

<210> SEQ ID NO 66
<211> LENGTH: 795
<212> TYPE: DNA
<213> ORGANISM: Artificial Sequence
<220> FEATURE:
<223> OTHER INFORMATION: Synthetic Construct

<400> SEQUENCE: 66

| | |
|---|---|
| atggagcaaa agctcatttct tgaagaggac ttgaatgaaa tggagcaaaa gctcatttct | 60 |
| gaagaggact tgaatgaaat ggagcaaaag ctcatttctg aagaggactt gaatgaaatg | 120 |
| gagcaaaagc tcatttctga agaggacttg aatgaaatgg agcaaaagct catttctgaa | 180 |
| gaggacttga atgaaatgga gcttgggc gacctcacca tgggccctaa aaagaagcgt | 240 |
| aaagtcgccc ccccgaccga tgtcagcctg ggggacgagc tccacttaga cggcgaggac | 300 |
| gtggcgatgg cgcatgccga cgcgctagac gatttcgatc tggacatgtt gggggacggg | 360 |
| gattccccgg gtccgggatt tacccccac gactccgccc cctacggcgc tctggatatg | 420 |
| gccgacttcg agtttgagca gatgtttacc gatgcccttg gaattgacga gtacggtggg | 480 |
| gaattcccgg ggatcctcga tgacagaccc tatgcttgcc cagtggaaag ctgcgaccgc | 540 |
| cgcttttcta gatcggatga gcttaccgc catatccgca tccacaccgg ccaaaaaccc | 600 |
| tttcaatgcc gtatctgcat gaggaatttc agcagccgcg atgtcctgag cgccataac | 660 |
| aggacccaca caggggaaaa gccattcgca tgtgacatct gcggtcgaaa gtttgcaagc | 720 |
| cgcgatgtcc tgaggcgcca taacaggata catttgaggc aaaatgatct cgaccgtacg | 780 |
| tacaagatcc gttag | 795 |

<210> SEQ ID NO 67
<211> LENGTH: 897
<212> TYPE: DNA
<213> ORGANISM: Artificial Sequence
<220> FEATURE:
<223> OTHER INFORMATION: Synthetic Construct

<400> SEQUENCE: 67

```
atggagcaaa agctcatttc tgaagaggac ttgaatgaaa tggagcaaaa gctcatttct      60
gaagaggact tgaatgaaat ggagcaaaag ctcatttctg aagaggactt gaatgaaatg     120
gagcaaaagc tcatttctga agaggacttg aatgaaatgg agcaaaagct catttctgaa     180
gaggacttga atgaaatgga gcttgggc gacctcacca tgggccctaa aaagaagcgt       240
aaagtcgccc cccgaccga tgtcagcctg ggggacgagc tccacttaga cggcgaggac      300
gtggcgatgg cgcatgccga cgcgctagac gatttcgatc tggacatgtt ggggacggg     360
gattccccgg gtccgggatt tacccccac gactccgccc cctacggcgc tctggatatg     420
gccgacttcg agtttgagca gatgtttacc gatgcccttg gaattgacga gtacggtggg     480
gaattcccgg ggatcctcga tgacagaccc tatgcttgcc cagtgaaaag ctgcgaccgc     540
cgcttttcta gatcggatga gcttacccgc catatccgca tccacaccgg ccaaaaaccc     600
tttcaatgcc gtatctgcat gaggaatttc agcagccgcg atgtcctgag cgccataac     660
aggacccaca caggggaaaa gccattcgca tgtgacatct gcggtcgaaa gtttgcaagc     720
cgcgatgtcc tgaggcgcca taacaggata catttgaggc aaggtccag atctcacgtc     780
tgtgcagaat gtggcaaagc gttcgttgag agctcaaagc taaaacgaca ccagctggtt     840
catgagctgg agagaagccc ttttagctcg agagatctac gggtggcatc cctgtga       897
```

<210> SEQ ID NO 68
<211> LENGTH: 1509
<212> TYPE: DNA
<213> ORGANISM: Artificial Sequence
<220> FEATURE:
<223> OTHER INFORMATION: Synthetic Construct

<400> SEQUENCE: 68

```
atggagcaaa agctcatttc tgaagaggac ttgaatgaaa tggagcaaaa gctcatttct      60
gaagaggact tgaatgaaat ggagcaaaag ctcatttctg aagaggactt gaatgaaatg     120
gagcaaaagc tcatttctga agaggacttg aatgaaatgg agcaaaagct catttctgaa     180
gaggacttga atgaaatgga gcttgggc gacctcacca tgggccctaa aaagaagcgt       240
aaagtcgccc cccgaccga tgtcagcctg ggggacgagc tccacttaga cggcgaggac      300
gtggcgatgg cgcatgccga cgcgctagac gatttcgatc tggacatgtt ggggacggg     360
gattccccgg gtccgggatt tacccccac gactccgccc cctacggcgc tctggatatg     420
gccgacttcg agtttgagca gatgtttacc gatgcccttg gaattgacga gtacggtggg     480
gaattcccgg ggatcttggc aaagcgcttt gccgacttta cagtctacag gaaccgcaca     540
cttcagaaat ggcacgataa gaccaaactg gcttctggaa actggggaa gggttttggt      600
gcctttgaac gctcaatctt gactcagatc gaccatattc tgatggacaa agagagatta     660
cttcgaagga cacagaccaa gcgctctgtc tatcgagttc ttggcaaacc tgagccagca     720
gctcagcctg tccagagag tttgccaggg aaccgggaga tccttcctca gcccctgct      780
aatgctcatc tgaaggactt ggatgaagaa atctttgatg atgatgactt ttaccaccag     840
```

| | |
|---|---:|
| ctccttcgag aactcataga acggaagacc agctccttgg ggatcctgga tcgcccttac | 900 |
| gcctgccctg tggaatcttg cgaccgccgg ttctcccgca gcgataacct ggtgcggcac | 960 |
| atccggattc acaccggcca gaaacctttc cagtgcagga tctgcatgag aaatttctcc | 1020 |
| cggtccgacc acctgaccac ccacaatagg cccacaccg gcgagaaacc ctttgcctgc | 1080 |
| gacatctgcg ggagaaagtt cgccgacccc ggccacctgg tgagacacaa tagaatccac | 1140 |
| accggtgaaa agcccttcgc ctgtcccgtg gagagctgcg atcgcagatt cagccgcagc | 1200 |
| gacgagctga caaggcacat cagaatccac accgggcaga agccttttca gtgccggatc | 1260 |
| tgcatgagga acttcagctc ccgggacgtg ctgagacgcc acaatcgcac acacaccggc | 1320 |
| gaaaagccct tcgcctgtga tatttgcggg cggaaatttg cctccagaga tgtgctgcgc | 1380 |
| cgccacaacc gcattcacct gagacagaac gatctcgaga gatctacggg tggcatccct | 1440 |
| gtgacccctc cccagtgcct ctcctggccc tggaagttgc cactccagtg cccaccagcc | 1500 |
| ttgtcctaa | 1509 |

<210> SEQ ID NO 69
<211> LENGTH: 1632
<212> TYPE: DNA
<213> ORGANISM: Artificial Sequence
<220> FEATURE:
<223> OTHER INFORMATION: Synthetic Construct

<400> SEQUENCE: 69

| | |
|---|---:|
| atggccgctg ccaaggccga gatgcagctg atgagccccc tgcagatcag cgacccttc | 60 |
| ggcagcttcc cccacagccc caccatggac aactacccca gctggaagaa gatgatgctg | 120 |
| ctgagcaatg gcgctcctca gttcctggga gccgctggcg cccctgaggg cagcggcagc | 180 |
| aatagcagca gcagctctag cggcggaggc ggaggggag gcggcggaag caatagctcc | 240 |
| agctccagca gcacattcaa tccacaagcc gacaccggcg agcagcccta tgagcacctg | 300 |
| accgccgaga gcttccccga catcagcctg aacaacgaga aggtgctggt ggaaaccagc | 360 |
| taccccagcc agaccacccg gctgcccct atcacctaca caggccggtt cagcctggaa | 420 |
| cccgcccta cagcggcaa cacccctgtgg cccgagcccc tgtttagcct ggtgtccggc | 480 |
| ctggtgtcta tgaccaaccc ccctgccagc agctcctctg ccccaagccc tgccgccagc | 540 |
| tctgcctctg ccagccagag ccctccactg agctgcgccg tgcccagcaa cgacagcagc | 600 |
| cccatctaca gcgccgctcc caccttcccc accccaaca ccgacatctt ccccgagcct | 660 |
| cagagccagg cctttcctgg atctgccggc accgccctgc agtacccacc tcctgcctat | 720 |
| cctgccgcca agggcggctt ccaggtgccc atgatccccg actacctgtt cccccagcag | 780 |
| cagggcgatc tgggcctggg cacccccgac cagaagcctt ccagggcct cgaaagccgg | 840 |
| acccagcagc caagcctgac cccctgagc accatcaagg ccttcgccac cagagcggc | 900 |
| agccaggacc tgaaggccct gaacaccagc taccagagcc agctgatcaa gcccagccgg | 960 |
| atgcggaagt accccaaccg gcccagcaag accccccac acgagaggcc ttacgcctgc | 1020 |
| cccgtggaaa gctgcgacag acggttcagc agaagcgacg agctgacccg gcacatccgg | 1080 |
| atccacaccg gccagaaacc cttccagtgc cggatctgca tgcggaactt cagcagccgg | 1140 |
| gacgtgctgc ggcggcacaa tagaacccac acaggcgaga agccttcgc ctgcgacatc | 1200 |
| tgcggccgga gttcgccag cagagatgtg ctgcggagac acaacaggat ccacctgaga | 1260 |
| cagaaggaca gaaagccga caagagcgtg gtcgccagca cgctaccag cagcctgagc | 1320 |
| agctacccctt ctcctgtggc cacctcctac ccaagcccag tgaccacaag ctacccatcc | 1380 |

```
cccgccacca cctcttatcc cagccccgtg cctaccagct tcagctctcc cggcagctcc    1440 acataccccea gccctgtgca tagcggcttc cctagccceta gcgtggecac cacatacagce   1500 agcgtgecce ctgecttece agctcaagtg tccagcttcc ccagctccgce cgtgaccaac    1560 agcttcagcg ccagcaccgg cctgagcgac atgaccgcca ccttcagccc ccggaccatc    1620
gagatctgct ga                                                       1632
```

<210> SEQ ID NO 70
<211> LENGTH: 1632
<212> TYPE: DNA
<213> ORGANISM: Artificial Sequence
<220> FEATURE:
<223> OTHER INFORMATION: Synthetic Construct

<400> SEQUENCE: 70

```
atggccgctg ccaaggccga gatgcagctg atgagccccc tgcagatcag cgacccctte     60 ggcagcttcc cccacagccc caccatggac aactacccca gctggaaga dgatgatgctg    120 ctgagcaatg cgctcctca gttcctggga gccgctggcg cccctgaggg cagcggcagc    180
aatagcagca gcagctctag cggcggaggc ggaggggggag cggcggaag caatagctcc    240 agctccagca gcacattcaa tccacaagcc gacaccggcg agcagcccta tgagcacctg    300
accgccgaga gcttcccega catcagcctg aacaacgaga aggtgctggt ggaaaccagc    360
taccccagcc agaccaccecg gctgcccect atcacctaca caggccggtt cagectggaa    420 cccgcccceta acagcggcaa caccctgtgg cccgagccec tgtttagcct ggtgtccggc    480
ctggtgtcta tgaccaaccc ccctgccagc agctcctctg ccccaagccc tgccgccagc    540
tctgcctctg ccagcagag ccctccactg agctgcgccg tgcccagcaa cgacagcagce    600 cccatctaca gcgcecgctcc caccttcccc acccccaaca ccgacatctt ccccgagcct    660
cagagccagg ccttttcectgg atctgccggce accgccctgc agtacccace tcectgccectat    720 cctgccgcca agggcggctt ccaggtgccc atgatccccg actaccectgtt ccccccagcag    780 cagggcgatc tgggcctggg caccccccgac cagaagccctt ccagggcct cgaaagccgg    840 acccagcagc caagcctgac cccectgagc accatcaagg ccttcgccac ccagagcggc    900
agccaggacc tgaaggccct gaacaccagce taccagagcc agctgatcaa gcccagccgg    960
atgcggaagt accccaaccg gcccagcaag acccccccac acgagaggcc ttacgcctgc   1020
cccgtggaaa gctgcgacag acggttcagc agaagcgaca acctggtccg gcacatccgg   1080
atccacaccg gccagaaacc cttccagtgc cggatctgca tgcggaactt ctctcggagce   1140 gaccacctga ccacccacat cagaacccac acaggcgaga gcccttcgc ctgcgacatc   1200 tgcggccgga agttcgccga ccccggccac ctcgtcagac acaacaggat tcacctgaga   1260
cagaaggaca agaaagccga caagagcgtg gtcgccagca cgctaccag cagcctgagce   1320 agctaccctt ctcctgtggc cacctccctac ccaagcccag tgaccacaag ctacccatcc   1380
cccgccacca cctcttatcc cagccccgtg cctaccagct tcagctctcc cggcagctcc   1440 acataccceca gccctgtgca tagcggcttc cctagcccta gcgtggccac cacatacagce   1500 agcgtgecce ctgecttece agctcaagtg tccagcttcc ccagctccgce cgtgaccaac   1560 agcttcagcg ccagcaccgg cctgagcgac atgaccgcca ccttcagccc ccggaccatc   1620
gagatctgct ga                                                      1632
```

<210> SEQ ID NO 71

<211> LENGTH: 169
<212> TYPE: PRT
<213> ORGANISM: Artificial Sequence
<220> FEATURE:
<223> OTHER INFORMATION: Synthetic Construct

<400> SEQUENCE: 71

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
        35                  40                  45

Asp Ser Ala Pro Tyr Gly Ala Leu Asp Met Ala Asp Phe Glu Phe Glu
    50                  55                  60

Gln Met Phe Thr Asp Ala Leu Gly Ile Asp Glu Tyr Gly Gly Glu Phe
65                  70                  75                  80

Pro Gly Ile Leu Asp Asp Arg Pro Tyr Ala Cys Pro Val Glu Ser Cys
                85                  90                  95

Asp Arg Arg Phe Ser Arg Ser Asp Glu Leu Thr Arg His Ile Arg Ile
            100                 105                 110

His Thr Gly Gln Lys Pro Phe Gln Cys Arg Ile Cys Met Arg Asn Phe
        115                 120                 125

Ser Ser Arg Asp Val Leu Arg Arg His Asn Arg Thr His Thr Gly Glu
    130                 135                 140

Lys Pro Phe Ala Cys Asp Ile Cys Gly Arg Lys Phe Ala Ser Arg Asp
145                 150                 155                 160

Val Leu Arg Arg His Asn Arg Ile His
                165

<210> SEQ ID NO 72
<211> LENGTH: 199
<212> TYPE: PRT
<213> ORGANISM: Artificial Sequence
<220> FEATURE:
<223> OTHER INFORMATION: Synthetic Construct

<400> SEQUENCE: 72

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
        35                  40                  45

Asp Ser Ala Pro Tyr Gly Ala Leu Asp Met Ala Asp Phe Glu Phe Glu
    50                  55                  60

Gln Met Phe Thr Asp Ala Leu Gly Ile Asp Glu Tyr Gly Gly Glu Phe
65                  70                  75                  80

Pro Gly Ile Leu Asp Asp Arg Pro Tyr Ala Cys Pro Val Glu Ser Cys
                85                  90                  95

Asp Arg Arg Phe Ser Arg Ser Asp Glu Leu Thr Arg His Ile Arg Ile
            100                 105                 110

His Thr Gly Gln Lys Pro Phe Gln Cys Arg Ile Cys Met Arg Asn Phe
        115                 120                 125

Ser Ser Arg Asp Val Leu Arg Arg His Asn Arg Thr His Thr Gly Glu
    130                 135                 140

Lys Pro Phe Ala Cys Asp Ile Cys Gly Arg Lys Phe Ala Ser Arg Asp

```
            145                 150                 155                 160
Val Leu Arg Arg His Asn Arg Ile His Leu Arg Gln Gly Pro Arg Ser
                165                 170                 175

His Val Cys Ala Glu Cys Gly Lys Ala Phe Val Glu Ser Ser Lys Leu
                180                 185                 190

Lys Arg His Gln Leu Val His
        195

<210> SEQ ID NO 73
<211> LENGTH: 384
<212> TYPE: PRT
<213> ORGANISM: Artificial Sequence
<220> FEATURE:
<223> OTHER INFORMATION: Synthetic Construct

<400> SEQUENCE: 73

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
                20                  25                  30

Asp Met Leu Gly Asp Gly Asp Ser Pro Gly Pro Gly Phe Thr Pro His
            35                  40                  45

Asp Ser Ala Pro Tyr Gly Ala Leu Asp Met Ala Asp Phe Glu Phe Glu
        50                  55                  60

Gln Met Phe Thr Asp Ala Leu Gly Ile Asp Glu Tyr Gly Gly Glu Phe
65                  70                  75                  80

Pro Gly Ile Leu Ala Lys Arg Phe Ala Asp Phe Thr Val Tyr Arg Asn
                85                  90                  95

Arg Thr Leu Gln Lys Trp His Asp Lys Thr Lys Leu Ala Ser Gly Lys
                100                 105                 110

Leu Gly Lys Gly Phe Gly Ala Phe Glu Arg Ser Ile Leu Thr Gln Ile
            115                 120                 125

Asp His Ile Leu Met Asp Lys Glu Arg Leu Leu Arg Arg Thr Gln Thr
        130                 135                 140

Lys Arg Ser Val Tyr Arg Val Leu Gly Lys Pro Glu Pro Ala Ala Gln
145                 150                 155                 160

Pro Val Pro Glu Ser Leu Pro Gly Glu Pro Glu Ile Leu Pro Gln Ala
                165                 170                 175

Pro Ala Asn Ala His Leu Lys Asp Leu Asp Glu Glu Ile Phe Asp Asp
                180                 185                 190

Asp Asp Phe Tyr His Gln Leu Leu Arg Glu Leu Ile Glu Arg Lys Thr
            195                 200                 205

Ser Ser Leu Gly Ile Leu Asp Arg Pro Tyr Ala Cys Pro Val Glu Ser
        210                 215                 220

Cys Asp Arg Arg Phe Ser Arg Ser Asp Asn Leu Val Arg His Ile Arg
225                 230                 235                 240

Ile His Thr Gly Gln Lys Pro Phe Gln Cys Arg Ile Cys Met Arg Asn
                245                 250                 255

Phe Ser Arg Ser Asp His Leu Thr Thr His Asn Arg Thr His Thr Gly
                260                 265                 270

Glu Lys Pro Phe Ala Cys Asp Ile Cys Gly Arg Lys Phe Ala Asp Pro
            275                 280                 285

Gly His Leu Val Arg His Asn Arg Ile His Thr Gly Glu Lys Pro Phe
        290                 295                 300

Ala Cys Pro Val Glu Ser Cys Asp Arg Arg Phe Ser Arg Ser Asp Glu
```

```
                305                 310                 315                 320
Leu Thr Arg His Ile Arg Ile His Thr Gly Gln Lys Pro Phe Gln Cys
                    325                 330                 335
Arg Ile Cys Met Arg Asn Phe Ser Ser Arg Asp Val Leu Arg Arg His
                340                 345                 350
Asn Arg Thr His Thr Gly Glu Lys Pro Phe Ala Cys Asp Ile Cys Gly
            355                 360                 365
Arg Lys Phe Ala Ser Arg Asp Val Leu Arg Arg His Asn Arg Ile His
    370                 375                 380
```

<210> SEQ ID NO 74
<211> LENGTH: 127
<212> TYPE: PRT
<213> ORGANISM: Artificial Sequence
<220> FEATURE:
<223> OTHER INFORMATION: Synthetic Construct

<400> SEQUENCE: 74

```
Ala Lys Arg Phe Ala Asp Phe Thr Val Tyr Arg Asn Arg Thr Leu Gln
1               5                   10                  15
Lys Trp His Asp Lys Thr Lys Leu Ala Ser Gly Lys Leu Gly Lys Gly
            20                  25                  30
Phe Gly Ala Phe Glu Arg Ser Ile Leu Thr Gln Ile Asp His Ile Leu
        35                  40                  45
Met Asp Lys Glu Arg Leu Leu Arg Arg Thr Gln Thr Lys Arg Ser Val
    50                  55                  60
Tyr Arg Val Leu Gly Lys Pro Glu Pro Ala Ala Gln Pro Val Pro Glu
65                  70                  75                  80
Ser Leu Pro Gly Glu Pro Glu Ile Leu Pro Gln Ala Pro Ala Asn Ala
                85                  90                  95
His Leu Lys Asp Leu Asp Glu Ile Phe Asp Asp Asp Phe Tyr
            100                 105                 110
His Gln Leu Leu Arg Glu Leu Ile Glu Arg Lys Thr Ser Ser Leu
        115                 120                 125
```

<210> SEQ ID NO 75
<211> LENGTH: 73
<212> TYPE: PRT
<213> ORGANISM: Artificial Sequence
<220> FEATURE:
<223> OTHER INFORMATION: Synthetic Construct

<400> SEQUENCE: 75

```
Met Glu Gln Lys Leu Ile Ser Glu Glu Asp Leu Asn Glu Met Glu Gln
1               5                   10                  15
Lys Leu Ile Ser Glu Glu Asp Leu Asn Glu Met Glu Gln Lys Leu Ile
            20                  25                  30
Ser Glu Glu Asp Leu Asn Glu Met Glu Gln Lys Leu Ile Ser Glu Glu
        35                  40                  45
Asp Leu Asn Glu Met Glu Gln Lys Leu Ile Ser Glu Glu Asp Leu Asn
    50                  55                  60
Glu Met Glu Ser Leu Gly Asp Leu Thr
65                  70
```

<210> SEQ ID NO 76
<211> LENGTH: 16
<212> TYPE: DNA
<213> ORGANISM: Artificial Sequence
<220> FEATURE:

<223> OTHER INFORMATION: Synthetic Construct

<400> SEQUENCE: 76
cgagccgaga gtagca                                                    16

<210> SEQ ID NO 77
<211> LENGTH: 23
<212> TYPE: DNA
<213> ORGANISM: Artificial Sequence
<220> FEATURE:
<223> OTHER INFORMATION: Synthetic Construct

<400> SEQUENCE: 77
catggtgagg tcgcccaagc tct                                            23

<210> SEQ ID NO 78
<211> LENGTH: 16
<212> TYPE: DNA
<213> ORGANISM: Artificial Sequence
<220> FEATURE:
<223> OTHER INFORMATION: Synthetic Construct

<400> SEQUENCE: 78
cgagccgaga gtagca                                                    16

<210> SEQ ID NO 79
<211> LENGTH: 20
<212> TYPE: DNA
<213> ORGANISM: Artificial Sequence
<220> FEATURE:
<223> OTHER INFORMATION: Synthetic Construct

<400> SEQUENCE: 79
gagctggagc tattgcttcc                                                20

<210> SEQ ID NO 80
<211> LENGTH: 6303
<212> TYPE: DNA
<213> ORGANISM: Artificial Sequence
<220> FEATURE:
<223> OTHER INFORMATION: Synthetic Construct

<400> SEQUENCE: 80
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtcacca actgggtaac ctctgctgac    180
ccccactcta ctttaccata gtagctccaa atccttcta gaaaatctga aaggcatagc    240
cccatatatc agtgatataa atagaacctg cagcaggctc tggtaaatga tgactacaag    300
gtggactggg aggcagcccg gccttggcag gcatcatcct ctaaatataa agatgagttt    360
gttcagcctt tgcagaagga aaaactgcca cccatcctag agtgccgcgt ccttgtcccc    420
ccaccccctc caatttattg ggaggaagga ccagctaagc ctcatctagg aagagcccct    480
cacccatctc cacctccact ccaggtctag ccagtcctgg gttgtgaccc ttgtctttca    540
gccccaggag agggacacac atagtgccac caaagaggct gggggagggc ctcagcccac    600
caaaacctgg ggccagtgcg tcctacagga ggggaaccct caccccttca atcccttag    660 gagacccaag ggcgctgcgc gtccctgagg cggacagctc cgtgtgctca ggctttgcgc    720
ctgacaggcc tatccccggg agccccgcg cctcctcccc ggcgctccgc cctcgcctcc    780
ccccgccagt tgtctatcct gcgacagctg cgcgccctcc ggccgccggt ggccctctgt    840

```
gcggtggggg aagggggtcga cgtggctcag cttttttggat tcaggagct cgggggtggg      900
aagagagaaa tggagttcca ggggcgtaaa ggagaggggag ttcgccttcc ttcccttcct      960
gagactcagg agtgactgct tctccaatcc tcccaagccc accactccac acgactccct     1020
cttcccggta gtcgcaagtg ggagtttggg gatctgagca agaacccga agaggagttg     1080
aaatattgga agtcagcagt caggcacctt cccgagcgcc cagggcgctc agagtggaca     1140
tggttgggga ggccttttggg acaggtgcgg ttcccggagc gcaggcgcac acatgcaccc     1200
accggcgaac gcggtgaccc tcgccccacc ccatcccctc cggcgggcaa ctgggtcggg     1260
tcaggaggggg caaacccgct agggagacac tccatatacg gcccggcccg cgttacctgg     1320
gaccgggcca acccgctcct tctttggtca acgcagggga cccgggcggg ggcccaggcc     1380
gcgaaccggc cgagggaggg ggctctagtg cccaacaccc aaatatggct cgagaagggc     1440
agcgacattc ctgcggggtg gcgcggaggg aatgcccgcg ggctatataa aacctgagca     1500
gagggacaag cggccaccgc agcggacagc gccaagtgaa gcctcgcttc ccctccgcgg     1560
cgaccagggc ccgagccgag agtagcagtt gtagctaccc gcccaggtag ggcaggagtt     1620
gggaggggac aggggggacag ggcactaccg aggggaacct gaaggactcc ggggcagaac     1680
ccagtcggtt cacctggtaa gcttgctagc tgtttagtga accgtcagat cgcctggaga     1740
cgccatccac gctgttttga cctccataga agacaccggg accgatccag cctccgcgga     1800
ttcgaatccc ggccgggaac ggtgcattgg aacgcggatt ccccgtgcca agagtgacgt     1860
aagtaccgcc tatagagtct ataggcccac aaaaaatgct ttcttctttt aatatacttt     1920
tttgtttatc ttatttctaa tactttccct aatctctttc tttcagggca ataatgatac     1980
aatgtatcat gcctctttgc accattctaa agaataacag tgataatttc tgggttaagg     2040
caatagcaat atttctgcat ataaatattt ctgcatataa attgtaactg atgtaagagg     2100
tttcatattg ctaatagcag ctacaatcca gctaccattc tgcttttatt ttatggttgg     2160
gataaggctg gattattctg agtccaagct aggcccttttt gctaatcatg ttcataccctc     2220
ttatcttcct cccacagctc ctgggcaacg tgctggtctg tgtgctggcc catcactttg     2280
gcaaagaatt gggattcgaa catcgattta aagctatggt gagtaaacaa atattgaaga     2340
acactggatt gcaggagatc atgtcgttta aagtgaatct ggaaggtgta gtaaacaatc     2400
atgtgttcac aatggaaggt tgtggaaaag gaaatatttt attcggaaac caactggttc     2460
agattcgtgt cacaaaaggg gctccgcttc catttgcatt tgatattctc tcaccagctt     2520
tccaatacgc caaccgtaca ttcacgaaat acccggagga tatatcagac tttttttatac     2580
aatcattttcc agcgggattt gtatacgaaa gaacgttgcg ttacgaagat ggtggactgg     2640
ttgaaatccg ttcagatata aatttaatcg aggagatgtt tgtctacaga gtggaatata     2700
aaggtagtaa cttcccgaat gatggtccag tgatgaagaa gacaatcaca ggattacaac     2760
cttcgttcga agttgtgtat atgaacgatg gcgtcttggt tggccaagtc attcttgttt     2820
atagattaaa ctctggcaaa ttttattcgt gtcacatgag aacactgatg aaatcaaagg     2880
gtgtagtgaa ggatttttccc gaataccatt tcattcaaca tcgtttagag aagacgtatg     2940
tggaagacgg aggttttgtt gagcaacacg agacggccat tgctcaactg acatcgctgg     3000
ggaaaccact tggatcctta cacgaatggg tttaactcga gagatctacg ggtggcatcc     3060
ctgtgacccc tccccagtgc ctctcctggc cctggaagtt gccactccag tgcccaccag     3120
ccttgtccta ataaaattaa gttgcatcat tttgtctgac taggtgtcct tctataatat     3180
```

```
tatggggtgg aggggggtgg tatggagcaa ggggcaagtt gggaagacaa cctgtagggc    3240
ctgcggggtc tattgggaac caagctggag tgcagtggca caatcttggc tcactgcaat    3300
ctccgcctcc tgggttcaag cgattctcct gcctcagcct cccgagttgt tgggattcca    3360
ggcatgcatg accaggctca gctaattttt gttttttttgg tagagacggg gtttcaccat    3420
attggccagg ctggtctcca actcctaatc tcaggtgatc tacccacctt ggcctcccaa    3480
attgctggga ttacaggcgt gaaccactgc tcccttccct gtccttctga ttttgtaggt    3540
aaccacgtgc ggaccgagcg gccgcaggaa ccctagtga tggagttggc cactccctct    3600
ctgcgcgctc gctcgctcac tgaggccggg cgaccaaagg tcgcccgacg cccgggcttt    3660
gcccgggcgg cctcagtgag cgagcgagcg cgcagctgcc tgcaggggcg cctgatgcgg    3720
tattttctcc ttacgcatct gtgcggtatt tcacaccgca tacgtcaaag caaccatagt    3780
acgcgccctg tagcggcgca ttaagcgcgg cgggtgtggt ggttacgcgc agcgtgaccg    3840
ctacacttgc cagcgcccta cgcccgctc ctttcgcttt cttcccttcc tttctcgcca    3900
cgttcgccgg ctttccccgt caagctctaa atcgggggct cccttaggg ttccgattta    3960
gtgctttacg gcacctcgac cccaaaaaac ttgatttggg tgatggttca cgtagtgggc    4020
catcgccctg atagacggtt tttcgccctt gacgttgga gtccacgttc tttaatagtg    4080
gactcttgtt ccaaactgga caacactca accctatctc gggctattct tttgatttat    4140
aagggatttt gccgatttcg gcctattggt taaaaatga gctgatttaa caaaatttta    4200
acgcgaattt taacaaaata ttaacgttta caattttatg gtgcactctc agtacaatct    4260
gctctgatgc cgcatagtta agccagcccc gacacccgcc aacacccgct gacgcgccct    4320
gacgggcttg tctgctcccg gcatccgctt acagacaagc tgtgaccgtc tccgggagct    4380
gcatgtgtca gaggttttca ccgtcatcac cgaaacgcgc gagacgaaag gcctcgtga    4440
tacgcctatt tttataggtt aatgtcatga taataatggt ttcttagacg tcaggtggca    4500
cttttcgggg aaatgtgcgc ggaaccccta tttgtttatt tttctaaata cattcaaata    4560
tgtatccgct catgagacaa taaccctgat aaatgcttca ataatattga aaaggaaga    4620
gtatgagtat tcaacatttc cgtgtcgccc ttattccctt ttttgcggca ttttgccttc    4680
ctgtttttgc tcacccagaa acgctggtga agtaaaaga tgctgaagat cagttgggtg    4740
cacgagtggg ttacatcgaa ctggatctca acagcggtaa gatccttgag agttttcgcc    4800
ccgaagaacg ttttccaatg atgagcactt ttaaagttct gctatgtggc gcggtattat    4860
cccgtattga cgccgggcaa gagcaactcg gtcgccgcat acactattct cagaatgact    4920
tggttgagta ctcaccagtc acagaaaagc atcttacgga tggcatgaca gtaagagaat    4980
tatgcagtgc tgccataacc atgagtgata acactgcggc caacttactt ctgacaacga    5040
tcggaggacc gaaggagcta accgcttttt tgcacaacat gggggatcat gtaactcgcc    5100
ttgatcgttg ggaaccggag ctgaatgaag ccataccaaa cgacgagcgt gacaccacga    5160
tgcctgtagc aatggcaaca acgttgcgca aactattaac tggcgaacta cttactctag    5220
cttcccggca caattaata gactggatgg aggcggataa agttgcagga ccacttctgc    5280
gctcggccct tccggctggc tggtttattg ctgataaatc tggagccggt gagcgtgggt    5340
ctcgcggtat cattgcagca ctggggccag atggtaagcc ctcccgtatc gtagttatct    5400
acacgacggg gagtcaggca actatggatg aacgaaatag acagatcgct gagataggtg    5460
cctcactgat taagcattgg taactgtcag accaagttta ctcatatata ctttagattg    5520
atttaaaact tcatttttaa tttaaaagga tctaggtgaa gatcctttt gataatctca    5580
```

```
tgaccaaaat cccttaacgt gagttttcgt tccactgagc gtcagacccc gtagaaaaga    5640
tcaaaggatc ttcttgagat cctttttttc tgcgcgtaat ctgctgcttg caaacaaaaa    5700
aaccaccgct accagcggtg gtttgtttgc cggatcaaga gctaccaact cttttttccga   5760 aggtaactgg cttcagcaga gcgcagatac caaatactgt ccttctagtg tagccgtagt    5820
taggccacca cttcaagaac tctgtagcac cgcctacata cctcgctctg ctaatcctgt    5880
taccagtggc tgctgccagt ggcgataagt cgtgtcttac cgggttggac tcaagacgat    5940
agttaccgga taaggcgcag cggtcgggct gaacggggggg ttcgtgcaca cagcccagct   6000
tggagcgaac gacctacacc gaactgagat acctacagcg tgagctatga aaagcgcca    6060 cgcttcccga agggagaaag gcggacaggt atccggtaag cggcagggtc ggaacaggag    6120
agcgcacgag ggagcttcca gggggaaacg cctggtatct ttatagtcct gtcgggtttc    6180
gccacctctg acttgagcgt cgattttgt gatgctcgtc agggggggcgg agcctatgga    6240 aaaacgccag caacgcggcc ttttacggtt cctggcctt tgctggcct tttgctcaca     6300 tgt                                                                  6303
```

<210> SEQ ID NO 81
<211> LENGTH: 1645
<212> TYPE: DNA
<213> ORGANISM: Artificial Sequence
<220> FEATURE:
<223> OTHER INFORMATION: Synthetic Construct

<400> SEQUENCE: 81

```
gaattcaatg gccgcggcca aggccgagat gcagctgatg tccccgctgc agatctctga     60
cccgttcgga tcctttcctc actcgcccac catggacaac taccctaagc tggaggagat    120
gatgctgctg agcaacgggg ctccccagtt cctcggcgcc gccggggccc cagagggcag    180
cggcagcaac agcagcagca gcagcagcgg gggcggtgga ggcggcgggg cggcagcaa    240 cagcagcagc agcagcagca ccttcaaccc tcaggcggac acgggcgagc agccctacga    300
gcacctgacc gcagagtctt ttcctgacat ctctctgaac aacgagaagg tgctggtgga    360
gaccagttac cccagccaaa ccactcgact gccccccatc acctatactg gccgcttttc    420
cctggagcct gcacccaaca gtggcaacac cttgtggccc gagcccctct tcagcttggt    480
cagtggccta gtgagcatga ccaacccacc ggcctcctcg tcctcagcac catctccagc    540
ggcctcctcc gcctccgcct cccagagccc acccctgagc tgcgcagtgc catccaacga    600
cagcagtccc atttactcag cggcacccac cttcccacg ccgaacactg acattttccc    660
tgagccacaa agccaggcct tcccgggctc ggcagggaca gcgctccagt acccgcctcc    720
tgcctaccct gccgccaagg gtggcttcca ggttcccatg atccccgact acctgttccc    780
acagcagcag ggggatctgg gcctgggcac cccagaccag aagcccttcc agggcctgga    840
gagccgcacc cagcagcctt cgctaacccc tctgtctact attaaggcct ttgccactca    900
gtcgggctcc caggacctga aggccctcaa taccagctac cagtcccagc tcatcaaacc    960
cagccgcatg cgcaagtacc ccaaccggcc cagcaagacg ccccccacg aacgccctta   1020 cgcttgccca gtggagtcct gtgatcgccg cttctcccgc tccgacgagc tcacccgcca   1080
catccgcatc cacacaggcc agaagccctt ccagtgccgc atctgcatgc gcaacttcag   1140
cagccgcgac gtcctcaggc gccacaaccg caccacacaca ggcgaaaagc ccttcgcctg   1200
cgacatctgt ggaagaaagt ttgccagcag ggatgtcctg aggaggcata acaggatcca   1260
```

| | |
|---|---|
| cttgcggcag aaggacaaga aagcagacaa aagtgttgtg gcctcttcgg ccacctcctc | 1320 |
| tctctcttcc tacccgtccc cggttgctac ctcttacccg tccccggtta ctacctctta | 1380 |
| tccatccccg gccaccacct catacccatc ccctgtgccc acctccttct cctctcccgg | 1440 |
| ctcctcgacc tacccatccc ctgtgcacag tggcttcccc tccccgtcgg tggccaccac | 1500 |
| gtactcctct gttcccctg ctttcccggc ccaggtcagc agcttcccct cctcagctgt | 1560 |
| caccaactcc ttcagcgcct ccacagggct ttcggacatg acagcaacct tttctcccag | 1620 |
| gacaattgaa atttgctaac tcgag | 1645 |

<210> SEQ ID NO 82
<211> LENGTH: 1645
<212> TYPE: DNA
<213> ORGANISM: Artificial Sequence
<220> FEATURE:
<223> OTHER INFORMATION: Synthetic Construct

<400> SEQUENCE: 82

| | |
|---|---|
| gaattcaatg gccgcggcca aggccgagat gcagctgatg tccccgctgc agatctctga | 60 |
| cccgttcgga tcctttcctc actcgcccac catggacaac taccctaagc tggaggagat | 120 |
| gatgctgctg agcaacgggg ctcccccagtt cctcggcgcc gccggggccc cagagggcag | 180 |
| cggcagcaac agcagcagca gcagcagcgg gggcggtgga ggcggcgggg cggcagcaa | 240 |
| cagcagcagc agcagcagca ccttcaaccc tcaggcggac acgggcgagc agccctacga | 300 |
| gcacctgacc gcagagtctt ttcctgacat ctctctgaac aacgagaagg tgctggtgga | 360 |
| gaccagttac cccagccaaa ccactcgact gcccccatc acctatactg ccgcttttc | 420 |
| cctggagcct gcacccaaca gtggcaacac cttgtggccc gagcccctct tcagcttggt | 480 |
| cagtggccta gtgagcatga ccaacccacc ggcctcctcg tcctcagcac catctccagc | 540 |
| ggcctcctcc gcctccgcct cccagagccc accctgagc tgcgcagtgc catccaacga | 600 |
| cagcagtccc atttactcag cggcacccac cttcccacg ccgaacactg acatttcccc | 660 |
| tgagccacaa agccaggcct ccccgggctc ggcagggaca gcgctccagt accgcctcc | 720 |
| tgcctaccct gccgccaagg gtggcttcca ggttcccatg atccccgact acctgttcc | 780 |
| acagcagcag ggggatctgg gcctgggcac cccagaccag aagccttcc agggcctgga | 840 |
| gagccgcacc cagcagcctt cgctaacccc tctgtctact attaaggcct ttgccactca | 900 |
| gtcgggctcc caggacctga aggccctcaa taccagctac cagtcccagc tcatcaaacc | 960 |
| cagccgcatg cgcaagtacc caaccggcc cagcaagacg ccccccacg aacgcccta | 1020 |
| cgcttgccca gtggagtcct gtgatcgccg cttctcccgc tccgacgagc tcacccgcca | 1080 |
| catccgcatc cacacaggcc agaagccctt ccagtgccgc atctgcatgc gcaacttcag | 1140 |
| cagccgcgac gtcctcaggc gccacaaccg cacccacaca ggcgaaaagc ccttcgcctg | 1200 |
| cgacatctgt ggaagaaagt ttgccagcag ggatgtcctg aggaggcata acaggatcca | 1260 |
| cttgcggcag aaggacaaga aagcagacaa aagtgttgtg gcctcttcgg ccacctcctc | 1320 |
| tctctcttcc tacccgtccc cggttgctac ctcttacccg tccccggtta ctacctctta | 1380 |
| tccatccccg gccaccacct catacccatc ccctgtgccc acctccttct cctctcccgg | 1440 |
| ctcctcgacc tacccatccc ctgtgcacag tggcttcccc tccccgtcgg tggccaccac | 1500 |
| gtactcctct gttcccctg ctttcccggc ccaggtcagc agcttcccct cctcagctgt | 1560 |
| caccaactcc ttcagcgcct ccacagggct ttcggacatg acagcaacct tttctcccag | 1620 |
| gacaattgaa atttgctaac tcgag | 1645 |

<210> SEQ ID NO 83
<211> LENGTH: 3539
<212> TYPE: DNA
<213> ORGANISM: Artificial Sequence
<220> FEATURE:
<223> OTHER INFORMATION: Synthetic Construct

<400> SEQUENCE: 83

```
gcggccgcac gcgtcaccaa ctgggtaacc tctgctgacc cccactctac tttaccataa      60
gtagctccaa atccttctag aaaatctgaa aggcatagcc ccatatatca gtgatataaa     120
tagaacctgc agcaggctct ggtaaatgat gactacaagg tggactggga ggcagcccgg     180
ccttggcagg catcatcctc taaatataaa gatgagtttg ttcagccttt gcagaaggaa     240
aaactgccac ccatcctaga gtgccgcgtc cttgtccccc cacccctcc aatttattgg      300
gaggaaggac cagctaagcc tcatctagga agagccccte acccatctcc acctccactc     360
caggtctagc cagtcctggg ttgtgaccct tgtctttcag ccccaggaga gggacacaca     420
tagtgccacc aaagaggctg ggggagggcc tcagcccacc aaaacctggg gccagtgcgt     480
cctacaggag gggaaccctc acccccttcaa tcccctttagg agacccaagg gcgctgcgcg     540
tccctgaggc ggacagctcc gtgtgctcag gctttgcgcc tgacaggcct atccccggga     600
gcccccgcgc tcctccccg gcgctccgcc ctcgcctccc cccgcagtt gtctatcctg       660
cgacagctgc gcgccctccg gccgccggtg gccctctgtg cggtggggga aggggtcgac     720
gtggctcagc tttttggatt cagggagctc ggggtggga agagagaaat ggagttccag      780
gggcgtaaag gagagggagt tcgccttcct tcccttcctg agactcagga gtgactgctt     840
ctccaatcct cccaagccca ccactccaca cgactccctc ttcccggtag tcgcaagtgg     900
gagtttgggg atctgagcaa agaacccgaa gaggagttga atattggaa gtcagcagtc      960
aggcaccttc ccgagcgccc agggcgctca gagtggacat ggttgggggag gccttttggga   1020
caggtgcggt tcccggagcg caggcgcaca catgcaccca ccggcgaacg cggtgaccct    1080
cgccccaccc catcccctcc ggcgggcaac tgggtcgggt caggaggggc aaacccgcta    1140
gggagacact ccatatacgg cccggcccgc gttacctggg accgggccaa cccgctcctt    1200
ctttggtcaa cgcaggggac ccgggcgggg gcccaggccg cgaaccggcc gaggagggg     1260
gctctagtgc ccaacaccca aatatggctc gagaagggca gcgacattcc tgcggggtgg    1320
cgcggaggga atgcccgcgg gctatataaa acctgagcag agggacaagc ggccaccgca    1380
gcggacagcg ccaagtgaag cctcgcttcc cctccgcggc gaccagggcc cgagccgaga    1440
gtagcagttg tagctacccg cccaggtagg gcaggagttg ggagggggaca ggggacagg    1500
gcactaccga ggggaacctg aaggactccg ggcagaacc cagtcggttc acctggtaag    1560
cttgctagct ccgcggattc gaatcccggc cgggaacggt gcattggaac gcggattccc    1620
cgtgccaaga gtgacgtaag taccgcctat agagtctata ggcccacaaa aaatgctttc    1680
ttctttttaat atacttttttt gtttatctta tttctaatac tttccctaat ctctttcttt    1740
cagggcaata atgatacaat gtatcatgcc tctttgcacc attctaaaga ataacagtga    1800
taatttctgg gttaaggcaa tagcaatatt tctgcatata aatatttctg catataaatt    1860
gtaactgatg taagaggttt catattgcta atagcagcta caatccagct accattctgc    1920
ttttatttta tggttgggat aaggctggat tattctgagt ccaagctagg ccctttttgct    1980
aatcatgttc ataccctctta tcttcctccc acagctcctg ggcaacgtgc tggtctgtgt    2040
```

```
gctggcccat cactttggca aagaattggg attcgaacat cgatttaaag ctatggagca    2100
aaagctcatt tctgaagagg acttgaatga aatggagcaa aagctcattt ctgaagagga    2160
cttgaatgaa atggagcaaa agctcatttc tgaagaggac ttgaatgaaa tggagcaaaa    2220
gctcatttct gaagaggact tgaatgaaat ggagcaaaag ctcatttctg aagaggactt    2280
gaatgaaatg gagagcttgg gcgacctcac catgggccct aaaaagaagc gtaaagtcgc    2340 cccccccgacc gatgtcagcc tggggacga gctccactta cggcgagg acgtggcgat      2400 ggcgcatgcc gacgcgctag acgatttcga tctggacatg ttggggacg gggattcccc    2460 gggtccggga tttacccccc acgactccgc ccctacggc gctctggata tggccgactt     2520
cgagtttgag cagatgttta ccgatgccct tggaattgac gagtacggtg gggaattccc    2580
ggggatcctc gatgacagac cctatgcttg cccagtggaa agctgcgacc gccgcttttc    2640
tagatcggat gagcttaccc gccatatccg catccacacc ggccaaaaac cctttcaatg    2700
ccgtatctgc atgaggaatt tcagcagccg cgatgtcctg aggcgccata acaggaccca    2760 cacagggggaa aagccattcg catgtgacat ctgcggtcga agtttgcaa gccgcgatgt    2820 cctgaggcgc cataacagga tacatttgag gcaaaatgat ctcgaccgta cgtacaagat    2880
ccgttagcat atgctaacag atccacgggt ggcatccctg tgacccctcc ccagtgcctc    2940
tcctggccct ggaagttgcc actccagtgc ccaccagcct tgtcctaata aaattaagtt    3000
gcatcatttt gtctgactag tacgggtggc atccctgtga cccctcccca gtgcctctcc    3060
tggccctgga agttgccact ccagtgccca ccagccttgt cctaataaaa ttaagttgca    3120
tcattttgtc tgactaggtg tccttctata atattatggg gtggagggg gtggtatgga    3180 gcaaggggca agttgggaag acaacctgta gggcctgcgg ggtctattgg gaaccaagct    3240
ggagtgcagt ggcacaatct tggctcactg caatctccgc ctcctgggtt caagcgattc    3300
tcctgcctca gcctcccgag ttgttgggat tccaggcatg catgaccagg ctcagctaat    3360
ttttgttttt tggtagaga cggggtttca ccatattggc caggctggtc tccaactcct    3420
aatctcaggt gatctaccca ccttggcctc ccaaattgct gggattacag gcgtgaacca    3480
ctgctccctt ccctgtcctt ctgattttgt aggtaaccac gtgcggaccg agcggccgc    3539
```

<210> SEQ ID NO 84
<211> LENGTH: 3488
<212> TYPE: DNA
<213> ORGANISM: Artificial Sequence
<220> FEATURE:
<223> OTHER INFORMATION: Synthetic Construct

<400> SEQUENCE: 84

```
gcggccgcac gcgtcaccaa ctgggtaacc tctgctgacc cccactctac tttaccataa      60
gtagctccaa atccttctag aaaatctgaa aggcatagcc ccatatatca gtgatataaa     120
tagaacctgc agcaggctct ggtaaatgat gactacaagg tggactggga ggcagcccgg     180
ccttggcagg catcatcctc taaatataaa gatgagtttg ttcagccttt gcagaaggaa     240
aaactgccac ccatcctaga gtgccgcgtc cttgtccccc caccccctcc aatttattgg     300
gaggaaggac cagctaagcc tcatctagga agagcccctc acccatctcc acctccactc     360
caggtctagc cagtcctggg ttgtgaccct tgtctttcag cccaggagg ggacacaca      420 tagtgccacc aaagaggctg ggggagggcc tcagcccacc aaaacctggg gccagtgcgt    480
cctacaggag gggaaccctc accccttcaa tcccttaggg agacccaagg gcgctgcgcg    540
tccctgaggc ggacagctcc gtgtgctcag gctttgcgcc tgacaggcct atccccggga    600
```

-continued

```
gcccccgcgc ctcctcccccg gcgctccgcc ctcgcctccc cccgccagtt gtctatcctg    660
cgacagctgc gcgccctccg gccgccggtg gccctctgtg cggtggggga aggggtcgac    720
gtggctcagc tttttggatt cagggagctc gggggtggga agagagaaat ggagttccag    780
gggcgtaaag gagagggagt tcgccttcct tcccttcctg agactcagga gtgactgctt    840
ctccaatcct cccaagccca ccactccaca cgactccctc ttcccggtag tcgcaagtgg    900
gagtttgggg atctgagcaa agaacccgaa gaggagttga aatattggaa gtcagcagtc    960
aggcaccttc ccgagcgccc agggcgctca gagtggacat ggttggggag gcctttggga    1020
caggtgcggt tcccggagcg caggcgcaca catgcaccca ccggcgaacg cggtgaccct    1080
cgccccaccc catcccctcc ggcgggcaac tgggtcgggt caggaggggc aaacccgcta    1140
gggagacact ccatatacgg cccggcccgc gttacctggg accgggccaa cccgctcctt    1200
ctttggtcaa cgcaggggac ccgggcgggg gcccaggccg cgaaccggcc gagggagggg    1260
gctctagtgc ccaacaccca aatatggctc gagaagggca gcgacattcc tgcggggtgg    1320
cgcggaggga atgcccgcgg gctatataaa acctgagcag agggacaagc ggccaccgca    1380
gcggacagcg ccaagtgaag cctcgcttcc cctccgcggc gaccagggcc cgagccgaga    1440
gtagcagttg tagctacccg cccaggtagg gcaggagttg ggaggggaca ggggacagg    1500 gcactaccga ggggaacctg aaggactccg gggcagaacc cagtcggttc acctggtaag    1560
cttgctagct ccgcggattc gaatcccggc cgggaacggt gcattggaac gcggattccc    1620
cgtgccaaga gtgacgtaag taccgcctat agagtctata ggcccacaaa aaatgctttc    1680 ttctttttaat atactttttt gtttatctta tttctaatac tttccctaat ctctttcttt    1740
cagggcaata atgatacaat gtatcatgcc tctttgcacc attctaaaga ataacagtga    1800
taatttctgg gttaaggcaa tagcaatatt tctgcatata aatatttctg catataaatt    1860
gtaactgatg taagaggttt catattgcta atagcagcta caatccagct accattctgc    1920
ttttatttta tggttgggat aaggctggat tattctgagt ccaagctagg ccttttgct    1980 aatcatgttc atacctctta tcttcctccc acagctcctg gcaacgtgc tggtctgtgt    2040 gctggcccat cactttggca aagaattggg attcgaacat cgatttaaag ctatggagca    2100
aaagctcatt tctgaagagg acttgaatga aatggagcaa aagctcattt ctgaagagga    2160
cttgaatgaa atggagcaaa agctcatttc tgaagaggac ttgaatgaaa tggagcaaaa    2220
gctcatttct gaagaggact tgaatgaaat ggagcaaaag ctcatttctg aagaggactt    2280
gaatgaaatg gagagcttgg gcgacctcac catgggccct aaaaagaagc gtaaagtcgc    2340
ccccccgacc gatgtcagcc tgggggacga gctccactta gacggcgagg acgtggcgat    2400
ggcgcatgcc gacgcgctag acgatttcga tctggacatg ttgggggacg gggattcccc    2460
gggtccggga tttaccccccc acgactccgc cccctacggc gctctggata tggccgactt    2520
cgagtttgag cagatgttta ccgatgccct tggaattgac gagtacggtg gggaattccc    2580
ggggatcctc gatgacagac cctatgcttg cccagtggaa agctgcgacc gccgcttttc    2640
tagatcggat gagcttaccc gccatatccg catccacacc ggccaaaaac cctttcaatg    2700
ccgtatctgc atgaggaatt tcagcagccg cgatgtcctg aggcgccata acaggaccca    2760
cacaggggaa aagccattcg catgtgacat ctgcggtcga aagtttgcaa gccgcgatgt    2820
cctgaggcgc cataacagga tacatttgag gcaaggtccc agatctcacg tctgtgcaga    2880
atgtggcaaa gcgttcgttg agagctcaaa gctaaaacga caccagctgg ttcatgagct    2940
```

```
ggagagaagc cctttagct cgagagatct acgggtggca tccctgtgac ccctccccag    3000
tgcctctcct ggccctggaa gttgccactc cagtgcccac cagccttgtc ctaataaaat    3060
taagttgcat cattttgtct gactaggtgt ccttctataa tattatgggg tggaggggg    3120 tggtatggag caaggggcaa gttgggaaga caacctgtag ggcctgcggg gtctattggg    3180
aaccaagctg gagtgcagtg gcacaatctt ggctcactgc aatctccgcc tcctgggttc    3240
aagcgattct cctgcctcag cctcccgagt tgttgggatt ccaggcatgc atgaccaggc    3300
tcagctaatt tttgtttttt tggtagagac ggggtttcac catattggcc aggctggtct    3360
ccaactccta atctcaggtg atctaccac cttggcctcc caaattgctg ggattacagg     3420
cgtgaaccac tgctcccttc cctgtccttc tgattttgta ggtaaccacg tgcggaccga    3480
gcggccgc                                                             3488

<210> SEQ ID NO 85
<211> LENGTH: 4035
<212> TYPE: DNA
<213> ORGANISM: Artificial Sequence
<220> FEATURE:
<223> OTHER INFORMATION: Synthetic Construct

<400> SEQUENCE: 85
gcggccgcac gcgtcaccaa ctgggtaacc tctgctgacc cccactctac tttaccataa      60
gtagctccaa atccttctag aaaatctgaa aggcatagcc ccatatatca gtgatataaa     120
tagaacctgc agcaggctct ggtaaatgat gactacaagg tggactggga ggcagcccgg    180
ccttggcagg catcatcctc taaatataaa gatgagtttg ttcagccttt gcagaaggaa    240
aaactgccac ccatcctaga gtgccgcgtc cttgtccccc caccccctcc aatttattgg    300
gaggaaggac cagctaagcc tcatctagga agagcccctc acccatctcc acctccactc    360
caggtctagc cagtcctggg ttgtgaccct tgtctttcag cccaggaga gggacacaca     420 tagtgccacc aaagaggctg ggggagggcc tcagcccacc aaaacctggg gccagtgcgt    480
cctacaggag gggaaccctc acccccttcaa tcccctttagg agacccaagg gcgctgcgcg    540
tccctgaggc ggacagctcc gtgtgctcag gcttgcgcc tgacaggcct atccccggga    600
gcccccgcgc ctcctccccg gcgctccgcc ctcgcctccc cccgccagtt gtctatcctg    660
cgacagctgc gcgccctccg gccgccggtg gccctctgtg cggtggggga aggggtcgac    720
gtggctcagc ttttttggatt cagggagctc gggggtggga agagagaaat ggagttccag    780
gggcgtaaag gagagggagt tcgccttcct tcccttcctg agactcagga gtgactgctt    840
ctccaatcct cccaagccca ccactccaca cgactccctc ttcccggtag tcgcaagtgg    900
gagtttgggg atctgagcaa agaacccgaa gaggagttga aatattggaa gtcagcagtc    960
aggcaccttc ccgagcgccc agggcgctca gagtggacat ggttggggag gcctttggga   1020
caggtgcggt tcccggagcg caggcgcaca catgcaccca ccggcgaacg cggtgaccct    1080
cgccccaccc catcccctcc ggcgggcaac tgggtcgggt caggaggggc aaacccgcta   1140
gggagacact ccatatacgg cccggcccgc gttacctggg accgggccaa cccgctcctt    1200 cttttggtcaa cgcaggggac ccgggcgggg gccaggccg cgaaccggcc gagggaggg    1260 gctctagtgc ccaacaccca aatatggctc gagaagggca gcgacattcc tgcggggtgg   1320
cgcggaggga atgcccgcgg gctatataaa acctgagcag agggacaagc ggccaccgca   1380
gcggacagcg ccaagtgaag cctcgcttcc cctccgcggc gaccagggcc cgagccgaga   1440
gtagcagttg tagctacccg cccaggtagg gcaggagttg ggaggggaca gggggacagg   1500
```

```
gcactaccga ggggaacctg aaggactccg gggcagaacc cagtcggttc acctggtaag    1560
cttgctagct ccgcggattc gaatcccggc cgggaacggt gcattggaac gcggattccc    1620
cgtgccaaga gtgacgtaag taccgcctat agagtctata ggcccacaaa aaatgctttc    1680 ttctttaat atacttttt gtttatctta tttctaatac tttccctaat ctctttcttt      1740
cagggcaata atgatacaat gtatcatgcc tctttgcacc attctaaaga ataacagtga    1800
taatttctgg gttaaggcaa tagcaatatt tctgcatata aatatttctg catataaatt    1860
gtaactgatg taagaggttt catattgcta atagcagcta caatccagct accattctgc    1920 tttattta tggttgggat aaggctggat tattctgagt ccaagctagg ccctttgct       1980 aatcatgttc atacctctta tcttcctccc acagctcctg gcaacgtgc tggtctgtgt     2040 gctggcccat cactttggca aagaattggg attcgaacat cgatttaaag ctatggagca    2100
aaagctcatt tctgaagagg acttgaatga aatggagcaa aagctcattt ctgaagagga    2160
cttgaatgaa atggagcaaa agctcatttc tgaagaggac ttgaatgaaa tggagcaaaa    2220
gctcatttct gaagaggact tgaatgaaat ggagcaaaag ctcatttctg aagaggactt    2280
gaatgaaatg gagagcttgg gcgacctcac catgggccct aaaaagaagc gtaaagtcgc    2340 cccccccgacc gatgtcagcc tggggggacga gctccactta gacggcgagg acgtggcgat   2400
ggcgcatgcc gacgcgctag acgatttcga tctggacatg ttgggggacg gggattcccc    2460
gggtccggga tttaccccccc acgactccgc cccctacggc gctctggata tggccgactt    2520
cgagtttgag cagatgttta ccgatgccct tggaattgac gagtacggtg gggaattccc    2580
ggggatcttg gcaaagcgct tgccgactt tacagtctac aggaaccgca cacttcagaa      2640
atggcacgat aagaccaaac tggcttctgg aaaactgggg aagggttttg gtgcctttga    2700
acgctcaatc ttgactcaga tcgaccatat tctgatggac aaagagagat tacttcgaag    2760
gacacagacc aagcgctctg tctatcgagt tcttggcaaa cctgagccag cagctcagcc    2820
tgtcccagag agtttgccag gggaaccgga gatccttcct caagcccctg ctaatgctca    2880
tctgaaggac ttggatgaag aaatctttga tgatgatgac ttttaccacc agctccttcg    2940
agaactcata gaacggaaga ccagctcctt ggggatcctg gatcgccctt acgcctgccc    3000
tgtggaatct gcgaccgcc ggttctcccg cagcgataac ctggtgcggc acatccggat     3060
tcacaccggc cagaaacctt tccagtgcag gatctgcatg agaaatttct cccgtccga     3120 ccacctgacc acccacaata ggacccacac cggcgagaaa ccctttgcct gcgacatctg    3180
cgggagaaag ttcgccgacc ccggccacct ggtgagacac aatagaatcc acaccggtga    3240
aaagcccttc gcctgtcccg tggagagctg cgatcgcaga ttcagccgca gcgacgagct    3300
gacaaggcac atcagaatcc acaccgggca gaagcctttt cagtgccgga tctgcatgag    3360
gaacttcagc tcccgggacg tgctgagacg ccacaatcgc acacacaccg gcgaaaagcc    3420
cttcgcctgt gatatttgcg ggcggaaatt tgcctccaga gatgtgctgc gccgccacaa    3480
ccgcattcac ctgagacaga acgatctcga gagatctacg ggtggcatcc ctgtgacccc    3540 tcccccagtgc ctctcctggc cctggaagtt gccactccag tgcccaccag ccttgtccta   3600
ataaaattaa gttgcatcat tttgtctgac taggtgtcct tctataatat tatgggggtgg   3660 agggggggtgg tatggagcaa ggggcaagtt gggaagacaa cctgtagggc ctgcggggtc    3720
tattgggaac caagctggag tgcagtggca caatcttggc tcactgcaat ctccgcctcc    3780
tgggttcaag cgattctcct gcctcagcct cccgagttgt tgggattcca ggcatgcatg    3840
```

```
accaggctca gctaatttt gtttttttgg tagagacggg gtttcaccat attggccagg    3900
ctggtctcca actcctaatc tcaggtgatc tacccacctt ggcctcccaa attgctggga    3960
ttacaggcgt gaaccactgc tcccttccct gtccttctga ttttgtaggt aaccacgtgc    4020
ggaccgagcg gccgc                                                    4035

<210> SEQ ID NO 86
<211> LENGTH: 4259
<212> TYPE: DNA
<213> ORGANISM: Artificial Sequence
<220> FEATURE:
<223> OTHER INFORMATION: Synthetic Construct

<400> SEQUENCE: 86
gcggccgcac gcgtcaccaa ctgggtaacc tctgctgacc cccactctac tttaccataa      60
gtagctccaa atccttctag aaaatctgaa aggcatagcc ccatatatca gtgatataaa     120
tagaacctgc agcaggctct ggtaaatgat gactacaagg tggactggga ggcagcccgg     180
ccttggcagg catcatcctc taaatataaa gatgagtttg ttcagccttt gcagaaggaa     240
aaactgccac ccatcctaga gtgccgcgtc cttgtccccc cacccctcc aatttattgg     300 gaggaaggac cagctaagcc tcatctagga agagcccctc acccatctcc acctccactc     360
caggtctagc cagtcctggg ttgtgaccct tgtctttcag ccccaggaga gggacacaca     420
tagtgccacc aaagaggctg ggggaggggcc tcagcccacc aaaacctggg gccagtgcgt     480
cctacaggag gggaaccctc accccttcaa tcccttagg agacccaagg gcgctgcgcg     540
tccctgaggc ggacagctcc gtgtgctcag gctttgcgcc tgacaggcct atccccggga     600
gcccccgcgc ctcctccccg gcgctccgcc ctcgcctccc cccgccagtt gtctatcctg     660
cgacagctgc gcgccctccg gccgccgtg gccctctgtg cggtggggga aggggtcgac     720
gtggctcagc ttttggatt cagggagctc ggggggtggga agagagaaat ggagttccag     780
gggcgtaaag gagagggagt tcgccttcct tccccttcctg agactcagga gtgactgctt     840
ctccaatcct cccaagccca ccactccaca cgactccctc ttcccggtag tcgcaagtgg     900
gagtttgggg atctgagcaa agaacccgaa gaggagttga atattggaa gtcagcagtc     960 aggcaccttc ccgagcgccc agggcgctca gagtggacat ggttggggag gcctttggga    1020
caggtgcggt tcccggagcg caggcgcaca catgcaccca ccggcgaacg cggtgaccct    1080
cgccccaccc catcccctcc ggcgggcaac tgggtcgggt caggaggggc aaacccgcta    1140
gggagacact ccatatacgg cccggccgcc gttacctggg accgggccaa cccgctcctt    1200 cttttggtcaa cgcaggggac ccgggcgggg gcccaggccg cgaaccggcc gagggagggg    1260
gctctagtgc ccaacaccca aatatggctc gagaagggca gcgacattcc tgcggggtgg    1320
cgcggaggga atgcccgcgg gctatataaa acctgagcag agggacaagc ggccaccgca    1380
gcggacagcg ccaagtgaag cctcgcttcc cctccgcggc gaccagggcc cgagccgaga    1440
gtagcagttg tagctacccg cccaggtagg gcaggagttg gaggggaca ggggacagg     1500 gcactaccga ggggaaccctg aaggactccg gggcagaacc cagtcggttc acctggtaag    1560
cttgctagct ccgcggattc gaatcccggc cgggaacggt gcattggaac gcggattccc    1620
cgtgccaaga gtgacgtaag taccgcctat agagtctata ggcccacaaa aaatgctttc    1680 ttctttaat atacttttt gtttatctta tttctaatac ttcccctaat ctctttcttt    1740
cagggcaata atgatacaat gtatcatgcc tctttgcacc attctaaaga ataacagtga    1800
taatttctgg gttaaggcaa tagcaatatt tctgcatata aatatttctg catataaatt    1860
```

```
gtaactgatg taagaggttt catattgcta atagcagcta caatccagct accattctgc   1920 tttttatttta tggttgggat aaggctggat tattctgagt ccaagctagg ccctttttgct  1980 aatcatgttc atacctctta tcttcctccc acagctcctg gcaacgtgc tggtctgtgt    2040 gctggcccat cactttggca aagaattggg attcgaacat cgatggtacc gaattcaatg   2100
gccgctgcca aggccgagat gcagctgatg agcccctgc agatcagcga ccccttcggc   2160
agcttccccc acagccccac catggacaac taccccaagc tggaagagat gatgctgctg    2220
agcaatggcg ctcctcagtt cctgggagcc gctggcgccc tgagggcag cggcagcaat    2280 agcagcagca gctctagcgg cggaggcgga ggggggaggcg gcggaagcaa tagctccagc   2340
tccagcagca cattcaatcc acaagccgac accggcgagc agccctatga gcacctgacc   2400
gccgagagct tccccgacat cagcctgaac aacgagaagg tgctggtgga aaccagctac   2460
cccagccaga ccacccggct gccccctatc acctacacag gccggttcag cctggaaccc   2520 gccccctaaca gcggcaacac cctgtggccc gagcccctgt ttagcctggt gtccggcctg   2580
gtgtctatga ccaaccccccc tgccagcagc tcctctgccc caagccctgc cgccagctct   2640
gcctctgcca gccagagccc tccactgagc tgcgccgtgc ccagcaacga cagcagcccc   2700
atctacagcg ccgctcccac cttccccacc cccaacaccg acatcttccc cgagcctcag   2760
agccaggcct ttcctggatc tgccggcacc gccctgcagt acccacctcc tgcctatcct   2820
gccgccaagg gcggcttcca ggtgcccatg atccccgact acctgttccc ccagcagcag   2880
ggcgatctgg gcctgggcac ccccgaccag aagccttttcc agggcctcga agcggacc   2940 cagcagccaa gcctgacccc cctgagcacc atcaaggcct cgccaccca gagcggcagc   3000 caggacctga aggccctgaa caccagctac cagagccagc tgatcaagcc cagccggatg   3060
cggaagtacc ccaaccggcc cagcaagacc ccccacacg agaggcctta cgcctgcccc   3120
gtggaaagct gcgacagacg gttcagcaga agcgacgagc tgacccggca catccggatc   3180
cacaccggcc agaaacccctt ccagtgccgg atctgcatgc ggaacttcag cagccgggac   3240
gtgctgcggc ggcacaatag aacccacaca ggcgagaagc ccttcgcctg cgacatctgc   3300
ggccggaagt tcgccagcag agatgtgctg cggagacaca acaggatcca cctgagacag   3360
aaggacaaga aagccgacaa gagcgtggtc gccagcagcg ctaccagcag cctgagcagc   3420 taccccttctc ctgtggccac ctcctaccca agcccagtga ccacaagcta cccatccccc   3480
gccaccacct cttatcccag ccccgtgcct accagcttca gctctcccgg cagctccaca   3540 tacccccagcc ctgtgcatag cggcttccct agccctagcg tggccaccac atacagcagc   3600 gtgcccccctg ccttcccagc tcaagtgtcc agcttcccca gctccgccgt gaccaacagc   3660
ttcagcgcca gcaccggcct gagcgacatg accgccacct tcagccccg gaccatcgag   3720 atctgctgac tcgagagatc tacgggtggc atccctgtga ccccctcccca gtgcctctcc   3780 tggccctgga agttgccact ccagtgccca ccagccttgt cctaataaaa ttaagttgca   3840
tcattttgtc tgactaggtg tccttctata atattatggg gtggagggg gtggtatgga   3900 gcaagggca agttgggaag acaacctgta gggcctgcgg ggtctattgg gaaccaagct   3960
ggagtgcagt ggcacaatct tggctcactg caatctccgc ctcctgggtt caagcgattc   4020
tcctgcctca gcctcccgag ttgttgggat tccaggcatg catgaccagg ctcagctaat   4080
ttttgttttt ttggtagaga cggggtttca ccatattggc caggctggtc tccaactcct   4140
aatctcaggt gatctaccca ccttggcctc ccaaattgct gggattacag gcgtgaacca   4200
```

```
ctgctccctt ccctgtcctt ctgattttgt aggtaaccac gtgcggaccg agcggccgc   4259
```

<210> SEQ ID NO 87
<211> LENGTH: 4259
<212> TYPE: DNA
<213> ORGANISM: Artificial Sequence
<220> FEATURE:
<223> OTHER INFORMATION: Synthetic Construct

<400> SEQUENCE: 87

```
gcggccgcac gcgtcaccaa ctgggtaacc tctgctgacc cccactctac tttaccataa     60
gtagctccaa atccttctag aaaatctgaa aggcatagcc ccatatatca gtgatataaa    120
tagaacctgc agcaggctct ggtaaatgat gactacaagg tggactggga ggcagcccgg    180
ccttggcagg catcatcctc taaatataaa gatgagtttg ttcagccttt gcagaaggaa    240
aaactgccac ccatcctaga gtgccgcgtc cttgtccccc cacccctcc aatttattgg     300
gaggaaggac cagctaagcc tcatctagga gagcccctc acccatctcc acctccactc     360
caggtctagc cagtcctggg ttgtgaccct tgtctttcag ccccaggaga gggacacaca    420
tagtgccacc aaagaggctg ggggagggcc tcagcccacc aaaacctggg gccagtgcgt    480
cctacaggag gggaaccctc acccttcaa tcccttagg agacccaagg gcgctgcgcg      540
tccctgaggc ggacagctcc gtgtgctcag gctttgcgcc tgacaggcct atccccggga    600
gccccgcgc ctcctcccg gcgctccgcc ctcgcctccc ccgccagtt gtctatcctg       660
cgacagctgc gcgccctccg gccgccggtg gccctctgtg cggtgggga aggggtcgac     720
gtggctcagc ttttttggatt cagggagctc ggggggtggga agagagaaat ggagttccag  780
gggcgtaaag gagagggagt tcgccttcct tccctcctg agactcagga gtgactgctt    840
ctccaatcct cccaagccca ccactccaca cgactccctc ttcccggtag tcgcaagtgg   900
gagtttgggg atctgagcaa agaacccgaa gaggagttga atattggaa gtcagcagtc    960
aggcaccttc ccgagcgccc agggcgctca gagtggacat ggttggggag gcctttggga   1020
caggtgcggt tcccggagcg caggcgcaca catgcaccca ccggcgaacg cggtgaccct    1080
cgccccaccc catcccctcc ggcgggcaac tgggtcgggt caggaggggc aaacccgcta   1140
gggagacact ccatatacgg cccggcccgc gttacctggg accgggccaa cccgctcctt   1200
ctttggtcaa cgcaggggac ccgggcgggg gcccaggccg cgaaccggcc gagggagggg   1260
gctctagtgc ccaacaccca aatatggctc gagaagggca gcgacattcc tgcgggtgg    1320
cgcggaggga atgcccgcgg gctatataaa acctgagcag agggacaagc ggccaccgca   1380
gcggacagcg ccaagtgaag cctcgcttcc cctccgcggc gaccagggcc cgagccgaga   1440
gtagcagttg tagctacccg cccaggtagg gcaggagttg ggaggggaca ggggacagg    1500
gcactaccga ggggaacctg aaggactccg gggcagaacc cagtcggttc acctggtaag   1560
cttgctagct ccgcggattc gaatcccggc cgggaacggt gcattggaac gcggattccc    1620
cgtgccaaga gtgacgtaag taccgcctat agagtctata ggcccacaaa aaatgctttc   1680
ttctttaat atactttttt gtttatctta tttctaatac tttccctaat ctctttcttt    1740
cagggcaata atgatacaat gtatcatgcc tctttgcacc attctaaaga ataacagtga   1800
taatttctgg gttaaggcaa tagcaatatt tctgcatata aatatttctg catataaatt   1860
gtaactgatg taagaggttt catattgcta atagcagcta caatccagct accattctgc   1920
ttttatttta tggttgggat aaggctggat tattctgagt ccaagctagg ccctttttgct  1980
aatcatgttc atacctctta tcttcctccc acagctcctg ggcaacgtgc tggtctgtgt    2040
```

```
gctggcccat cactttggca aagaattggg attcgaacat cgatggtacc gaattcaatg    2100
gccgctgcca aggccgagat gcagctgatg agcccctgc agatcagcga cccttcggc     2160
agcttccccc acagccccac catggacaac taccccaagc tggaagagat gatgctgctg    2220
agcaatggcg ctcctcagtt cctgggagcc gctggcgccc tgagggcag cggcagcaat     2280
agcagcagca gctctagcgg cggaggcgga gggggaggcg gcggaagcaa tagctccagc    2340
tccagcagca cattcaatcc acaagccgac accggcgagc agccctatga gcacctgacc    2400
gccgagagct tccccgacat cagcctgaac aacgagaagg tgctggtgga aaccagctac    2460
cccagccaga ccacccggct gccccctatc acctacacag gccggttcag cctggaaccc    2520
gcccctaaca cggcaacac cctgtggccc gagcccctgt ttagcctggt gtccggcctg      2580
gtgtctatga ccaaccccc tgccagcagc tcctctgccc caagccctgc cgccagctct      2640
gcctctgcca gccagagccc tccactgagc tgcgccgtgc ccagcaacga cagcagcccc    2700
atctacagcg ccgctcccac cttccccacc cccaacaccg acatcttccc cgagcctcag    2760
agccaggcct ttcctggatc tgccggcacc gccctgcagt acccacctcc tgcctatcct    2820
gccgccaagg gcggcttcca ggtgcccatg atccccgact acctgttccc ccagcagcag    2880
ggcgatctgg gcctgggcac ccccgaccag aagcctttcc agggcctcga aagccggacc    2940
cagcagccaa gctgaccccc ctgagcacc atcaaggcct cgccaccca gagcggcagc       3000
caggacctga aggccctgaa caccagctac cagagccagc tgatcaagcc cagccggatg    3060
cggaagtacc ccaaccggcc cagcaagacc cccccacacg agaggcctta cgcctgcccc    3120
gtggaaagct gcgacagacg gttcagcaga agcgacaacc tggtccggca catccggatc    3180
cacaccggcc agaaacccct tccagtgccgg atctgcatgc ggaacttctc tcggagcgac    3240
cacctgacca cccacatcag aacccacaca ggcgagaagc ccttcgcctg cgacatctgc   3300
ggccggaagt tcgccgaccc cggccacctc gtcagacaca caggattca cctgagacag    3360
aaggacaaga aagccgacaa gagcgtggtc gccagcagcg ctaccagcag cctgagcagc    3420
taccttctc ctgtggccac ctcctaccca agcccagtga ccacaagcta cccatccccc      3480
gccaccacct cttatcccag ccccgtgcct accagcttca gctctcccgg cagctccaca    3540
taccccagcc ctgtgcatag cggcttccct agccctagcg tggccaccac atacagcagc    3600
gtgcccctg ccttcccagc tcaagtgtcc agcttccca gctccgccgt gaccaacagc       3660
ttcagcgcca gcaccggcct gagcgacatg accgccacct tcagccccg gaccatcgag     3720
atctgctgac tcgagagatc tacgggtggc atccctgtga cccctcccca gtgcctctcc     3780
tggccctgga agttgccact ccagtgccca ccagccttgt cctaataaaa ttaagttgca   3840
tcattttgtc tgactaggtg tccttctata atattatggg gtggaggggg gtggtatgga    3900
gcaaggggca agttgggaag acaacctgta gggcctgcgg ggtctattgg gaaccaagct    3960
ggagtgcagt ggcacaatct tggctcactg caatctccgc ctcctgggtt caagcgattc    4020
tcctgcctca gcctcccgag ttgttgggat tccaggcatg catgaccagg ctcagctaat    4080
ttttgttttt ttggtagaga cggggtttca ccatattggc caggctggtc tccaactcct    4140
aatctcaggt gatctaccca ccttggcctc ccaaattgct gggattacag gcgtgaacca    4200
ctgctccctt ccctgtcctt ctgattttgt aggtaaccac gtgcggaccg agcggccgc     4259
```